(12) United States Patent
Hamamura et al.

(10) Patent No.: US 7,553,867 B2
(45) Date of Patent: Jun. 30, 2009

(54) FURAN OR THIOPHENE DERIVATIVE AND MEDICINAL USE THEREOF

(75) Inventors: Kazumasa Hamamura, Osaka (JP); Shigekazu Sasaki, Osaka (JP); Yuichiro Amano, Osaka (JP); Junichi Sakamoto, Osaka (JP); Kohji Fukatsu, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 152 days.

(21) Appl. No.: 10/526,507

(22) PCT Filed: Sep. 4, 2003

(86) PCT No.: PCT/JP03/11308

§ 371 (c)(1),
(2), (4) Date: Sep. 29, 2005

(87) PCT Pub. No.: WO2004/022551

PCT Pub. Date: Mar. 18, 2004

(65) Prior Publication Data

US 2006/0100261 A1   May 11, 2006

(30) Foreign Application Priority Data

Sep. 6, 2002 (JP) ............... 2002-261873
Jun. 27, 2003 (JP) ............... 2003-185241

(51) Int. Cl.
*A61K 31/341* (2006.01)
*A61K 31/381* (2006.01)
*C07D 307/40* (2006.01)
*C07D 333/14* (2006.01)
*C07D 333/18* (2006.01)

(52) U.S. Cl. .................. 514/438; 514/461; 549/78; 549/484; 549/497; 549/505

(58) Field of Classification Search ........... 514/438, 514/461; 549/78, 484, 497, 505
See application file for complete search history.

(56) References Cited

U.S. PATENT DOCUMENTS

| 6,020,339 | A  | * | 2/2000 | Perrier et al. ............ 514/269 |
| 6,506,757 | B1 |   | 1/2003 | Tajima et al. |
| 6,589,969 | B1 |   | 7/2003 | Tajima et al. |
| 2004/0097739 | A1 |   | 5/2004 | Sakuma et al. |

FOREIGN PATENT DOCUMENTS

| WO | WO 99/46232   | 9/1999  |
| WO | WO 00/23442   | 4/2000  |
| WO | WO 02/14291   | 2/2002  |
| WO | WO 02/057783  | 7/2002  |
| WO | WO 02/059098  | 8/2002  |
| WO | WO 02/083616  | 10/2002 |
| WO | WO 02/092590  | 11/2002 |
| WO | WO 02/096893  | 12/2002 |
| WO | WO 02/096894  | 12/2002 |
| WO | WO 02/096895  | 12/2002 |
| WO | WO 02/100403  | 12/2002 |
| WO | WO 03/000649  | 1/2003  |
| WO | WO 03/059875  | 7/2003  |
| WO | WO 2004/041266 | 5/2004 |

OTHER PUBLICATIONS

Hsueh et al. Arterioscler. Thromb. Vasc. Biol. 2001, 1891-5.*
Duriez et al. Exp. Opin. Invest. Drugs 1998, 7(11), pp. 1997-2009.*
Rumi et al. Curr. Med. Chem. Anti-Cancer Agents 2004, 4(6), 465-477.*
J. Alzeer, et al., "Phenyl B-Methoxyacrylates: A New Antimalarial Pharmacophore", *J. Med. Chem.*, (2000), vol. 43, No. 4, pp. 560-568.
I. M. Lapina, et al., "Acylation of Amino Acids with Furancarboxylic Acid Chlorides", *Russian Journal of General Chemistry*, (2001), vol. 71, No. 9, pp. 1479-1483.
Chemcats, RN. 381673-50-3 and RN 352338-59-1, 2002.

* cited by examiner

*Primary Examiner*—Joseph K McKane
*Assistant Examiner*—Jason Nolan
(74) *Attorney, Agent, or Firm*—Wenderoth, Lind & Ponack, L.L.P.

(57) ABSTRACT

The present invention provides a compound represented by the formula (I):

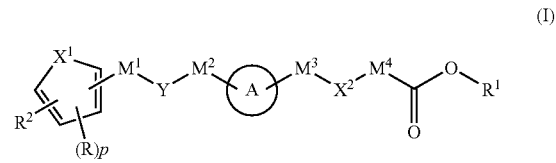

[wherein R is an optionally substituted hydrocarbon group or an optionally substituted heterocyclic group, p is 0, 1 or 2, and when p is 2, each R may be the same or different, $R^1$ is a hydrogen atom or an optionally substituted hydrocarbon group, $R^2$ is an optionally substituted aromatic group, Ring A is an optionally substituted monocyclic aromatic ring or optionally substituted bicyclic aromatic fused ring, $X^1$ is an oxygen atom or a sulfur atom, $X^2$ is a bond, an oxygen atom or —S(O)$_n$— (wherein n is 0, 1 or 2), Y is a bond, an oxygen atom, —S(O)$_m$—, —C(=O)—N($R^3$)— or —N($R^3$)—C (=O)— ($R^3$ is a hydrogen atom, an optionally substituted hydrocarbon group or an optionally substituted heterocyclic group, and m is 0, 1 or 2), $M^1$, $M^2$ and $M^3$ may be the same or different and are each independently a bond or an optionally substituted divalent aliphatic hydrocarbon group, and $M^4$ is an optionally substituted divalent aliphatic hydrocarbon group] or a salt thereof, which is useful as a prophylactic and/or therapeutic agent for lipid metabolism abnormality, arteriosclerotic disease and sequelae thereof, diabetes mellitus and the like.

27 Claims, No Drawings

SEQUENCE LISTING

<160> NUMBER OF SEQ ID NOS: 12

<210> SEQ ID NO 1
<211> LENGTH: 34
<212> TYPE: DNA
<213> ORGANISM: Artificial Sequence
<220> FEATURE:
<223> OTHER INFORMATION: A nucleotide sequence of primer PARD-U

<400> SEQUENCE: 1
aacggtacct cagccatgga gcagcctcag gagg                                   34

<210> SEQ ID NO 2
<211> LENGTH: 34
<212> TYPE: DNA
<213> ORGANISM: Artificial Sequence
<220> FEATURE:
<223> OTHER INFORMATION: A nucleotide sequence of primer PARD-L

<400> SEQUENCE: 2
taagtcgacc cgttagtaca tgtccttgta gatc                                   34

<210> SEQ ID NO 3
<211> LENGTH: 33
<212> TYPE: DNA
<213> ORGANISM: Artificial Sequence
<220> FEATURE:
<223> OTHER INFORMATION: A nucleotide sequence of primer XRA-U

<400> SEQUENCE: 3
ttagaattcg acatggacac caaacatttc ctg                                    33

<210> SEQ ID NO 4
<211> LENGTH: 33
<212> TYPE: DNA
<213> ORGANISM: Artificial Sequence
<220> FEATURE:
<223> OTHER INFORMATION: A nucleotide sequence of primer XRA-L

<400> SEQUENCE: 4
cccctcgagc taagtcattt ggtgcggcgc ctc                                    33

<210> SEQ ID NO 5
<211> LENGTH: 36
<212> TYPE: DNA
<213> ORGANISM: Artificial Sequence
<220> FEATURE:
<223> OTHER INFORMATION: A nucleotide sequence of primer PPRE-U

<400> SEQUENCE: 5
tcgacagggg accaggacaa aggtcacgtt cgggag                                 36

<210> SEQ ID NO 6
<211> LENGTH: 36
<212> TYPE: DNA
<213> ORGANISM: Artificial Sequence
<220> FEATURE:
<223> OTHER INFORMATION: A nucleotide sequence of primer PPRE-L

<400> SEQUENCE: 6
tcgactcccg aacgtgacct ttgtcctggt cccctg                                 36

<210> SEQ ID NO 7
<211> LENGTH: 28

```
<212> TYPE: DNA
<213> ORGANISM: Artificial Sequence
<220> FEATURE:
<223> OTHER INFORMATION: A nucleotide sequence of primer TK-U

<400> SEQUENCE: 7
cccagatctc cccagcgtct tgtcattg                                              28

<210> SEQ ID NO 8
<211> LENGTH: 28
<212> TYPE: DNA
<213> ORGANISM: Artificial Sequence
<220> FEATURE:
<223> OTHER INFORMATION: A nucleotide sequence of primer TK-L

<400> SEQUENCE: 8
tcaccatggt caagctttta agcgggtc                                              28

<210> SEQ ID NO 9
<211> LENGTH: 33
<212> TYPE: DNA
<213> ORGANISM: Artificial Sequence
<220> FEATURE:
<223> OTHER INFORMATION: A nucleotide sequence of primer PAG-U

<400> SEQUENCE: 9
gtgggtaccg aaatgaccat ggttgacaca gag                                        33

<210> SEQ ID NO 10
<211> LENGTH: 33
<212> TYPE: DNA
<213> ORGANISM: Artificial Sequence
<220> FEATURE:
<223> OTHER INFORMATION: A nucleotide sequence of primer PAG-L

<400> SEQUENCE: 10
ggggtcgacc aggactctct gctagtacaa gtc                                        33

<210> SEQ ID NO 11
<211> LENGTH: 33
<212> TYPE: DNA
<213> ORGANISM: Artificial Sequence
<220> FEATURE:
<223> OTHER INFORMATION: A nucleotide sequence of primer PAA-U

<400> SEQUENCE: 11
aaaggatccc gcgatggtgg acacagaaag ccc                                        33

<210> SEQ ID NO 12
<211> LENGTH: 33
<212> TYPE: DNA
<213> ORGANISM: Artificial Sequence
<220> FEATURE:
<223> OTHER INFORMATION: A nucleotide sequence of primer PAA-L

<400> SEQUENCE: 12
cccgtcgact cagtacatgt ccctgtagat ctc                                        33
```

FURAN OR THIOPHENE DERIVATIVE AND MEDICINAL USE THEREOF

This application is the National Phase filing of International Patent Application No. PCT/JP03/11308, filed Sep. 4, 2003.

TECHNICAL FIELD

The present invention relates to a novel furan or thiophene derivative which has excellent blood lipid metabolism ameliorating action and blood glucose lowering action, and is useful as a prophylactic and/or therapeutic agent for lipid metabolism abnormality, arteriosclerotic disease and sequelae thereof (for example, ischemic cardiac disease, cerebral disease or peripheral arterial occlusion and the like), diabetes mellitus, impaired glucose tolerance and the like.

BACKGROUND ART

Peroxisome proliferator activated receptor (PPAR) is a receptor which was cloned in 1990 as a protein mediating actions of increasing peroxisome that is an intracellular small organ associated with lipolysis (Nature, vol. 347, p. 645 (1990)), and a transcription factor that belongs to a nuclear receptor having a ligand such as estrogen, thyroid hormone, fat-soluble vitamin, etc. Three isoforms of PPARα, PPARδ and PPARγ have been identified so far. It is known that PPARα is mainly expressed in the liver, heart, kidney, adrenal, digestive tract and skeletal muscle and PPARγ in immune systemic organs, large intestine, small intestine, adrenal and adipocytes, and PPARδ is ubiquitarily expressed with no specificity for tissues. Any PPAR forms a stable hetero dimer with retinoid X receptor (RXR) and binds to a specific DNA recognizing sequence of the target gene (PPRE) to control it.

PPARα agonist increases lipoprotein lipase (EMBO Journal, vol. 15, p. 5336 (1996)) and suppresses expression of apoC-III (Journal of Clinical Investigation, vol. 95, p. 705 (1995)) to promote catabolism of triglyceride-rich lipoprotein. Furthermore, a fatty acid transport protein and a binding protein specific for each tissue of liver, muscle, fat, small intestine and the like are induced (Journal of Biological Chemistry, vol. 273, p. 16710 (1998)), to promote uptake of free fatty acid. Furthermore, it strongly increases fatty acid β oxidase localized in the mitochondria and peroxisome (Journal of Biological Chemistry, vol. 273, p. 5678 (1998)). Furthermore, PPARα is reported to regulate positively apoA-I gene in human (Journal of Biological Chemistry, vol. 269, p. 31012 (1994)). As the results, PPARα agonist promotes loss of triglyceride from the blood, decreases triglyceride synthesis and ultra-low-density lipoprotein secretion to decrease serum triglyceride, and increases blood high-density lipoprotein, to ameliorate blood lipid composition. For PPARα agonist, a lipid lowering agent known as fibrate type drugs has been already clinically used, and it is clear that PPARα agonist is useful as a prophylactic and/or therapeutic agent for hyperlipidemia and the like. Furthermore, PPARα agonist is known to have physiological actions induce UCP2 (uncoupling protein-2) which is one of uncoupling proteins inhibiting oxidative phosphorylation which is the last step of ATP production system in the liver and small intestine (Biochemical and Biophysical Research Communications, vol. 257, p. 879 (1999), and Biochimica et Biophysica Acta, vol. 1530, p. 15 (2001)), and also known to induce UCP-3 (uncoupling protein-3) in skeletal muscle (FASEB Journal, vol. 15, p. 833 (2001)). From these facts, it is expected to have anti-obesity action by increase of energy consumption or insulin resistance ameliorating action (Diabetes, vol. 50, p. 411 (2001)).

Furthermore, it is reported that PPARα is expressed in human aortic smooth muscle cells, that PPARα agonist suppresses IL-6 induction by the stimulation of IL-1β (Nature, vol. 393, p. 790 (1998)), and that PPARα agonist suppresses VCAM-1 expression of endothelial cells by TNF-α or IL-1β (Circulation, vol. 99, p. 3125 (1999)), which suggests that it suppresses formation of atherosclerosis involving inflammatory process. Furthermore, PPARα agonist is found to increase expression of SR-BI (scavenger receptor B class I) and ABCA1 (ATP binding cassette transporter A1) (Circulation, vol. 101, p. 2411 (2000), and Nature Medicine, vol. 7, p. 53 (2001)), which suggests that it increases cholesterol reverse transport system to act against arteriosclerosis. Furthermore, from the fact that potentiation of ABCA1 expression in the small intestine promotes enteral excretion of free cholesterol (Journal of Clinical Investigation, vol. 108, p. 303 (2001)), PPARα agonist is expected to also have serum cholesterol lowering action. On the other hand, PPARα agonist is reported to reduce fibrinogen serum level in mice (Blood, vol. 93, p. 2991 (1999)), which suggests possibility of suppressing cardiovascular event following plaque formation by suppression of thrombus formation.

Endogenous ligand candidates of PPARδ (also referred to as PPARβ or NUCI for human) includes long chain fatty acid and carbaprostacyclin. PPARδ is universally expressed, especially intensively in intestines, kidney and heart. It is reported that PPARδ selective agonist promotes export of cholesterol dependently on apoA-I in macrophage, fibroblast and enteral cells, increases blood high-density lipoprotein and decreases low-density lipoprotein, fast triglyceride and fast insulin in obesity Rhesus monkey (Proceedings of the National Academy of Sciences of the United States of America, vol. 98, p. 5306 (2001)), and shows an action of increasing HDL-C in db/db mouse (FEBS letters, vol. 473, p. 333 (2000)). Therefore, PPARδ agonist is considered to be able to be a blood lipid composition ameliorating agent, and is likely to be an agent of suppressing or treating arteriosclerotic progress, and further an agent of preventing attack of ischemic cardiac disease and the like by reducing syndrome X risk factor. Furthermore, PPARδ agonist is known to induce differentiation and proliferation of glia cells (Molecular and Cellular Biology, vol. 20, p. 5119 (2000) and Glia, vol. 33, p. 191 (2001)). Furthermore, PPARδ agonist is reported to show an action of promoting differentiation of mouse precursor adipocytes (Journal of Biological Chemistry, vol. 274, p. 21920 (1999); Journal of Biological Chemistry, vol. 275, p. 38768 (2000); Journal of Biological Chemistry, vol. 276, p. 3175 (2001)); an action of promoting expression of UCP-2 and UCP-3 of skeletal muscle cells in rat and human (Journal of Biological Chemistry, 2001, 276, p. 10853 and Endocrinology, vol. 142, p. 4189 (2001)); and an action of inhibiting adrenal medulla cell death by hyperosmolar stress (Journal of Biological Chemistry, vol. 277, p. 21341 (2002)). Furthermore, PPARδ is reported to be involved in colon cancer (Cell, vol. 99, p. 335 (1999) and Proceedings of the National Academy of Sciences of the United States of America, vol. 98, p. 2598 (2001)), implantation in pregnancy (Genes and Development, vol. 13, p. 1561 (1999)), bone resorption action in osteoclasts (Journal of Biological Chemistry, vol. 275, p. 8126 (2000)), apoptosis in inflammation (Genes and Development., vol. 15, p. 3263 (2001)), and control of type II acyl-CoA synthase in brain (Journal of Biological Chemistry, vol. 274, p. 35881 (1999)). Also, for PPARδ agonist, use as a prophylactic and/or therapeutic agent for atherosclerosis is disclosed in the pamphlet of WO92/10468, and use as a therapeutic agent for diabetes mellitus or an anti-obesity agent is disclosed in the pamphlet of WO97/28115.

PPARγ is induced to be expressed in the very beginning of adipocyte differentiation, and plays important roles in adipocyte differentiation as master regulator. In recent years, it is suggested that 15-deoxy-$\Delta^{12, 14}$ prostaglandin J2, which is a metabolite of prostaglandin D2, is an endogenous ligand of PPARγ, and it has been clarified that certain insulin sensitizers represented by thiazolidinedione derivatives have a PPARγ ligand activity and the strength of the activity parallels with a hypoglycemic action or adipocyte differentiation promoting action [Cell, vol. 83, p. 803 (1995); Journal of Biological Chemistry, vol. 270, p. 12953, (1995); Journal of Medicinal Chemistry, vol. 39, p. 655 (1996)]. More recently, it has been elucidated that 1) PPARγ is expressed in the cultured cell derived from human liposarcoma and the addition of PPARγ ligand stops its growth [Proceedings of The National Academy of Sciences of The United States of America, vol. 94, p. 237 (1997)], 2) nonsteroidal anti-inflammatory drugs represented by indomethacin and phenoprofen have a PPARγ ligand activity [Journal of Biological Chemistry, vol. 272, p. 3406 (1997)], 3) PPARγ is highly expressed in activated macrophage, and the addition of its ligand leads to the inhibition of the transcription of the gene involved in inflammation [Nature, vol. 391, p. 79 (1998)], 4) PPARγ ligand inhibits production of inflammatory cytokines (TNFα, IL-1β, IL-6) by monocyte [Nature, vol. 391, p. 82 (1998)] and the like.

Agents of binding to PPAR receptor are disclosed, for example, in the pamphlet of WO00/64876, the pamphlet of WO02/144291, the pamphlet of WO01/79197, the pamphlet of WO00/23442, the pamphlet of WO99/46232, JP-A-2001-261612, the pamphlet of WO01/92201, the pamphlet of WO0/75103, the pamphlet of WO01/60807, the specification of US-A-2002/0037911, the specification of U.S. Pat. No. 6,369,055, the specification of US-A-2002/0022656, the pamphlet of WO97/28149, the specification of US-A-2002/0042441, the pamphlet of WO01/00603, the pamphlet of WO02/18355, the pamphlet of WO02/16331, the pamphlet of WO02/16332, the pamphlet of WO01/16120, the pamphlet of WO97/36579 and the like.

Recently, it has been shown that by the action of free fatty acid on G protein-coupled receptor GPR40 which is expressed in pancreas, insulin secretion from pancreatic β cell is promoted (Nature (advance online publication), Feb. 23, 2003, doi:10.1038/nature01478).

On the other hand, compounds having a furan or thiophene structure are known as those described in the following documents and the like.

The pamphlet of WO00/23442 has described a compound as an agent of binding to PPAR ligand receptor represented by the formula:

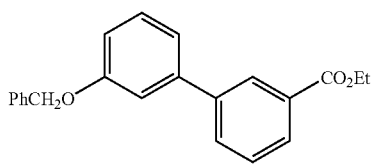

[wherein $R^{21}$ groups are each independently a hydrogen atom, C1-8 alkyl, a halogen atom, C1-4 alkoxy, C1-4 alkylthio, nitro, $NR^{24}R^{25}$ (wherein $R^{24}$ and $R^{25}$ are each independently C1-4 alkyl.), cyano, trifluoromethyl, trifluoromethyloxy, carbocycle or heterocycle (the carbocycle and heterocycle may be substituted with a group selected from C1-4 alkyl, C1-4 alkoxy, a halogen atom or trifluoromethyl.), $R^{22}$ is a hydrogen atom, C1-8 alkyl, a halogen atom, C1-4 alkoxy, C1-4 alkylthio, nitro, $NR^{24}R^{25}$ (wherein $R^{24}$ and $R^{25}$ are each independently C1-4 alkyl.), cyano, trifluoromethyl or trifluoromethyloxy, $R^{23}$ is a hydrogen atom or C1-4 alkyl, $X^{21}$ is —N— or —CH—, $X^{22}$ and $Y^{20}$ are each independently —O—, —S— or —$NR^{26}$— (wherein $R^{26}$ is a hydrogen atom or C1-4 alkyl.), $Z^{20}$ is —O— or —S(O)$_p$'— (wherein p' is 0, 1 or 2.), $R^{27}$ and $R^{28}$ are each independently a hydrogen atom or C1-4 alkyl, or C3-7 cycloalkylene with the carbon atom to which they are attached,

is carbocycle or heterocycle,

⹀⹀ is a double a bond or a triple bond, and q and r are each independently 1 to 3.], a non-toxic salt and a hydrate thereof.

JP-A-1989-143856 has disclosed a compound as an antiallergic and anti-inflammatory agent represented by the formula:

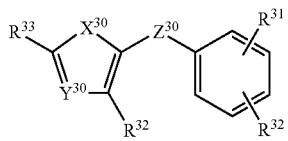

[wherein $X^{30}$ is —C($R^{34}$)═ or —N═, $Y^{30}$ is —C($R^{34}$)═N—, —N═C($R^{34}$)—, —C($R^{34}$)═C($R^{34}$)—, —O—, —S— or —N($R^{34}$)—, $Z^{30}$ is —($CH_2$)n'O—, —($CH_2$)n'-S—, —($CH_2$)n'-N($R^{34}$)—, —C(═O)—N($R^{34}$)—, —($CH_2$)n'S(O)—, —($CH_2$)n'$SO_2$—, —C($R^{34}$)═C($R^{34}$)— or —C≡C—, $R^{31}$ is —(CHR$^{37}$)$_n$COOR$^{33}$, n' is each independently 0 to 5, $R^{32}$ is each independently hydrogen, lower alkyl, lower alkoxy, lower alkoxycarbonyl, trifluoromethyl, nitro, cyano or halogen, $R^{33}$ is

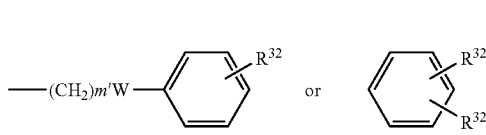

W is a bond or —O—, —S—, —N($R^{34}$)—, m' is 1 to 15, $R^{34}$ is each independently hydrogen or lower alkyl, and $R^{37}$ is hydrogen or methyl] (the definitions in the formula are excerpted for necessary part), and a pharmaceutically acceptable salt thereof.

PCT Japanese Translation Patent Application Publication No. 1993-507920 has described that a compound represented by the formula:

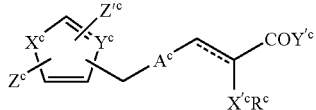

[wherein $A^c$ is

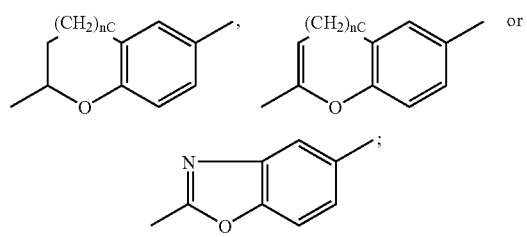

nC is 0 or 1;

----- is a bond or not;

$R^c$ is C1-C8 alkyl, C3-C7 cycloalkyl, C3-C8 alkenyl, C3-C8 alkynylphenyl, C7-C8 phenylalkyl, C2-C8 alkanoyl, or, C1-C3 alkyl, trifluoromethyl, hydroxy, C1-C3 alkoxy, or one of the above-mentioned groups mono- or di-substituted with fluorine or chlorine;

$X^c$ is S, O, $NR^{2c}$, —CH=CH—, —CH=N— or —N=CH—;

$R^{2c}$ is hydrogen, C1-C3 alkyl, phenyl or benzyl;

$Y^c$ is CH or N;

$Z^c$ is hydrogen, C1-C7 alkyl, C3-C7 cycloalkyl, phenyl, or C1-C 3 alkyl, trifluoromethyl, C1-C3 alkoxy, phenyl, phenoxy, benzyl, benzyloxy, phenyl mono- or di-substituted with fluorine or chlorine;

$X'^c$ is O, S, SO or $SO_2$;

$Y'^c$ is hydroxy, C1-C3 alkoxy and the like; and $Z'^c$ is hydrogen or C1-C3 alkyl] has hypoglycemic action and blood lipid lowering action.

The pamphlet of WO01/93840 has described compounds represented by the formula:

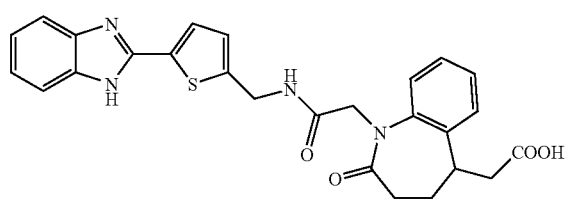

as an integrin receptor ligand.

The pamphlet of WO01/10847 has described a compound represented by the formulae:

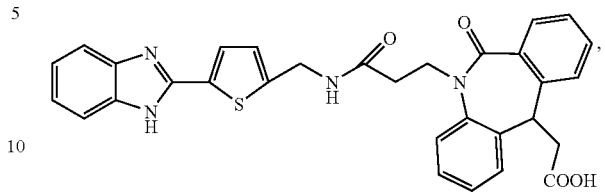

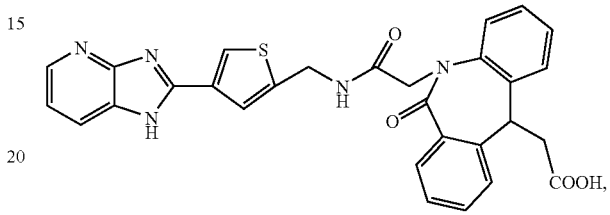

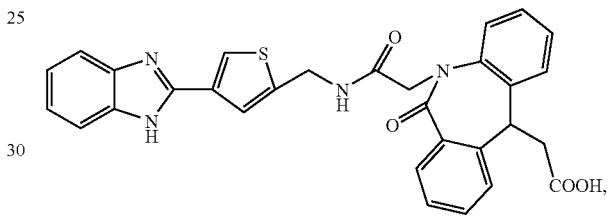

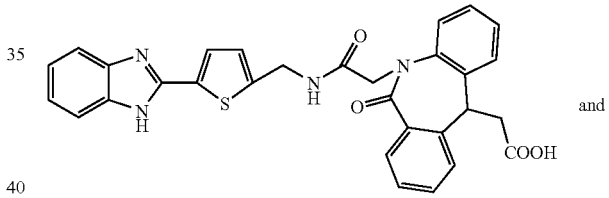

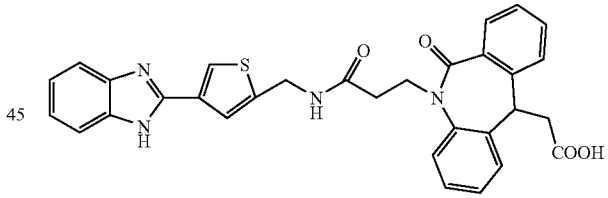

as an integrin receptor ligand.

The pamphlet of WO01/23357 has described a compound represented by the formula:

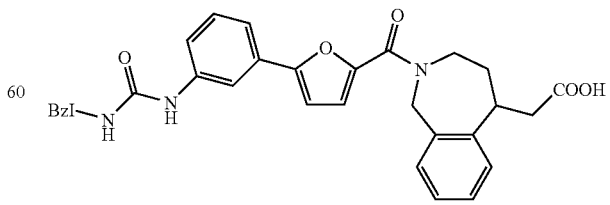

as an integrin receptor ligand.

The pamphlet of WO01/87038 has described a compound represented by the formula:

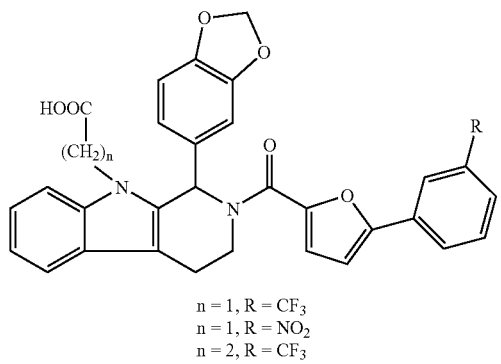

n = 1, R = CF₃
n = 1, R = NO₂
n = 2, R = CF₃ as a phosphodiesterase inhibitor.

The pamphlet of WO99/6393 has described a compound represented by the formula:

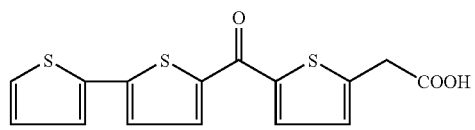

as an anticancer agent or metastasis suppresser.

JP-A-1997-221476 has described a compound represented by the formulae:

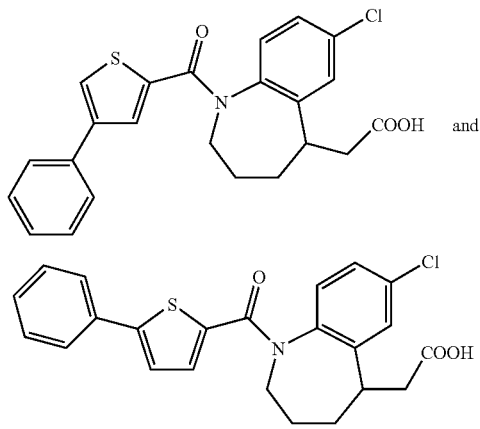

as starting materials of the compound having affinity for vasopressin receptor.

Journal of Medicinal Chemistry, vol. 39, p. 3636 (1996) has described a compound represented by the formula:

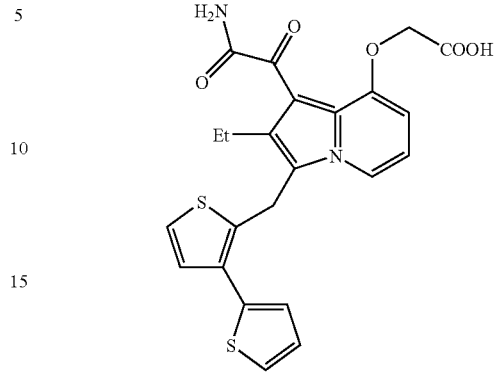

as a secretory phospholipase $A_2$ inhibitor.

The pamphlet of WO01/53267 has described a compound represented by the formula:

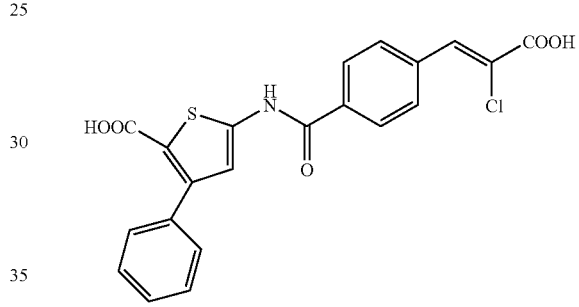

as a starting material of thrombopoietin receptor agonist.

The pamphlet of WO99/19300 has described a compound represented by the formula:

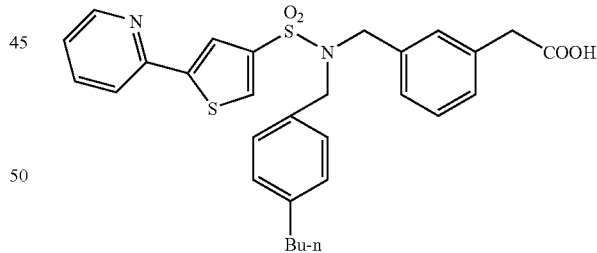

as a prostaglandin agonist.

CHEMCATS [online] has disclosed compounds represented by the formulae:

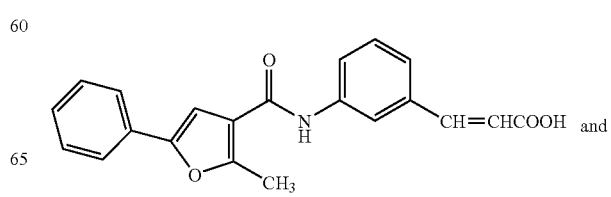

-continued

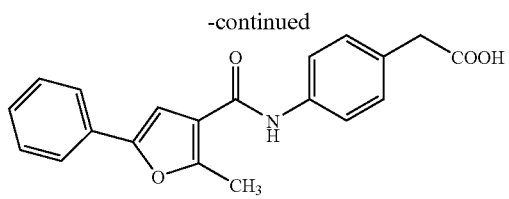

As a PPAR agonist, the pamphlet of WO02/092590 has described a furan derivative, the pamphlet of WO02/083616 has described a thiophene derivative, and the pamphlet of WO02/096893, the pamphlet of WO02/096894 and the pamphlet of WO02/096895 have described a thiazole derivative.

DISCLOSURE OF INVENTION

It is desired to develop a novel compound which is useful as a prophylactic and/or therapeutic agent for PPAR-related diseases (for example, lipid metabolism abnormality, arteriosclerotic disease and sequelae thereof (for example, ischemic cardiac disease, cerebral disease or peripheral arterial occlusion and the like), diabetes mellitus, impaired glucose tolerance and the like), and, has excellent properties such as little side-effects and the like as a pharmaceutical.

Furthermore, a non-peptide low molecular agonist or antagonist for GPR40 receptor has not been known so far, and it is desired to develop a novel compound which has an action of regulating GPR40 receptor functions and is useful as an insulin secretion enhancer or a prophylactic and/or therapeutic agent for diabetes mellitus and the like.

The present inventors have made extensive study under above circumstances, and firstly synthesized a furan derivative and a thiophene derivative having the following particular structure, and found unexpectedly that such compound exerts excellent preventing and treating action for PPAR-related conditions or diseases by regulating PPAR, and exerts excellent preventing and treating action for GPR40 receptor-associated conditions or diseases by excellent GPR40 receptor agonist activity. Based on these findings, the present inventors have reached completion of the present invention.

That is, the present invention relates to:

(1) A compound represented by the formula (I):

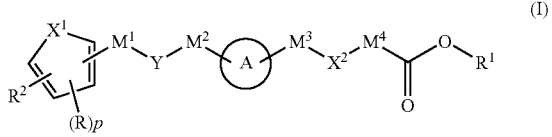

[wherein R is an optionally substituted hydrocarbon group or an optionally substituted heterocyclic group, p is 0, 1 or 2, and when p is 2, each R may be the same or different, $R^1$ is a hydrogen atom or an optionally substituted hydrocarbon group, $R^2$ is an optionally substituted aromatic group, Ring A is an optionally substituted monocyclic aromatic ring or optionally substituted bicyclic aromatic fused ring, $X^1$ is an oxygen atom or a sulfur atom, $X^2$ is a bond, an oxygen atom or —S(O)$_n$— (wherein n is 0, 1 or 2), Y is a bond, an oxygen atom, —S(O)$_m$—, —C(=O)—N(R$^3$)— or —N(R$^3$)—C(=O)— ($R^3$ is a hydrogen atom, an optionally substituted hydrocarbon group or an optionally substituted heterocyclic group, and m is 0, 1 or 2), $M^1$, $M^2$ and $M^3$ may be the same or different and are each independently a bond or an optionally substituted divalent aliphatic hydrocarbon group, and $M^4$ is an optionally substituted divalent aliphatic hydrocarbon group (provided that (1) when Y is an oxygen atom or —S(O)$_m$—, $M^1$ is not a bond, (2) when Y is a bond and one of $M^1$ and $M^2$ is a bond, the other of $M^1$ and $M^2$ is neither a bond nor methylene, and (3) it does not include 3-[3-[[(2-methyl-5-phenyl-3-furanyl)carbonyl]amino]phenyl]-2-propenoic acid, 4-[[(2-methyl-5-phenyl-3-furanyl)carbonyl]amino] benzeneacetic acid, 5-[[4-[(1Z)-2-carboxy-2-chloroethenyl] benzoyl]amino]-3-phenyl-2-thiophenecarboxylic acid, 3-[3-[[(2-methyl-5-phenyl-3-furanyl)carbonyl]amino]phenyl]-2-propenoic acid and 4-[[(2-methyl-5-phenyl-3-furanyl) carbonyl]amino]benzeneacetic acid)] or a pharmacologically acceptable salt thereof;

(2) The compound as described in the above-mentioned (1), wherein R is an optionally substituted alkyl, an optionally substituted aralkyl, an optionally substituted cycloalkyl or an optionally substituted aryl;

(3) The compound as described in the above-mentioned (1), wherein p is 1;

(4) The compound as described in the above-mentioned (1), wherein $R^1$ is a hydrogen atom;

(5) The compound as described in the above-mentioned (1), wherein $R^2$ is an optionally substituted phenyl;

(6) The compound as described in the above-mentioned (1), wherein Ring A is an optionally substituted monocyclic aromatic ring;

(7) The compound as described in the above-mentioned (6), wherein the monocyclic aromatic ring is a monocyclic aromatic heterocycle;

(8) The compound as described in the above-mentioned (6), wherein the monocyclic aromatic ring is a benzene ring or a thiazole ring;

(9) The compound as described in the above-mentioned (1), wherein the formula:

is the formula:

(wherein Ring A' is an optionally further substituted benzene ring);

(10) The compound as described in the above-mentioned (1), wherein $X^1$ is an oxygen atom;

(11) The compound as described in the above-mentioned (1), wherein $X^2$ is a bond, an oxygen atom or a sulfur atom;

(12) The compound as described in the above-mentioned (1), wherein Y is an oxygen atom or a sulfur atom;

(13) The compound as described in the above-mentioned (1), wherein Y is —C(=O)—N(R$^3$)— ($R^3$ is a hydrogen atom, an optionally substituted hydrocarbon group or an optionally substituted heterocyclic group, and the carbon atom is bonded to $M^1$, and the nitrogen atom to $M^2$);

(14) The compound as described in the above-mentioned (13), wherein $R^3$ is a hydrogen atom, an optionally substituted alkyl, an optionally substituted aralkyl, an optionally substituted cycloalkyl or an optionally substituted aryl;

(15) The compound as described in the above-mentioned (1), wherein $M^1$ is an alkylene having 3 or more carbon atoms;

(16) The compound as described in the above-mentioned (1), wherein $M^1$, $M^2$ and $M^3$ may be the same or different and are each independently a bond, an alkylene, an alkenylene or an alkynylene, and $M^4$ is an alkylene, an alkenylene or an alkynylene;

(17) The compound as described in the above-mentioned (1), wherein $x^2$ is an oxygen atom or —S(O)$_n$— (wherein n is 0, 1 or 2) and $M^3$ is an optionally substituted divalent aliphatic hydrocarbon group;

(18) The compound as described in the above-mentioned (1), wherein the formula (I) is

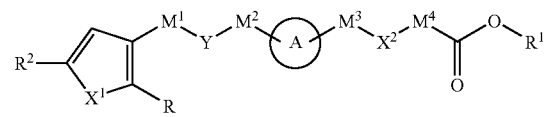

(I')

(wherein each of the symbols is as defined in the above-mentioned (1));

(19) The compound as described in the above-mentioned (18), wherein the formula (I') is

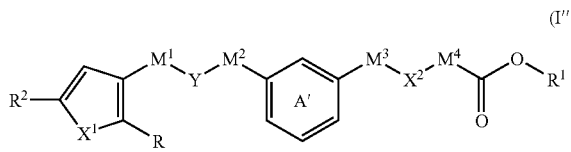

(I'')

(wherein the symbols are as defined in the above-mentioned (1) and (9));

(20) The compound as described in the above-mentioned (19), wherein $X^1$ is an oxygen atom, $X^2$ is an oxygen atom or —S(O)$_n$— (wherein n is 0, 1 or 2), Y is an oxygen atom, $M^1$ is an optionally substituted $C_{1-3}$ alkylene, $M^2$ is a bond, $M^3$ is a bond or an optionally substituted methylene, and $M^4$ is an optionally substituted methylene;

(21) The compound as described in the above-mentioned (20), wherein $M^1$ and $M^3$ may be the same or different and are each independently an optionally substituted methylene;

(22) The compound as described in the above-mentioned (19), wherein $X^1$ is an oxygen atom, $X^2$ is a bond, Y is an oxygen atom, $M^1$ is an optionally substituted n-propylene, $M^2$ and $M^3$ are a bond, and $M^4$ is an optionally substituted methylene;

(23) The compound as described in the above-mentioned (18), wherein Ring A is an optionally substituted monocyclic aromatic heterocycle;

(24) The compound as described in the above-mentioned (18), wherein Ring A is an optionally substituted thiazole ring or an optionally substituted oxazole ring, $X^1$ is an oxygen atom, $X^2$ is a bond, Y is an oxygen atom or —S(O)$_n$— (wherein n is 0, 1 or 2), $M^1$ is an optionally substituted $C_{1-3}$ alkylene, $M^2$ and $M^3$ are a bond, and $M^4$ is an optionally substituted methylene;

(25) The compound as described in the above-mentioned (18), wherein Ring A is an optionally substituted thiazole ring, $X^1$ is an oxygen atom, $X^2$ is a bond, Y is —S—, $M^1$ is an optionally substituted methylene or an optionally substituted n-propylene, $M^2$ and $M^3$ are a bond, and $M^4$ is an optionally substituted methylene;

(26) The compound as described in the above-mentioned (18), wherein the formula (I') is

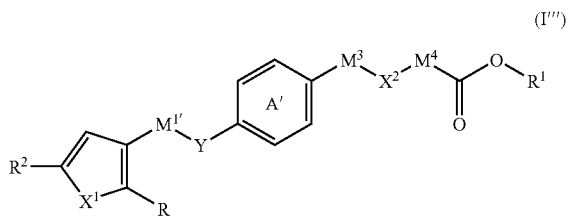

(I''')

(wherein $M^{1'}$ is an alkylene group having 3 or more carbon atoms, and the other symbols are as defined in the above-mentioned (1) and (9));

(27) The compound as described in the above-mentioned (1), wherein R is an optionally substituted alkyl, aryl or cycloalkyl group, p is 0 or 1, $R^1$ is a hydrogen atom, $R^2$ is an optionally substituted phenyl group, Ring A is an optionally substituted benzene ring or an optionally substituted thiazole ring, $X^1$ is an oxygen atom, $X^2$ is a bond or an oxygen atom, Y is an oxygen atom or —C(=O)—N($R^3$)— (wherein $R^3$ is a hydrogen atom, alkyl or aralkyl, and the carbon atom is bonded to $M^1$, and the nitrogen atom to $M^2$), $M^1$, M and $M^3$ may be the same or different and are each independently a bond or alkylene, and $M^4$ is alkylene;

(28) The compound as described in the above-mentioned (1), wherein R is an optionally substituted alkyl, aryl or cycloalkyl group, p is 0 or 1, $R^1$ is a hydrogen atom, $R^2$ is an optionally substituted phenyl group, Ring A is an optionally substituted benzene ring or an optionally substituted thiazole ring, $X^1$ is an oxygen atom, $X^2$ is a bond or —S(O)$_n$— (wherein n is 0, 1 or 2), Y is an oxygen atom or —C(=O)—N($R^3$)— (wherein $R^3$ is a hydrogen atom, alkyl or aralkyl, and the carbon atom is bonded to $M^1$, and the nitrogen atom to $M^2$), $M^1$, $M^2$ and $M^3$ may be the same or different and are each independently a bond or alkylene, and $M^4$ is alkylene;

(29) A prodrug of the compound as described in the above-mentioned (1);

(30) A medicine comprising the compound as described in the above-mentioned (1) or a prodrug thereof;

(31) An agent of regulating nuclear receptor PPAR comprising the compound as described in the above-mentioned (1) or a prodrug thereof;

(32) A prophylactic or therapeutic agent for nuclear receptor PPAR-related diseases comprising the compound as described in the above-mentioned (1) or a prodrug thereof;

(33) The prophylactic or therapeutic agent as described in the above-mentioned (32), wherein the nuclear receptor PPAR-related diseases are lipid metabolism abnormality or sequelae thereof, arteriosclerotic disease or sequelae thereof, diabetes mellitus, or impaired glucose tolerance;

(34) The medicine as described in the above-mentioned (30), which is an agent of raising high-density lipoprotein cholesterol, an agent of lowering triglyceride, an agent of lowering a low-density lipoprotein cholesterol or an agent of suppressing progress of arteriosclerotic plaque;

(35) An agent of regulating GPR40 receptor function comprising the compound as described in the above-mentioned (1) or a prodrug thereof;

(36) The agent as described in the above-mentioned (35) which is an agent of regulating insulin secretion, an agent of lowering blood glucose or an agent of protecting pancreatic β cell;

(37) The agent as described in the above-mentioned (35), which is a prophylactic or therapeutic agent for diabetes mellitus, glucose intolerance, ketosis, acidosis, diabetic neuropathy, diabetic nephropathy, diabetic retinopathy, hyperlipidemia, sexual dysfunction, cutaneous diseases, arthropathy, osteopenia, arteriosclerosis, thrombotic diseases, dyspepsia, memory and learning disorders, obesity, hypoglycaemia, hypertension, edema, insulin resistant syndrome, unstable diabetes mellitus, lipoatrophy, insulin allergy, insulinoma, lipotoxicity or cancer;

(38) A method of regulating nuclear receptor PPAR, which comprises administering to a mammal an effective amount of the compound as described in the above-mentioned (1) or a prodrug thereof;

(39) A method of preventing or treating nuclear receptor PPAR-related disease, which comprises administering to a mammal an effective amount of the compound as described in the above-mentioned (1) or a prodrug thereof;

(40) The method as described in the above-mentioned (39), wherein the nuclear receptor PPAR-related diseases is lipid metabolism abnormality or sequelae thereof, arteriosclerotic disease or sequelae thereof, diabetes mellitus, or impaired glucose tolerance;

(41) A method of raising high-density lipoprotein cholesterol, lowering triglyceride, lowering low-density lipoprotein cholesterol or suppressing progress of arteriosclerotic plaque, which comprises administering to a mammal an effective amount of the compound as described in the above-mentioned (1) or a prodrug thereof;

(42) A method of regulating GPR40 receptor function, which comprises administering to a mammal an effective amount of the compound as described in the above-mentioned (1) or a prodrug thereof;

(43) A method of regulating insulin secretion, lowering blood glucose or protecting pancreatic β cell, which comprises administering to a mammal an effective amount of the compound as described in the above-mentioned (1) or a prodrug thereof;

(44) A method of preventing or treating diabetes mellitus, glucose intolerance, ketosis, acidosis, diabetic neuropathy, diabetic nephropathy, diabetic retinopathy, hyperlipidemia, sexual dysfunction, cutaneous diseases, arthropathy, osteopenia, arteriosclerosis, thrombotic diseases, dyspepsia, memory and learning disorders, obesity, hypoglycaemia, hypertension, edema, insulin resistant syndrome, unstable diabetes mellitus, lipoatrophy, insulin allergy, insulinoma, lipotoxicity or cancer, which comprises administering to a mammal an effective amount of the compound as described in the above-mentioned (1) or a prodrug thereof;

(45) Use of the compound as described in the above-mentioned (1) or a prodrug thereof for manufacturing an agent of regulating nuclear receptor PPAR;

(46) Use of the compound as described in the above-mentioned (1) or a prodrug thereof for manufacturing a prophylactic or therapeutic agent for nuclear receptor PPAR-related diseases;

(47) Use of the compound as described in the above-mentioned (1) or a prodrug thereof for manufacturing a prophylactic or therapeutic agent for lipid metabolism abnormality or sequelae thereof, arteriosclerotic disease or sequelae thereof, diabetes mellitus, or impaired glucose tolerance;

(48) Use of the compound as described in the above-mentioned (1) or a prodrug thereof for manufacturing an agent of raising high-density lipoprotein cholesterol, an agent of lowering triglyceride, an agent of lowering a low-density lipoprotein cholesterol or an agent of suppressing progress of arteriosclerotic plaque;

(49) Use of the compound as described in the above-mentioned (1) or a prodrug thereof for manufacturing an agent of regulating GPR40 receptor function;

(50) Use of the compound as described in the above-mentioned (1) or a prodrug thereof for manufacturing an agent of regulating insulin secretion, an agent of lowering blood glucose or an agent of protecting pancreatic β cell; and

(51) Use of the compound as described in the above-mentioned (1) or a prodrug thereof for manufacturing a prophylactic or therapeutic agent for diabetes mellitus, glucose intolerance, ketosis, acidosis, diabetic neuropathy, diabetic nephropathy, diabetic retinopathy, hyperlipidemia, sexual dysfunction, cutaneous diseases, arthropathy, osteopenia, arteriosclerosis, thrombotic diseases, dyspepsia, memory and learning disorders, obesity, hypoglycaemia, hypertension, edema, insulin resistant syndrome, unstable diabetes mellitus, lipoatrophy, insulin allergy, insulinoma, lipotoxicity or cancer.

In the following, definitions of each symbol will be explained.

R is an optionally substituted hydrocarbon group or an optionally substituted heterocyclic group.

The hydrocarbon group in the "optionally substituted hydrocarbon group" represented by R includes, for example, an aliphatic hydrocarbon group, an alicyclic hydrocarbon group, an alicyclic-aliphatic hydrocarbon group, an aromatic aliphatic hydrocarbon group, an aromatic hydrocarbon group and the like. Such a hydrocarbon group has preferably 1 to 15 carbon atoms.

The aliphatic hydrocarbon group includes a straight or branched aliphatic hydrocarbon group having 1 to 15 carbon atoms, for example, alkyl, alkenyl, alkynyl and the like.

Suitable examples of alkyl include an alkyl group having 1 to 10 carbon atoms, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like, among those preferably, an alkyl group having 1 to 4 carbon atoms (especially, methyl, ethyl, isopropyl, butyl).

Suitable examples of alkenyl include an alkenyl group having 2 to 10 carbon atoms, for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

Suitable examples of alkynyl include an alkynyl group having 2 to 10 carbon atoms, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like.

The alicyclic hydrocarbon group includes a saturated or unsaturated alicyclic hydrocarbon group having 3 to 12 carbon atoms, for example, cycloalkyl, cycloalkenyl, cycloalkadienyl and the like.

Suitable examples of cycloalkyl include a cycloalkyl group having 3 to 10 carbon atoms, for example, cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like, among those preferably, cyclohexyl.

Suitable examples of cycloalkenyl include a cycloalkenyl group having 3 to 10 carbon atoms, for example, 2-cyclopenten-1-yl, 3-cyclopenten-1-yl, 2-cyclohexen-1-yl, 3-cyclohexen-1-yl and the like.

Suitable examples of cycloalkadienyl include a cycloalkadienyl group having 4 to 10 carbon atoms, for example, 2,4-cyclopentadien-1-yl, 2,4-cyclohexadien-1-yl, 2,5-cyclohexadien-1-yl and the like.

The alicyclic-aliphatic hydrocarbon group includes, for example, those formed by binding of the above-mentioned alicyclic hydrocarbon group and aliphatic hydrocarbon group (e.g., cycloalkyl-alkyl, cycloalkenyl-alkyl and the like), among those preferably, an alicyclic-aliphatic hydrocarbon group having 4 to 9 carbon atoms. Suitable examples of the alicyclic-aliphatic hydrocarbon group include cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl and the like.

The aromatic aliphatic hydrocarbon group includes, for example, an aromatic aliphatic hydrocarbon group having 7 to 13 carbon atoms (e.g., an aralkyl group having 7 to 13 carbon atoms, an arylalkenyl group having 8 to 13 carbon atoms and the like) and the like. Suitable examples of the aromatic aliphatic hydrocarbon group include a phenylalkyl group having 7 to 9 carbon atoms such as benzyl, phenethyl, 1-phenylethyl, 1-phenylpropyl, 2-phenylpropyl, 3-phenylpropyl and the like; a naphthylalkyl group having 11 to 13 carbon atoms such as 1-naphthylmethyl, 1-naphthylethyl, 2-naphthylmethyl, 2-naphthylethyl and the like; a phenylalkenyl group having 8 to 10 carbon atoms such as styryl and the like; a naphthylalkenyl group having 12 to 13 carbon atoms such as 2-(2-naphthylvinyl) and the like, and the like.

The aromatic hydrocarbon group (aryl) includes an aromatic hydrocarbon group having 6 to 14 carbon atoms, for example, phenyl, naphthyl, anthryl, phenanthryl, acenaphthylenyl, biphenylyl and the like, among those preferably, phenyl, 1-naphthyl, 2-naphthyl and the like. The aromatic hydrocarbon group may be partially hydrogenated, and the partially hydrogenated aromatic hydrocarbon group includes, for example, tetrahydronaphthalenyl and the like.

The "hydrocarbon group" represented by R is preferably an alkyl group having 1 to 10 carbon atoms, a cycloalkyl group having 3 to 10 carbon atoms, an aralkyl group having 7 to 13 carbon atoms, an aryl group having 6 to 14 carbon atoms and the like.

The heterocycle in the "optionally substituted heterocyclic group" represented by R includes, for example, aromatic heterocycle and non-aromatic heterocycle.

The aromatic heterocycle includes, for example, a 5- to 7-membered monocyclic aromatic heterocycle or fused aromatic heterocycle containing 1 to 4 heteroatoms selected from an oxygen atom, a sulfur atom and a nitrogen atom in addition to carbon atoms as ring-constituting atoms. The fused aromatic heterocycle includes, for example, a ring in which such a 5- to 7-membered monocyclic aromatic heterocycle is fused with a 6-membered ring containing 1 to 2 nitrogen atoms, a benzene ring or a 5-membered ring containing 1 sulfur atom and the like. Suitable examples of the aromatic heterocycle include furan, thiophene, pyridine, pyrimidine, pyridazine, pyrazine, pyrrole, imidazole, pyrazole, isoxazole, isothiazole, oxazole, thiazole, oxadiazole, thiadiazole, triazole, tetrazole, quinoline, quinazoline, quinoxaline, benzofuran, benzothiophene, benzoxazole, benzothiazole, benzimidazole, indole, 1H-indazole, 1H-pyrrolo[2,3-b]pyrazine, 1H-pyrrolopyridine, 1H-imidazopyridine, 1H-imidazopyrazine, triazine, isoquinoline, benzothiadiazole and the like. The aromatic heterocycle is preferably 5 or 6-membered aromatic heterocycle, further preferably, furan, thiophene, pyridine, pyrimidine, pyrazole, oxazole, thiazole and the like.

The non-aromatic heterocycle includes, for example, 5- to 7-membered monocyclic non-aromatic heterocycle or fused non-aromatic heterocycle containing 1 to 4 heteroatoms selected from an oxygen atom, a sulfur atom and a nitrogen atom in addition to carbon atoms as ring-constituting atoms. The non-aromatic fused heterocycle includes, for example, a ring in which such 5- to 7-membered monocyclic non-aromatic heterocycle is fused with a 6-membered ring containing 1 to 2 nitrogen atoms, a benzene ring or a 5-membered ring containing 1 sulfur atom and the like. Suitable examples of the non-aromatic heterocycle include pyrrolidine, pyrroline, pyrazolidine, piperidine, piperazine, morpholine, thiomorpholine, hexamethyleneimine, oxazolidine, thiazolidine, imidazolidine, imidazoline, tetrahydrofuran, azepane, tetrahydropyridine and the like.

The hydrocarbon group and heterocyclic group represented by R may have 1 to 3 substituents at substitutable position. Such substituent includes, for example, a halogen atom (e.g., fluorine, chlorine, bromine, iodine); sulfo; cyano; azido; nitro; nitroso; a $C_{1-6}$ alkyl group optionally substituted with 1 to 3 halogen atoms (e.g., fluorine, chlorine, bromine, iodine and the like)(e.g., methyl, ethyl, propyl, isopropyl, trifluoromethyl and the like); a $C_{2-6}$ alkenyl group optionally substituted with 1 to 3 halogen atoms (e.g., fluorine, chlorine, bromine, iodine and the like)(e.g., ethenyl, 1-propenyl, 2-propenyl and the like); an alkynyl group having 1 to 6 carbon atoms optionally substituted with 1 to 3 halogen atoms (e.g., fluorine, chlorine, bromine, iodine and the like)(e.g., ethynyl, 1-propynyl and the like); a $C_{3-10}$ cycloalkyl group optionally substituted with 1 to 3 halogen atoms (e.g., fluorine, chlorine, bromine, iodine and the like)(e.g., cyclopropyl, cyclobutyl, cyclopentyl, cyclohexyl and the like); a $C_{6-14}$ aryl group optionally substituted with 1 to 3 halogen atoms (e.g., fluorine, chlorine, bromine, iodine and the like)(e.g., phenyl, naphthyl and the like); an aromatic heterocyclic group optionally substituted with 1 to 3 halogen atoms (e.g., fluorine, chlorine, bromine, iodine and the like)(e.g., thienyl, furyl, pyridyl, oxazolyl, thiazolyl and the like); non-aromatic heterocyclic group optionally substituted with 1 to 3 halogen atoms (e.g., fluorine, chlorine, bromine, iodine and the like) (e.g., tetrahydrofuryl, morpholinyl, thiomorpholinyl, piperidinyl, pyrrolidinyl, piperazinyl and the like); a $C_{7-13}$ aralkyl group optionally substituted with 1 to 3 halogen atoms (e.g., fluorine, chlorine, bromine, iodine and the like)(e.g., benzyl, phenethyl, naphthylmethyl and the like); amino optionally mono- or di-substituted with a substituent (s) selected from a $C_{1-4}$ alkyl group optionally substituted with 1 to 3 halogen atoms (e.g., fluorine, chlorine, bromine, iodine and the like)(e.g., methyl, ethyl, propyl, isopropyl and the like), formyl, a $C_{2-8}$ acyl group optionally substituted with 1 to 3 halogen atoms (e.g., fluorine, chlorine, bromine, iodine and the like), and a $C_{1-8}$ sulfonyl group optionally substituted with 1 to 3 halogen atoms (e.g., fluorine, chlorine, bromine, iodine and the like); amidino; formyl; a $C_{2-8}$ acyl group optionally substituted with 1 to 3 halogen atoms (e.g., fluorine, chlorine, bromine, iodine and the like); a $C_{1-8}$ sulfonyl group optionally substituted with 1 to 3 halogen atoms (e.g., fluorine, chlorine, bromine, iodine and the like); a $C_{1-8}$ sulfinyl group optionally substituted with 1 to 3 halogen atoms (e.g., fluorine, chlorine, bromine, iodine and the like); phosphono optionally mono- or di-substituted with a $C_{1-4}$ alkyl group optionally substituted with 1 to 3 halogen atoms (e.g., fluorine, chlorine, bromine, iodine and the like)(e.g., methyl, ethyl, propyl, isopropyl and the like); carbamoyl optionally mono- or di-substituted with a $C_{1-4}$ alkyl group optionally substituted with 1 to 3 halogen atoms (e.g., fluorine, chlorine, bromine, iodine and the like)(e.g., methyl, ethyl, propyl, isopropyl and the like); sulfamoyl optionally mono- or di-substituted with a $C_{1-4}$ alkyl group optionally substituted with 1 to 3 halogen atoms (e.g., fluorine, chlorine, bromine, iodine and the like)(e.g., methyl, ethyl, propyl, isopropyl and the like); carboxy; a $C_{2-8}$ alkoxycarbonyl group optionally substituted with 1 to 3 halogen atoms (e.g., fluorine, chlorine, bromine, iodine and the like) (e.g., methoxycarbonyl, ethoxycarbonyl, propoxycarbonyl, tert-butoxycarbonyl and the like); hydroxy; a $C_{1-6}$ alkoxy group optionally substituted with 1 to 3 halogen atoms (e.g., fluorine, chlorine, bromine, iodine and the like)(e.g., methoxy, ethoxy, propoxy, isopropoxy, trifluoromethoxy and the like); a $C_{2-5}$ alkenyloxy group optionally substituted with 1 to 3 halogen atoms (e.g., fluorine, chlorine, bromine, iodine and the like)(e.g., allyloxy, crotyloxy, 2-pentenyloxy and the like); a $C_{7-13}$ aralkyloxy group optionally substituted with 1 to 3 halogen atoms (e.g., fluorine, chlorine, bromine, iodine and the like) (e.g., benzyloxy, phenethyloxy and the like); a $C_{6-14}$ aryloxy group optionally substituted with 1 to 3 halogen atoms (e.g., fluorine, chlorine, bromine, iodine and the like) (e.g., phenyloxy, naphthyloxy and the like); mercapto; a $C_{1-6}$ alkylthio group optionally substituted with 1 to 3 halogen atoms (e.g., fluorine, chlorine, bromine, iodine and the like)(e.g., methylthio, ethylthio, propylthio, isopropylthio, trifluoromethylthio and the like); a $C_{7-13}$ aralkylthio group optionally substituted with 1 to 3 halogen atoms (e.g., fluorine, chlorine, bromine, iodine and the like) (e.g., benzylthio, phenethylthio and the like); a $C_{6-14}$ arylthio group optionally substituted with 1 to 3 halogen atoms (e.g., fluorine, chlorine, bromine, iodine and the like) (e.g., phenylthio, naphthylthio and the like); oxo; thioxo, and the like. Preferred is a halogen atom (especially, fluorine), a $C_{1-6}$ alkoxy group optionally substituted with 1 to 3 halogen atoms and the like.

Suitable examples of the acyl group which the hydrocarbon group or the heterocyclic group represented by R may have as the substituent include, for example, a $C_{2-8}$ acyl group optionally substituted with 1 to 3 halogen atoms (e.g., fluorine, chlorine, bromine, iodine and the like) (e.g., acetyl, propionyl, butyryl, isobutyryl, valeryl, isovaleryl, pivaloyl, hexanoyl, cyclobutanecarbonyl, cyclopentanecarbonyl, cyclohexanecarbonyl, crotonyl, benzoyl, nicotinoyl, isonicotinoyl, trifluoroacetyl and the like) and the like.

Suitable examples of the sulfonyl group which the hydrocarbon group or the heterocyclic group represented by R may have as the substituent include, for example, a $C_{1-8}$ sulfonyl group optionally substituted with 1 to 3 halogen atoms (e.g., fluorine, chlorine, bromine, iodine and the like) (e.g., methanesulfonyl, ethanesulfonyl, benzenesulfonyl, p-toluenesulfonyl, trifluoromethanesulfonyl and the like) and the like.

Suitable examples of the sulfinyl group which the hydrocarbon group or the heterocyclic group represented by R may have as the substituent include, for example, a $C_{1-8}$ sulfinyl group optionally substituted with 1 to 3 halogen atoms (e.g., fluorine, chlorine, bromine, iodine and the like) (e.g., methanesulfinyl, ethanesulfinyl, benzenesulfinyl, p-toluenesulfinyl, trifluoromethanesulfinyl and the like) and the like.

Suitable examples of the phosphono group which the hydrocarbon group or the heterocyclic group represented by R may have as the substituent include, for example, (a $C_{1-4}$ monoalkyl or dialkyl)phosphono (e.g., dimethylphosphono; diethylphosphono; diisopropylphosphono; dibutylphosphono; 2-oxido-1,3,2-dioxaphosphinan-2-yl and the like) which may form a ring and the like.

Among those, R is preferably an optionally substituted alkyl, an optionally substituted aryl, an optionally substituted aralkyl, an optionally substituted cycloalkyl and the like, and the substituent is preferably 1) a halogen atom; 2) a $C_{1-6}$ alkyl group optionally substituted with 1 to 3 halogen atoms (e.g., methyl, ethyl, propyl, isopropyl, trifluoromethyl and the like); 3) hydroxy; 4) a $C_{1-6}$ alkoxy group optionally substituted with 1 to 3 halogen atoms (e.g., fluorine, chlorine, bromine, iodine and the like)(e.g., methoxy, ethoxy, trifluoromethoxy and the like) and the like.

Among those, R is especially preferably a $C_{1-4}$ alkyl group optionally substituted with 1 to 3 halogen atoms or hydroxy, a phenyl group optionally substituted with 1 to 3 halogen atoms, a $C_{3-10}$ cycloalkyl group and the like.

p is 0, 1 or 2. That is, the substituent R is not present, or present at one or two. When R is present at two (p is 2), each R may be the same or different.

R is preferably present at one (p is 1).

$R^1$ is a hydrogen atom or an optionally substituted hydrocarbon group.

The "hydrocarbon group" in $R^1$ has the same meaning as the "hydrocarbon group" in R, among those preferably, an alkyl such as ethyl and the like (especially, an alkyl group having 1 to 4 carbon atoms). The hydrocarbon group may be substituted with the substituents exemplified as the substituent which the "hydrocarbon group" in R may have, and the like. The position of the substituent may be any substitutable position. The number of the substituent may be one or more. When the number of the substituents is two or more, the respective substituents may be the same or different.

$R^1$ is preferably a hydrogen atom.

$R^2$ is an optionally substituted aromatic group.

The "aromatic group" in $R^2$ includes an aromatic hydrocarbon group and an aromatic heterocyclic group. The "aromatic hydrocarbon group" has the same meaning as the "aromatic hydrocarbon group" exemplified as one of the "hydrocarbon group" in R, and may be substituted with the substituents exemplified as the substituent which the "hydrocarbon group" in R may have, and the like. The position of the substituent may be any substitutable position. The number of the substituent may be one or more. When the number of the substituents is two or more, the respective substituents may be the same or different.

The "aromatic heterocyclic group" in $R^2$ has the same meaning as the "aromatic heterocyclic group" exemplified as one of the "heterocyclic group" in R, and may be substituted with the substituents exemplified as the substituent which the "heterocyclic group" in R may have, and the like. The position of the substituent may be any substitutable position. The number of the substituent may be one or more. When the number of the substituents is two or more, the respective substituents may be the same or different.

$R^2$ is preferably optionally substituted, an aromatic hydrocarbon group having 6 to 14 carbon atoms (preferably phenyl) and a 5- or 6-membered aromatic heterocyclic group (preferably pyridyl, furyl, thienyl), among those preferably, optionally substituted phenyl. Preferred substituent includes 1) a halogen atom (e.g., fluorine, chlorine, bromine, iodine and the like); 2) a $C_{1-6}$ alkyl group optionally substituted with 1 to 3 halogen atoms (e.g., fluorine, chlorine, bromine, iodine and the like)(e.g., methyl, ethyl, propyl, isopropyl, trifluoromethyl and the like); 3) a $C_{6-14}$ aryl group (e.g., phenyl and the like); 4) a $C_{1-6}$ alkoxy group optionally substituted with 1 to 3 halogen atoms (e.g., fluorine, chlorine, bromine, iodine and the like) (e.g., methoxy, ethoxy, trifluoromethoxy and the like); 5) a $C_{1-6}$ alkylthio group optionally substituted with 1 to 3 halogen atoms (e.g., fluorine, chlorine, bromine, iodine and the like) (e.g., methylthio and the like) and the like.

$R^2$ is more preferably a $C_{6-14}$ aromatic hydrocarbon group (preferably phenyl) or 5 or 6-membered aromatic heterocyclic group (preferably pyridyl, furyl, thienyl) which may have respectively 1 to 3 substituents selected from the above-mentioned 1)-5), among those especially preferably, phenyl which may have 1 to 3 substituents selected from the above-mentioned 1), 2) and 4).

$X^1$ is an oxygen atom or a sulfur atom.

$X^1$ is preferably an oxygen atom.

$X^2$ is a bond, an oxygen atom or —S(O)$_n$— (wherein n is 0, 1 or 2).

$X^2$ is preferably a bond, an oxygen atom or a sulfur atom (n is 0).

Y is a bond, an oxygen atom, —S(O)$_m$—, —C(=O)—N($R^3$)— or —N($R^3$)—C(=O)— ($R^3$ is a hydrogen atom, an optionally substituted hydrocarbon group or an optionally substituted heterocyclic group, and m is 0, 1 or 2).

Y is preferably —O—, —S—, or —C(=O)—N($R^3$)— ($R^3$ has the same meaning as defined above).

The "hydrocarbon group" in $R^3$ has the same meaning as the "hydrocarbon group" in R, and is preferably aliphatic hydrocarbon group such as methyl, propyl, heptyl and the like, an aromatic aliphatic hydrocarbon group such as benzyl group and the like. The hydrocarbon group may be substituted with the substituents exemplified as the substituent which the "hydrocarbon group" in R may have, and the like, and the like. The position of the substituent may be any substitutable position. The number of the substituent may be one or more. When the number of the substituents is two or more, the respective substituents may be the same or different.

The "heterocyclic group" in $R^3$ has the same meaning as the "heterocyclic group" in R, and may be substituted with the substituents exemplified as the substituent which the "heterocyclic group" in R may have, and the like. The position of the substituent may be any substitutable position. The number of the substituent may be one or more. When the number of the substituents is two or more, the respective substituents may be the same or different.

$R^3$ is preferably a hydrogen atom, an optionally substituted alkyl, an optionally substituted aralkyl, an optionally substituted cycloalkyl, an optionally substituted aryl, and the substituent is preferably 1) a halogen atom; 2) a $C_{1-6}$ alkyl group optionally substituted with 1 to 3 halogen atoms (e.g., methyl, ethyl, propyl, isopropyl, trifluoromethyl and the like); 3) hydroxy; 4) a $C_{1-6}$ alkoxy group optionally substituted with 1 to 3 halogen atoms (e.g., fluorine, chlorine, bromine, iodine and the like)(e.g., methoxy, ethoxy, trifluoromethoxy and the like) and the like.

Among those, $R^3$ is more preferably a hydrogen atom, a $C_{1-4}$ alkyl group optionally substituted with 1 to 3 halogen atoms and the like, especially preferably, a hydrogen atom.

Ring A is an optionally substituted monocyclic aromatic ring or optionally substituted bicyclic aromatic fused ring, preferably an optionally substituted monocyclic aromatic ring.

The "monocyclic aromatic ring" in Ring A is a ring which may have a heteroatom (for example, an oxygen atom, nitrogen atom, a sulfur atom and the like) as ring-constituting atoms in addition to carbon atoms, and is aromatic. It includes benzene and a monocyclic aromatic heterocycle such as furan, thiophene, pyridine, pyrimidine, pyridazine, pyrazine, pyrrole, imidazole, pyrazole, isoxazole, isothiazole, oxazole, thiazole, oxadiazole, thiadiazole, triazole, tetrazole and the like, among those preferably, benzene, thiazole and oxazole and the like, especially preferably, benzene and thiazole. The monocyclic aromatic ring may be substituted with the substituent exemplified as the substituent which the "hydrocarbon group" and "heterocyclic group" in R may have, and the like, preferably with a $C_{1-6}$ alkyl group or a $C_{1-6}$ alkoxy group. The aromatic ring in Ring A may be substituted with such substituents of 1 or 2. Of course, the substituent is bonded at the substitutable position of the aromatic ring.

The "bicyclic aromatic fused ring" in Ring A is a ring obtained by fusion of two rings and is aromatic, and may contain a heteroatom (for example, an oxygen atom, nitrogen atom, a sulfur atom and the like) as each ring-constituting atom in addition to carbon atoms. The fused ring includes, for example, naphthalene, quinoline, quinazoline, quinoxaline, benzofuran, benzothiophene, benzoxazole, benzothiazole, benzimidazole, indole, 1H-indazole, 1H-pyrrolo[2,3-b]pyrazine, 1H-pyrrolopyridine, 1H-imidazopyridine, 1H-imidazopyrazine, triazine, isoquinoline, benzothiadiazole, among those preferably, naphthalene, benzofuran, benzothiophene, benzoxazole, benzothiazole and the like. The fused ring may be substituted with the substituents exemplified as the substituent which the "hydrocarbon group" and "heterocyclic group" in R may have, and the like. The bicyclic aromatic fused ring in Ring A may be substituted with such substituents of 1 or 2. Of course, the substituent is bonded at the substitutable position of the bicyclic aromatic fused ring.

When Ring A is the optionally further substituted benzene ring, binding positions of $M^2$ and $M^3$ on the benzene ring is preferably para or meta, among those especially preferably, meta substitution, that is, the formula:

in the formula (I) is the formula:

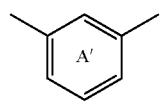

(wherein Ring A' is an optionally further substituted benzene ring).

$M^1$, $M^2$ and $M^3$ may be the same or different and are each independently a bond or an optionally substituted divalent aliphatic hydrocarbon group, and $M^4$ is an optionally substituted divalent aliphatic hydrocarbon group.

The "divalent aliphatic hydrocarbon group" represented by $M^1$, $M^2$, $M^3$ and $M^4$ includes, for example, alkylene, alkenylene, alkynylene and the like. It is preferably a $C_{1-20}$, more preferably a $C_{1-6}$ divalent aliphatic hydrocarbon group, and further preferably, (1) $C_{1-20}$ alkylene (preferably $C_{1-6}$ alkylene, for example, —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —CH(CH$_3$)$_2$—, —(CH$_2$)$_2$C(CH$_3$)$_2$—, —(CH$_2$)$_3$C(CH$_3$)$_2$— or —CH(CH$_2$CH$_2$CH$_3$)—;

(2) $C_{2-20}$ alkenylene (preferably $C_{2-6}$ alkenylene, for example, —CH=CH—, —CH$_2$—CH=CH—, —C(CH$_3$)$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$— and the like)

(3) $C_{2-20}$ alkynylene (preferably $C_{2-6}$ alkynylene, for example, —C≡C—, —CH$_2$—C≡C—, —CH$_2$—C≡C—CH$_2$—CH$_2$— and the like); and the like, among those especially preferably, $C_{1-6}$alkylene and $C_{2-6}$alkenylene and the like.

The "aliphatic hydrocarbon group" may have a substituent, and the substituent includes, for example, the substituents exemplified as the substituent which the "hydrocarbon group" in R may have, and the like. The "divalent aliphatic hydrocarbon group" in $M^1$, $M^2$, $M^3$ and $M^4$ may be substituted with such substituents of 1 or 2. Of course, the substituent is bonded at the substitutable position of the "aliphatic hydrocarbon group".

$M^1$ is also preferably an alkylene group having 3 or more (especially preferably propylene). Furthermore, $M^1$, $M^2$ and $M^3$ may be the same or different and are each independently preferably a bond, alkylene, alkenylene or alkynylene, and $M^4$ is preferably alkylene, alkenylene or alkynylene.

The combination of $X^2$ and $M^3$ is preferably such that $X^2$ is an oxygen atom or —S(O)$_n$— (wherein n is 0, 1 or 2) and $M^3$ is an optionally substituted divalent aliphatic hydrocarbon group.

R, $R^2$ and the group represented by the formula:

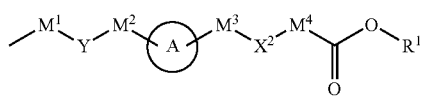

(wherein the symbols are as defined above) may be substituted at any substitutable position of the ring

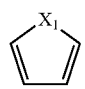

(wherein the symbols are as defined above), among those preferably at the substitution position represented by

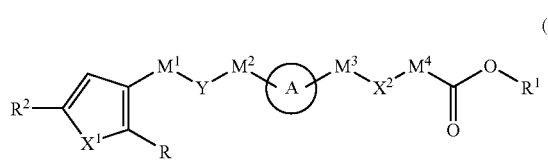

(wherein the symbols are as defined above).

A compound of the formula (I') is preferably a compound of the formula (I''):

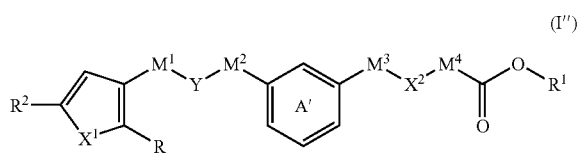

(wherein the symbols are as defined above), especially in the formula (I'') preferably wherein $X^1$ is an oxygen atom, $X^2$ is an oxygen atom or —S(O)$_n$— (wherein n is 0, 1 or 2), Y is an oxygen atom, $M^1$ is optionally substituted $C_{1-3}$ alkylene ($M^1$ is preferably an optionally substituted methylene), $M^2$ is a bond, $M^3$ is a bond or optionally substituted methylene ($M^3$ is preferably an optionally substituted methylene), and $M^4$ is optionally substituted methylene.

Among the compound of the formula (I''), also preferred is a compound of the formula (I'') wherein $X^1$ is an oxygen atom, $X^2$ is a bond, Y is an oxygen atom, $M^1$ is optionally substituted n-propylene, $M^2$ and $M^3$ are a bond, and $M^4$ is optionally substituted methylene.

Among the compound of the formula (I'), also preferred is a compound of the formula (I') wherein Ring A is an optionally substituted monocyclic aromatic heterocycle. Among those, preferred is a compound of the formula (I') wherein Ring A is an optionally substituted thiazole ring or an optionally substituted oxazole ring, $X^1$ is an oxygen atom, X is a bond, Y is an oxygen atom or —S(O)$_n$— (wherein n is 0, 1 or 2), $M^1$ is optionally substituted $C_{1-3}$ alkylene, $M^2$ and $M^3$ are a bond, and $M^4$ is optionally substituted methylene. Among those, especially preferred is a compound of the formula (I') wherein Ring A is an optionally substituted thiazole ring, $X^1$ is an oxygen atom, $X^2$ is a bond, Y is —S—, $M^1$ is optionally substituted methylene or optionally substituted n-propylene, $M^2$ and $M^3$ are a bond, and $M^4$ is optionally substituted methylene.

A compound of the formula (I'''):

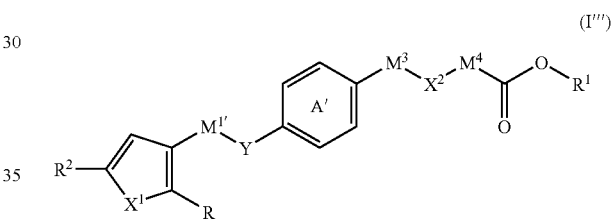

(wherein the symbols are as defined above) among the compound of formula (I'), is also included in one of the preferable embodiments of the present invention.

Preferable embodiments of the compound represented by the formula (I) of the present invention (hereinafter, referred to as Compound (I)) include a compound of the formula (I) wherein R is optionally substituted alkyl, aryl or cycloalkyl, p is 0 or 1, $R^1$ is a hydrogen atom, $R^2$ is an optionally substituted phenyl group, Ring A is an optionally substituted benzene ring or an optionally substituted thiazole ring, $X^1$ is an oxygen atom, $X^2$ is a bond, an oxygen atom or —S(O)$_n$— (wherein n is 0, 1 or 2), Y is an oxygen atom or —C(=O)—N($R^3$)— (wherein $R^3$ is a hydrogen atom, alkyl or aralkyl, and the carbon atom is bonded to $M^1$, and the nitrogen atom to $M^2$), $M^1$, $M^2$ and $M^3$ may be the same or different and are each independently a bond or alkylene, and $M^4$ is alkylene.

Salts of Compound (I) is preferably pharmacologically acceptable salts, and include, for example, a salt with an inorganic base, a salt with an organic base, a salt with an inorganic acid, a salt with an organic acid, a salt with a basic or acidic amino acid, etc.

Preferable examples of the salt with an inorganic base include an alkali metal salt such as sodium salt, potassium salt, lithium salt, etc.; an alkaline earth metal salt such as calcium salt, magnesium salt, etc.; aluminum salt; ammonium salt; etc.

Preferable examples of the salt with an organic base include a salt with trimethylamine, triethylamine, pyridine, picoline, ethanolamine, diethanolamine, triethanolamine, dicyclohexylamine, N,N'-dibenzylethylenediamine, etc.

Preferable examples of the salt with an inorganic acid include a salt with hydrochloric acid, hydrobromic acid, nitric acid, sulfuric acid, phosphoric acid, etc.

Preferable examples of the salt with an organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc.

Preferable examples of the salt with a basic amino acid include a salt with arginine, lysine, ornithine, etc.

Preferable examples of the salt with an acidic amino acid include a salt with aspartic acid, glutamic acid, etc.

The prodrug of Compound (I) or a salt thereof means a compound which is converted to Compound (I) under the physiological condition or with a reaction by an enzyme, an gastric acid, etc. in the living body, that is, a compound which is converted to Compound (I) by enzymatic oxidation, reduction, hydrolysis, etc.; a compound which is converted to Compound (I) with hydrolysis by gastric acid, etc.; etc. Examples of the prodrug of Compound (I) include a compound wherein an amino group of Compound (I) is substituted with acyl, alkyl, phosphoric acid, etc. (e.g. a compound wherein an amino group of Compound (I) is substituted with eicosanoyl, alanyl, pentylaminocarbonyl, (5-methyl-2-oxo-1,3-dioxolen-4-yl)methoxycarbonyl, tetrahydrofuranyl, tetrahydropyranyl, pyrrolidylmethyl, pivaloyloxymethyl, tert-butyl, etc.); a compound wherein an hydroxy group of Compound (I) is substituted with acyl, alkyl, phosphoric acid, boric acid, etc. (e.g. a compound wherein an hydroxy group of Compound (I) is modified with acetyl, palmitoyl, propanoyl, pivaloyl, succinyl, fumaryl, alanyl, dimethylaminomethylcarbonyl, tetrahydropyranyl, etc.); a compound wherein a carboxy group of Compound (I) is modified with ester, amide, etc. (e.g. a compound wherein a carboxy group of Compound (I) is modified with ethyl ester, phenyl ester, carboxymethyl ester, dimethylaminomethyl ester, pivaloyloxymethyl ester, ethoxycarbony-loxyethyl ester, phthalidyl ester, (5-methyl-2-oxo-1,3-dioxolen-4-yl) methyl ester, cyclohexyloxycarbonylethyl ester, methyl amide, etc.); etc. These compounds can be manufactured by per se known method from Compound (I).

In addition, the prodrug of Compound (I) may be a compound which is converted into Compound (I) under the physiological conditions as described in "Pharmaceutical Research and Development", Vol. 7 (Drug Design), pages 163-198 published in 1990 by Hirokawa Publishing Co.

Compound (I) may be labeled with an isotope (e.g., $^3H$, $^{14}C$, $^{35}S$, $^{125}I$ and the like) and the like.

Compound (I) may be anhydride or hydrate.

Compound (I) or a salt thereof (hereinafter, sometimes simply referred to as the compound of the present invention) has low toxicity and can be used as a medicine for mammals (e.g., human, mouse, rat, rabbit, dog, cat, bovine, horse, pig, monkey etc.), preferably a prophylactic or therapeutic agent for various diseases to be mentioned below as itself or as an admixture with a pharmacologically acceptable carrier.

Examples of the pharmacologically acceptable carriers include various organic or inorganic carriers which are generally used in this field. For example, an excipient, a lubricant, a binder, a disintegrating agent, etc. are used in solid formulations; and a solvent, a solubilizer, a suspending agent, an isotonizing agent, a buffer, a soothing agent, etc. are used in liquid formulations. In addition, if desired, an additive such as a preservative, antioxidant, a colorant, a sweetener, etc. may be used.

The suitable examples of the excipient include lactose, sucrose, D-mannitol, D-sorbitol, starch, dextrin, α-nized starch, crystalline cellulose, low-substituted hydroxypropylcellulose, carboxymethylcellulose sodium, arabia gum, dextrin, pullulan, light silicic anhydride, synthetic aluminum silicate, magnesium aluminometasilicate, etc.

Suitable examples of the lubricant include magnesium stearate, calcium stearate, talc, colloidal silica, etc.

The suitable examples of the binder include, for example, α-nized starch, cane sugar, gelatin, arabia gum, methylcellulose, carboxymethylcellulose, carboxymethylcellulose sodium, crystalline cellulose, sucrose, D-mannitol, trehalose, dextrin, pullulan, hydroxypropylcellulose, hydroxypropylmethylcellulose, polyvinylpyrrolidone, etc.

The suitable examples of the disintegrator include, for example, lactose, sucrose, starch, carboxymethylcellulose, carboxymethylcellulose calcium, croscarmellose sodium, carboxymethylstarch sodium, light silicic anhydride, low-substituted hydroxypropylcellulose, etc.

The suitable examples of the solvent include, for example, water for injection, physiological saline, Ringer's solution, alcohol, propylene glycol, polyethylene glycol, sesame oil, corn oil, olive oil, cotton oil, etc.

The suitable examples of the solubilizer include, for example, polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate, etc.

The suitable examples of the suspending agent include, for example, surfactants such as stearyltriethanolamine, sodium lauryl sulfate, laurylaminopropionic acid, lecithin, benzalkonium chloride, benzethonium chloride, glyceryl monostearate, etc.; and hydrophilic macromolecular substances such as polyvinyl alcohol, polyvinylpyrrolidone, carboxymethylcellulose sodium, methylcellulose, hydroxymethylcellulose, hydroxyethylcellulose, hydroxypropylcellulose, etc.; polysorbates, polyoxyethylene hydrogenated castor oil, etc.

The suitable examples of the isotonizing agent include, for example, sodium chloride, glycerin, D-mannitol, D-sorbitol, glucose, etc.

The suitable examples of the buffer include, for example, a buffer solution such as phosphate, acetate, carbonate, citrate, etc.

The suitable examples of the soothing agent include, for example, benzyl alcohol, etc.

The suitable examples of the preservative include, for example, p-hydroxybenzoic acid esters, chlorobutanol, benzyl alcohol, phenethyl alcohol, dehydroacetic acid, sorbic acid, etc.

The suitable examples of the antioxidant include, for example, sulfites, ascorbic acid salts, etc.

The suitable examples of the colorant include, for example, water-soluble food tar colors (e.g., Food Color Red No. 2 and 3, Food Color Yellow No. 4 and No. 5, and Food Color Blue No. 1 and No. 2; and water-insoluble lake colors (e.g., aluminate of the above-mentioned water-soluble food tar colors), natural colors (e.g., β-carotene, chlorophyll, colcothar and the like), etc.

The suitable examples of the sweetener include, for example, saccharin sodium, dipotassium glycyrrhizinate, aspartame, stevia, etc.

Formulation of the medicine of the present invention includes, for example, oral preparations such as tablets, capsules (including softcapsule and microcapsule), granules, powders, syrups, emulsion, suspension, etc.; and non-oral preparations such as injections (e.g., subcutaneous injections, intravenous injections, intramuscular injections, peritoneal injections, etc.), external preparations (e.g., nasal preparations, transdermal preparations, ointments, etc.), suppositories (e.g., rectal suppositories, vaginal suppositories, etc.), pellet, drops, sustained release preparations (e.g., sustained microcapsule, etc.), eye-drops and the like, which can be safely administered orally or non-orally, respectively.

The medicine of the present invention can be produced according to a publicly known method used in the field of a preparation technique, for example, the method described in the Japanese Pharmacopoeia. Specific methods of preparing the preparations will be decribed below.

The oral preparation can be produced by adding an excipient (e.g., lactose, sucrose, starch, D-mannitol, etc.), a disintegrant (e.g., carboxymethylcellulose calcium, etc.), a binder (e.g., α-nized starch, arabia gum, carboxymethylcellulose, hydroxypropylcellulose, polyvinylpyrrolidone, etc.), or a lubricant (e.g., talc, magnesium stearate, polyethylene glycol 6000, etc.), etc. to active ingredients, followed by compressing it and, coating the formulated product with a coating agent for the purpose of taste masking, enteric dissolution or sustained release according to a publicly known method, if necessary.

The coating agent includes, for example, sugar-coating agent, water-soluble film-coating agent, enteric film-coating agent, sustained release film-coating agent and the like.

The sugar-coating agent includes, for example, sucrose, which may be used in combination with one or more of talc, precipitated calcium carbonate, gelatin, arabia gum, pullulan, Carnauba Wax, etc.

The water-soluble film-coating agent includes, for example, cellulose polymers such as hydroxypropylcellulose, hydroxypropylmethylcellulose, hydroxyethylcellulose and methylhydroxyethylcellulose; synthetic polymers such as polyvinylacetal diethylaminoacetate, aminoalkylmethacrylate copolymer E [Eudragit E (trademark), Rohm and Haas Company], polyvinylpyrrolidone; polysaccharides such as pullulan and the like.

The enteric film-coating agent includes, for example, cellulose polymers such as hydroxypropylmethylcellulose phthalate, hydroxypropylmethylcellulose acetatosuccinate, carboxymethylethylcellulose and cellulose acetate phthalate; acrylate polymers such as methacrylate copolymer L [Eudragit L (trademark), Rohm and Haas Company], methacrylate copolymer LD [Eudragit L-30D55 (trademark), Rohm and Haas Company] and methacrylate copolymer S [Eudragit S (trademark), Rohm and Haas Company]; natural substances such as Shellac and the like.

The sustained release film-coating agent includes, for example, cellulose polymers such as ethylcellulose; acrylate polymers such as aminoalkylmethacrylate copolymer RS [Eudragit RS (trademark), Rohm and Haas Company], ethyl acrylate and/or methyl methacrylate copolymer suspension [Eudragit NE (trademark), Rohm and Haas Company], etc.

The above-mentioned coating agents may be used in a suitable mixture of two or more. Also, a light-blocking agent such as titanium oxide and iron sesquioxide may be used in coating.

The injection preparation can be produced by dissolving, suspending or emulsifying active ingredients in aqueous solvent (e.g., distilled water, physiological saline, Ringer's solution, etc.) or oily solvent (e.g., vegetable oils such as olive oil, sesame oil, cotton oil and corn oil, propylene glycol, etc.) with a dispersing agent (e.g., polysorbate 80, polyoxyethylene hydrogenated castor oil 60, polyethylene glycol, carboxymethylcellulose, and sodium alginate, etc.), a preservative (e.g., methyl paraben, propyl parabens, benzyl alcohol, chlorobutanol, phenol, etc.), an isotonizing agent (e.g., sodium chloride, glycerin, D-mannitol, D-sorbitol, glucose, etc), etc. If desired, additives such as a solubilizer (e.g., sodium salicylate, sodium acetate, etc.), a stabilizer (e.g., human serum albumin, etc.), a soothing agent (e.g., benzyl alcohol, etc.) may be used.

The compound of the present invention has actions of ameliorating blood lipid metabolism, ameliorating plasma lipid composition, lowering blood glucose, lowering blood insulin, ameliorating insulin resistance, potentiating insulin sensitivity, controlling retinoid-related receptor or the like.

The controlling action means any of agonist action and antagonist action.

Furthermore, the retinoid-related receptor is included in a nucleus receptor, and is a DNA-binding transcription factor whose ligand is a signal molecule such as oil-soluble vitamins etc., which may be any of a monomer receptor, a homodimer receptor and a heterodimer receptor.

Herein, examples of the monomer receptor include retinoid 0 receptor (hereinafter also abbreviated as ROR) α (GenBank Accession No. L14611), RORβ (GenBank Accession No. L14160), RORγ (GenBank Accession No. U16997); Rev-erbα (GenBank Accession No. M24898), Rev-erbβ (GenBank Accession No. L31785); ERRα (GenBank Accession No. X51416), ERRβ (GenBank Accession No. X51417); Ftz-FIα (GenBank Accession No. S65876), Ftz-FIβ (GenBank Accession No. M81385); TIx (GenBank Accession No. S77482); GCNF (GenBank Accession No. U14666) and the like.

Examples of the homodimer receptor include homodimers formed by retinoid X receptor (hereinafter also abbreviated as RXR) α (GenBank Accession No. X52733), RXRβ (GenBank Accession No. M84820), RXRγ (GenBank Accession No. U38480); COUPα (GenBank Accession No. X12795), COUPβ (GenBank Accession No. M64497), COUPγ (GenBank Accession No. X12794); TR 2α (GenBank Accession No. M29960), TR 2β (GenBank Accession No. L27586); HNF 4α (GenBank Accession No. X76930), HNF 4γ (GenBank Accession No. Z49826) and the like.

Examples of the heterodimer receptor include heterodimers formed by the above-mentioned retinoid X receptor (RXRα, RXRβ or RXRγ) and one receptor selected from retinoid A receptor (hereinafter also abbreviated as RAR) α (GenBank Accession No. X06614), RARβ (GenBank Accession No. Y00291), RARγ (GenBank Accession No. M24857); thyroid hormone receptor (hereinafter also abbreviated as TR) α (GenBank Accession No. M24748), TRβ (GenBank Accession No. M26747); vitamin D receptor (VDR) (GenBank Accession No. J03258); peroxisome proliferator-activated receptor (hereinafter also abbreviated as PPAR) α (GenBank Accession No. L02932), PPARβ (PPARδ) (GenBank Accession No. U10375), PPARγ (GenBank Accession No. L40904); LXRα (GenBank Accession No. U22662), LXRβ (GenBank Accession No. U14534); FXR (GenBank Accession No. U18374); MB67 (GenBank Accession No. L29263); ONR (GenBank Accession No. X75163); and NURa (GenBank Accession No. L13740), NURβ (GenBank Accession No. X75918) and NURγ (GenBank Accession No. U12767).

The compound of the present invention has an excellent ligand activity for peroxisome proliferator-activated receptors (PPARα, PPARβ (PPARδ), PPARγ) among the above-mentioned retinoid-involved receptors, and is useful as an agonist, a partial agonist, an antagonist or a partial antagonist.

Further, the compound of the present invention has an excellent ligand activity for the peroxisome proliferator-activated receptors in heterodimer receptors formed from a retinoid X receptor and the peroxisome proliferator-activated receptor (e.g., heterodimer receptors formed from RXRα and PPARδ, heterodimer receptors formed from RXRα and PPARγ, etc.).

Accordingly, the compound of the present invention can be used advantageously as a peroxisome proliferator-activated receptor ligand.

Therefore, the compound of the present invention is useful as a prophylactic or therapeutic agent for PPAR-related diseases (for example, lipid metabolism abnormality and sequelae thereof, arteriosclerotic disease and sequelae thereof, diabetes mellitus, impaired glucose tolerance and the like).

Since the compound of the present invention has an action of increasing high-density lipoprotein (HDL) cholesterol while lowering low-density lipoprotein (LDL) cholesterol, it has an action of increasing plasma anti-arteriosclerotic index [(HDL cholesterol/total cholesterol)×100] with an action of lowering plasma triglyceride. Therefore, the compound of the present invention is useful as an agent of increasing high-density lipoprotein (HDL) cholesterol, an agent of lowering low-density lipoprotein (LDL) cholesterol and an agent of lowering triglyceride. The agent of the present invention is useful as a prophylactic or therapeutic agent for diseases based on such pharmacological actions. That is, it is particularly useful as a prophylactic or therapeutic agent in a mammal (e.g., mouse, rat, hamster, rabbit, cat, dog, bovine, horse, sheep, monkey, human and the like) for hyperlipidemia, especially hyper-LDL cholesterolemia, hyperlipoproteinemia and hypertriglyceridemia, hypo-HDL cholesterolemia, and arteriosclerotic disease and sequelae thereof generated from them, acute coronary syndrome such as atherosclerosis, peripheral arterial occlusion, acute myocardial infarction, unstable angina pectoris and the like, re-stenosis following percutaneous transluminal coronary angioplasty (PTCA), ischemic cardiac diseases such as myocardial infarction, angina pectoris and the like, arteriosclerosis involving vascular calcification and the like, intermittent claudication, cerebral stroke (cerebral infarction, cerebral embolism, cerebral hemorrhage and the like), lacunar infarction, cerebrovascular dementia, gangrene, glomerulosclerosis, renopathy, Tangier disease and the like.

The compound of the present invention is useful as a prophylactic or therapeutic agent for primary hypo-HDL-emia and the like which is not curable only by LDL cholesterol lowering action, as compared with an agent having only LDL cholesterol lowering action but not having HDL cholesterol increasing action. The eventual object of a therapeutic agent for hyperlipidemia is to prevent onset of lethal diseases such as cardiac infarction and the like, and thus an HDL cholesterol increasing agent can prevent more strongly onset of cardiac infarction and the like although an agent having only LDL cholesterol lowering action but not having HDL cholesterol increasing action is also recognized to have prophylactic effects somewhat for onset of cardiac infarction and the like. Furthermore, the compound of the present invention is also effective for patients or diseases or symptoms for which an agent having only LDL cholesterol lowering action but not having HDL cholesterol increasing action is not recognized to show therapeutic effects (for example, refractory hyperlipidemia and the like), and can suppress onset rate of lethal diseases such as cardiac infarction and the like even in human having normal serum lipid level, and ameliorate the therapeutic effects.

Furthermore, the compound of the present invention is suitable for the treatment of diseases associated with excessive cell growth. A main example of the diseases associated with excessive cell growth is tumor. It has been reported that tumor growth can be suppressed by lowering total serum cholesterol or LDL cholesterol or VLDL cholesterol (Lancet, 339, p 1154 (1992)). Therefore, the compound of the present invention can treat tumor because they have an LDL cholesterol or VLDL cholesterol lowering action. It can be used for the treatment of tumor alone or in combination with known therapeutic methods. Other applicable diseases include hyperproliferative skin diseases such as psoriasis, basal cell cancer, squamous cell carcinoma, keratosis and keratosis diseases.

The hyperproliferative vascular diseases such as angiostenosis and occlusion caused by surgical means such as PTCA (percutaneous transluminal coronary angioplasty) or bypass surgery are based on the growth of smooth muscle cells, and the compound of the present invention is also suitable for the treatment or prophylaxis of these diseases in view of its LDL cholesterol and VLDL cholesterol lowering action. For this end, the compound is used alone or in combination with known active compound such as heparin and the like that can be administered intravenously, preferably given by oral administration.

The compound of the present invention has a blood HDL cholesterol increasing action. By the increase in the blood HDL cholesterol, export of cholesterol from the cell with excess cholesterol is promoted (Current Opinion in Lipidology 4: 392-400). Thus, the compound of the present invention is suitable for the prophylaxis or treatment of atherosclerosis. In consideration of biological characteristics thereof, the Compounds are particularly suitable for the prophylaxis or treatment of arteriosclerotic vascular lesion and sequelae thereof, such as coronary disease (CHD), cerebral ischemia, intermittent claudication, gangrene and the like.

Another use of the compound of the present invention is based on anti-oxidant action of HDL. The blood lipid peroxide concentration is far higher in HDL than in LDL, and HDL has a role of preventing peroxidation of lipid that occurs in living organisms, such as oxidation of LDL and the like (Current Opinion in Lipidology 4: 392-400, Current Opinion in Lipidology 5: 354-364).

Yet another use of the compound of the present invention includes hypertension and sequelae thereof. Hyperlipidemia aggravates arteriosclerosis and induces hypertension. In contrast, HDL is known to prevent biosynthesis and to inhibit release of EDRF (epithelium-derived relaxing factor) by oxidized LDL, and increase prostacyclin, which is a vascular relaxing factor, in macrophages (Current Opinion in Lipidology 5: 354-364). In view of the lipid-lowering action and blood HDL cholesterol increasing action of the compound of the present invention, it is suitable for the prophylaxis or treatment of hypertension and sequelae thereof, such as coronary heart disease (CHD), cerebral ischemia and the like. For this end, the compound of the present invention or a salt thereof is used alone or in combination with a pharmaceutical agent exemplified below and can be administered. The possible combinations includes, for example, angiotensin-II antagonists [e.g., losartan potassium (NU-LOTAN), candesartan cilexetil (BLOPRESS) and the like], ACE inhibitors [e.g., enalapril maleate (RENIVASE), lisinopril (ZESTRIL, LONGES), delapril hydrochloride (ADECUT), captopril and the like], calcium antagonists [e.g., amlodipine tosilate (AMLODIN, NORVASC), manidipine hydrochloride (CALSLOT) and the like], hypotensive diuretic, a receptor blocker, β receptor blocker and the like.

Some of the possible use of the compound of the present invention is based on the cell protective action from cytotoxic secretions such as gastric juice, pancreatic juice, bile and the like. Body fluid-tissue interfacial cells mainly expresses apo J, and form a natural barrier against cytotoxic secretions such as gastric juice, pancreatic juice, bile and the like, and HDL is a carrier of apo J (clusterin) (Current Opinion in Lipidology 4: 392-400). In consideration of the blood HDL cholesterol increasing action of the compound of the present invention, the compound of the present invention is suitable for the prophylaxis or treatment of gastric ulcer, pancreatitis, hepatitis and the like.

Some of still other possible use of the compound of the present invention is based on cell growth activity. HDL promotes cell growth of vascular endothelial cells (EC), corneal endothelium and the like, alone or together with growth factor, and HDL promotes growth of human lymphocytes (Current Opinion in Lipidology 3: 222-226). The compound of the present invention has a blood HDL cholesterol increasing action. In consideration of these cell growth activities, it is suitable for the prophylaxis or treatment of arteriosclerotic vascular lesion and sequelae thereof, such as coronary disease, corneal injury and the like. In addition, it is also suitable for the prophylaxis or treatment of diseases based on lowered immunity, such as infectious diseases, malignant tumor and the like. Furthermore, HDL specifically acts on human placental transplanted tissue to cause secretion of lactogen, as well as promotes secretion of apoE from macrophages (Current Opinion in Lipidology 3: 222-226). In consideration of the secretion promoting activity, the compound of the present invention is also suitable for the prophylaxis or treatment of fetal hypoplasia and the like.

A more noteworthy application example of the compound of the present invention includes secondary hyperlipidemia. This includes diabetes mellitus, insulin resistance (syndrome X), hypothyroidism, nephrotic syndrome, chronic renal failure and the like, and these diseases cause onset of hyperlipidemia. In most cases, it is said that hyperlipidemia aggravates these diseases, thereby forming what is called a vicious circle. In view of the lipid lowering action, the compound of the present invention is also suitable for the treatment of these diseases and prevention of progression thereof. For this end, the compounds of the present invention are used alone or in combination with a known active compound, i.e., for combined use with therapeutic drugs of diabetes mellitus, for example, (1) diuretic (e.g., furosemide, spironolactone, etc.), (2) sympathetic suppressant (e.g., atenolol, etc.), (3) angiotensin II antagonists (e.g., losartan, candesartan, etc.), (4) angiotensin I-converting enzyme inhibitors (e.g., enalapril maleate, delapril hydrochloride, etc.), (5) calcium antagonists (e.g., nifedipine, manidipine hydrochloride, etc.) and the like, for combined use with a therapeutic drug of hypothyroidism, dry thyroid, levothyroxine sodium, liothyronine sodium and the like, for combined use with a therapeutic drug of renal disease, prednisolone, sodium methylprednisolone succinate, furosemide, bumetanide, azosemide and the like, preferably by oral administration.

The compound of the present invention is also useful for the prophylaxis or treatment of Alzheimer's disease. Increase of blood cholesterol is known as a risk factor of Alzheimer's disease. The compound of the present invention can be used for the prophylaxis or treatment of Alzheimer's disease, based on its superior HDL cholesterol increasing and lipid lowering action thereof. For this end, the compound of the present invention can be administered alone or in combination with pharmaceutical agents exemplified in the following. The possible combination in this case includes, for example, acetylcholine esterase inhibitors (e.g., ARICEPT, EXELON and the like), amyloid β production and/or secretion inhibitors (e.g., γ or β selectase inhibitors such as JT-52, LY-374973 and the like, SIB-1848 and the like), amyloid P coagulation inhibitors (e.g., PTI-00703, BETABLOC (AN-1792) and the like) and the like.

A still noteworthy indication for the use of the compound of the present invention is osteoporosis associated with increase of blood cholesterol. By the superior lipid-lowering action, the compound of the present invention can be used for the prophylaxis or treatment of osteoporosis associated with increase of blood cholesterol. For this end, the compound of the present invention can be administered alone or in combination with pharmaceutical agents exemplified in the following. The possible combination in this case includes, for example, sex hormone and related pharmaceutical agents [e.g., estrogen preparations, ipriflavone (osten), raloxifene, osateron, tibolone and the like], calcitonins, vitamin D preparations [e.g., alfacalcidol, calcitriol and the like], bone resorption inhibitors such as bisphosphonic acids (e.g., etidronate, clodronate, etc.) and the like, osteogenesis promoters such as fluorine compounds, PTH and the like, and the like.

In addition, the compound of the present invention is suitable for the treatment of the diseases related to hyperchylomicronemia such as acute pancreatitis. As the onset mechanism of pancreatitis, it is said that chylomicron produces fine thrombus in pancreatic capillary, or triglyceride is decomposed by pancreatic lipase due to hyperchylomicronemia and the resulting free fatty acid increases to cause strong focal irritation. Since the compound of the present invention has a triglyceride-lowering action, it can treat pancreatitis, wherein it can be used alone or in combination with known treatment method for the treatment of pancreatitis. For the treatment of this disease, the compound of the present invention can be administered orally or topically, wherein it can be used alone or in combination with known active compounds. The components that can be combined in this case include, for example, aprotinin (trasylol), gabexate mesylate (FOY), nafamostat mesylate (futhan), citicoline (nicholin), urinastatin (miraclid) and the like for enzyme inhibition therapy. In addition, for removal of pain, anticholinergic drugs, normarcotic analgesics or narcotic is also used.

A yet still possible use of the compound of the present invention is inhibition of thrombus formation. Blood triglyceride level and factor VII involved in blood coagulation are in positive correlation, wherein an intake of α-3 fatty acid lowers triglyceride level as well as inhibits coagulation. Therefore, hypertriglyceridemia promotes formation of thrombus. In addition, since VLDL of hyperlipidemia patients increased secretion of plasminogen activator inhibitor from vascular endothelial cells more strongly than did regular lipidemia patients, triglyceride is also considered to degrade fibrinolytic activity. Therefore, in view of the triglyceride-lowering action, the compound of the present invention is suitable for the prophylaxis or treatment of thrombus formation. For this end, it can be used alone or in combination with known therapeutic drugs mentioned below, preferably by oral administration.

Prophylactic or therapeutic drug of thrombus formation: blood coagulation inhibitors [e.g., heparin sodium, heparin calcium, warfarin calcium (warfarin), Xa inhibitor], thrombolytic agents [e.g., tPA, urokinase], anti-platelet drugs [e.g., aspirin, sulfinpyrazone (Anturan), dipyridamole (Persantin), ticlopidine (Panaldine), cilostazol (Pletal), GPIIb/IIIa antagonists (reopro)] coronary vasodilators: nifedipine, diltiazem, nicoradil, nitrous acid agents; cardiac muscle protective drug: heart ATP-K opener, endothelin antagonists, urotensin antagonists and the like.

A yet still possible use of the compound of the present invention is based on increase of ABCA1m or LXR (liver X receptor) a expression. The peroxisome proliferators-activated receptor agonist is known to increase expression of ABCA1m or LXRA (Nat. Med., vol. 7, p53 (2001), Proc. Natl. Acad. Sci. U.S.A., vol. 98, p5306 (2001), Mol. Cell, vol. 7, p161 (2001), Mol. Endocrinol., vol. 14, p741 (2000)). ABCA1 binds to apoprotein (e.g., apoAI, apoAII and the like) or apolipoprotein (e.g., high-density lipoprotein, HDL) present in the living body, whereby it can export intracellular cholesterol to the outside of the cells. Furthermore, the cholesterol exported to the outside of the cells is transported to a tissue having low cholesterol content. That is, the compound of the present invention is useful for regulating cholesterol distribution in the body.

Therefore, based on the action of exporting intracellular cholesterol, the compound of the present invention is useful as a prophylactic and/or therapeutic agent for diseases such as hypo-HDL-emia; Tangier disease; coronary disease (e.g., myocardial infarction, angina pectoris, silent myocardial ischemia and the like); carotid arteriosclerosis; cerebrovascular disorders (e.g., cerebral stroke, cerebral infarction and the like); occlusive arteriosclerosis; fatty liver; cirrhosis; diabetic complications; cutaneous diseases; xanthoma; joint diseases; proliferative diseases; peripheral arterial occlusion; ischemic peripheral circulation disorders; obesity; cerebrotendinous xanthomatosis (CTX); glomerulonephritis; vascular hypertrophy; vascular hypertrophy following intervention (percutaneous transluminal coronary angioplasty, percutaneous transluminal coronary revascularization, stent implantation, coronary endoscopy, intravascular ultrasound, intracoronary thrombolytic therapy and the like); re-occlusion and/or re-stenosis following bypass surgery; hyperlipidemia-related potent renopathy and/or nephritis or pancreatitis; hyperlipidemia (e.g., postprandial hyperlipidemia); intermittent claudication; deep vein thrombosis; malarial encephalopathy and the like, or an agent of suppressing progress thereof (comprising suppressing progress of arteriosclerotic plaque in type II diabetes mellitus and the like).

Furthermore, based on the action of transporting cholesterol to a tissue having low cholesterol content, the compound of the present invention is useful as a prophylactic and/or therapeutic agent, for example, for diseases involved with Alzheimer's disease, wound, hypoplasia and the like; and an agent of promoting cure after surgery, including accident or organ transplant.

Furthermore, based on the action of increasing LXRa expression, the compound of the present invention can increase intracellular LXRA content. Since the LXRA can express ABCA1 mRNA, the compound of the present invention is useful as a prophylactic and/or therapeutic agent for the above-mentioned various diseases exemplified as the diseases involving ABCA1 expression increase.

The compound of the present invention can be used as, for example, a prophylactic or therapeutic agent of diabetes mellitus (e.g., type I diabetes mellitus, type II diabetes mellitus, gestational diabetes mellitus, etc.); a prophylactic or therapeutic agent of hyperlipidemia (e.g., hypertriglyceridemia, hypercholesterolemia, hypo-HDL-emia, postprandial hyperlipemia, etc.); an agent for ameliorating insulin resistance; an insulin sensitizer; a prophylactic or therapeutic agent of impaired glucose tolerance (IGT); and an agent for preventing progress from impaired glucose tolerance to diabetes mellitus.

Regarding diagnostic criteria of diabetes mellitus, new diagnostic criteria were reported by the Japan Diabetes Society in 1999.

According to this report, diabetes mellitus is a condition wherein the fasting blood glucose level (glucose concentration in venous plasma) is not less than 126 mg/dl, the 2-hour value (glucose concentration in venous plasma) of the 75 g oral glucose tolerance test (75 g OGTT) is not less than 200 mg/dl, or the non-fasting blood glucose level (glucose concentration in venous plasma) is not less than 200 mg/dl. In addition, a condition that does not fall within the scope of the above definition of diabetes mellitus, and which is not a "condition wherein the fasting blood glucose level (glucose concentration in venous plasma) is less than 110 mg/dl or the 2-hour value (glucose concentration in venous plasma) of the 75 g oral glucose tolerance test (75 g OGTT) is less than 140 mg/dl" (normal type), is called the "borderline type".

As regards the diagnostic criteria for diabetes mellitus, moreover, new diagnostic criteria were reported by ADA (American Diabetic Association) in 1997 and by WHO in 1998.

According to these reports, diabetes mellitus is a condition where the fasting blood glucose level (glucose concentration in venous plasma) is not less than 126 mg/dl, and the 2-hour value (glucose concentration in venous plasma) of the 75 g oral glucose tolerance test is not less than 200 mg/dl.

In addition, according to the above reports, impaired glucose tolerance is a condition where the fasting blood glucose level (glucose concentration in venous plasma) is less than 126 mg/dl, and the 2-hour value (glucose concentration in venous plasma) of the 75 g oral glucose tolerance test is not less than 140 mg/dl and less than 200 mg/dl. Furthermore, according to the ADA report, a condition where the fasting blood glucose level (glucose concentration in venous plasma) is not less than 110 mg/dl and less than 126 mg/dl, is called IFG (Impaired Fasting Glucose). On the other hand, according to the WHO report, a condition of IFG (Impaired Fasting Glucose) as such, where the 2-hour value (glucose concentration in venous plasma) of the 75 g oral glucose tolerance test is less than 140 mg/dl, is called IFG (Impaired Fasting Glycemia).

The compound of the present invention can also be used as a prophylactic or therapeutic agent of diabetes mellitus, borderline type, impaired glucose tolerance, IFG (Impaired Fasting Glucose) and IFG (Impaired Fasting Glycemia) as defined by the foregoing new diagnostic criteria. Furthermore, the compound of the present invention can be also used to prevent the progression of the borderline type, impaired glucose tolerance, IFG (Impaired Fasting Glucose) or IFG (Impaired Fasting Glycemia) to diabetes mellitus.

The compound of the present invention has both action of blood glucose lowering action and plasma lipid composition ameliorating action, and therefore, it is very useful as a prophylactic and/or therapeutic agent for arteriosclerotic symptoms in a diabetes mellitus patient.

The compound of the present invention can be also used as a prophylactic or therapeutic agent of diabetic complications (e.g., neuropathy, nephropathy, retinopathy, cataract, macroangiopathy, osteopenia, diabetic hyperosmolar coma, infectious diseases (e.g., respiratory infection, urinary tract infection, gastrointestinal tract infection, dermal soft tissue infection, lower limb infection, etc.), diabetic gangrene, xerostomia, decreased sense of hearing, cerebrovascular disease, peripheral circulatory disturbance, etc.), obesity, osteoporosis, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, terminal renal disorder, etc.), muscular dystrophy, myocardiac infarction, angina pectoris, cerebrovascular disease (e.g., cerebral infarction, cerebral stroke), insulin resistant syndrome, syndrome X, hyperinsulinemia, hyperinsulinemia-induced sensory disorder, tumor (e.g., leukemia, breast cancer, prostate cancer, skin cancer, etc.), irritable bowel syndrome, acute or chronic diarrhea, inflammatory diseases (e.g., Alzheimer's disease, chronic rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, pancreatitis, inflammatory colitis, ulcerative colitis), visceral obesity syndrome and the like.

Also, the compound of the present invention can be used for ameliorating bellyache, nausea, vomiting, or dysphoria in epigastrium, each of which is accompanied by gastrointestinal ulcer, acute or chronic gastritis, biliary dyskinesia, cholecystitis and the like.

Furthermore, the compound of the present invention can control (enhance or inhibit) appetite, and therefore, can be used as a therapeutic agent of leanness and cibophobia (the weight increase in administration subjects suffering from leanness or cibophobia) or a therapeutic agent of obesity.

The compound of the present invention has TNF-α suppressing effects (TNF-α production amount lowering effects in a living tissue and TNF-α activity lowering effects) can be also used as a prophylactic or therapeutic agent of TNF-α mediated inflammatory diseases. Examples of such inflammatory diseases include diabetic complications (e.g., retinopathy, nephropathy, neuropathy, macroangiopathy, etc.), chronic rheumatoid arthritis, spondylitis deformans, osteoarthritis, lumbago, gout, postoperative or traumatic inflammation, remission of swelling, neuralgia, pharyngolaryngitis, cystitis, hepatitis, pneumonia, gastric mucosal injury (including aspirin-induced gastric mucosal injury) and the like.

The compound of the present invention has an apoptosis inhibitory activity, and can be used as a prophylactic or therapeutic agent of diseases mediated by promotion of apoptosis. Examples of the diseases mediated by promotion of apoptosis include viral diseases (e.g., AIDS, fulminant hepatitis, etc.), neurodegenerative diseases (e.g., Alzheimer's disease, Parkinson's disease, amyotropic lateral sclerosis, retinitis pigmentosa, cerebellar degeneration, etc.), myelodysplasia (e.g., aplastic anemia, etc.), ischemic diseases (e.g., myocardial infarction, cerebral stroke, etc.), hepatic diseases (e.g., alcoholic hepatitis, hepatitis B, hepatitis C, etc.), joint-diseases (e.g., osteoarthritis, etc.), atherosclerosis and the like.

The compound of the present invention can be used for reducing visceral fats, inhibiting accumulation of visceral fats, ameliorating glycometabolism, ameliorating lipid metabolism, ameliorating insulin resistance, inhibiting production of oxidized LDL, ameliorating lipoprotein metabolism, ameliorating coronary artery metabolism, preventing or treating cardiovascular complications, preventing or treating heart failure complications, lowering blood remnant, preventing or treating anovulation, preventing or treating hirsutism, preventing or treating hyperandrogenism and the like.

The compound of the present invention can be used for prognosis amelioration, for secondary prevention and for inhibition of progress of the various diseases described above (e.g., cardiovascular events such as myocardial infarction, etc.).

Since the compound of the present invention has an action of changing binding property between fatty acid which is a ligand of GPR40 receptor, and GPR40 receptor, especially GPR40 receptor agonist action, and has low toxicity, and has few side-effects, it is safe and useful as an agent of regulating GPR40 receptor function, preferably GPR40 agonist.

The compound of the present invention has excellent regulating action for GPR40 receptor function in a mammal (for example, mouse, rat, hamster, rabbit, cat, dog, bovine, sheep, monkey, human and the like), and therefore, is useful as an agent of regulating GPR40 receptor-associated physiological functions or a prophylactic and/or therapeutic agent for GPR40 receptor-associated conditions or diseases.

Specifically, a medicine comprising the compound of the present invention is useful as an agent of regulating insulin secretion (preferably insulin secretion promoter) or an agent of protecting pancreatic β cell. Furthermore, a medicine comprising the compound of the present invention is useful as a prophylactic and/or therapeutic agent for diseases such as diabetes mellitus, glucose intolerance, ketosis, acidosis, diabetic neuropathy, diabetic nephropathy, diabetic retinopathy, hyperlipidemia, sexual dysfunction, cutaneous diseases, arthropathy, osteopenia, arteriosclerosis, thrombotic diseases, dyspepsia, memory and learning disorders, obesity, hypoglycaemia, hypertension, edema, insulin resistance, unstable diabetes mellitus, lipoatrophy, insulin allergy, insulinoma, lipotoxicity, cancer and the like such as disease, especially, diabetes mellitus, glucose intolerance, ketosis, acidosis, diabetic neuropathy, diabetic nephropathy, diabetic retinopathy, hyperlipidemia, sexual dysfunction, cutaneous diseases, arthropathy, osteopenia, arteriosclerosis, thrombotic diseases, dyspepsia, memory and learning disorders and the like. Diabetes mellitus includes insulin dependent (Type I) diabetes mellitus and insulin non-dependent (Type II) diabetes mellitus.

The content of Compound (I) of the present invention or a pharmacologically acceptable salt thereof in the medicine of the present invention is about 0.1% by weight to 90% by weight, usually 0.5% by weight to 50% by weight based on the total weight of the medicine. The dose may vary depending on administration subject, administration route, the disease and the like, but for example, when orally administered to an adult (60 kg) as a therapeutic agent for arteriosclerosis, an agent of lowering blood glucose or a therapeutic agent for diabetic complications, the dose as active ingredient is about 0.1 to 1000 mg/day, preferably about 0.5 to 200 mg/day. Compound (I) of the present invention or a pharmacologically acceptable salt thereof may be administered once or twice or three times daily.

The compound of the present invention can be used in combination with a drug such as a therapeutic agent for diabetes mellitus, a therapeutic agent for diabetic complications, an antihyperlipidemic agent, a hypotensive agent, an antiobesity agent, a diuretic agent, a chemotherapeutic agent, an immunotherapeutic agent, anti-thrombic agent, an agent of ameliorating cachexia, etc. (hereinafter, abbreviated as a combination drug). The combination drug may be a compound having a low molecular weight, or may be a protein, a polypeptide or an antibody, each of which has a high molecular weight, or may be a vaccine and the like. The administration mode of the compound of the present invention and the combination drug is not particularly limited, and it is sufficient that the compound of the present invention and the combination drug are combined in administration. Examples of such administration mode include: (1) administration of single preparation, which is produced by formulating the compound of the present invention and the combination drug simultaneously, (2) simultaneous administration of two kinds of preparations by the same administration route, which are produced by formulating the compound of the present invention and the combination drug separately, (3) staggered administration of two kinds of preparations by the same administration route, which are produced by formulating the compound of the present invention and the combination drug separately, (4) simultaneous administration of two kinds of preparations by different administration route, which are produced by formulating the compound of the present invention and the combination drug separately, and (5) staggered administration of two kinds of preparations by different administration route (for example, the compound of the present invention and the combination drug are administered in this order, or in the reverse order), which are produced by formulating the compound of the present invention and the combination drug separately. The dose of the combination drug can be appropriately selected based on a clinically employed dose. The compound ratio of the compound of the present invention and the combination drug can be appropriately determined according to the administration subject, the administration route, the target disease, the clinical condition, the combination, and other factors. In cases where the administration subject is a human, for instance, the combination drug may be used in an amount of 0.01 to 100 parts by weight per part by weight of the compound of the present invention.

Examples of the therapeutic agent for diabetes mellitus include insulin preparations (e.g., animal insulin preparations extracted from the bovine or swine pancreas; human insulin preparations synthesized by a genetic engineering technique using *Escherichia coli* or a yeast); insulin zinc; protamine insulin zinc; fragment of insulin or derivatives thereof (e.g., INS-1, etc.), agents for ameliorating insulin resistance (e.g., pioglitazone hydrochloride, troglitazone, rosiglitazone or its maleate, GI-262570, JTT-501, MCC-555, YM-440, KRP-297, CS-011, FK-614, the compound described in WO99/58510, etc.), α-glucosidase inhibitors (e.g., voglibose, acarbose, miglitol, emiglitate, etc.), biguanides (e.g., phenformin, metformin, buformin, etc.), insulin secretagogues [sulfonylureas (e.g., tolbutamide, glibenclamide, gliclazide, chlorpropamide, tolazamide, acetohexamide, glyclopyramide, glimepiride, glipizide, glybuzole, etc.), repaglinide, nateglinide, mitiglinide or its calcium salt hydrate, GLP-1, etc.], dipeptidylpeptidase IV inhibitors (e.g., NVP-DPP-278, PT-100, etc.), β3 agonists (e.g., CL-316243, SR-58611-A, UL-TG-307, SB-226552, AJ-9677, BMS-196085, AZ-40140, etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLUT (sodium-glucose cotransporter) inhibitors (e.g., T-1095, etc.) and the like.

Examples of the therapeutic agent for diabetic complications include aldose reductase inhibitors (e.g., tolrestat, epalrestat, zenarestat, zopolrestat, minalrestat, fidarestat (SNK-860), CT-112, etc.), neurotrophic factors (e.g., NGF, NT-3, BDNF, etc.), neurotrophic factor production and/or secretion promoters (neurotrophic factor production and/or secretion promoters described in WO01/14372), PKC inhibitors (e.g., LY-333531, etc.), AGE inhibitors (e.g., ALT946, pimagedine, pyratoxathine, N-phenacylthiazolium bromide (ALT766), EXO-226, etc.), active oxygen scavengers (e.g. thioctic acid, etc.), and cerebral vasodilators (e.g., tiapuride, mexiletine, etc.).

Examples of the antihyperlipidemic agent include an agent of inhibiting biosynthesis of cholesterol such as HMG-CoA reductase inhibitors such as pravastatin, simvastatin lovastatin, atorvastatin, fluvastatin, lipantil, cerivastatin, itavastatin, ZD-4522 or salts thereof (e.g., sodium salt and the like) and the like), squalene synthase inhibitors (e.g., the compound as described in WO97/10224)), oxide squalene cyclase inhibitors (e.g., WO96/11201), squalene epoxidase inhibitors (e.g., NB-598 and the like) and the like, fibrate compounds (e.g., bezafibrate, beclofibrate, binifibrate, ciprofibrate, clinofibrate, clofibrate, clofibric acid, etofibrate, phenofibrate, gemfibrozil, nicofibrate, pirifibrate, ronifibrate, simfibrate, theofibrate and the like), ACAT inhibitor (e.g., Avasimibe, Eflucimibe and the like), anion-exchange resin (e.g., cholestyramine and the like), cholesterol absorption inhibitors (e.g., Ezetimibe, vegetable sterol (e.g., soysterol, γ-oryzanol and the like) and the like), probucol, nicotinic acids (e.g., nicomol, niceritrol and the like), ethyl eicosapentaenoic acid, and the like.

Examples of the hypotensive agent include angiotensin converting enzyme inhibitors (e.g., captopril, enalapril, delapril), angiotensin II antagonists (e.g., candesartan cilexetil, losartan, eprosartan, valsartan, termisartan, irbesartan, tasosartan, etc.), calcium antagonists (e.g., manidipine, nifedipine, nicardipine, amlodipine, efonidipine, etc.), potassium channel opener (e.g., levcromakalim, L-27152, AL 0671, NIP-121 and the like), and clonidine.

Examples of the antiobesity agent include antiobesity drugs acting on the central nervous system (e.g. dexfenfluramine, fenfluramine, phentermine, sibutramine, anfepramon, dexamphetamine, mazindol, phenylpropanolamine, clobenzorex, etc.), pancreatic lipase inhibitors (e.g. orlistat, etc.), β3 agonists (e.g. CL-316243, SR-58611-A, UL-TG-307, SB-226552, AJ-9677, BMS-196085, AZ-40140, etc.), anorectic peptides (e.g. leptin, CNTF (Ciliary Neurotrophic Factor), etc.) and cholecystokinin agonists (e.g. lintitript, FPL-15849, etc.).

Examples of the diuretic agent include xanthine derivatives (e.g., theobromine and sodium salicylate, theobromine and calcium salicylate, etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), anti-aldosterone preparations (e.g., spironolactone, triamterene, etc.), carbonate dehydratase inhibitors (e.g., acetazolamide, etc.), chlorobenzenesulfonamide preparations (e.g., chlorthalidone, mefruside, indapamide, etc.), azosemide, isosorbide, ethacrynic acid, piretanide, bumetanide, furosemide and the like.

Examples of the chemotherapeutic agent include alkylating agents (e.g., cyclophosphamide, ifosfamide, etc.), metabolic antagonists (e.g., methotrexate, 5-fluorouracil and a derivative thereof, etc.), antitumor antibiotics (e.g., mitomycin, adriamycin, etc.), plant-derived antitumor agents (e.g., vincristine, vindesine, taxol, etc.), cisplatin, carboplatin, etopoxide and the like, among those preferably, 5-fluorouracil derivatives such as Furtulon and Neo-Furtulon.

Examples of the immunotherapeutic agent include microorganism- or bacterium-derived components (e.g., muramyl dipeptide derivatives, Picibanil, etc.), immunopotentiator polysaccharides (e.g., lentinan, schizophyllan, krestin, etc.), genetically engineered cytokines (e.g., interferons, interleukins (IL), etc.), colony stimulating agents (e.g., granulocyte colony stimulating factor, erythropoietin, etc.) and the like, among those preferably, interleukins such as IL-1, IL-2, IL-12 and the like.

The anti-thrombic agent includes, for example, heparin (e.g., heparin sodium, heparin calcium, dalteparin sodium and the like), warfarin (e.g., warfarin potassium and the like), anti-thrombin agents (e.g., argatroban and the like), thrombolytic agents (e.g., urokinase, tisokinase, alteplase, nateplase, monteplase, pamiteplase and the like), platelet aggregation inhibitors (e.g., ticlopidine hydrochloride, cilostazol, ethyl eicosapentaenoic acid, beraprost sodium, sarpogrelate hydrochloride and the like) and the like.

The agents of ameliorating cachexia include, for example, cyclooxygenase inhibitors (e.g., indomethacin, etc.) (Cancer Research, vol. 49, pp. 5935-5939, 1989), progesterone derivatives (e.g., megestrol acetate) (Journal of Clinical Oncology, vol. 12, pp. 213-225, 1994), glucocorticoids (e.g. dexamethasone, etc.), metoclopramide pharmaceuticals, tetrahydrocannabinol pharmaceuticals (the above references are applied to both), fat metabolism ameliorating agents (e.g., eicosapentanoic acid, etc.) (British Journal of Cancer, vol. 68, pp. 314-318, 1993), growth hormones, IGF-1, and antibodies to the cachexia-inducing factor TNF-α, LIF, IL-6 or oncostatin M, can also be used as the combination drug.

Furthermore, the combination drug includes neuranagenesis promoters (e.g., Y-128, VX-853, prosaptide, etc.), antidepressants (e.g., desipramine, amitriptyline, imipramine, etc.), antiepileptics (e.g., lamotrigine, etc.), antiarrhythmic drug (e.g., mexiletine, etc.), acetylcholine receptor ligands (e.g., ABT-594, etc.), endothelin receptor antagonists (e.g., ABT-627, etc.), monoamine uptake inhibitor (e.g., tramadol, etc.), narcotic analgesics (e.g., morphine, etc.), GABA receptor agonists (e.g., gabapentin, etc.), α2 receptor agonists (e.g., clonidine, etc.), local analgesics (e.g., capsaicin, etc.), protein kinase C inhibitors (e.g., LY-333531, etc.), antianxiety drugs (e.g., benzodiazepine, etc.), phosphodiesterase inhibitors (e.g., sildenafil (citrate), etc.), dopamine agonists (e.g., apomorphine, etc.), therapeutic agents for osteoporosis (e.g., alfacalcidol, calcitriol, elcatonin, calcitonin salmon, estriol, ipriflavone, pamidronate disodium, alendronate sodium hydrate, incadronate disodium, etc.), antidementia agents (e.g., tacrine, donepezil, rivastigmine, galantamine, etc.), therapeutic agents for incontinentia or pollakiuria (e.g., flavoxate hydrochloride, oxybutynin hydrochloride, propiverine hydrochloride, etc.) midazolam, ketoconazole and the like.

When the compound of the present invention is applied to the above-mentioned diseases, it can be used in combination with biological preparations (e.g.: antibody, vaccine preparations and the like), and it is also possible to apply as a combination therapy by combining with a gene therapy method and the like. The antibody and vaccine preparation include, for example, vaccine preparations for angiotensin II, vaccine preparations for CETP, CETP antibody, TNFα antibody and antibody for other cytokines, amyloid β vaccine preparations, diabetes mellitus I vaccines (DIAPEP-277 of Peptor Corp. and the like) and the like, as well as antibody or vaccine preparation for cytokine, renin-angiotensin enzymes and the products thereof, antibody or vaccine preparation for enzyme or protein involved blood lipid metabolism, antibody or vaccine related to enzyme and protein involved in blood coagulation-fibrinolytic system, antibody or vaccine preparation for protein involved in glucose metabolism and insulin resistance and the like. The gene therapy method includes, for example, a therapy method using gene related to cytokine, rennin-angiotensin enzymes and products thereof, a therapy method using DNA decoys such as NFκB decoy and the like, a therapy method using antisense, a therapy method using a gene related to the enzyme and protein involved blood lipid metabolism (e.g., gene relating for metabolism, excretion and absorption of cholesterol or triglyceride or HDL cholesterol or blood phospholipid and the like), a therapy method using a gene related to enzyme and protein (e.g., growth factors such as HGF, VEGF, etc., and the like) involved in angiogenesis therapy targeting peripheral vascular obstruction and the like, a therapy method using a gene related to protein involved in glucose metabolism and insulin resistance, antisense for cytokines such as TNF and the like, and the like. It is also possible to use concurrently with various regeneration methods of organs such as heart regeneration, renal regeneration, pancreatic regeneration, revascularization and the like, and angiogenesis therapy utilizing transplantation of bone marrow cells (bone marrow mononuclear cells, bone marrow stem cells and the like).

In the following, methods of producing Compound (I) will be explained in detail.

Compound (I) can be prepared by a per se known method, for example, Methods A to Bb or a method analogous thereto shown below. The amount of the solvent to be used in the preparation is not limited as long as the mixture can be stirred. In each of the following production methods, the starting compound may be used in the form of a salt, and such salt includes those exemplified as the salt of the aforementioned Compound (I).

[Method A]

Compound (I-1) which is Compound (I) of the present invention wherein $R^1$ is a hydrogen atom can be synthesized, for example, by the following method and the like.

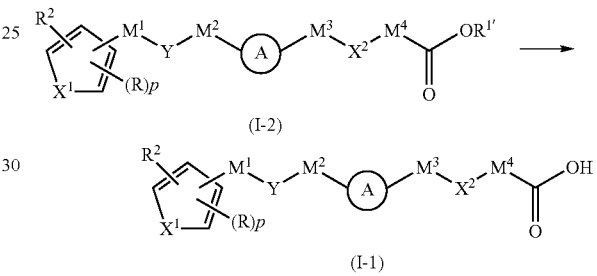

[wherein $R^{1\prime}$ is an optionally substituted hydrocarbon group, and the other symbols are as defined above.]

The "optionally substituted hydrocarbon group" in $R^1$, has the same meaning as the above-mentioned "optionally substituted hydrocarbon group" in $R^1$, preferably a $C_{1-6}$ alkyl group, further preferably, methyl, ethyl and the like.

In this method, Compound (I-2) is hydrolyzed to give Compound (I-1). This reaction is carried out in the presence of an acid or base in a suitable solvent according to a conventional method.

The acid includes, for example, inorganic acid such as hydrochloric acid, sulfuric acid, hydrobromic acid and the like; organic acid such as acetic acid and the like, and the like. The base includes, for example, alkali metal carbonate such as potassium carbonate, sodium carbonate and the like; alkali metal alkoxide such as sodium methoxide and the like; alkali metal hydroxide such as potassium hydroxide, sodium hydroxide, lithium hydroxide and the like, and the like. The amount of the acid and base is usually excessive amount relative to Compound (I-2). The amount of the acid is preferably about 2 to about 50 equivalents relative to Compound (I-2), and the amount of the base is about 1.2 to about 5 equivalents relative to Compound (I-2).

The suitable solvent includes, for example, alcohols such as methanol, ethanol and the like; ethers such as tetrahydrofuran, dioxane, diethyl ether and the like; dimethylsulfoxide; acetone and water and the like. Such solvent may be mixed in a suitable ratio.

The reaction temperature is usually about –20 to about 150° C., preferably about –10 to about 100° C. The reaction time is usually about 0.1 to about 20 hours.

[Method B]

Compound (I-3) which is Compound (I) of the present invention wherein Y is —SO$_m$— (m is 1 or 2) can be synthesized, for example, by the following method and the like.

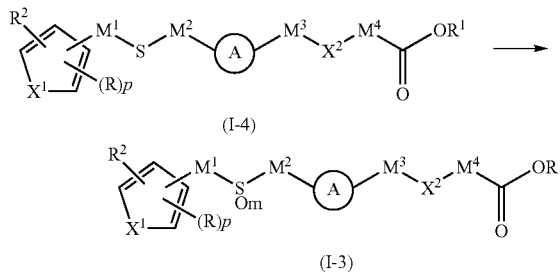

(I-4)

(I-3)

[wherein the symbols are as defined above.]

In this method, Compound (I-4) is oxidized to give Compound (I-3). This reaction is usually carried out using an oxidizing agent in a solvent which does not interfere with the reaction solvent.

The oxidizing agent includes, for example, 3-chlorophenylperbenzoic acid, sodium periodate, hydrogen peroxide water, peracetic acid and the like. The amount of the oxidizing agent is about 1 equivalent to excessive amount, preferably about 1 to about 10 equivalents relative to Compound (I-4).

The reaction solvent which does not interfere with the reaction includes, for example, ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; alcohols such as ethanol, methanol and the like, and the like. Such solvent may be mixed in a suitable ratio.

The reaction temperature is usually about −50 to about 150° C., preferably about −10 to about 100° C. The reaction time is usually about 0.5 to about 20 hours.

[Method C]

Compound (I-5) which is Compound (I) of the present invention wherein X$^2$ is —SO$_n$— (n is 1 or 2) can be synthesized, for example, by the following method and the like.

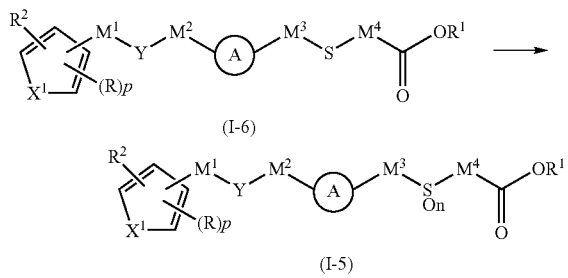

(I-6)

(I-5)

[wherein the symbols are as defined above.]

In this method, Compound (I-6) is oxidized to give Compound (I-5). The present method is carried out, for example, under the same reaction conditions as those of the conversion from Compound (I-4) to Compound (I-3) in the above-mentioned Method B.

[Method D]

Compound (I-7) which is Compound (I) of the present invention wherein Y is —O— or —S— and M$^2$ is not a bond can be synthesized, for example, by the following method and the like.

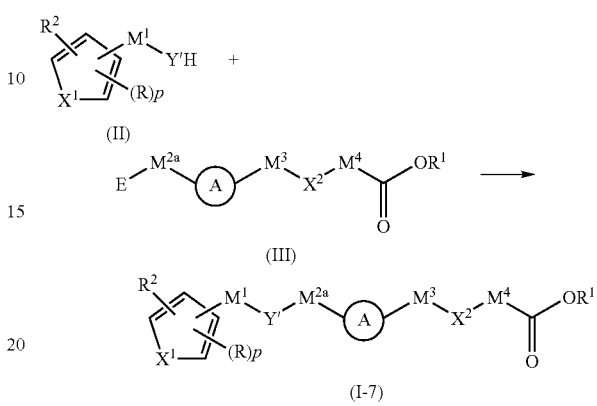

(II)

(III)

(I-7)

[wherein Y' is —O— or —S—, M$^{2a}$ is an optionally substituted divalent aliphatic hydrocarbon group, E is halogen such as a chlorine atom, bromine atom, iodine atom and the like, a leaving group such as methanesulfonyloxy, p-toluenesulfonyloxy and the like, and the other symbols are as defined above.]

The "optionally substituted divalent aliphatic hydrocarbon group" in M$^{2a}$ has the same meaning as the above-mentioned "optionally substituted divalent aliphatic hydrocarbon group" in M$^2$.

In this method, Compound (II) is reacted with Compound (III) to give Compound (I-7). This reaction is carried out according to a conventional method in the presence of a base in a reaction solvent which does not interfere with the reaction.

The base includes, for example, alkali metal carbonate such as potassium carbonate, sodium carbonate and the like; alkali metal hydrogen carbonate such as potassium hydrogen carbonate, sodium hydrogen carbonate and the like; alkali metal hydroxide such as potassium hydroxide, sodium hydroxide, lithium hydroxide and the like; amines such as pyridine, triethylamine, N,N-dimethylaniline, 1,8-diazabicyclo[5.4.0]undec-7-ene and the like; metal hydride such as potassium hydride, sodium hydride and the like; alkali metal alkoxide such as sodium methoxide, sodium ethoxide, potassium tert-butoxide and the like. The amount of such base is preferably about 1 to about 5 molar equivalents relative to Compound (II).

The reaction solvent which does not interfere with the reaction includes, for example, aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethylsulfoxide and the like, and the like. Such solvent may be mixed in a suitable ratio.

The reaction temperature is usually about −50 to about 150° C., preferably about −10 to about 100° C. The reaction time is usually about 0.5 to about 20 hours.

[Method E]

Compound (I-9) which is Compound (I) of the present invention wherein Y is —O— or —S—, M$^1$ is an optionally substituted divalent aliphatic hydrocarbon group can be synthesized, for example, by the following method and the like.

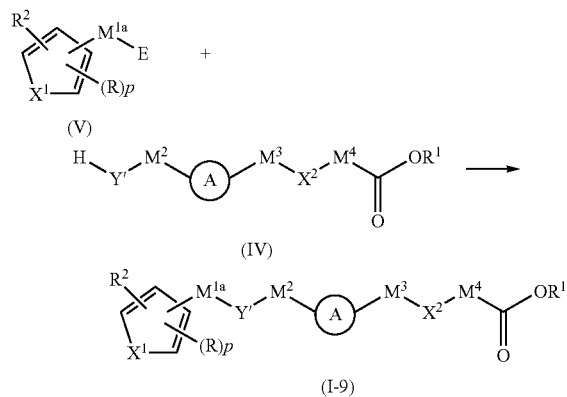

[wherein $M^{1a}$ is an optionally substituted divalent aliphatic hydrocarbon group, and the other symbols are as defined above.]

The "optionally substituted divalent aliphatic hydrocarbon group" in $M^{1a}$ has the same meaning as the above-mentioned "optionally substituted divalent aliphatic hydrocarbon group" in $M^1$.

In this method, Compound (V) is reacted with Compound (IV) to give Compound (I-9). The present method is carried out for example under the same reaction conditions as those of the above-mentioned Method D by reacting Compound (II) with Compound (III) to give compound (1-7).

[Method F]

Compound (I-8) which is Compound (I) of the present invention wherein Y is —O— or —S—, and $M^2$ is a bond can be synthesized, for example, by the following method and the like.

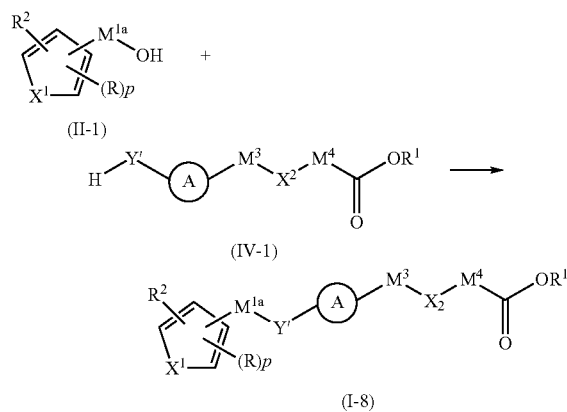

[wherein the symbols are as defined above.]

In this method, Compound (II-1) is reacted with Compound (IV-1) to give Compound (I-8). This reaction is carried out according to the method known per se, which is known as a so called ester interchange reaction, such as the method described in Synthesis, page 1 (1981), or a method analogous thereto. That is, this reaction is generally carried out in the presence of an organic phosphorus compound and electrophile in a solvent that does not adversely affect the reaction.

The organic phosphorus compound includes, for example, triphenylphosphine, tributylphosphine and the like. The electrophile includes, for example, diethyl azodicarboxylate, diisopropyl azodicarboxylate, azodicarbonyldipiperazine, 1,1'-(azodicarbonyl)dipiperidine and the like. The amount of the organic phosphorus compound and the electrophile is preferably about 1 to about 5 molar equivalents, respectively relative to Compound (II-1).

The reaction solvent which does not interfere with the reaction includes, for example, ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethylsulfoxide and the like, and the like. Such solvent may be mixed in a suitable ratio.

The reaction temperature is usually about −50 to about 150° C., preferably about −10 to about 100° C. The reaction time is usually about 0.5 to about 20 hours.

[Method G]

Compound (I-10) which is Compound (I) of the present invention wherein Y is —CON($R^3$)— (provided that the carbonyl carbon atom is bonded to $M^1$) can be synthesized, for example, by the following method and the like.

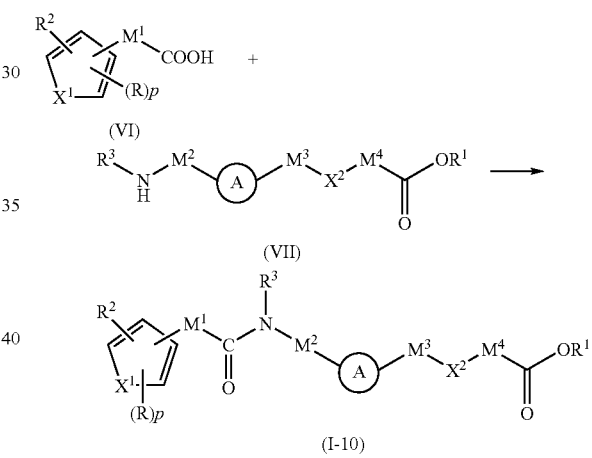

[wherein the symbols are as defined above.]

This method is a method of condensing (amidation) Compound (VI) with Compound (VII) to give Compound (I-10). This reaction is carried out by a per se known method, for example, (1) a method of directly condensing Compound (VI) and Compound (VII) with a condensing agent, or (2) a method of reacting suitably a reactive derivative of Compound (VI) and Compound (VII) and the like.

Firstly, the method (1) will be explained.

The above-mentioned condensing agent includes generally known condensing agent, for example, a carbodiimide-based condensing reagent such as dicyclohexylcarbodiimide, diisopropylcarbodiimide, 1-ethyl-3-(3-dimethylaminopropyl)carbodiimide and hydrochloride thereof and the like; a phosphate-based condensing reagent such as diethyl cyanophosphate, diphenylphosphoryl azide and the like; carbonyldiimidazole, 2-chloro-1,3-dimethylimidazolium tetrafluoroborate and the like.

The method (1) is usually carried out in a solvent, and the solvent includes, for example, amides such as N,N-dimethylformamide, N,N-dimethylacetoamide and the like; halogenated hydrocarbons such as chloroform, dichloromethane and the like; aromatic hydrocarbons such as benzene, toluene and the like; ethers such as tetrahydrofuran, dioxane, diethyl ether and the like; ethyl acetate, water and the like. Such solvent may be mixed in a suitable ratio.

The amount of Compound (VII) is 0.1 to 10 molar equivalents, preferably 0.3 to 3 molar equivalents relative to Compound (VI).

The amount of the condensing agent is 0.1 to 10 molar equivalents, preferably 0.3 to 3 molar equivalents relative to Compound (VI).

When carbodiimide-based condensing reagent such as dicyclohexylcarbodiimide, diisopropylcarbodiimide, 1-ethyl-3-(3-dimethylaminopropyl)carbodiimide and hydrochloride thereof and the like is used as the condensing agent, if necessary, suitable condensing promoter (e.g., 1-hydroxy-7-azabenzotriazole, 1-hydroxybenzotriazole, N-hydroxysuccinimide, N-hydroxyphthalimide and the like) may be used. Furthermore, when phosphate-based condensing reagent such as diethyl cyanophosphate, diphenylphosphoryl azide and the like is used as the condensing agent, organic amine base such as triethylamine and the like may be also added.

The amount of the above-mentioned condensing promoter or organic amine base is 0.1 to 10 molar equivalents, preferably 0.3 to 3 molar equivalents relative to Compound (VI).

The reaction temperature is usually −30° C. to 100° C. The reaction time is usually 0.5 to 60 hours.

In the following, the method (2) will be explained.

The reactive derivative of Compound (VI) includes, for example, acid anhydride, acid halide (e.g., acid chloride, acid bromide), acid imidazolide, active ester (for example, phenyl ester, nitro-or halogen-substituted phenyl ester (for example, 4-nitrophenyl ester, pentafluorophenyl ester and the like), 1-hydroxy-7-azabenzotriazole ester, 1-hydroxybenzotriazole ester, N-hydroxysuccinimide ester, N-hydroxyphthalimide ester and the like), or mixed acid anhydride (for example, anhydride with methyl carbonate, ethyl carbonate, isobutyl carbonate and the like) and the like.

For example, when acid anhydride, acid halide, acid imidazolide or active ester is used as the above-mentioned reactive derivative, the reaction is carried out in the presence or absence of a base in a reaction solvent which does not interfere with the reaction.

The base includes, for example, amines such as triethylamine, N-methylmorpholine, N,N-dimethylaniline and the like; alkali metal carbonate such as potassium carbonate, sodium carbonate and the like; alkali metal hydrogen carbonate such as potassium hydrogen carbonate, sodium hydrogen carbonate and the like; alkali metal hydroxide such as potassium hydroxide, sodium hydroxide, lithium hydroxide and the like; and the like. The amount of the base is 0.1 to 10 molar equivalents, preferably 0.3 to 3 molar equivalents relative to Compound (VI) or a reactive derivative thereof.

The reaction solvent which does not interfere with the reaction includes, for example, halogenated hydrocarbons such as chloroform, dichloromethane and the like; aromatic hydrocarbons such as benzene, toluene and the like; ethers such as tetrahydrofuran, dioxane, diethyl ether and the like; ethyl acetate, water, N,N-dimethylformamide and the like. Such solvent may be mixed in a suitable ratio.

The amount of Compound (VII) is 0.1 to 10 molar equivalents, preferably 0.3 to 3 molar equivalents relative to Compound (VI) or a reactive derivative thereof.

The reaction temperature is usually −30° C. to 100° C. The reaction time is usually 0.5 to 20 hours.

Furthermore, when the mixed acid anhydride is used, Compound (VI) is reacted with chlorocarbonate ester (e.g., methyl chlorocarbonate, ethyl chlorocarbonate, isobutyl chlorocarbonate and the like) in the presence of a base (e.g., amines such as triethylamine, N-methylmorpholine, N,N-dimethylaniline and the like; alkali metal carbonate such as potassium carbonate, sodium carbonate and the like; alkali metal hydrogen carbonate such as potassium hydrogen carbonate, sodium hydrogen carbonate and the like; alkali metal hydroxide such as potassium hydroxide, sodium hydroxide, lithium hydroxide and the like, and the like), and further with Compound (VII).

The amount of Compound (VII) is usually 0.1 to 10 molar equivalents, preferably 0.3 to 3 molar equivalents relative to Compound (VI) or mixed acid anhydride thereof.

The reaction temperature is usually −30° C. to 100° C. The reaction time is usually 0.5 to 20 hours.

[Method H]

Compound (I-11) which is Compound (I) of the present invention wherein Y is —N($R^3$)CO— (provided that the carbonyl carbon is bonded to $M^2$) can be synthesized, for example, by the following method and the like.

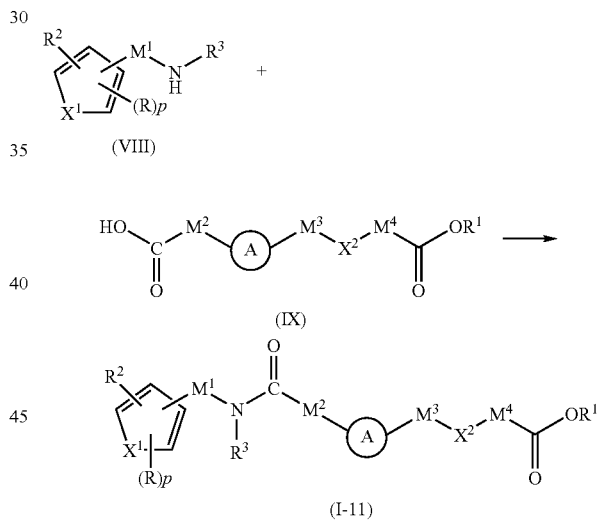

[wherein the symbols are as defined above.]

This method is a method of condensing (amidation) Compound (VIII) with Compound (IX) to give Compound (I-11). The present method is carried out, for example, under the same reaction conditions as those of the above-mentioned Method G by reacting Compound (VI) with Compound (VII) to give Compound (I-10).

[Method I-1] [Method I-2]

Compounds (I-12a'), (I-12b'), (I-12a) and (I-12b) which are Compound (I) of the present invention wherein Y is a bond, and $M^1$ is an optionally substituted divalent aliphatic hydrocarbon group having 2 or more carbon atoms can be synthesized, for example, by the following methods (I-1) and (I-2) and the like.

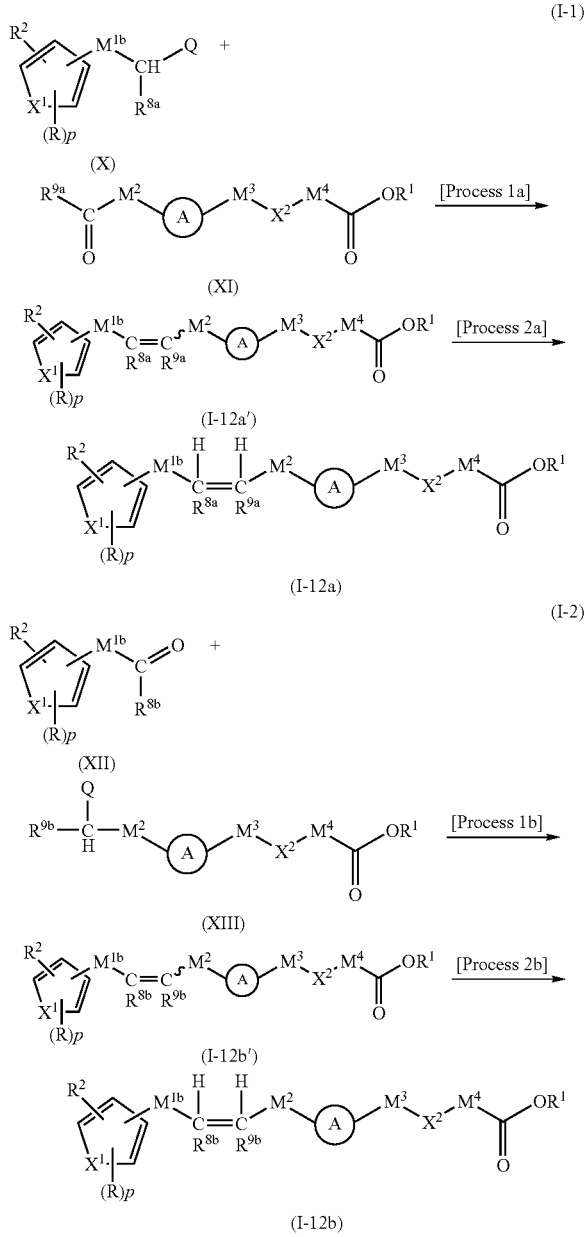

[wherein Q is P(O) (OR$^7$)$_2$ or PR$^7_3$ (wherein R$^7$ is a C$_{1-4}$ alkyl group (for example, methyl, ethyl, propyl, isopropyl, butyl, isobutyl, sec-butyl, tert-butyl and the like) or a C$_{6-10}$ aryl group (for example, phenyl, naphthyl and the like) optionally substituted with a C$_{1-4}$ alkyl group, preferably methyl, ethyl, phenyl and the like.), M$^{1b}$ is a bond or an optionally substituted divalent aliphatic hydrocarbon group, R$^{8a}$, R$^{8b}$, R$^{9a}$ and R$^{9b}$ may be the same or different and are each independently a substituent suitably selected from a hydrogen atom, an alkyl group or the substituent which the "divalent aliphatic hydrocarbon group" in the above-mentioned M$^1$ may have, and the other symbols are as defined above.]

The "optionally substituted divalent aliphatic hydrocarbon group" in M$^{1b}$ is has the same meaning as the above-mentioned "optionally substituted divalent aliphatic hydrocarbon group" in the M$^1$. The "alkyl group f in R$^{8a}$, R$^{8b}$, R$^{9a}$ and R$^{9b}$ is straight or branched alkyl group, and the number of the carbon atoms is not particularly limited, preferably less than 18, for example, methyl, ethyl, propyl, isopropyl, butyl, isobutyl, sec-butyl, tert-butyl and the like.

[Process 1a] Preparation of Compound (I-12a')

Compound (I-12a') is obtained by reacting Compound (XI) (1) with phosphonium ylide induced from phosphonium salt (X) (Q=PR$^7_3$) to give olefin, which is so-called Wittig reaction, or (2) with phosphonate carboanion induced from alkylphosphorous diester (X) (Q=P(O) (OR$^7$)$_2$) to give olefin, which is so-called Wittig-Horner-Emmons reaction.

[Process 1b] Preparation of Compound (I-12b')

Compound (I-12b') is obtained by reacting Compound (XII)

(1) with phosphonium ylide induced from phosphonium salt (XIII) (Q=PR$^7_3$) to give olefin, which is so-called Wittig reaction, or (2) with phosphonate carboanion induced from alkylphosphorous diester (XIII) (Q=P(O) (OR$^7$)$_2$) to give olefin, which is so-called Wittig-Horner-Emmons reaction.

The reaction is known per se, and can be carried out according to or by referring to the conditions described or cited in, for example, 4th ed. Jikken Kagaku Koza (Maruzen) vol. 19, Organic Synthesis I, pp. 57-78.

[Process 2a] Preparation of Compound (I-12a)

The double bond of Compound (I-12a') obtained in Process 1a is reduced to give Compound (I-12a).

[Process 2b] Preparation of Compound (I-12b)

The double bond of Compound (I-12b') obtained in Process 1b is reduced to give Compound (I-12b).

In such reduction reaction, catalytic hydrogenation and the like can be used in the presence of a catalyst.

The catalyst to be used for catalytic hydrogenation, includes metals such as palladium, platinum, nickel, rhodium and the like, oxides, salts and complexes of thereof, and the like. These catalysts can be also used by being carried on various carriers such as carbon and the like. The hydrogenation can be conducted under normal pressure or under pressurization.

The solvent to be used therefor can be appropriately determined, for example, alcohols (for example, methanol or ethanol and the like), ethers (for example, tetrahydrofuran, dioxane, diethyl ether and the like), hydrocarbons (for example, hexane, pentane and the like), aromatic hydrocarbons (for example, benzene, toluene and the like), halogenated hydrocarbon (for example, dichloromethane, chloroform and the like), esters (for example, ethyl acetate and the like), aprotic polar solvent (for example, N,N-dimethylformamide, dimethylsulfoxide, acetonitrile and the like) and the like. Such solvent may be mixed in a suitable ratio.

The reaction time is 0.5 to 72 hours, preferably 1 to 24 hours. The reaction temperature is from −100 to 100° C. (preferably from −70 to 50° C.).

Compound (I-2) which is used as a starting compound in Method A is prepared by, for example, the above-mentioned Method B to Method I.

Compound (I-4) which is used as a starting compound in Method B is prepared, for example, by the above-mentioned Method A or Method C to Method F.

Compound (I-6) which is used as a starting compound in Method C is prepared, for example, by the above-mentioned Method A, Method B or Method D to Method I.

Compound (II-1') which is Compound (II) wherein Y is —O— and the moiety adjacent to Y' of M¹ is non-substituted methylene (also including a compound of Compound (II-1) wherein the moiety adjacent to OH group of M$^{1a}$ a is non-substituted methylene, and used as a starting compound in Method F, and a compound of Compound (II-1") wherein R⁸ is a hydrogen atom, and used as a starting compound In the below-described Method P), and used as a starting compound in Method D is prepared, for example, by the following Method J.

[Method J]

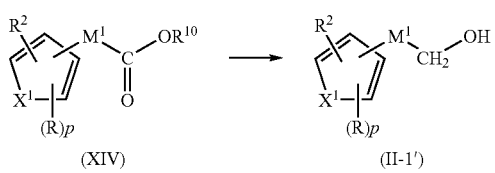

[wherein R¹⁰ is a hydrogen atom or an optionally substituted hydrocarbon group, and the other symbols are as defined above.]

Herein, the "optionally substituted hydrocarbon group" represented by the above-mentioned R¹⁰ includes those exemplified as the above-mentioned R¹.

In this method, Compound (XIV) is reduced to give Compound (II-1').

In this reduction reaction, the reducing agent is used in an amount of 1 equivalent to large excess (preferably 1 to 10 equivalents) relative to Compound (XIV). The reducing agent includes, for example, metal hydrogen complex compound such as sodium borohydride, sodium cyanoborohydride, aluminium lithium hydride, diisobutylaluminium hydride and the like or diborane and the like.

Method J is usually carried out in a solvent. The solvent to be used therefor can be appropriately determined depending on the kind of the reducing agent, for example, alcohols (for example, methanol or ethanol and the like), ethers (for example, tetrahydrofuran, dioxane, diethyl ether and the like), hydrocarbons (for example, hexane, pentane and the like), aromatic hydrocarbons (for example, benzene, toluene and the like), halogenated hydrocarbon (for example, dichloromethane, chloroform and the like), aprotic polar solvent (for example, N,N-dimethylformamide, dimethylsulfoxide, acetonitrile and the like) and the like. The reaction time is 0.5 to 72 hours, preferably 1 to 24 hours. The reaction temperature is −30 to 100° C.

Compound (II-2) which is Compound (II) wherein Y' is —S—, and used as a starting compound in Method D is prepared, for example, by the following Method K.

[Method K]

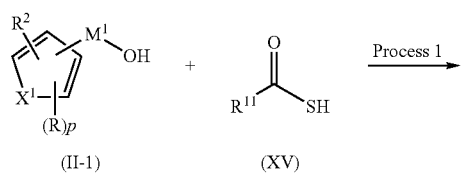

-continued

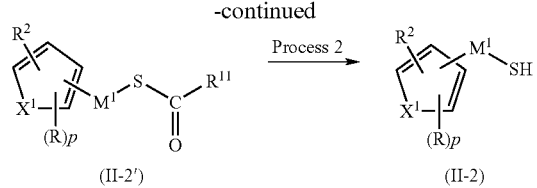

[wherein R" is an optionally substituted hydrocarbon group, and the other symbols are as defined above.]

The "optionally substituted hydrocarbon group" in R¹¹ has the same meaning as the above-mentioned "optionally substituted hydrocarbon group" in R¹, preferably a C$_{1-4}$ alkyl group, or a phenyl group optionally substituted with a C$_{1-4}$ alkyl group or 1 to 3 halogen atoms and the like.

[Process 1]

In this method, Compound (II-1) is reacted with Compound (XV) to give Compound (II-2'). This reaction is carried out in the same manner as in that of Compound (II-1) and Compound (IV-1) in the above-mentioned Method F.

Compound (XV) can be prepared by a per se known method, or is available as a commercial product.

[Process 2]

In this method, Compound (II-2') obtained in Process 1 is hydrolyzed to give Compound (II-2). This reaction is carried out in the same manner as the preparation of Compound (I-1) by hydrolyzing Compound (I-2) in the above-mentioned Method A.

Moreover, Compound (II-2) may be separated and purified as thiol, and if the above-mentioned hydrolyzation is carried out in the presence of a base, it may be separated and purified as alkyl metal thiolate, or without separating alkylmetal thiolate, it may be used in the preparation of Compound (I-7) shown in Method D.

Compound (V) which is used as a starting compound in Method E is prepared, for example, by the following Method L.

[Method L]

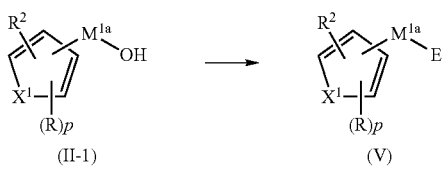

[wherein the symbols are as defined above.]

The reaction of converting the hydroxy group of Compound (II-1) to a leaving group E is carried out by, for example, the reaction of Compound (II-1) and a halogenating agent when E is halogen. The halogenating agent includes, for example, phosphorus halide such as phosphorus trichloride, phosphorus oxychloride, phosphorus pentachloride, phosphorus tribromide and the like, red phosphorus and halogen or thionyl chloride and the like. The amount of the halogenating agent is 1 to 5 equivalents to 1 equivalent of Compound (II-1).

When E is sulfonyloxy such as toluenesulfonyloxy or methanesulfonyloxy and the like, it is carried out by the reaction of Compound (II-1) and a sulfonylating agent. The sulfonylating agent includes, for example, corresponding sulfonyl chloride or sulfonic acid anhydride (for example, toluenesulfonyl chloride, methanesulfonyl chloride, methanesulfonic acid anhydride and the like) and the like. The amount of the sulfonylating agent is 1 to 5 equivalents to 1 equivalent of Compound (II-1). An inorganic base such as potassium carbonate, sodium hydrogen carbonate and the like, or organic base such as 4-(N,N-dimethylamino)pyridine, triethylamine, pyridine, dimethylaniline, 1,4-diazabicyclo[2.2.2]octane (DABCO) and the like may be also used in 1 to 10 equivalents.

Method E is usually carried out in a solvent. The solvent to be conveniently used therefor includes, for example, halogenated hydrocarbons (for example, dichloromethane, chloroform, dichloroethane and the like), hydrocarbons (for example, hexane, pentane and the like), aromatic hydrocarbons (for example, benzene, toluene and the like), ethers (for example, diethyl ether, tetrahydrofuran and the like), esters (for example, methyl acetate, ethyl acetate and the like), aprotic polar solvent (for example, N,N-dimethylformamide, dimethylsulfoxide, acetonitrile and the like) and the like.

The reaction temperature is −30° C. to 100° C., preferably −10° C. to 50° C. The reaction time is usually 10 minutes to 100 hours, preferably 3 to 24 hours.

Compound (VI) which is used as a starting compound in Method G is prepared, for example, by the following Method M.

[Method M]

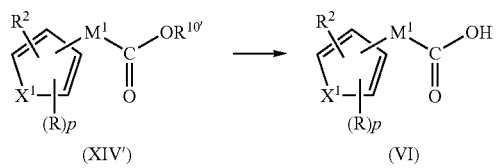

[wherein $R^{10'}$ is an optionally substituted hydrocarbon group, and the other symbols are as defined above.]

The "optionally substituted hydrocarbon group" in $R^{10'}$ has the same meaning as the above-mentioned "optionally substituted hydrocarbon group" in $R^1$.

In this method, Compound (XIV') is hydrolyzed to give Compound (VI). This reaction is carried out in the same manner as the preparation of Compound (I-1) by hydrolyzing Compound (I-2) in the above-mentioned Method A.

Compound (VIII) which is used as a starting compound in Method H is prepared, for example, by the following Method N-1 or Method N-2.

[Method N-1]

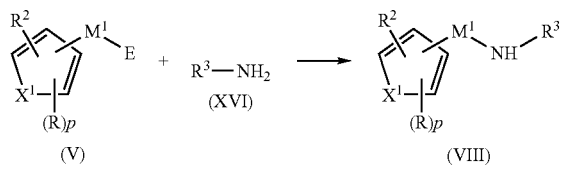

[wherein the symbols are as defined above.]

In this method, Compound (V) is reacted with Compound (XVI) to give Compound (VIII). This reaction is carried out in the same manner as that of Compound (II) with Compound (III) in the above-mentioned Method D.

[Method N-2]

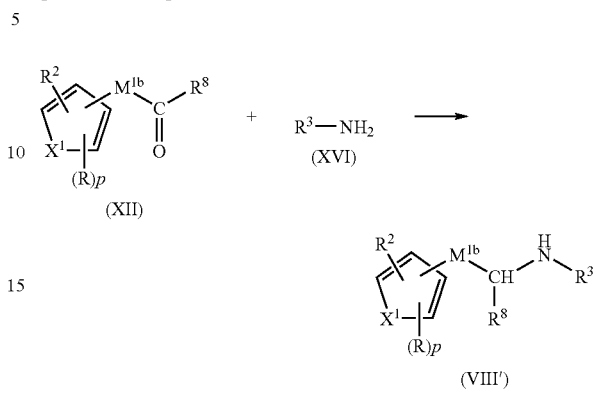

[wherein the symbols are as defined above.]

The present method is a method of reacting Compound (XII) with ammonia or primary amine (XVI), and reducing the produced imine or iminium ion to synthesize amines, i.e., a method of obtaining Compound (VIII') by so-called reductive amination reaction.

In this reaction, ammonia or primary amine (XVI) is used in 1 equivalent or large excess (preferably 1 to 10 equivalents) relative to Compound (XII).

An acid (for example, mineral acid such as hydrochloric acid, phosphoric acid, sulfuric acid and the like or organic acid such as toluenesulfonic acid, methanesulfonic acid, acetic acid and the like) may be added in 0.1 to 2 equivalents. The reduction method includes reduction with a reducing agent such as metal hydrogen complex compound such as sodium borohydride, sodium cyanoborohydride, aluminium lithium hydride and the like, diborane and the like, catalytic hydrogenation in the presence of a catalyst such as palladium or Raney nickel and the like, electrolytic reduction using lead or platinum as a negative electrode. The reducing agent is used in 1 equivalent to large excess (preferably 1 to 10 equivalents).

Method N-2 is usually carried out in a solvent. The solvent to be used therefor can be appropriately determined depending on methods of reducing, for example, alcohols (for example, methanol or ethanol and the like), ethers (for example, tetrahydrofuran, dioxane, diethyl ether and the like), halogenated hydrocarbon (for example, dichloromethane, chloroform and the like), hydrocarbons (for example, hexane, pentane and the like), aromatic hydrocarbons (for example, benzene, toluene and the like), aprotic polar solvent (for example, N,N-dimethylformamide, dimethylsulfoxide, acetonitrile and the like) and the like. The reaction time is 0.5 to 72 hours, preferably 1 to 24 hours. The reaction temperature is −30° C. to 100° C., preferably 0° C. to 60° C.

Compound (XVI) can be prepared by a per se known method, or is available as a commercial product.

Compound (X) which is used as a starting compound in Method I-1 is prepared, for example, by the following Method O.

[Method O]

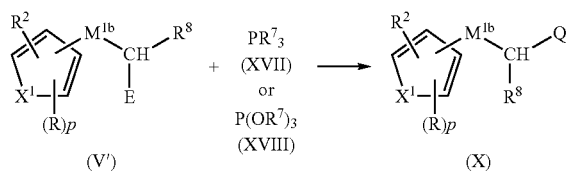

[wherein the symbols are as defined above.]

This reaction is a method of reacting Compound (V') with Compound (XVII) when Q is $P(O)(OR^7)_2$ in Compound (X), or reacting Compound (V') with Compound (XVIII) when Q is $PR^7_3$ in Compound (X), to produce Compound (X).

In this reaction, Compound (XVII) or Compound (XVIII) is used in 1 equivalent or large excess (preferably 1 to 10 equivalents) relative to Compound (V').

The reaction can be carried out without solvent, or in a solvent suitably selected from, for example, ethers (for example, tetrahydrofuran, dioxane, diethyl ether and the like), halogenated hydrocarbon (for example, dichloromethane, chloroform and the like), hydrocarbons (for example, hexane, pentane and the like), aromatic hydrocarbons (for example, benzene, toluene and the like), aprotic polar solvent (for example, N,N-dimethylformamide, dimethylsulfoxide, acetonitrile and the like) and the like.

The reaction time is 0.5 to 72 hours, preferably 1 to 24 hours. The reaction temperature is 0° C. to 20° C.

Compound (XVII) and (XVIII) can be prepared by a per se known method, or is available as a commercial product. Furthermore, Compound (V') is prepared by the above-mentioned Method L.

Compound (XII) which is used as a starting compound in Method I-2 is prepared, for example, by the following Method P.

[Method P]

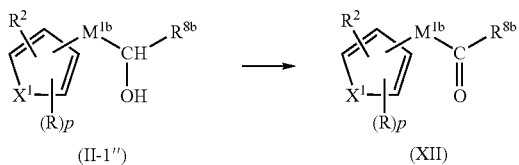

[wherein the symbols are as defined above.]

In this method, Compound (II-1") is oxidized to give Compound (XII).

In the oxidation reaction, an oxidizing agent is used, for example, in 1 equivalent to 20 equivalents relative to Compound (II-1"). The oxidizing agent includes activated manganese dioxide, pyridinium chlorochromate (PCC), pyridinium dichromate (PDC), dimethylsulfoxide-acid anhydride (acetic anhydride, trifluoroacetic anhydride and the like), dimethylsulfoxide-thionyl chloride, dimethylsulfoxide-sulfuryl chloride, dimethylsulfoxide-oxalyl chloride, dimethylsulfoxide-chlorine, and dimethylsulfoxide-dicyclohexylcarbodiimide (DCC) in the presence of acid (phosphoric acid, trifluoroacetic acid, dichloroacetic acid and the like) and the like.

The oxidation reaction is usually carried out in a solvent. The solvent to be used therefor is can be appropriately determined depending on the kind of the oxidizing agent, for example, ethers (for example, tetrahydrofuran, dioxane, diethyl ether and the like), halogenated hydrocarbon (for example, dichloromethane, chloroform and the like), ketones (for example, acetone, methyl ethyl ketone and the like), aprotic polar solvent (for example, N,N-dimethylformamide, dimethylsulfoxide, acetonitrile and the like) and the like.

The reaction time is 0.5 to 48 hours, preferably 1 to 24 hours. The reaction temperature is appropriately determined depending on the kind of an oxidizing agent, and is −80 to 100° C.

Compound (II-2) which is Compound (II-1") wherein $R^8$ is not a hydrogen atom, and used as a starting compound in Method P is prepared, for example, by the following Method P'.

[Method P']

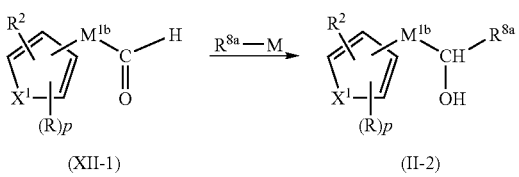

[wherein $R^{8a}$ is an optionally substituted hydrocarbon group, M is a hydrogen atom or metal atom such as sodium, lithium, magnesium and the like (in the case of a divalent metal, the remaining monovalent may be occupied by halogen atom and the like), and the other symbols are as defined above.]

The "optionally substituted hydrocarbon group" in $R^{8a}$ has the same meaning as the above-mentioned "optionally substituted hydrocarbon group" in $R^1$.

In this method, Compound (XII-1) is reacted with $R^{8a}$-M to give Compound (II-2). This reaction is in accordance with a conventional method in a reaction solvent which does not interfere with the reaction. $R^{8a}$-M is used in 1 equivalent or large excess, preferably about 1 to about 5 molar equivalents relative to Compound (XII-1). When M is a hydrogen atom, the reaction is carried out in the presence of a basic compound. The basic compound to be used includes inorganic basic compounds such as sodium hydroxide and potassium carbonate, alkoxides such as sodium methoxide and potassium tert-butoxide, organic lithium reagents such as n-butyl lithium, phenyl lithium and lithium diisopropylamide, alkyl metal amides such as sodium amide and the like.

The reaction solvent which does not interfere with the reaction includes, for example, hydrocarbons such as pentane, hexane and the like; aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethylsulfoxide and the like, and the like. Such solvent may be mixed in a suitable ratio.

Moreover, Compound (II-1') is oxidized to give Compound (XII-1) in the above-mentioned Method P.

Compound (VI') which is Compound (VI) wherein $M^1$ is an optionally substituted divalent aliphatic hydrocarbon group, and used as a starting compound in Method G or, Compound (VI') which is Compound (XIV) wherein $M^1$ is an optionally substituted divalent aliphatic hydrocarbon group, and $R^{10}$ is hydrogen, and used as a starting compound in Method J, is prepared, for example, by the following Method Q.

[Method Q]

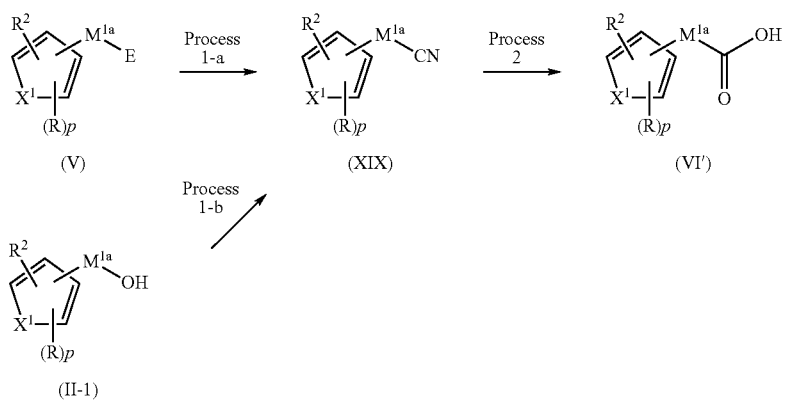

[wherein the symbols are as defined above.]

[Process 1-a]

In this method, Compound (V) is reacted with inorganic cyanide to give Compound (XIX). This reaction is carried out according to a conventional method in a reaction solvent which does not interfere with the reaction.

The inorganic cyanide to be used includes, for example, cyanide sodium, cyanide potassium, cyanide copper (I) and the like. The amount of such inorganic cyanide is preferably 1 equivalent to large excess (preferably 1 to 10 equivalents) relative to Compound (V).

Furthermore, for the reaction, alkali metal iodide such as iodide sodium and the like may be added in 1 equivalent or large excess (preferably 1 to 10 equivalents) as a reaction promoter.

The reaction solvent which does not interfere with the reaction includes, for example, water, alcohols (for example, methanol or ethanol and the like), ethers (for example, tetrahydrofuran, dioxane, diethyl ether and the like), halogenated hydrocarbon (for example, dichloromethane, chloroform and the like), hydrocarbons (for example, hexane, pentane and the like), aromatic hydrocarbons (for example, benzene, toluene and the like), aprotic polar solvent (for example, N,N-dimethylformamide, dimethylsulfoxide, acetonitrile and the like) and the like. Such solvent may be mixed in a suitable ratio. The reaction temperature is usually about 0° C. to about 200° C. The reaction time is usually about 0.5 to about 20 hours.

[Process 1-b]

In this method, Compound (II-1) is reacted with hydrogen cyanide by so-called Mitsunobu reaction to give Compound (XIX). This reaction carried out in the same manner as the preparation of Compound (I-8) by reacting Compound (II-1) with Compound (IV-1) in the above-mentioned Method F.

Moreover, in the above-mentioned reaction, cyanohydrin (for example, acetonecyanohydrin and the like) may be used as hydrogen cyanide source instead of hydrogen cyanide.

[Process 2]

In this method, Compound (XIX) obtained in Process 1-a or Process 1-b is hydrolyzed to give Compound (VI'). This reaction is carried out in the same manner as the preparation of Compound (I-1) by hydrolyzing Compound (I-2) in the above-mentioned Method A.

Compound (XXI) and Compound (XIV″) which is Compound (XIV) in Method J (also including Compound (XIV') which is used as a starting compound in Method M) wherein $M^1$ is optionally substituted divalent aliphatic hydrocarbon group having 2 or more, is prepared, for example, by the following Method R.

[Method R]

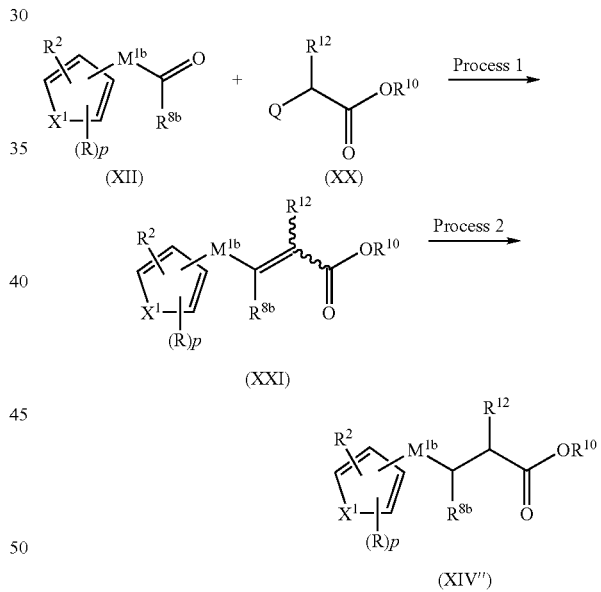

[wherein $R^{12}$ is a substituent suitably selected from a hydrogen atom, an alkyl group or the substituent which the "divalent aliphatic hydrocarbon group" may have in the above-mentioned $M^1$, and the other symbols are as defined above.]

The alkyl group in $R^{12}$ is straight or branched alkyl group, and the number of carbon atoms is not particularly limited, preferably less than 18, for example, methyl, ethyl, propyl, isopropyl, butyl, isobutyl, sec-butyl, tert-butyl and the like.

[Process 1] Preparation of Compound (XXI)

Compound (XXI) is obtained by reacting Compound (XII) (1) with phosphonium ylide induced from phosphonium salt (XX) ($Q=PR^7_3$) to give olefin, which is so-called Wittig reaction, or (2) with phosphonate carboanion induced from alkylphosphorous diester (XX) (Q=P(O)(OR$^7$)$_2$) to give olefin, which is so-called Wittig-Horner-Emmons reaction.

This reaction is carried out in the same manner as the preparation of Compound (I-12a') by Wittig reaction or Wittig-Horner-Emmons reaction in the above-mentioned [Process 1a] of Method I-1.

Compound (XX) is can be prepared by a per se known method or a method analogous thereto, or is available as a commercial product.

[Process 2] Preparation of Compound (XIV")

This reaction is a method of reducing the double bond of Compound (XXI) obtained in Process 1 to give Compound (XIV"). This reaction is carried out in the same manner as the preparation of Compound (I-12a) by hydrogenation of Compound (I-12a') in [Process 2a] of the above-mentioned Method I.

Compound (III) in Method D is prepared, for example, by the following Method S.

[Method S]

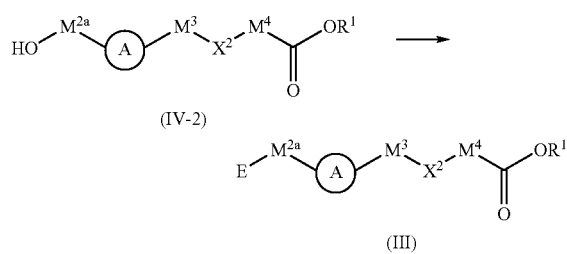

[wherein the symbols are as defined above.]

In this method, the hydroxy group of Compound (IV-2) is converted to a leaving group E to give Compound (III). This reaction is carried out in the same manner as the preparation of Compound (V) by converting the hydroxy group of Compound (II-1) to a leaving group E in the above-mentioned Method L.

Compound (XI) in Method I-1 is prepared, for example, by the following Method T.

[Method T]

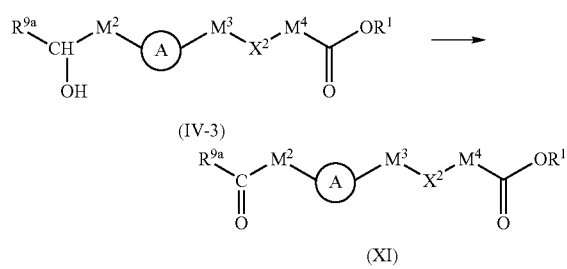

[wherein the symbols are as defined above.]

In this method, Compound (IV-3) is oxidized to give Compound (XI). This reaction is carried out in the same manner as the preparation of Compound (XII) by oxidation of Compound (II-1") in the above-mentioned Method P.

Compound (XIII) in Method I-2 is prepared, for example, by the following Method U.

[Method U]

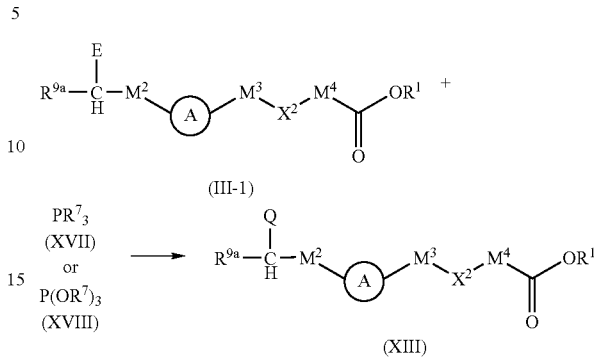

[wherein the symbols are as defined above.]

This reaction is a method of reacting Compound (III-1) with Compound (XVII) when Q is P(O)(OR$^7$)$_2$ in Compound (XIII), or reacting Compound (III-1) with Compound (XVIII) when Q is PR$^7$$_3$ in Compound (XIII), to give Compound (XIII). This reaction is carried out in the same manner as the preparation of Compound (X) by a reaction of Compound (V') with Compound (XVII) or Compound (XVIII) in the above-mentioned Method Q.

Moreover, in this process, Compound (III-1) is included in Compound (III), and prepared by the method shown in the above-mentioned Method S.

Compound (IV) in Method E, Compound (IV-1) in Method F, Compound (VII) in Method G, Compound (IX) in Method H, Compound (IV-2) in Method S, and, Compound (IV-3) in Method T (such compounds are all included in Compound (XXII) in Method V of the following formula), are prepared, for example, by the following Method V.

[Method V]

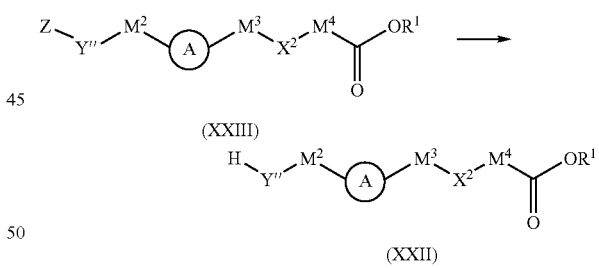

[wherein Z is a protective group for amino, a protective group for carboxy, a protective group for hydroxy or a protective group for mercapto, —Y"— is —O—, —S—, —N(R$^3$)— or —C(=O)—O— (provided that carbonyl carbon is boned to M$^2$), and the other symbols are as defined above.]

The "protective group" represented by Z includes the protective groups described below and the like. In this method, the protective group of Compound (XXIII) is deprotected to give Compound (XXII). The reaction of deprotecting the protective group is carried out by a per se known method or a method analogous thereto, for example, according to or by referring to the conditions described or cited in, for example, "PROTECTIVE GROUPS IN ORGANIC SYNTHESIS", Second Edition (JOHN WILEY & SONS, INC.) and the like.

Compound (XXIII-1) which is Compound (XXIII) in Method V wherein $X^2$ is —O— or —S—, $M^3$ is not a bond is prepared, for example, by the following Method W.

[Method W]

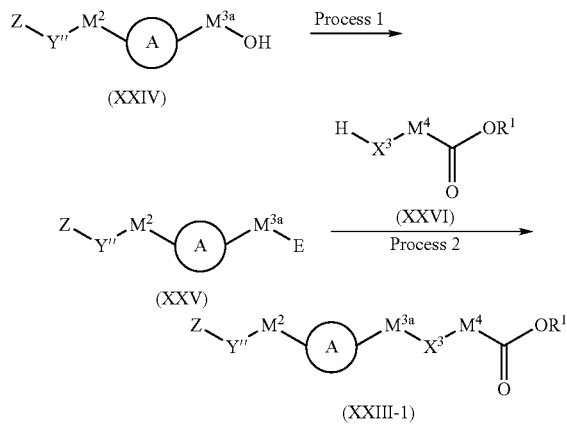

[wherein $X^3$ is —O— or —S—, $M^{3a}$ is an optionally substituted divalent aliphatic hydrocarbon group, and the other symbols are as defined above.]

The "optionally substituted divalent aliphatic hydrocarbon group" in $M^{3a}$ has the same meaning as the above-mentioned "optionally substituted divalent aliphatic hydrocarbon group" in the $M^1$.

[Process 1]

In this method, the hydroxy group of Compound (XXIV) is converted to a leaving group E to give Compound (XXV). This reaction is carried out in the same manner as the preparation of Compound (V) by converting the hydroxy group of Compound (II-1) to a leaving group E in the above-mentioned Method L.

[Process 2]

In this method, Compound (XXV) obtained in Process 1 is reacted with Compound (XXVI) to give Compound (XXIII-1). The present method is carried out, for example, under the same reaction conditions as those of the above-mentioned Method D by reacting Compound (II) with Compound (III) to give Compound (I-7).

Compound (XXVI) in [Process 2] of Method W can be prepared by a per se known method, or is also available as a commercial product.

Compound (XXIII-2) which is Compound (XXIII) in Method V wherein $X^2$ is —O— or —S— is prepared, for example, by the following Method X.

[Method X]

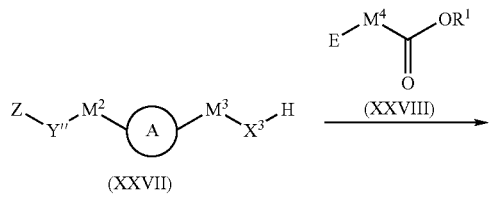

-continued

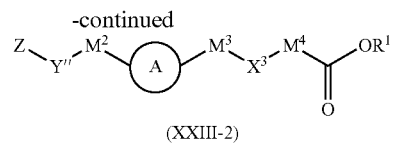

[wherein the symbols are as defined above.]

In this method, Compound (XXVII) is reacted with Compound (XXVIII) to give Compound (XXIII-2). The present method for example, is carried out under the same reaction conditions as those of the above-mentioned Method D by reacting Compound (II) with Compound (III) to give Compound (I-7).

Moreover, Compound (XXVIII) in the above-mentioned Method X can be prepared by a per se known method, or is also available as a commercial product.

Compound (XXIII-3) which is Compound (XXIII) wherein $x^2$ is —O— or —S— and $M^3$ is a bond, and used as a starting compound in Method V is prepared, for example, by the following Method Y.

[Method Y]

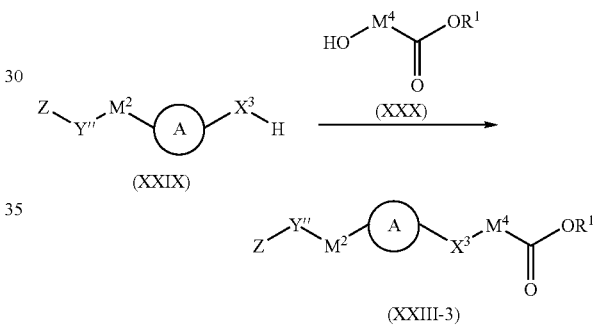

[wherein the symbols are as defined above.]

In this method, Compound (XXIX) is reacted with Compound (XXX) by so-called Mitsunobu reaction to give Compound (XXIII-3). This reaction is carried out in the same manner as the preparation of Compound (I-8) by reacting Compound (II-1) with Compound (IV-1) in the above-mentioned Method F.

Moreover, Compound (XXX) in the above-mentioned Method Y can be prepared by a per se known method, or is also available as a commercial product.

Compound (XXIII-4) which is Compound (XXIII) in Method V wherein $X^2$ and $M^4$ are a bond together, $M^3$ is optionally substituted divalent aliphatic hydrocarbon group having 2 or more carbon atoms, or Compound (XXIII-5) is prepared, for example, by the following Method Z.

[Method Z]

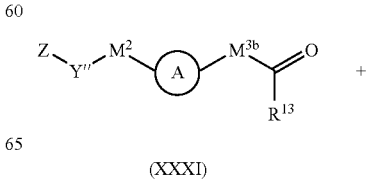

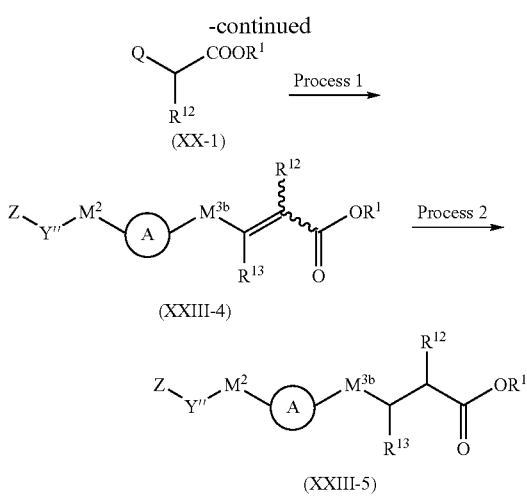

[wherein $M^{3b}$ is a bond or an optionally substituted divalent aliphatic hydrocarbon group, $R^{13}$ is a substituent suitably selected from a hydrogen atom, an alkyl group or the substituent which the "divalent aliphatic hydrocarbon group" may have in the above-mentioned $M^1$, and the other symbols are as defined above.]

The "optionally substituted divalent aliphatic hydrocarbon group" in $M^{3b}$ has the same meaning as the above-mentioned "optionally substituted divalent aliphatic hydrocarbon group" in the $M^1$. The alkyl group in $R^{13}$ is straight or branched alkyl group, and the number of carbon atoms is not particularly limited, preferably less than 18, for example, methyl, ethyl, propyl, isopropyl, butyl, isobutyl, sec-butyl, tert-butyl and the like, and the like.

[Process 1] Preparation of Compound (XXIII-4)

Compound (XXIII-4) is obtained by reacting Compound (XXXI)

(1) with phosphonium ylide induced from phosphonium salt (XX-I) ($Q=PR^7_3$) to give olefin, which is so-called Wittig reaction, or (2) with phosphonate carboanion induced from alkylphosphorous diester (XX-I) ($Q=P(O)(OR^7)_2$) to give olefin, which is so-called Wittig-Horner-Emmons reaction.

This reaction is carried out in the same manner as the preparation of Compound (I-12a') by Wittig reaction or Wittig-Horner-Emmons reaction in the above-mentioned [Process 1a] of Method I-1.

Compound (XX-I) is can be prepared by a per se known method or a method analogous thereto, or is available as a commercial product, or is also available as a commercial product.

[Process 2] Preparation of Compound (XXIII-5)

This reaction is a method of reducing the double bond of Compound (XXIII-4) obtained in Process 1 to give Compound (XXIII-5). This reaction is carried out in the same manner as the preparation of Compound (I-12a) by hydrogenation of Compound (I-12a') in [Process 2a] of the above-mentioned Method I.

Compound (XXIII-6) which is Compound (XXIII) in Method V wherein $X^2$ and $M^4$ are a bond together, $R^1$ is a hydrogen atom and $M^3$ is an optionally substituted divalent aliphatic hydrocarbon group, and Compound (XXIII-7) which is Compound (XXIII) wherein $X^2$ and $M^4$ are a bond together, $M^3$ is an optionally substituted divalent aliphatic hydrocarbon group and $R^1$ is not a hydrogen atom is prepared, for example, by the following Method Aa.

[Method Aa]

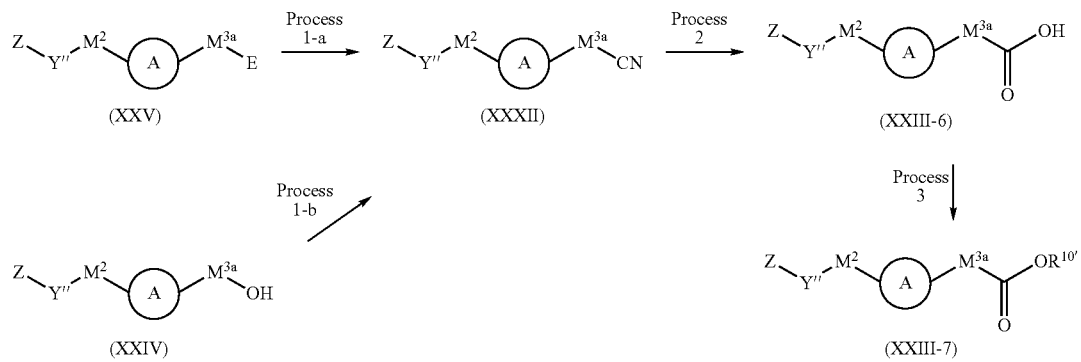

[wherein the symbols are as defined above.]

[Process 1-a]

In this method, Compound (XXV) is reacted with inorganic cyanide to give Compound (XXXII). This reaction is carried out in the same manner as the preparation of Compound (XIX) by reacting Compound (V) with inorganic cyanide in [Process 1-a] of the above-mentioned Method Q.

[Process 1-b]

In this method, Compound (XXIV) is reacted with hydrogen cyanide by so-called Mitsunobu reaction to give Compound (XXXII). This reaction is carried out in the same manner as the preparation of Compound (I-8) by reacting Compound (II-1) with Compound (IV-1) in the above-mentioned Method F.

Moreover, in the above-mentioned reaction, cyanohydrin (for example, acetonecyanohydrin and the like) may be used as hydrogen cyanide source instead of hydrogen cyanide.

[Process 2]

In this method, Compound (XXXII) obtained in Process 1-a or Process 1-b is hydrolyzed to give Compound (XXIII-6). This reaction is carried out in the same manner as the preparation of Compound (I-1) by hydrolyzing Compound (I-2) in the above-mentioned Method A.

[Process 3]

In this method, Compound (XXIII-6) obtained in Process 2 is esterified to give Compound (XXIII-7). This reaction can be carried out by a per se known method for example, according to or by referring to the conditions described or cited in, for example, 4th ed. Jikken Kagaku Koza (Maruzen) vol. 22, Organic Synthesis IV, pp. 43-51.

Compound (XXIV) in [Process 1] of Method W, and Compound (XXXI) in Method Z are known compounds, and can be prepared by a per se known method, or are also available as a commercial product. Furthermore, Compound (XXIV) (Compound (XXIV-1) or Compound (XXIV-2) in the following Method Bb) and Compound (XXXI) (Compound (XXXI-1) or Compound (XXXI-2) in the following Method Bb) are prepared, for example, by the following Method Bb from Compound (XXIII-8) (the compound combining Compound (XXIII-6) and Compound (XXIII-7) prepared in Method Aa, and Compound (XXIII-4) and Compound (XXIII-5) prepared in Method Z).

[Method Bb]

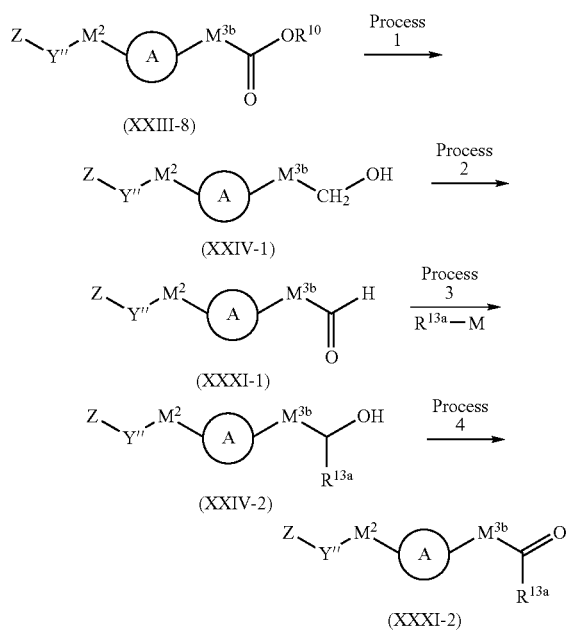

[wherein $R^{13a}$ is an optionally substituted hydrocarbon group, and the other symbols are as defined above.]

Herein, the above-mentioned "optionally substituted hydrocarbon group" in $R^{13a}$ has the same meaning as the above-mentioned "optionally substituted hydrocarbon group" in $R^1$.

[Process 1]

Compound (XXIV-1) is prepared by reducing Compound (XXIII-8) in Method J under the same conditions as the preparation of Compound (II-1) by reducing Compound (XIV).

[Process 2]

Compound (XXXI-1) is prepared by oxidizing Compound (XXIV-1) under the same conditions as the preparation of Compound (XII) by oxidizing Compound (II-1") in the above-mentioned Method P.

[Process 3]

Compound (XXIV-2) is prepared by reacting Compound (XXXI-1) with $R^{13a}$-M under the same conditions as the preparation of Compound (II-2) by reacting Compound (XII-1) and $R^{8a}$-M in the above-mentioned Method P'.

[Process 4]

Compound (XXXI-2) is prepared by oxidizing Compound (XXIV-2) under the same conditions as the preparation of Compound (XII) by oxidizing Compound (II-1") in the above-mentioned Method P.

The compound which is Compound (XIV) in Method J wherein $M^1$ is a bond and $R^{10}$ is an optionally substituted hydrocarbon group, or Compound (XIV') in Method M wherein $M^1$ is a bond, can be prepared by a per se known method. Furan carboxylic acid ester wherein $X^1$ is an oxygen atom can be prepared by, for example, the method described or cited in, for example, 4th ed. Jikken Kagaku Koza (Maruzen) vol. 24, Organic Synthesis VI, pp. 500-504, JP-A-1999-60569, Synthesis 12, p. 1027 (1983) and the like. Thiophenecarboxylic acid ester wherein $X^1$ is a sulfur atom can be prepared by, for example, the method described or cited in, for example, 4th ed. Jikken Kagaku Koza (Maruzen) vol. 24, Organic Synthesis VI, pp. 513-517 and the like.

In the substituent which R, $R^1$, $R^2$, $R^3$, Ring A, $M^1$, $M^2$ or $M^3$ of Compound (I) may have respectively, when the substituent has a convertible functional group (for example, a carboxy group, an amino group, a hydroxy group, a carbonyl group, a mercapto group, ester, cyano group, a sulfo group, a halogen atom and the like), the functional group can be converted by a per se known method or a method analogous thereto to give a variety of compounds.

For example, a carboxy group is convertible by a reaction such as esterification, reduction, amidation, conversion to optionally protected amino group and the like. An amino group is convertible by a reaction such as amidation, sulfonylation, nitrosation, alkylation, arylation, imidation and the like. A hydroxy group is convertible by a reaction such as esterification, carbamoylation, sulfonylation, alkylation, arylation, oxidation, halogenation and the like. A carbonyl group is convertible by a reaction such as reduction, oxidation, imination (containing oximation and hydrazonation), (thio) ketalation, alkylidenation, thiocarbonylation and the like. A mercapto group is convertible by a reaction such as alkylation, oxidation and the like. Ester or a cyano group is convertible by a reaction such as reduction, hydrolyzation and the like. A sulfo group is convertible by a reaction such as sulfonamidation, reduction and the like. A halogen atom is convertible by various nucleophilic substitution reactions, various coupling reactions and the like.

In each of the reactions for synthesizing the above-mentioned objective compounds and the starting compounds, a starting compound used having an amino, carboxy, hydroxyl or mercapto as its substituent may be present as a compound in which a protective group used ordinarily in a peptide chemistry has been introduced into such a substituent, and an objective compound can be obtained by deprotection if necessary after the reaction.

A protective group for amino includes, for example, optionally substituted $C_{1-6}$ alkyl-carbonyl (e.g., acetyl, ethylcarbonyl and the like), phenylcarbonyl, $C_{1-6}$ alkyloxy-carbonyl (e.g., methoxycarbonyl, ethoxycarbonyl and the like), $C_{6-10}$ aryloxy-carbonyl (e.g., phenyloxycarbonyl and the like), $C_{7-10}$ aralkyloxy-carbonyl (e.g., benzyloxycarbonyl and the like), formyl, trityl, phthaloyl and the like. Such protective group may be substituted with about 1 to 4 of a halogen atom (e.g., fluorine, chlorine, bromine and iodine and the like), $C_{1-6}$ alkyl-carbonyl (e.g., acetyl, ethylcarbonyl, butylcarbonyl and the like), nitro and the like.

A protective group for carboxy includes, for example, optionally substituted $C_{1-6}$ alkyl (e.g., methyl, ethyl, n-propyl, isopropyl, n-butyl, tert-butyl and the like), phenyl, trityl, silyl and the like. Such protective group may be substituted with about 1 to 4 of a halogen atom (e.g., fluorine, chlorine, bromine and iodine and the like), $C_{1-6}$ alkyl-carbonyl (e.g., acetyl, ethylcarbonyl, butylcarbonyl and the like), formyl, nitro, and the like.

A protective group for hydroxy includes, for example, optionally substituted $C_{1-6}$ alkyl (e.g., methyl, ethyl, n-propyl, isopropyl, n-butyl, tert-butyl and the like), phenyl, $C_{7-10}$ aralkyl (e.g., benzyl and the like), $C_{1-6}$ alkyl-carbonyl (e.g., acetyl, ethylcarbonyl and the like), $C_{6-10}$ aryloxy-carbonyl (e.g., phenoxycarbonyl and the like), $C_{7-10}$ aralkyloxy-carbonyl (e.g., benzyloxycarbonyl and the like), formyl, pyranyl, furanyl, silyl and the like. Such protective group may be substituted with 1 to 4 of a halogen atom (e.g., fluorine, chlorine, bromine and iodine and the like), $C_{1-6}$ alkyl (e.g., methyl, ethyl, n-propyl, isopropyl, n-butyl, tert-butyl and the like), phenyl, $C_{7-10}$ aralkyl (e.g., benzyl and the like), nitro and the like. A protective group for mercapto includes, for example, the same as those used as the protective group for hydroxy.

A deprotection method may be a per se known method or a method analogous thereto such as a treatment with an acid, base, reduction, UV, hydrazine, phenylhydrazine, sodium N-methyldithiocarbamate, tetrabutylammonium fluoride, palladium acetate and the like.

Isolation and purification of Compound (I) of the present invention and starting materials thereof from the reaction mixture, can be carried out by the conventional separation and purification means such as extraction, concentration, filtration, recrystallization, distillation, column chromatography and thin layer chromatography.

When compound (I) thus obtained is obtained as a free form by a reaction described above, it may be converted in accordance with a per se known method or a method analogous thereto (e.g., neutralization, etc.) into a salt, and conversely, when it is obtained as a salt then it may be converted in accordance with a per se known method or a method analogous thereto into a free form or another salt.

When compound (I) is obtained as an enantiomer, a stereoisomer, a positional isomer or a rotational isomer, these isomers are also encompassed in compound (I), and each isomer can be obtained as a single product according to a synthetic method and separation method known per se. For example, when compound (I) has an enantiomer, an enantiomer resolved from this compound is also encompassed in compound (I).

The enantiomer can be produced by a method known per se. To be specific, an optically active synthetic intermediate is used, or the final racemate product is subjected to optical resolution according to a conventional method to give an enantiomer.

The method of optical resolution may be a method known per se, such as a fractional recrystallization method, a chiral column method, a diastereomer method and the like.

1) Fractional recrystallization method

A salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and a free enantiomer is obtained by a neutralization step where desired.

2) Chiral Column Method

A racemate or a salt thereof is applied to a column for separation of an enantiomer (chiral column) to allow separation. In the case of a liquid chromatography, for example, a mixture of an enantiomer is applied to a chiral column such as ENANTIO-OVM (manufactured by Tosoh Corporation) or CHIRAL series (manufactured by Daicel Chemical Industries, Ltd.) and the like, and developed with water, various buffers (e.g., phosphate buffer) and organic solvents (e.g., ethanol, methanol, isopropanol, acetonitrile, trifluoroacetic acid, diethylamine, etc.) solely or in admixture to separate the enantiomer. In the case of a gas chromatography, for example, a chiral column such as CP-Chirasil-DeX CB (manufactured by GL Sciences Inc.) and the like is used to allow separation.

3) Diastereomer Method

A racemic mixture is prepared into a diastereomeric mixture by chemical reaction with an optically active reagent, which is prepared into a single substance by a typical separation means (e.g., fractional recrystallization, chromatography method, etc.) and the like, and subjected to a chemical treatment such as hydrolysis and the like to separate an optically active reagent moiety, whereby an enantiomer is obtained. For example, when compound (I) contains hydroxy or primary or secondary amino in a molecule, the compound and an optically active organic acid (e.g., MTPA [α-methoxy-α-(trifluoromethyl)phenylacetic acid], (−)-menthoxyacetic acid, etc.) and the like are subjected to condensation reaction to give diastereomers of ester form or amide form, respectively. When compound (I) has a carboxylic acid group, this compound and an optically active amine or an alcohol reagent are subjected to condensation reaction to give diastereomers of amide form or ester form, respectively. The separated diastereomer is converted to an enantiomer of the original compound by acid hydrolysis or base hydrolysis.

Compound (I) of the present invention and a pharmacologically acceptable salt thereof shows excellent preventing and treating action for PPAR-related diseases (e.g., lipid metabolism abnormality and sequelae thereof, diabetes mellitus, hyperlipidemia, arteriosclerotic disease and sequelae thereof (for example, ischemic cardiac disease, cerebral disease or peripheral arterial occlusion and the like), impaired glucose tolerance and the like), by acting on PPAR. Therefore, it is useful as an agent of controlling PPAR and a prophylactic or therapeutic agent for PPAR-related diseases (e.g., lipid metabolism abnormality and sequelae thereof, diabetes mellitus, hyperlipidemia, arteriosclerotic diseases (for example, ischemic cardiac disease, cerebral disease or peripheral arterial occlusion and the like), impaired glucose tolerance and the like) in a mammal (e.g., human, monkey, sheep, bovine, horse, dog, cat, rabbit, rat, mouse and the like). Compound (I) of the present invention is also useful as an agent of raising high-density lipoprotein cholesterol, an agent of lowering triglyceride, an agent of lowering a low-density lipoprotein cholesterol, an agent of suppressing progress of arteriosclerotic plaque and the like. Furthermore, Compound (I) of the present invention has regulating action for GPR40 receptor function, and is also useful as an insulin secretion promoter or a prophylactic or therapeutic agent for diabetes mellitus and the like.

BEST MODE FOR CARRYING OUT THE INVENTION

The present invention is explained in more detail by the following Experimental Examples, which are not to be construed as limitative.

When a base, an amino acid and the like are expressed using abbreviations in the present specification, they are based on the abbreviations of IUPAC-IUB Commission on Biochemical Nomenclature or conventional abbreviations used in the pertinent field, which are exemplified by the following. When an amino acid has an enantiomer, it refers to an L form, unless specifically indicated.

EXPERIMENTAL EXAMPLE 1

PPARγ-RXRα Heterodimer Ligand Activity

The PPARγ:RXRα:4ERPP/CHO-K1 cells obtained in Reference Example 8a were cultured in Ham's F12 medium [produced by Life Technologies, Inc., USA] containing 10% fetal bovine serum [produced by Life Technologies, Inc., USA] and inoculated to a 96-well white plate [produced by Corning Coster Corporation, USA] at $2\times10^4$ cells/well and cultured overnight at 37° C. in a carbon dioxide gas incubator.

After removal of the medium from the 96-well white plate which had been cultured overnight, Ham's F12 medium containing 80 µl of 0.1% fatty acid-free bovine serum albumin (BSA) and 20 µl of a test compound were added, and the plate was incubated at 37° C. in a carbon dioxide gas incubator for 18 to 24 hours. After removal of the medium, 40 µl of PicaGene 7.5 (produced by Waco Pure Chemicals Industries, Ltd.) diluted twofold with HBSS (HANKS' BALANCED SALT SOLUTION) (produced by BIO WHITTAKER) was added, and after stirring, the luciferase activity was determined using 1420 ARVO Multilabel Counter [produced by Wallac].

A fold induction was calculated from the luciferase activity for addition of each 100 nM of the test compound relative to the luciferase activity of the test compound non-administration group as 1. Results are shown in [Table 1].

TABLE 1

| Example No. | Fold induction |
|---|---|
| 1 (3) | 2.8 |
| 5 (2) | 2.3 |

As shown above, it was clear that the compound of the present invention has excellent PPARγ-RXRα heterodimer ligand activity.

EXPERIMENTAL EXAMPLE 2

PPARδ-RXRα Heterodimer Ligand Activity

At 18 to 24 hours after transfection carried out in Reference Example 9a, COS-1 cells were collected, suspended in DMEM medium [manufactured by Life Technologies, Inc., USA] containing 0.1% fatty acid-free bovine serum albumin (BSA) (produced by Waco Pure Chemicals Industries, Ltd.), and inoculated to each well of a 96-well white plate (produced by Corning, USA) at $1\times10^4$ cells/well in 80 µl. Subsequently, 20 µl of a test compound was added, and the plate was incubated under the conditions of 37° C. and 5% $CO_2$ for 36 to 48 hours. After removal of the medium from the 96-well white plate, 40 µl of PicaGene. LT 7.5 (produced by Waco Pure Chemicals Industries, Ltd.) diluted twofold with HBSS (HANKS' BALANCED SALT SOLUTION) (produced by BIO WHITTAKER) was added, and after stirring, the luciferase activity was determined using 1420 ARVO Multilabel Counter [produced by Wallac].

The fold induction was calculated from the luciferase activity for addition of each 10 nM of the test compound relative to the luciferase activity of the test compound non-administration group as 1. Results are shown in [Table 2].

TABLE 2

| Example No. | Fold induction |
|---|---|
| 5 (9) | 6.7 |
| 6 (4) | 7.4 |
| 6 (6) | 6.6 |
| 6 (24) | 6.8 |
| 6 (26) | 5.6 |

As shown above, it was clear that the compound of the present invention has excellent PPARδ-RXRα heterodimer ligand activity.

EXPERIMENTAL EXAMPLE 3

PPARα-RXRα Heterodimer Ligand Activity

At 18 to 24 hours after transfection carried out in Reference Example 12a, COS-1 cells were collected, suspended in DMEM medium [manufactured by Life Technologies, Inc., USA] containing 0.1% BSA (fatty acid-free) (produced by Waco Pure Chemicals Industries, Ltd.), and inoculated to each well of a 96-well white plate (produced by Corning, USA) at $1\times10^4$ cells/well in 80 µl. Subsequently, 20 µl of a test compound was added, and the plate was incubated at 37° C. in a carbon dioxide gas incubator for 36 to 48 hours. After removal of the medium from the 96-well white plate, 40 µl of PicaGene LT 7.5 (produced by Waco Pure Chemicals Industries, Ltd.) diluted twofold with HBSS (HANKS' BALANCED SALT SOLUTION) (produced by BIO WHITTAKER) was added, and after stirring, the luciferase activity was determined using 1420 ARVO Multilabel Counter [produced by Wallac].

The fold induction was calculated from the luciferase activity for the well to which 10 nM of the compound is added, relative to the luciferase activity of a control to which the compound is not added as 1. Results are shown in [Table 3].

TABLE 3

| Example No. | Fold induction |
|---|---|
| 1 | 10.2 |
| 2 (1) | 10.9 |
| 5 (5) | 10.1 |
| 6 | 9.3 |
| 6 (1) | 8.9 |
| 6 (2) | 9.2 |

As shown above, it was clear that the compound of the present invention has excellent PPARα-RXRα heterodimer ligand activity.

EXPERIMENTAL EXAMPLE 4

Receptor Function Regulating Action (Agonist Action) for GPR40

CHO cell strain (No. 104) which have had expressed human GPR40 was diluted to contain $3\times10^4$ cells/100 µL, and added to a Black walled 96-well plate (Costar) at 100 µL/well, and incubated overnight in $CO_2$ incubator. Change of intracellular calcium concentration was measured with FLIPR (Molecular Device). The method is as follows. 50 μg of Fluo-3AM (DOJIN) was dissolved in 21 μL of DMSO (DOJIN), and the same amount of 20% pluronic acid (Molecular Probes) was further added thereto, and the mixture was mixed. The mixture was added to 10.6 mL of an assay buffer [prepared by adding 10 mL of solution which was produced by adding 20 mL of 1 M HEPES (pH 7.4) (DOJIN) to 1 L of HBSS (Invitrogen), dissolving 710 mg of probenecid (Sigma) in 5 mL of 1N NaOH, and further adding 5 mL of the above-mentioned HBSS/HEPES solution thereto and mixing it.] containing 105 μL of fetal bovine serum, to give a fluorescent dye solution. The medium of the cell plate was removed, and immediately, the fluorescent dye solution was added at 100 μL/well, and incubated in $CO_2$ incubator for 1 hour, allowing the fluorescent dye to be incorporated into the cells. The cells after incubation were washed with the above-mentioned assay buffer. The compound to be added to the cells was diluted with the assay buffer to each concentration, added to the plate for the test sample. After conducting the above-mentioned pretreatment, intracellular calcium concentration change after adding the compound was measured in FLIPR to investigate the agonist action. By dose-response curve with the change of fluorescence intensity value at 30 seconds after reaction initiation, $EC_{50}$ value was calculated.

TABLE 4

Action of regulating receptor function for GPR40

| Example No. | $EC_{50}$, μM |
|---|---|
| 5 (8) | 0.10 |
| 5 (10) | 0.87 |
| 5 (11) | 0.58 |
| 6 (4) | 0.18 |
| 6 (6) | 0.16 |
| 6 (7) | 0.29 |
| γ-linolenic acid | 2.0 |

From the results of Table 4, it was clear that the compound of the present invention has excellent regulating action for GPR40 receptor function.

The genetic engineering procedures described in the following Reference Examples 1a to 12a were based on the methods described in the textbook (Maniatis, et al., Molecular Cloning, Cold Spring Harbor Laboratory, 1989) or the methods described in the protocols attached to the reagents.

Reference Example 1a

Cloning of Human PPARδ Gene

A human PPARδ gene was cloned using a pancreatic cDNA (Toyobo Co., Ltd., QUICK-Clone cDNA) as a template by means of a PCR method employing a primer set shown below which was prepared with referring to the base sequence of PPARδ gene reported by Schmidt, A. et al. (Mol. Endocrinol., vol. 6: 1634-1641 (1992)).

PARD-U;
(SEQ ID NO: 1)
5'-AAC GGT ACC TCA GCC ATG GAG CAG CCT CAG GAG G-3'

PARD-L;
(SEQ ID NO: 2)
5'-TAA GTC GAC CCG TTA GTA CAT GTC CTT GTA GAT C-3'

The PCR reaction was carried out according to the Hot Start method using AmpliWax PCR Gem 100 (Takara Shuzo Co., Ltd.). First, 10×LA PCR Buffer (2 μl), 2.5 mM dNTP solution (3 μl), 12.5 μM primer solution (each 2.5 μl) and sterile distilled water (10 μl) were mixed to obtain a bottom layer solution mixture. Human heart cDNA (1 ng/ml, 1 μl) as a template, 10×LA PCR Buffer (3 μl), 2.5 mM dNTP solution (1 μl), TaKaRa LA Taq DNA polymerase (0.5 μl, Takara Shuzo Co., Ltd.) and sterile distilled water (24.5 μl) were mixed to obtain a top layer solution mixture. To the prepared bottom layer solution mixture was added one AmpliWax PCR Gem 100 (Takara Shuzo Co., Ltd.), and the mixture was treated at 70° C. for 5 minutes and in ice for 5 min, after which the top layer solution mixture was added to give a reaction mixture of PCR. A tube containing the reaction mixture was set in a thermal cycler (Perkin Elmer, USA) and treated at 95° C. for 2 minutes. The cycle of 95° C. for 15 seconds and 68° C. for 2 minutes was repeated 45 times and the tube was treated at 72° C. for 8 minutes. The obtained PCR product was subjected to electrophoresis on agarose gel (1%), and a 1.4 kb DNA fragment containing PPARδ gene was recovered from the gel and then inserted into pT7Blue-T vector (Takara Shuzo Co., Ltd.) to give a plasmid pTBT-hPPARδ.

Reference Example 2a

Cloning of Human RXRα Gene

A human RXRα gene was cloned using a kidney cDNA (produced by Toyobo Co., Ltd., trademark: QUICK-Clone cDNA) as a template by means of a PCR method employing a primer set shown below which was prepared with referring to the base sequence of RXRα gene reported by Mangelsdorf, D. J. et al. [Nature, vol. 345 (6272), pp. 224-229 (1990)].

XRA-U:
(SEQ ID NO: 3)
5'-TTA GAA TTC GAC ATG GAC ACC AAA CAT TTC CTG-3'

XRA-L:
(SEQ ID NO: 4)
5'-CCC CTC GAG CTA AGT CAT TTG GTG CGG CGC CTC-3'

The PCR reaction was carried out according to the Hot Start method using AmpliWax PCR Gem 100 (produced by Takara Shuzo Co., Ltd.). First, 10×LA PCR Buffer (2 μl), 2.5 mM DNTP solution (3 μl), 12.5 μM primer solution (each 2.5 μl) and sterile distilled water (10 μl) were mixed to obtain a bottom layer solution mixture. Human kidney cDNA (1 ng/ml, 1 μl) as a template, 10×LA PCR Buffer (3 μl), 2.5 mM dNTP solution (1 μl), TaKaRa LA Taq DNA polymerase (0.5 μl, produced by Takara Shuzo Co., Ltd.) and sterile distilled water (24.5 μl) were mixed to a top layer solution mixture.

To the aforementioned bottom layer solution mixture was added one AmpliWax PCR Gem 100 (produced by Takara Shuzo Co., Ltd.), and the mixture was treated at 70° C. for 5 minutes and in ice for 5 minutes, after which the top layer solution mixture was added to give a reaction mixture of PCR. A tube containing the reaction mixture was set in a thermal cycler (produced by Perkin Elmer, USA) and treated at 95° C. for 2 minutes. The cycle of 95° C. for 15 seconds and 68° C. for 2 minutes was repeated 35 times and the tube was treated at 72° C. for 8 minutes.

The obtained PCR product was subjected to electrophoresis on agarose gel (1%), and a 1.4 kb DNA fragment containing RXRα gene was recovered from the gel and inserted into pT7Blue-T vector (produced by Takara Shuzo Co., Ltd.) to give a plasmid pTBT-hRXRα.

Reference Example 3a

Preparation of Plasmids for Expressing Human PPARδ and RXRα

A 5.6 kb KpnI-SalI fragment of plasmid pMCMVneo and a 1.3 kb KpnI-SalI fragment containing hPPARδ gene of plasmid pTBT-hPPARδ described in Reference Example 1a were ligated to give plasmid pMCMVneo-hPPARδ.

Reference Example 4a

Preparation of Plasmids for Expressing Human PPARδ and RXRα

A 5.6 kb EcoRI-SalI fragment of plasmid pMCMVneo and a 1.4 kb EcoRI-XhoI fragment containing hRXRα gene of plasmid pTBT-hRXRα described in Reference Example 2a were ligated to give plasmid pMCMVneo-hRXRα.

Reference Example 5a

Preparation of Reporter Plasmids

A DNA fragment containing a PPAR-responding element (PPRE) of an acyl CoA oxidase was prepared using the following 5'-terminal phosphorylated synthetic DNA.

```
PPRE-U:
                                    (SEQ ID NO: 5)
5'-pTCGACAGGGGACCAGGACAAAGGTCACGTTCGGGAG-3'

PPRE-L:
                                    (SEQ ID NO: 6)
5'-pTCGACTCCCGAACGTGACCTTTGTCCTGGTCCCCTG-3'
```

First, PPRE-U and PPRE-L were annealed and inserted into a SalI site of plasmid pBlueScript SK. By determining the base sequence of the inserted fragment, based on which plasmid pBSS-PPRE4, plasmid pBSS-PPRE4 in which 4 PPREs were ligated in tandem was selected.

A HSV thymidine kinase minimum promoter (TK promoter) region was cloned using pRL-TK vector (produced by Promega, USA) as a template by means of a PCR method employing a primer set shown below which was prepared with referring to the base sequence of the promoter region of thymidine kinase gene reported by Luckow, B. et al. [Nucleic Acids Res., Vol. 15 (13), p. 5490 (1987)].

```
TK-U:
5'-CCCAGATCTCCCCAGCGTCTTGTCATTG-3'    (SEQ ID NO: 7)

TK-L:
5'-TCACCATGGTCAAGCTTTTAAGCGGGTC-3'    (SEQ ID NO: 8)
```

The PCR reaction was carried out according to the Hot Start method using AmpliWax PCR Gem 100 (Takara Shuzo Co., Ltd.). First, 10×LA PCR Buffer (2 μl), 2.5 mM dNTP solution (3 μl), 12.5 μM primer solution (each 2.5 μl) and sterile distilled water (10 μl) were mixed to obtain a bottom layer solution mixture. pRL-TK vector (produced by Promega, USA, 1 μl) as a template, 10×LA PCR Buffer (3 μl), 2.5 mM DNTP solution (1 μl), TaKaRa LA Taq DNA polymerase (0.5 μl, produced by Takara Shuzo Co., Ltd.) and sterile distilled water (24.5 μl) were mixed to obtain a top layer solution-mixture.

To the prepared bottom layer solution mixture was added one AmpliWax PCR Gem 100 (produced by Takara Shuzo Co., Ltd.), and the mixture was treated at 70° C. for 5 minutes and in ice for 5 minutes, after which the top layer solution mixture was added to give a reaction mixture of PCR. A tube containing the reaction mixture was set in a thermal cycler (produced by Perkin Elmer, USA) and treated at 95° C. for 2 minutes. The cycle of 95° C. for 15 seconds and 68° C. for 2 minutes was repeated 35 times and the tube was treated at 72° C. for 8 minutes.

The obtained PCR product was subjected to electrophoresis on agarose gel (1%), and a 140 b DNA fragment containing TK promoter was recovered from the gel and inserted into pT7 Blue-T vector (produced by Takara Shuzo Co., Ltd.). A fragment containing the TK promoter, which was obtained by cleaving this plasmid with restriction enzymes BglII and NcoI, was ligated with a BglII-NcoI fragment of plasmid pGL3-Basic vector [produced by Promega, USA] to give a plasmid pGL3-TK.

The NheI-XhoI fragment (4.9 kb) of the obtained plasmid pGL3-TK and the NheI-XhoI fragment (200 bp) of plasmid pBSS-PPRE4 were ligated to give a plasmid pGL3-4ERPP-TK. This plasmid pGL3-4ERPP-TK was cleaved with BamHI (produced by Takara Shuzo Co., Ltd.) and then treated with T4 DNA polymerase (produced by Takara Shuzo Co., Ltd.) to form a blunt terminal whereby obtaining a 1.6 kb of a DNA fragment. Both DNA fragments were ligated to construct a reporter plasmid pGL3-4ERPP-TK neo.

Subsequently, a reporter plasmid in which the direction of a PPAR-responding element (PPRE) of the reporter plasmid pGL3-4ERPP-TK neo is reversed was obtained. That is, a 4.9 kb KpnI-NheI fragment of plasmid pGL3-TK and a 200 bp KpnI-XbaI fragment of plasmid pBSS-PPRE4 were ligated to obtain a plasmid pGL3-PPRE4-TK. This plasmid pGL3-PPRE4-TK was cleaved with BamHI (produced by Takara Shuzo Co., Ltd.) and then treated with T4 DNA polymerase (produced by Takara Shuzo Co., Ltd.) to form a blunt terminal. On the other hand, pGFP-C1 (produced by Toyobo Co., Ltd.) was cleaved with Bsu36I (NEB) and then treated with T4 DNA polymerase (produced by Takara Shuzo Co., Ltd.) to form a blunt terminal whereby obtaining a 1.6 kb of a DNA fragment. Both DNA fragments were ligated to construct a reporter plasmid pGL3-4ERPP-TK neo.

Reference Example 6a

Cloning of Human PPARγ Gene

A human PPARγ gene was cloned using heart cDNA (produced by Toyobo Co., Ltd., trademark: QUICK-Clone cDNA) as a template by means of a PCR method empolying a primer set shown below which was prepared with referring to the base sequence of PPARγ gene reported by Greene et al. [Gene Expr., vol. 4 (4-5), pp. 281-299 (1995)].

```
PAG-U:
                                              (SEQ ID NO: 9)
5'-GTG GGT ACC GAA ATG ACC ATG GTT GAC ACA GAG-3'

PAG-L:
                                              (SEQ ID NO: 10)
5'-GGG GTC GAC CAG GAC TCT CTG CTA GTA CAA GTC-3'
```

The PCR reaction was carried out according to the Hot Start method using AmpliWax PCR Gem 100 (produced by Takara Shuzo Co., Ltd.). First, 10×LA PCR Buffer (2 μl), 2.5 mM dNTP solution (3 μl), 12.5 μM primer solution (each 2.5 μl) and sterile distilled water (10 μl) were mixed to obtain a bottom layer solution mixture. Human heart cDNA (1 ng/ml, 1 µl) as a template, 10×LA PCR Buffer (3 µl), 2.5 mM dNTP solution (1 µl), TaKaRa LA Taq DNA polymerase (0.5 µl, produced by Takara Shuzo Co., Ltd.) and sterile distilled water (24.5 µl) were mixed to obtain a top layer solution mixture.

To the prepared bottom layer solution mixture was added one AmpliWax PCR Gem 100 (produced by Takara Shuzo Co., Ltd.), and the mixture was treated at 70° C. for 5 minutes and in ice for 5 minutes, after which the top layer solution mixture was added to give a reaction mixture of PCR. A tube containing the reaction mixture was set in a thermal cycler (produced by Perkin Elmer, USA) and treated at 95° C. for 2 minutes. The cycle of 95° C. for 15 sec and 68° C. for 2 minutes was repeated 35 times and the tube was treated at 72° C. for 8 minutes.

The obtained PCR product was subjected to electrophoresis on agarose gel (1%), and a 1.4 kb DNA fragment containing PPARγ gene was recovered from the gel and inserted into pT7Blue-T vector (produced by Takara Shuzo Co., Ltd.) to give a plasmid pTBT-hPPARγ.

Reference Example 7a

Preparation of Plasmids for Expressing Human PPARγ and RXRα

A 7.8 kb FspI-NotI fragment of plasmid pVgRXR (produced by Invitrogen, USA) and a 0.9 kb FspI-NotI fragment containing the RXRα gene of the plasmid pTBT-hRXRα obtained in Reference Example 2a were ligated to give a plasmid pVgRXR2. The pVgRXR2 was cleaved with BstXI and then treated with T4 DNA polymerase (produced by Takara Shuzo Co., Ltd.) to form a blunt terminal. Then, cleavage with KpnI gave a 6.5 kb DNA fragment.

On the other hand, the plasmid pTBT-hPPARγ obtained in Reference Example 6a was cleaved with SalI and then treated with T4 DNA polymerase (produced by Takara Shuzo Co., Ltd.) to form a blunt terminal. Then, cleavage with KpnI gave a 1.4 kb DNA fragment containing human PPARγ gene.

Both DNA fragments were ligated to construct plasmid pVgRXR2-hPPARγ.

Reference Example 8a

Introduction of Plasmids for Expressing Human PPARγ and RXRα and Reporter Plasmid into CHO-K1 Cell and Establishment of Expressed Cell A CHO-K1 cell was grown in a cell culture flask of 150 cm² (produced by Corning Coaster Corporation, USA) using Ham's F12 Medium (produced by Life Technologies, Inc.) containing 10% fetal bovine serum (produced by Life Technologies, Inc., USA), and scraped by treating with 0.5 g/L tripsin-0.2 g/L EDTA (ethylenediaminetetraacetic acid, produced by Life Technologies, Inc., USA). The cell was washed with PBS (phosphate-buffered saline) (produced by Life Technologies, Inc., USA), centrifuged (1000 rpm, 5 minutes) and suspended in PBS. Using a gene pulser (produced by Bio-Rad Laboratories, USA), DNA was introduced into the cell under the following conditions.

Namely, $8\times10^6$ cells, 10 µg of plasmid pVgRXR2-hPPARγ obtained in Reference Example 7a and 10 µg of reporter plasmid pGL3-4ERPP-TK neo obtained in Reference Example 5a were placed in a cuvette having a 0.4 cm gap and subjected to electroporation at 0.25 kV voltage and 960 µF capacitance. Thereafter, the cell was placed in the 10% fetal bovine serum-containing Ham's F12 Medium, cultured for 24 hours, scraped again and centrifuged, and then suspended in Ham's F12 Medium containing 10% fetal bovine serum supplemented with geneticin (500 µg/ml, produced by Life Technologies, Inc. USA) and zeocin (250 µg/ml, produced by Invitrogen, USA), diluted to $10^4$ cell/ml, inoculated to a 96 well plate (produced by Corning Costar Corporation, USA) and cultured in a carbon dioxide gas incubator at 37° C. to give a geneticin-and zeocin-resistant transformant.

The obtained transformant strain was cultured in a 24-well plate (produced by Corning Costar Corporation, USA). 10 µM pibglitazone hydrochloride was added thereto and a strain in which the luciferase was expressed and induced, i.e., PPARγ:RXRα:4ERPP/CHO-K1, was selected.

Reference Example 9a

Introduction of Plasmids for Expressing Human PPARδ and RXRα and Reporter Plasmid into COS-1 Cell A COS-1 cell was inoculated in a cell culture flask (produced by Corning, USA) of 150 cm² at $5\times10^6$ cells/50 ml, and the plate was incubated under the conditions of 37° C. and 5% $CO_2$ for 24 hours. Transfection was carried out with lipofectamine (produced by Invitrogen, USA). A transfection mixture solution was prepared by mixing 125 µl of lipofectamine, 100 µl of PLUS Reagent, 2.5 µg of pMCMVneo-hPPARδ (obtained in Reference Example 3a), 2.5 µg of pMCMVneo-hRXRα (obtained in Reference Example 4a), 5 µg of reporter plasmid pGL3-4ERPP-TK neo (obtained in Reference Example 5a) and 5 µg of pRL-tk [produced by Promega, USA] with 5 ml of opti-MEM (produced by Invitrogen, USA). To the COS-1 cell washed with opti-MEM, the above-mentioned transfection mixture solution and 20 ml of opti-MEM were added, and then incubated under the conditions of 37° C. and 5% $CO_2$ for 3 hours. Then, 25 ml of DMEM medium [manufactured by Life Technologies, Inc., USA] containing 0.1% fatty acid-free bovine serum albumin (BSA) (produced by Waco Pure Chemicals Industries, Ltd.) was added thereto, and then incubated under the conditions of 37° C. and 5% $CO_2$ for 18 to 24 hours.

Reference Example 10a

Cloning of Human PPARα Gene

A human PPARα gene was cloned using hepatic cDNA (Toyobo Co., Ltd., QUICK-Clone cDNA) as a template by means of a PCR method employing a primer set shown below which was prepared with referring to the base sequence of PPARα gene reported by Sher, T. et al. (Biochemistry, vol. 32, pp5598-5604 (1993)).

PAA-U:
(SEQ ID NO: 11)
5'-AAA GGA TCC CGC GAT GGT GGA CAC AGA AAG CCC-3'

PAA-L:
(SEQ ID NO: 12)
5'-CCC GTC GAC TCA GTA CAT GTC CCT GTA GAT CTC-3'

The PCR reaction was carried out according to the Hot Start method using AmpliWax PCR Gem 100 (produced by Takara Shuzo Co., Ltd.). As a bottom layer solution mixture, 10×native pfu Buffer (2 μl), 2.5 mM dNTP solution (3 μl), 12.5 μM primer solution (each 2.5 μl) and sterile distilled water (10 μl) were mixed. As a top layer solution mixture, human hepatic cDNA (1 ng/ml, 1 μl) as a template, 10× native pfu Buffer (3 μl), 2.5 mM dNTP solution (1 μl), native pfu DNA polymerase (0.5 μl, produced by STRATAGENE, USA) and sterile distilled water (24.5 μl) were mixed. To the prepared bottom layer solution mixture was added one AmpliWax PCR Gem 100 (produced by Takara Shuzo Co., Ltd.), and the mixture was treated at 70° C. for 5 minutes and in ice for 5 minutes, after which the top layer solution mixture was added to give a reaction mixture of PCR. A tube containing the reaction mixture was set in a thermal cycler (produced by Perkin Elmer, USA) and treated at 95° C. for 2 minutes. The cycle of 95° C. for 15 seconds and 68° C. for 2 minutes was repeated 45 times and the tube was treated at 72° C. for 8 minutes.

The obtained PCR product was subjected to electrophoresis on agarose gel (1%), and a 1.4 kb DNA fragment containing PPARα gene was recovered from the gel and inserted into pT7Blue Blunt vector (produced by Takara Shuzo Co., Ltd.) to give a plasmid pTBB-hPPARα.

Reference Example 11a

Preparation of Plasmids for Expressing Human PPARα

A 5.6 kb KpnI-SalI fragment of plasmid pMCMVneo and a 1.4 kb KpnI-SalI fragment containing human PPARα gene of plasmid pTBB-hPPARα described in Reference Example 10a were ligated to give plasmid pMCMVneo-hPPARα.

Reference Example 12a

Co-Introduction of Plasmids for Expressing Human PPARα and RXRα and Reporter Plasmid into COS-1 Cell A COS-1 cell was inoculated in a cell culture flask (produced by Corning, USA) of 150 cm² at 5×10⁶ cells/50 ml, and incubated under the conditions of 37° C. and 5% $CO_2$ for 24 hours. Transfection was carried out with lipofectamine (produced by Invitrogen, USA). A transfection mixture solution was prepared by mixing 125 μl of lipofectamine, 100 μl of PLUS Reagent, 2.5 μg of pMCMVneo-hPPARα (obtained in Reference Example 11a), 2.5 μg of pMCMVneo-hRXRα (obtained in Reference Example 4a), 5 μg of reporter plasmid pGL3-4ERPP-TK neo (obtained in Reference Example 5a) and 5 μg of pRL-tk [produced by Promega, USA] with 5 ml of opti-MEM (produced by Invitrogen, USA). To COS-1 cell washed with opti-MEM, the above-mentioned transfection mixture solution and 20 ml of opti-MEM were added, and then incubated under the conditions of 37° C. and 5% $CO_2$ for 3 hours. Then, 25 ml of DMEM medium [manufactured by Life Technologies, Inc., USA] containing 0.1% fatty acid-free bovine serum albumin (BSA) (produced by Waco Pure Chemicals Industries, Ltd.) was added thereto, and then incubated under the conditions of 37° C. and 5% $CO_2$ for 18 to 24 hours.

The present invention is hereinafter described in more detail by means of the following Examples and Reference Examples which are not to be construed as limitative. Also, these Examples may be modified without departing from the scope of the present invention.

¹H-NMR spectra were recorded on a Varian Gemini-200 (200 MHz) or MERCURY 300 (300 MHz) spectrometer using tetramethylsilane as an internal standard and chemical shifts are given in δ values (ppm). In the mixture of solvents, the value indicated means the mixing ratio of volume of each solvent, unless otherwise stated. Unless otherwise stated, % indicates % by weight. Unless otherwise stated, an elution solvent in silica gel column chromatography is indicated as a capacity ratio. The term "room temperature" in the present specification usually means a temperature from about 20 to about 30° C.

Further, each symbol used in Examples and Reference Examples indicates the following meanings. s: singlet, d: doublet, t: triplet, q: quartet, br: broad, dd: double doublet, dt: double triplet, td: triple doublet, dq: double quartet, tt: triple triplet, ddd: double double doublet, m: multiplet, Hz: hertz, $CDCl_3$: deuterated chloroform, DMSO-$d_6$: deuterated dimethylsulfoxide, $CD_3OD$: deuterated methanol, and %: % by weight Reference Example 1

1-Fluoro-4-(2-nitro-1-propenyl)benzene

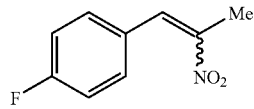

A mixture of 4-fluorobenzaldehyde (17.0 g), acetic acid (11.5 g), methylamine-hydrochloride (3.70 g), sodium acetate (4.50 g) and nitromethane (41.2 g) was stirred at 100° C. for 1.5 hours. The reaction solution was diluted with water, and then 3 times extracted with ethyl acetate. The collected organic layer was dried over anhydrous magnesium sulfate, and the solvent was distilled off under reduced pressure. The obtained crude product was crystallized from diethyl ether—hexane to obtain an objective product (18.4 g) as crystals.

Melting point 59-61° C. ¹H-NMR ($CDCl_3$) δ 2.45 (3H, s), 7.16 (2H, d), 7.44 (2H, dd), 8.06 (1H, s).

Reference Example 2

Methyl 4-(4-fluorophenyl)-2,5-dimethyl-3-furoate

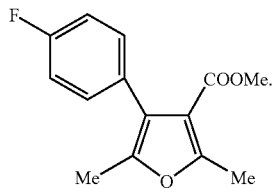

To a solution of 1-fluoro-4-(2-nitro-1-propenyl)benzene (2.49 g) in methanol (20 ml) was added piperidine (1.36 ml) and methyl acetoacetate (1.60 g) at room temperature, and the mixture was stirred as such overnight. After the reaction solution was concentrated under reduced pressure, water (10 ml) and concentrated hydrochloric acid (3 ml) were added thereto, and the mixture was stirred at room temperature for 1 hour. The reaction solution was twice extracted with ethyl acetate and the collected organic layer was dried over anhydrous magnesium sulfate. The solvent was distilled off under reduced pressure. The obtained crude product was purified by silica gel column chromatography (ethyl acetate:hexane=1:9) to obtain an objective product (1.59 g) as a solid matter. The obtained matter was recrystallized from cold methanol to obtain crystals. Melting point 34-35° C.; $^1$H-NMR (CDCl$_3$) δ 2.18 (3H, s), 2.56 (3H, s), 3.66 (3H, s), 7.05 (2H, t), 7.21 (2H, dd) Reference Example 2(1) to Reference Example 2(3)

In the same manner as in Reference Example 2, the below-described compounds were obtained from the β-ketoester form corresponding to 1-fluoro-4-(2-nitro-1-propenyl) benzene.

Reference Example 2(1)

Ethyl 2-cyclohexyl-4-(4-fluorophenyl)-5-methyl-3-furoate

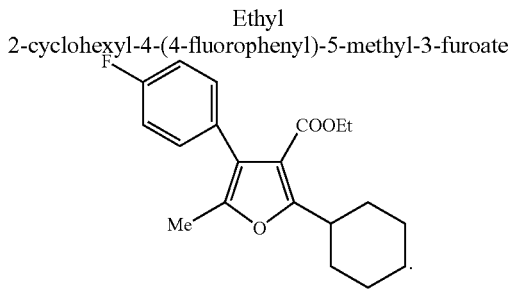

Melting point 71-72° C.; $^1$H-NMR (CDCl$_3$) δ 1.09 (3H, t), 1.24-1.93 (10H, m), 2.17 (3H, s), 3.78 (1H, tt), 4.10 (2H, q), 7.04 (2H, t), 7.21 (2H, dd).

Reference Example 2(2)

Ethyl 4-(4-fluorophenyl)-2-isopropyl-5-methyl-3-furoate

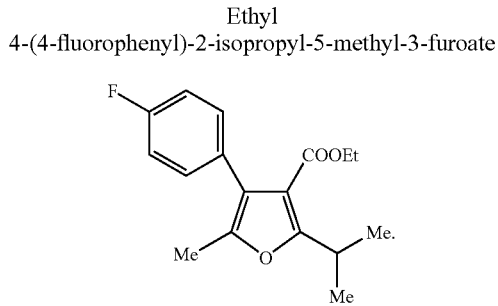

Melting point 27-28° C.; $^1$H-NMR (CDCl$_3$) δ 1.09 (3H, t), 1.30 (6H, d), 2.18 (3H, s), 3.65-3.79 (1H, m), 4.11 (2H, q), 7.04 (2H, t), 7.21 (2H, dd).

Reference Example 2(3)

Ethyl 4-(4-fluorophenyl)-5-methyl-2-phenyl-3-furoate

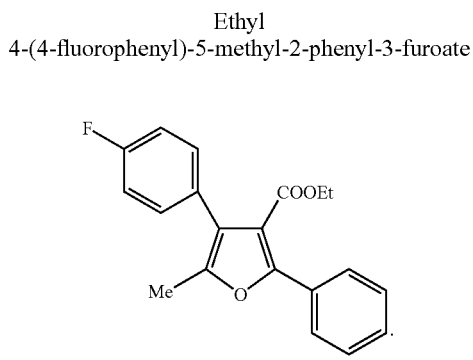

Melting point 78-79° C.; $^1$H-NMR (CDCl$_3$) δ 1.02 (3H, t), 2.30 (3H, s), 4.10 (2H, q), 7.09 (2H, t), 7.19-7.48 (5H, m), 7.82 (2H, dd).

Reference Example 3

Methyl 5-(4-fluorophenyl)-2-methyl-3-furoate

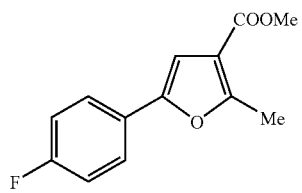

To a solution of 1,8-azabicyclo[5.4.0]-7-undecene (44.5 g) in toluene (100 ml) was added dropwise a solution of methyl acetoacetate (33.9 g) in toluene (50 ml) with ice-cooling. After the reaction solution was stirred as such for 10 minutes, a solution of 2-chloro-4'-fluoroacetophenone (50.4 g) in toluene (100 ml) was added dropwise with ice-cooling and the mixture was further stirred at room temperature for 2 hours. The resulting precipitate was filtered and washed with toluene. The obtained toluene solution was passed through silica gel, and the silica gel was washed with ethyl acetate-hexane (1:1). The collected solution was concentrated under reduced pressure, ethyl acetate-hexane was removed to obtain a toluene solution. To the toluene solution was added 4-toluenesulfonic acid•1 hydrate (5.55 g) and the mixture was stirred at 100° C. for 2 hours. The reaction solution was washed with an aqueous sodium hydrogen carbonate solution and the aqueous layer was extracted with ethyl acetate. The organic layer was collected and dried over magnesium sulfate. The solvent was distilled off under reduced pressure. The obtained crude product was crystallized from cold methanol to obtain an objective product (37.6 g) as crystals.

Melting point 96-97° C.; $^1$H-NMR (CDCl$_3$) δ 2.64 (3H, s), 3.85 (3H, s), 6.81 (1H, s), 7.08 (2H, t), 7.60 (2H, dd).

Reference Example 3(1) to Reference Example 3(9)

In the same manner as in Reference Example 3, the below-described compounds obtained from the β-ketoester form corresponding to the phenacyl halide.

Reference Example 3(1)

Methyl 2-methyl-5-[4-(trifluoromethyl)phenyl]-3-furoate

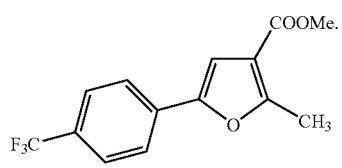

Melting point 91-92° C.; $^1$H-NMR (CDCl$_3$) δ 2.67 (3H, s), 3.87 (3H, s), 7.00 (1H, s), 7.63 (2H, d), 7.73 (2H, d).

Reference Example 3(2)

Methyl 2-ethyl-5-[4-(trifluoromethyl)phenyl]-3-furoate

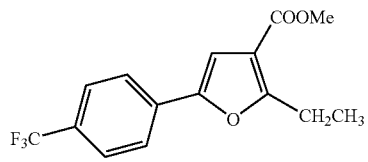

Melting point 81-82° C.; $^1$H-NMR (CDCl$_3$) δ 1.33 (3H, t), 3.09 (2H, q), 3.86 (3H, s), 6.99 (1H, s), 7.62 (2H, d), 7.72 (2H, d).

Reference Example 3(3)

Methyl 2-isopropyl-5-[4-(trifluoromethyl)phenyl]-3-furoate

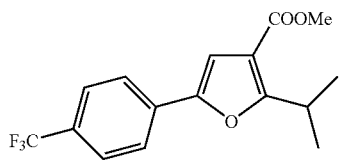

Melting point 61-62° C.; $^1$H-NMR (CDCl$_3$) □ 1.35 (6H, d), 3.77-3.87 (1H, m), 3.85 (3H, s), 6.98 (1H, s), 7.62 (2H, d), 7.72 (2H, d).

Reference Example 3(4)

15 Methyl 2-butyl-5-[4-(trifluoromethyl)phenyl]-3-furoate

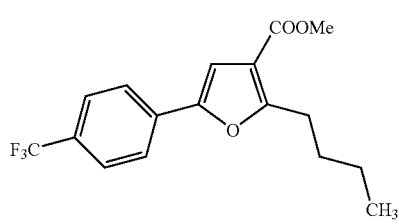

Melting point 172-174° C.; $^1$H-NMR (CDCl$_3$) δ 0.98 (3H, t), 1.38-1.50 (2H, m), 1.71-1.82 (2H, m), 3.11 (2H, t), 7.04 (1H, s), 7.64 (2H, d), 7.74 (2H, d).

Reference Example 3(5)

Methyl 2-methyl-5-[4-(trifluoromethoxy)phenyl]-3-furoate

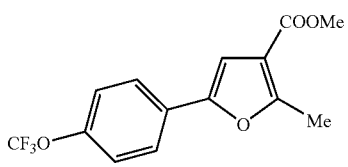

Melting point 66-67° C.; $^1$H-NMR (CDCl$_3$) δ 2.65 (3H, s), 3.85 (3H, s), 6.87 (1H, s), 7.23 (2H, d), 7.64 (2H, d).

Reference Example 3(6)

Methyl 5-(3-methoxyphenyl)-2-methyl-3-furoate

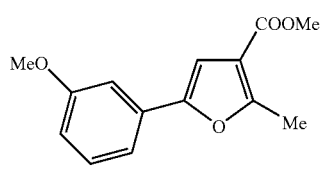

Melting point 67-68° C.; $^1$H-NMR (CDCl$_3$) δ 2.65 (3H, s), 3.85 (6H, s), 6.83 (1H, ddd), 6.88 (1H, s), 7.16-7.34 (3H, m).

Reference Example 3(7)

Methyl 2-methyl-5-[3-(trifluoromethyl)phenyl]-3-furoate

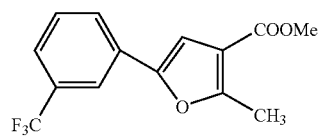

Melting point 74-75° C.; $^1$H-NMR (CDCl$_3$) δ 2.67 (3H, s), 3.86 (3H, s), 6.97 (1H, s), 7.49-7.51 (2H, m), 7.77-7.80 (1H, m), 7.87 (1H, s).

Reference Example 3(8)

Methyl 2-ethyl-5-(3-methoxyphenyl)-3-furoate

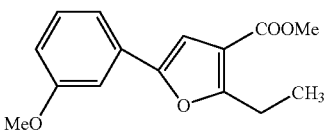

An oily matter; $^1$H-NMR (CDCl$_3$) δ 1.32 (3H, t), 3.07 (2H, q), 3.85 (3H, s), 3.85 (3H, s), 6.82 (1H, ddd), 6.86 (1H, s), 7.16-7.32 (3H, m).

Reference Example 3(9)

Methyl 5-(4-chlorophenyl)-2-methyl-3-furoate

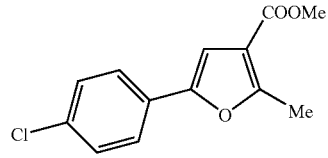

Melting point 105-106° C.; $^1$H-NMR (CDCl$_3$) δ 2.64 (3H, s), 3.85 (3H, s), 6.87 (1H, s), 7.35 (2H, d), 7.56 (2H, d).

Reference Example 4

Ethyl 5-phenyl-2-(trifluoromethyl)-3-furoate

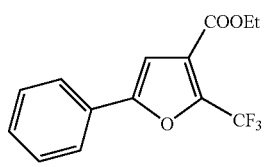

To a suspension of suspended matter (5.51 g) of 60% sodium hydride in liquid paraffin in 1,2-dimethoxyethane (100 ml) was added dropwise a solution of ethyl 4,4,4-trifluoroacetoacetate (23.1 g) in 1,2-dimethoxyethane (50 ml) at room temperature. The reaction solution was stirred for 0.5 hour, and then to the reaction solution was added dropwise 2-bromoacetophenone (24.9 g) at room temperature. The mixture was further stirred at 80° C. overnight. The reaction solution was poured into water and twice extracted with ethyl acetate. The collected organic layer was dried over anhydrous magnesium sulfate, and the solvent was distilled off under reduced pressure to obtain an oily matter. The obtained oily matter was dissolved in toluene (200 ml) and 4-toluenesulfonic acid.1 hydrate (4.77 g) was added thereto. The reaction mixture was heated under reflux for 8 hours under dehydration condition by using the reaction vessel equipped with a Dean-Stark trap. The reaction solution was washed with an aqueous sodium hydrogen carbonate solution and the aqueous layer was extracted with ethyl acetate. The collected organic layer was dried over anhydrous magnesium sulfate, and the solvent was distilled off under reduced pressure. The obtained crude product was purified by silica gel column chromatography (hexane to hexane:ethyl acetate=15:1) and crystallized from cold methanol to obtain an objective product (10.7 g) as crystals. Melting point 44-45° C.; $^1$H-NMR (CDCl$_3$) δ 1.39 (3H, t), 4.38 (2H, q), 7.05 (1H, s), 7.38-7.49 (3H, m), 7.68-7.74 (2H, m).

Reference Example 5

5-(4-Fluorophenyl)-2-methyl-3-furoic acid

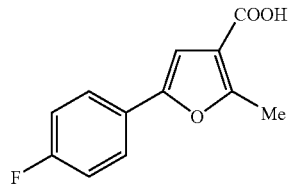

A mixture of methyl 5-(4-fluorophenyl)-2-methyl-3-furoate (15.36 g), sodium hydroxide (5.25 g), methanol (100 ml), water (50 ml) and tetrahydrofuran (50 ml) was stirred at room temperature overnight. The reaction solution was concentrated, diluted with water and acidified with dilute hydrochloric acid. Then, the reaction solution was twice extracted with ethyl acetate. The collected organic layer was dried over anhydrous sodium sulfate and the solvent was distilled off under reduced pressure. The obtained crude product was crystallized from diethyl ether-hexane to obtain an objective product (13.4 g) as crystals. Melting point 217-218° C.; $^1$H-NMR (CDCl$_3$-DMSO-d$_6$) δ 2.65 (3H, s), 6.83 (1H, s), 7.07 (2H, t), 7.60 (2H, dd).

Reference Example 5(1) to Reference Example 5(6)

In the same manner as in Reference Example 5, the below-described compounds were obtained from the 3-furancarboxylate derivative obtained in Reference Example 3(1) to Reference Example 3(5) and Reference Example 4.

Reference Example 5(1)

2-Methyl-5-[4-(trifluoromethyl)phenyl]-3-furoic acid

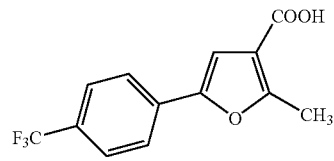

Melting point 199-200° C.; $^1$H-NMR (CDCl$_3$) δ 2.67 (3H, s), 7.02 (1H, s), 7.61 (2H, d), 7.72 (2H, d).

Reference Example 5(2)

2-Ethyl-5-[4-(trifluoromethyl)phenyl]-3-furoic acid

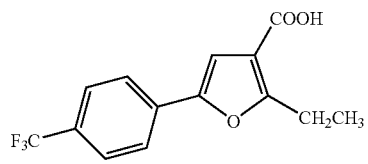

Melting point 186-187° C.; $^1$H-NMR (CDCl$_3$) δ 1.36 (3H, t) 3.14 (2H, q), 7.05 (1H, s), 7.65 (2H, d), 7.75 (2H, d).

Reference Example 5(3)

2-Isopropyl-5-[4-(trifluoromethyl)phenyl]-3-furoic acid

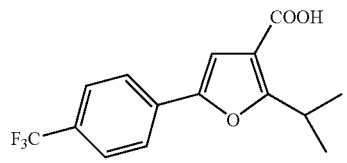

Melting point 187-188° C.; ¹H-NMR (CDCl₃) δ 1.38 (6H, d) 3.80-3.94 (1H, m), 7.04 (1H, s), 7.65 (2H, d), 7.75 (2H, d).

Reference Example 5(4)

2-Butyl-5-[4-(trifluoromethyl)phenyl]-3-furoic acid

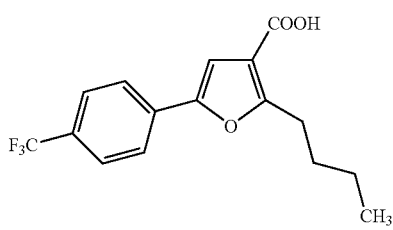

Melting point 172-174° C.; ¹H-NMR (CDCl₃) δ 0.98 (3H, t) 1.38-1.50 (2H, m), 1.71-1.82 (2H, m), 3.11 (2H, t), 7.04 (1H, s), 7.64 (2H, d), 7.74 (2H, d).

Reference Example 5(5)

2-Methyl-5-[4-(trifluoromethoxy)phenyl]-3-furoic acid

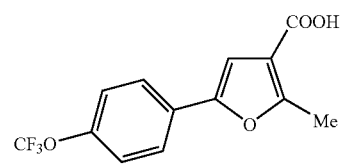

Melting point 145-146° C.; ¹H-NMR (CDCl₃) δ 2.70 (3H, s), 6.93 (1H, s), 7.24 (2H, d), 7.67 (2H, d).

Reference Example 5(6)

5-Phenyl-2-(trifluoromethyl)-3-furoic acid

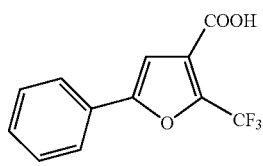

Melting point 171-173° C.; ¹H-NMR (CDCl₃) δ 7.09 (1H, s), 7.37-7.48 (3H, m), 7.72 (2H, d).

Reference Example 6

[5-(4-Fluorophenyl)-2-methyl-3-furyl]methanol

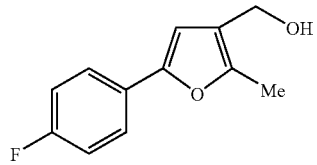

To a suspension of aluminum lithium hydride (3.67 g) in tetrahydrofuran (200 ml) was added dropwise a solution of methyl 5-(4-fluorophenyl)-2-methyl-3-furoate (15.1 g) in tetrahydrofuran (50 ml) with ice-cooling and the mixture was stirred at 0° C. for 1 hour. The reaction solution was ice-cooled, and water (3.5 ml), a 15% aqueous sodium hydroxide solution (3.5 ml) and water (8 ml) were sequentially added dropwise. Excess aluminum lithium hydride was decomposed and then the resulting mixture was stirred as such at room temperature for 2 hours. The produced precipitate was filtered off and then washed with ethyl acetate. The solvent of the collected filtrate was distilled off under reduced pressure. The obtained crude product was crystallized from hexane to obtain an objective product (11.9 g) as crystals. Melting point 80-82° C.; ¹H-NMR (CDCl₃) δ 1.61 (1H, br s), 2.35 (3H, s), 4.50 (2H, s), 6.56 (1H, s), 7.05 (2H, t), 7.58 (2H, dd).

Reference Example 6(1) to Reference Example 6(14)

In the same manner as in Reference Example 6, the below-described compounds were obtained from the 3-furancarboxylate derivative obtained in Reference Example 2, Reference Example 2(1) to Reference Example 2(3), Reference Example 3(1) to Reference Example 3(9) and Reference Example 4.

Reference Example 6(1)

[4-(4-Fluorophenyl)-2,5-dimethylfuran-3-yl]methanol

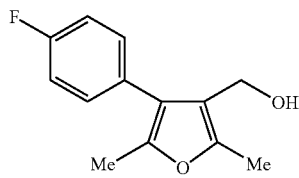

Paraffinoid solid; ¹H-NMR (CDCl₃) δ 2.26 (3H, s), 2.33 (3H, s), 4.41 (2H, s), 7.10 (2H, t), 7.36 (2H, dd).

Reference Example 6(2)

[4-(4-Fluorophenyl)-2-isopropyl-5-methylfuran-3-yl]methanol

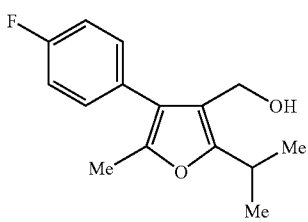

Melting point 72-73° C.; $^1$H-NMR (CDCl$_3$) δ 1.31 (6H, d), 2.27 (3H, s), 3.02-3.23 (1H, m), 4.41 (2H, s), 7.09 (2H, t), 7.36 (2H, dd).

Reference Example 6(3)

[2-Cyclohexyl-4-(4-fluorophenyl)-5-methylfuran-3-yl]methanol

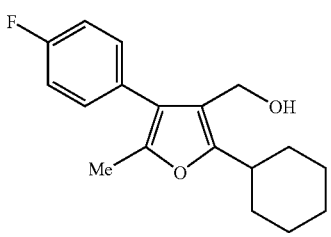

Melting point 137-138° C.; $^1$H-NMR (CDCl$_3$) δ 1.22-1.94 (10H, m), 2.26 (3H, s), 2.75 (1H, tt), 4.41 (2H, s), 7.09 (2H, t), 7.36 (2H, dd).

Reference Example 6(4)

[4-(4-Fluorophenyl)-5-methyl-2-phenylfuran-3-yl]methanol

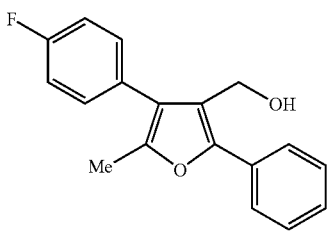

Melting point 153-154° C.; $^1$H-NMR (CDCl$_3$) δ 2.37 (3H, s) 4.57 (2H, s), 7.14 (2H, t), 7.29-7.49 (5H, m), 7.76 (2H, d).

Reference Example 6(5)

{2-Methyl-5-[4-(trifluoromethyl)phenyl]-3-furyl}methanol

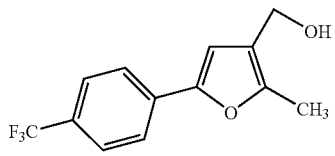

Melting point 90-91° C.; $^1$H-NMR (CDCl$_3$) δ 2.37 (3H, s), 4.52 (2H, s), 6.74 (1H, s), 7.59 (2H, d), 7.68 (2H, d)

Reference Example 6(6)

{2-Ethyl-5-[4-(trifluoromethyl)phenyl]-3-furyl}methanol

Melting point 52-53° C.; $^1$H-NMR (CDCl$_3$) δ 1.30 (3H, t), 1.41 (1H, br s), 2.74 (2H, q), 4.53 (2H, s), 6.75 (1H, s), 7.59 (2H, d), 7.70 (2H, d).

Reference Example 6(7)

{2-Isopropyl-5-[4-(trifluoromethyl)phenyl]-3-furyl}methanol

Melting point 100-101° C.; $^1$H-NMR (CDCl$_3$) δ 1.33 (6H, d), 1.39 (1H, br s), 3.10-3.19 (1H, m), 4.54 (2H, s), 6.74 (1H, s), 7.59 (2H, d), 7.69 (2H, d).

Reference Example 6(8)

{2-Butyl-5-[4-(trifluoromethyl)phenyl]-3-furyl}methanol

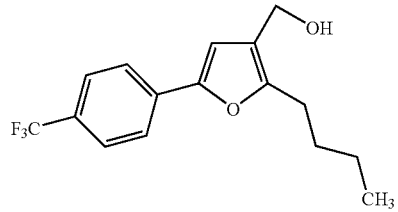

Melting point 74-75° C.; $^1$H-NMR (CDCl$_3$) δ 0.95 (3H, t), 1.33-1.45 (3H, m), 1.63-1.73 (2H, m), 2.71 (2H, t), 4.52 (2H, s), 6.76 (1H, s), 7.59 (2H, d) 7.69 (2H, d)

Reference Example 6(9)

{2-Methyl-5-[4-(trifluoromethoxy)phenyl]-3-furyl}methanol

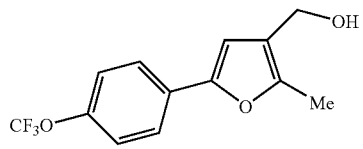

Melting point 53-55° C.; $^1$H-NMR (CDCl$_3$) δ 1.41 (1H, br t) 2.37 (3H, s), 4.52 (2H, d), 6.64 (1H, s), 7.20 (2H, d), 7.63 (2H, d)

Reference Example 6(10)

[5-Phenyl-2-(trifluoromethyl)-3-furyl]methanol

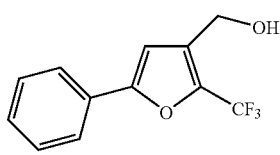

Melting point 57-58° C.; $^1$H-NMR (CDCl$_3$) δ 1.71 (1H, t), 4.73 (2H, d), 6.82 (1H, s), 7.32-7.44 (3H, m), 7.69 (2H, d).

Reference Example 6(11)

[5-(3-Methoxyphenyl)-2-methyl-3-furyl]methanol

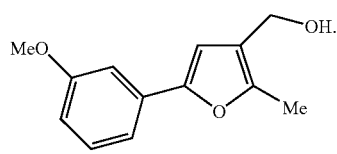

Melting point 61-62° C.; $^1$H-NMR (CDCl$_3$) δ 1.43 (1H, t), 2.37 (3H, s), 3.85 (3H, s), 4.51 (2H, d), 6.64 (1H, s), 6.79 (1H, ddd), 7.15-7.32 (3H, m).

Reference Example 6(12)

{2-Methyl-5-[3-(trifluoromethyl)phenyl]-3-furyl}methanol

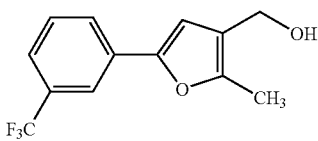

Melting point 39-41° C.; $^1$H-NMR (CDCl$_3$) δ 1.43 (1H, t), 2.38 (3H, s), 4.53 (2H, d), 6.73 (1H, s), 7.46 (2H, d), 7.77 (1H, t), 7.86 (1H, s).

Reference Example 6(13)

[2-Ethyl-5-(3-methoxyphenyl)-3-furyl]methanol

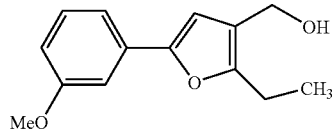

Melting point 66-67° C.; $^1$H-NMR (CDCl$_3$) δ 1.29 (3H, t), 1.38 (1H, t), 2.73 (2H, q), 3.85 (3H, s), 4.52 (2H, d), 6.63 (1H, s), 6.79 (1H, ddd), 7.17-7.32 (3H, m).

Reference Example 6(14)

[5-(4-Chlorophenyl)-2-methyl-3-furyl]methanol

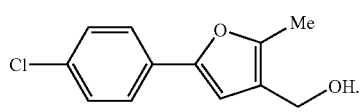

Melting point 129-130° C.; $^1$H-NMR (CDCl$_3$) δ 2.35 (3H, s) 4.50 (2H, s), 6.62 (1H, s), 7.31 (2H, d), 7.53 (2H, d).

Reference Example 7

2-Ethyl-5-[4-(trifluoromethyl)phenyl]-3-furaldehyde

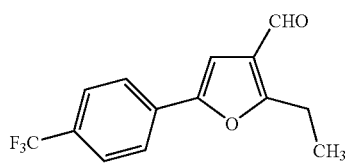

{2-Ethyl-5-[4-(trifluoromethyl)phenyl]-3-furyl}methanol (4.77 g) and active manganese dioxide (25 g) were stirred at room temperature in hexane (50 ml) and diethyl ether (10 ml) overnight. Insolubles were filtered and washed with ethyl acetate. The solvent of the collected filtrate was distilled off under reduced pressure. The obtained crude product was purified by silica gel column chromatography (hexane:ethyl acetate=6:1) to obtain an objective product (3.21 g) as a solid matter. The obtained matter was recrystallized from hexane to obtain crystals.

Melting point 95-96° C.; ¹H-NMR (CDCl₃) δ 1.42 (3H, t), 3.07 (2H, q), 7.03 (1H, s), 7.65 (2H, d), 7.75 (2H, d), 9.98 (1H, s).

Reference Example 7(1) to Reference Example 7(3)

In the same manner as in Reference Example 7, the below-described compounds were obtained from the 3-furylmethanol derivative obtained in Reference Example 6(5), Reference Example 6(8) and Reference Example 6.

Reference Example 7(1)

2-Methyl-5-[4-(trifluoromethyl)phenyl]-3-furaldehyde

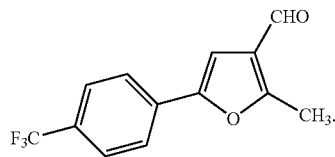

Melting point 106-107° C.; ¹H-NMR (CDCl₃) δ 2.69 (3H, s), 7.02 (1H, s), 7.63 (2H, d), 7.74 (2H, d), 9.96 (1H, s).

Reference Example 7(2)

2-Butyl-5-[4-(trifluoromethyl)phenyl]-3-furaldehyde

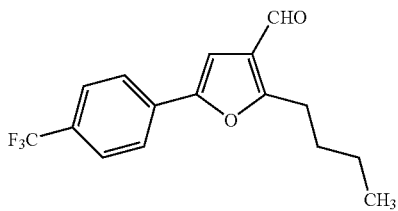

An oily matter; ¹H-NMR (CDCl₃) δ 0.98 (3H, t), 1.38-1.51 (2H, m), 1.75-1.85 (2H, m), 3.04 (2H, t), 7.03 (1H, s), 7.65 (2H, d), 7.75 (2H, d), 9.97 (1H, s).

Reference Example 7(3)

5-(4-Fluorophenyl)-2-methyl-3-furaldehyde

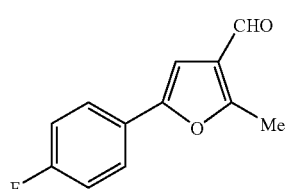

Melting point 60-61° C.; ¹H-NMR (CDCl₃) δ 2.66 (3H, s), 6.84 (1H, s), 7.09 (2H, t), 7.62 (2H, dd), 9.96 (1H, s).

Reference Example 8

Ethyl (2E)-3-{2-ethyl-5-[4-(trifluoromethyl)phenyl]-3-furyl}acrylate

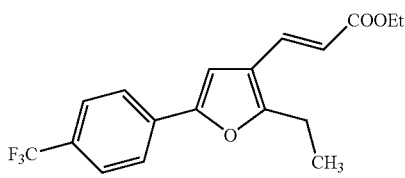

To a solution of ethyl diethylphosphonoacetate (3.02 g) in toluene (30 ml) was added a suspended matter (0.54 g) of 60% sodium hydride in liquid paraffin with ice-cooling and the mixture was stirred for 0.5 hour. A solution of 2-ethyl-5-[4-(trifluoromethyl)phenyl]-3-furaldehyde (3.01 g) in toluene (30 ml) was added thereto and the mixture was stirred at room temperature overnight. The reaction solution was poured into water and twice extracted with diethyl ether. The collected organic layer was dried over anhydrous magnesium sulfate, and the solvent was distilled off under reduced pressure. The obtained crude product was purified by silica gel column chromatography (hexane:ethyl acetate=15:1 to 9:1) to obtain an objective product (3.48 g) as a solid matter.

Melting point 82-83° C.; ¹H-NMR (CDCl₃) δ 1.33 (3H, t), 1.34 (3H, t), 2.85 (2H, q), 4.26 (2H, q), 6.14 (1H, d), 6.85 (1H, s), 7.57 (1H, d), 7.62 (2H, d), 7.73 (2H, d).

Reference Example 8(1) and Reference Example 8(2)

In the same manner as in Reference Example 8, the below-described compounds were obtained from the 3-furaldehyde derivative obtained in Reference Example 7(1) and Reference Example 7(2).

Reference Example 8(1)

Ethyl (2E)-3-{2-methyl-5-[4-(trifluoromethyl)phenyl]-3-furyl}acrylate

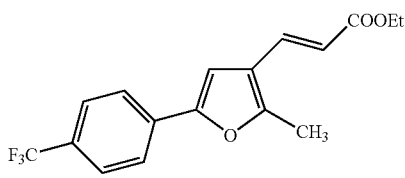

Melting point 78-79° C.; ¹H-NMR (CDCl₃) δ 1.33 (3H, t), 2.48 (3H, s), 4.26 (2H, q), 6.14 (1H, d), 6.84 (1H, s), 7.55 (1H, d), 7.62 (2H, d), 7.73 (2H, d).

Reference Example 8(2)

Ethyl (2E)-3-{2-butyl-5-[4-(trifluoromethyl)phenyl]-3-furyl}acrylate

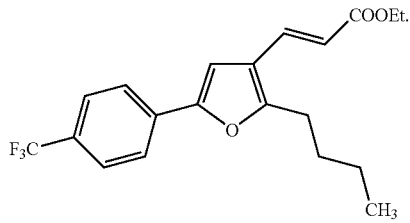

An oily matter; ¹H-NMR (CDCl₃) δ 0.96 (3H, t), 1.28-1.50 (2H, m), 1.34 (3H, t), 1.64-1.79 (2H, m), 2.82 (2H, t), 4.26 (2H, q), 6.15 (1H, d), 6.86 (1H, s), 7.57 (1H, d), 7.63 (2H, d), 7.74 (2H, d).

Reference Example 9

Ethyl 3-{2-ethyl-5-[4-(trifluoromethyl)phenyl]-3-furyl}propionate

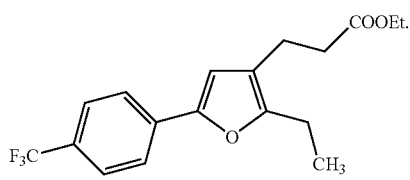

A solution of ethyl (2E)-3-{2-ethyl-5-[4-(trifluoromethyl)phenyl]-3-furyl}acrylate (3.30 g) in toluene (30 ml) and ethanol (5 ml) was hydrogenated using chlorotris(triphenylphosphine) rhodium (I) (0.45 g) as a catalyst at room temperature under normal pressure overnight. The obtained crude product was purified by silica gel column chromatography (hexane: ethyl acetate=9:1) to obtain an objective product (3.31 g) as an oily matter.
¹H-NMR (CDCl₃) δ 1.25 (3H, t), 1.27 (3H, t), 2.50-2.76 (6H, m), 4.14 (2H, q), 6.59 (1H, s), 7.58 (2H, d), 7.68 (2H, d).

Reference Example 9(1) and Reference Example 9(2)

In the same manner as in Reference Example 9, the below-described compounds were obtained from the ethyl acrylate derivative obtained in Reference Example 8(1) and Reference Example 8 (2).

Reference Example 9(1)

Ethyl 3-{2-methyl-5-[4-(trifluoromethyl)phenyl]-3-furyl}propionate

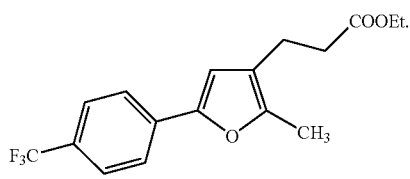

¹H-NMR (CDCl₃) δ 1.26 (3H, t), 2.31 (3H, s), 2.53 (2H, t), 2.69 (2H, t), 4.13 (2H, q), 6.57 (1H, s), 7.56 (2H, d), 7.65 (2H, d)

Reference Example 9(2)

Ethyl 3-{2-butyl-5-[4-(trifluoromethyl)phenyl]-3-furyl}propionate

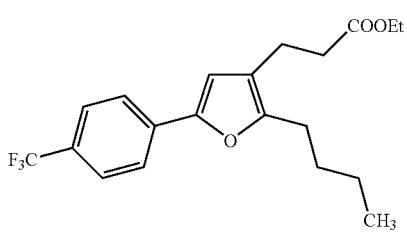

An oily matter; ¹H-NMR (CDCl₃) δ 0.95 (3H, t), 1.25 (3H, t) 1.32-1.45 (2H, m), 1.60-1.70 (2H, m), 2.54 (2H, t), 2.65 (2H, t), 2.71 (2H, t), 4.14 (2H, q), 6.58 (1H, s), 7.57 (2H, d), 7.66 (2H, d).

Reference Example 10

3-{2-Ethyl-5-[4-(trifluoromethyl)phenyl]-3-furyl}propionic acid

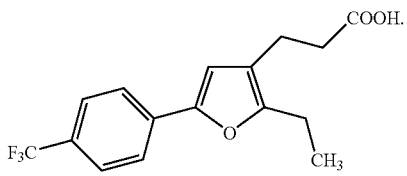

To a solution of ethyl 3-{2-ethyl-5-[4-(trifluoromethyl)phenyl]-3-furyl}propionate (0.540 g) in methanol (3 ml) and tetrahydrofuran (5 ml) was added a 1 N aqueous sodium hydroxide solution (3.2 ml) and the mixture was stirred at room temperature overnight. The reaction solution was concentrated and diluted with water. After the reaction solution was acidified with dilute hydrochloric acid, the resultant was twice extracted with ethyl acetate. The collected organic layer was dried over anhydrous sodium sulfate and the solvent was distilled off under reduced pressure. The obtained crude product was crystallized from hexane to obtain an objective product (0.413 g) as crystals. Melting point 94-95° C.; ¹H-NMR (CDCl₃) δ 1.26 (3H, t), 2.59-2.75 (6H, m), 6.59 (1H, s), 7.57 (2H, d), 7.67 (2H, d).

Reference Example 10(1) and Reference Example 10(2)

In the same manner as in Reference Example 10, the below-described compounds were obtained from the ethyl propionate derivative obtained in Reference Example 9(1) and Reference Example 9(2).

Reference Example 10(1)

3-{2-Methyl-5-[4-(trifluoromethyl)phenyl]-3-furyl}propionic acid

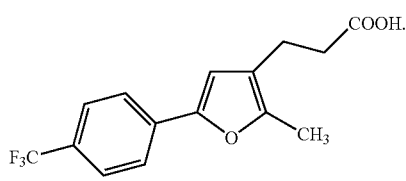

Melting point 112-113° C.; ¹H-NMR (CDCl₃) δ 2.31 (3H, s) 2.58-2.63 (2H, m), 2.69-2.74 (2H, m), 6.58 (1H, s), 7.57 (2H, d), 7.66 (2H, d).

Reference Example 10(2)

3-{2-Butyl-5-[4-(trifluoromethyl)phenyl]-3-furyl}propionic acid

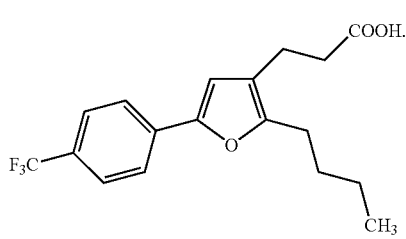

Melting point 79-80° C.; ¹H-NMR (CDCl₃) δ 0.94 (3H, t), 1.32-1.44 (2H, m), 1.60-1.70 (2H, m), 2.59-2.75 (6H, m), 6.59 (1H, s), 7.57 (2H, d), 7.67 (2H, d).

Reference Example 11

3-{2-Ethyl-5-[4-(trifluoromethyl)phenyl]-3-furyl}propan-1-ol

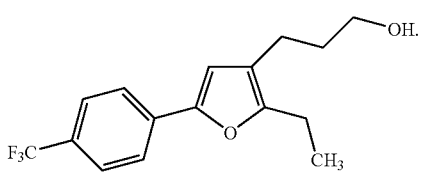

To a suspension of aluminum lithium hydride (0.46 g) in tetrahydrofuran (50 ml) was added dropwise a solution of ethyl 3-{2-ethyl-5-[4-(trifluoromethyl)phenyl]-3-furyl}propionate (2.76 g) in tetrahydrofuran (30 ml) with ice-cooling and the mixture was stirred at room temperature for 1 hour. The reaction solution was ice-cooled, and then water (0.5 ml), a 15% aqueous sodium hydroxide solution (0.5 ml) and water (1.5 ml) were sequentially added dropwise thereto. Excess aluminum lithium hydride was decomposed and then the resulting mixture was stirred as such at room temperature for 2 hours. The produced precipitate was filtered off and then washed with ethyl acetate. The solvent of the collected filtrate was distilled off under reduced pressure. The obtained crude product was purified by silica gel column chromatography (hexane:ethyl acetate=6:1 to 3:1) to obtain an objective product (1.64 g) as an oily matter.

¹H-NMR (CDCl₃) δ 1.27 (3H, t), 1.31 (1H, br s), 1.76-1.89 (2H, m), 2.48 (2H, t), 2.67 (2H, q), 3.70 (2H, t), 6.60 (1H, s), 7.58 (2H, d), 7.69 (2H, d).

Reference Example 11(1) and Reference Example 11(2)

In the same manner as in Reference Example 11, the below-described compounds were obtained from the ethyl propionate derivative obtained in Reference Example 9(1) and Reference Example 9(2).

Reference Example 11(1)

3-{2-Methyl-5-[4-(trifluoromethyl)phenyl]-3-furyl}propan-1-ol

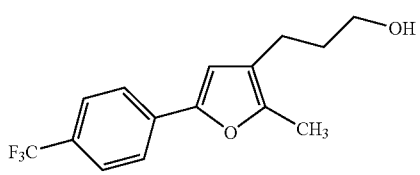

An oily matter; ¹H-NMR (CDCl₃) δ 1.77-1.86 (2H, m), 2.30 (3H, s), 2.47 (2H, t), 3.68 (2H, t), 6.57 (1H, s), 7.57 (2H, d), 7.67 (2H, d).

Reference Example 11(2)

3-{2-Butyl-5-[4-(trifluoromethyl)phenyl]-3-furyl}propan-1-ol

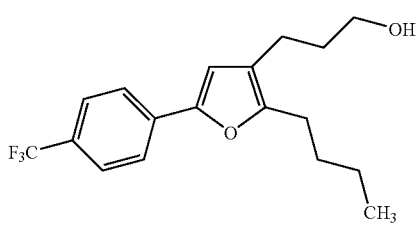

An oily matter; ¹H-NMR (CDCl₃) δ 0.95 (3H, t), 1.27 (1H, br s), 1.32-1.45 (2H, m), 1.61-1.71 (2H, m), 1.78-1.87 (2H, m), 2.48 (2H, t), 2.64 (2H, t), 3.69 (2H, br t), 6.59 (1H, s), 7.57 (2H, d), 7.67 (2H, d).

Reference Example 12

{2-Methyl-5-[4-(trifluoromethyl)phenyl]-3-furyl}acetic acid

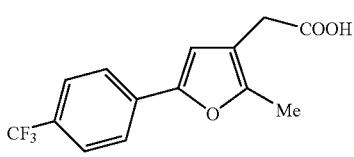

1) To a solution of {2-methyl-5-[4-(trifluoromethyl)phenyl]-3-furyl}methanol (1.48 g) in tetrahydrofuran (100 ml) was added acetone cyanohydrin (0.80 ml) and tributylphosphine (2.89 ml), and then finally 1,1'-(azodicarbonyl)dipiperidine (2.92 g) was added. The mixture was stirred at room temperature for 3 days. Hexane and toluene were added thereto, the solid matter was filtered and washed with toluene. The filtrate was concentrated under reduced pressure, and then the residue was purified by silica gel column chromatography (hexane:ethyl acetate=10:1 to 5:1) to obtain {2-methyl-5-[4-(trifluoromethyl)phenyl]-3-furyl}acetonitrile (1.76 g) as an oily matter.

$^1$H-NMR (CDCl$_3$) δ 2.37 (3H, s), 3.50 (2H, s), 6.70 (1H, s), 7.61 (2H, d), 7.70 (2H, d).

2) To a solution of {2-methyl-5-[4-(trifluoromethyl)phenyl]-3-furyl}acetonitrile (1.76 g) in ethanol (10 ml) was added 8 N sodium hydroxide (10 ml) and the mixture was heated under reflux overnight. After completing the reaction, the reaction mixture was acidified with concentrated hydrochloric acid and extracted with ethyl acetate. The organic layer was washed with saturated brine, and then purified by silica gel column chromatography (hexane:ethyl acetate=1:1) to obtain an objective product (0.68 g) as crystals.

Melting point 123-125° C.; $^1$H-NMR (CDCl$_3$) δ 2.34 (3H, s), 3.45 (2H, s), 6.70 (1H, s), 7.58 (2H, d), 7.68 (2H, d).

Reference Example 12(1)

[5-(4-Fluorophenyl)-2-methyl-3-furyl]acetic acid

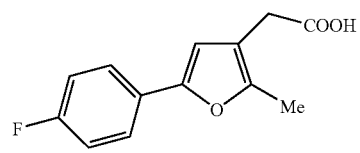

In the same manner as in Reference Example 12, an objective product was obtained from [5-(4-fluorophenyl)-2-methyl-3-furyl]methanol obtained in Reference Example 6.

Melting point 107-108° C.; $^1$H-NMR (CDCl$_3$) δ 2.31 (3H, s), 3.43 (2H, s), 6.50 (1H, s), 7.03 (2H, t), 7.56 (2H, dd).

Reference Example 13

2-{2-Methyl-5-[4-(trifluoromethyl)phenyl]-3-furyl}ethanol

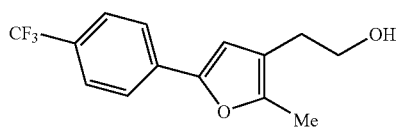

A suspension of aluminum lithium hydride (0.10 g) in tetrahydrofuran (5 ml) was ice-cooled and {2-methyl-5-[4-(trifluoromethyl)phenyl]-3-furyl}acetic acid (0.43 g) in tetrahydrofuran (5 ml) was added dropwise thereto. The mixture was stirred with ice-cooling for 30 minutes and then at room temperature for 1 hour. After completing the reaction, water (0.1 ml), 15% sodium hydroxide (0.1 ml) and water (0.3 ml) were sequentially added and the mixture was stirred at room temperature for 30 minutes. The precipitated crystals were filtered and washed with tetrahydrofuran. The filtrate was concentrated under reduced pressure and the residue was purified by silica gel column chromatography (hexane:ethyl acetate=5:1 to 1:1) to obtain an objective product (0.28 g) as an oily matter.

$^1$H-NMR (CDCl$_3$) δ 2.33 (3H, s), 2.64 (2H, t), 3.81 (2H, t), 6.63 (1H, s), 7.58 (2H, d), 7.68 (2H, d).

Reference Example 13(1)

2-[5-(4-Fluorophenyl)-2-methyl-3-furyl]ethanol

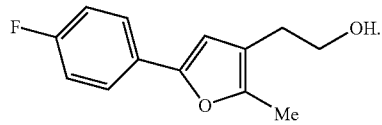

In the same manner as in Reference Example 13, an objective product was obtained from [5-(4-fluorophenyl)-2-methyl-3-furyl]acetic acid obtained in Reference Example 12(1).

Melting point 52-53° C.; $^1$H-NMR (CDCl$_3$) δ 1.46 (1H, br s) 2.31 (3H, s), 2.63 (2H, t), 3.79 (2H, br q), 6.44 (1H, s), 7.04 (2H, t), 7.57 (2H, dd).

Reference Example 14

1-[5-(4-Fluorophenyl)-2-methyl-3-furyl]ethanol

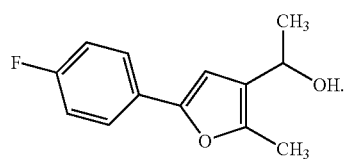

To a solution of 5-(4-fluorophenyl)-2-methyl-3-furaldehyde (2.54 g) in tetrahydrofuran (40 ml) was added dropwise a 1 N solution of methyl magnesium bromide (18.7 ml) in tetrahydrofuran at −78° C. and the reaction solution was stirred at room temperature overnight. The reaction solution was poured into an aqueous ammonium chloride solution and twice extracted with ethyl acetate. The collected organic layer was dried over anhydrous magnesium sulfate, and the solvent was distilled off under reduced pressure. The obtained crude product was purified by silica gel column chromatography (hexane-hexane:ethyl acetate=3:1) and crystallized from hexane to obtain an objective product (2.43 g) as powders.

Melting point 50-52° C.; $^1$H-NMR (CDCl$_3$) δ 1.48 (3H, d), 1.60 (1H, d), 2.35 (3H, s), 4.85 (1H, dq), 6.57 (1H, s), 7.04 (2H, t), 7.57 (2H, dd).

Reference Example 14(1)

1-[5-(4-Fluorophenyl)-2-methyl-3-furyl]butan-1-ol

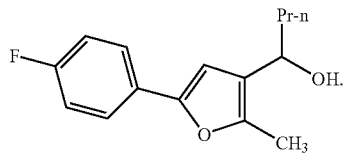

In the same manner as in Reference Example 14, an objective product was obtained using 5-(4-fluorophenyl)-2-methyl-3-furaldehyde and propylmagnesium bromide.

Melting point 73-74° C.; $^1$H-NMR (CDCl$_3$) δ 0.94 (3H, t), 1.26-1.47 (2H, m), 1.59 (1H, d), 1.62-1.72 (1H, m), 1.77-1.87 (1H, m), 2.34 (3H, s), 4.62 (1H, dt), 6.54 (1H, s), 7.04 (2H, t), 7.57 (2H, dd).

Reference Example 15

Ethyl 3-{[5-(4-fluorophenyl)-2-methyl-3-furoyl]amino}benzoate

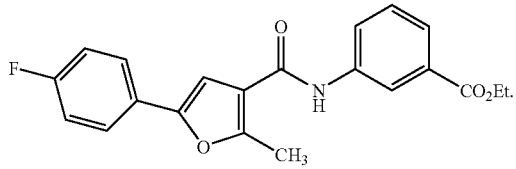

To a solution of 5-(4-fluorophenyl)-2-methyl-3-furoic acid (4.47 g) and N,N-dimethylformamide (2 drops) in tetrahydrofuran (50 ml) was added dropwise oxalyl chloride (3.54 ml) at room temperature and the mixture was stirred for 0.5 hour. The solvent of the reaction solution was distilled off under reduced pressure to obtain a crude product of acid chloride as a solid matter. Ethyl 3-aminobenzoate (3.69 g) and sodium hydrogen carbonate (3.41 g) were stirred in tetrahydrofuran (50 ml), and the obtained solid matter was dissolved in tetrahydrofuran (50 ml). The reactant was added dropwise at room temperature and the mixture was stirred as such overnight. The reaction solution was diluted with ethyl acetate, washed with water and dried over anhydrous magnesium sulfate, and then the solvent was distilled off under reduced pressure. The obtained residue was crystallized from diethyl ether-hexane to obtain an objective product (7.39 g) as crystals.

Melting point 171-172° C.; $^1$H-NMR (CDCl$_3$) δ 1.40 (3H, t), 2.70 (3H, s), 4.38 (2H, q), 6.72 (1H, s), 7.10 (2H, t), 7.44 (1H, t), 7.59-7.66 (3H, m), 7.81 (1H, td), 8.02-8.06 (2H, m).

Reference Example 15(1)

Ethyl 3-({2-methyl-5-[4-(trifluoromethyl)phenyl]-3-furoyl}amino)benzoate

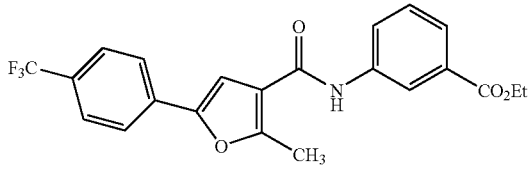

In the same manner as in Reference Example 15, an objective product was obtained from 2-methyl-5-[4-(trifluoromethyl)phenyl]-3-furoic acid in Reference Example 5(1).

Melting point 161-162° C.; $^1$H-NMR (CDCl$_3$) δ 1.39 (3H, t) 2.73 (3H, s), 4.38 (2H, q), 6.92 (1H, s), 7.40-7.48 (1H, m), 7.64-7.72 (3H, m), 7.77-7.84 (3H, m), 8.02-8.07 (2H, m).

Reference Example 16

Ethyl 3-{N-[5-(4-fluorophenyl)-2-methyl-3-furoyl]-N-methylamino}benzoate

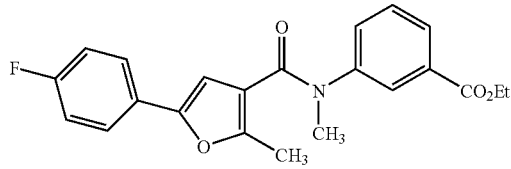

Ethyl 3-{N-[5-(4-fluorophenyl)-2-methyl-3-furoyl]amino}benzoate (1.07 g) was dissolved in N,N-dimethylformamide (5 ml) and tetrahydrofuran (5 ml), and a suspended matter (0.13 g) of 60% sodium hydride in liquid paraffin was added at room temperature. The mixture was stirred as such for 0.5 hour. To the mixture was added methyl iodide (0.36 ml) at room temperature and the mixture was stirred as such overnight. The reaction solution was poured into water and twice extracted with ethyl acetate. The collected organic layer was dried over anhydrous magnesium sulfate, and the solvent was distilled off under reduced pressure. The obtained residue was purified by silica gel column chromatography (hexane:ethyl acetate=6:1 to 2:1) to obtain an objective product (1.18 g) as an oily matter.

$^1$H-NMR (CDCl$_3$) δ 1.39 (3H, t), 2.47 (3H, s), 3.47 (3H, s), 4.38 (2H, q), 5.69 (1H, s), 6.98 (2H, t), 7.26-7.44 (4H, m), 7.89-7.97 (2H, m).

Reference Example 16(1) to 16 (3)

In the same manner as in Reference Example 16, ethyl 3-{N-[5-(4-fluorophenyl)-2-methyl-3-furoyl]amino}benzoate was alkylated with the corresponding alkyl halide to obtain the below-described compounds.

Reference Example 16(1)

Ethyl 3-{N-[5-(4-fluorophenyl)-2-methyl-3-furoyl]-N-propylamino}benzoate

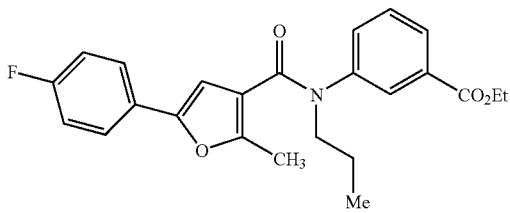

Melting point 119-120° C.; $^1$H-NMR (CDCl$_3$) δ 0.94 (3H, t) 1.39 (3H, t), 1.55-1.70 (2H, m), 2.47 (3H, s), 3.86 (2H, t), 4.38 (2H, q), 5.63 (1H, s), 6.97 (2H, t), 7.27-7.34 (3H, m), 7.40 (1H, t), 7.87 (1H, t), 7.95 (1H, td).

Reference Example 16(2)

Ethyl 3-{N-[5-(4-fluorophenyl)-2-methyl-3-furoyl]-N-heptylamino}benzoate

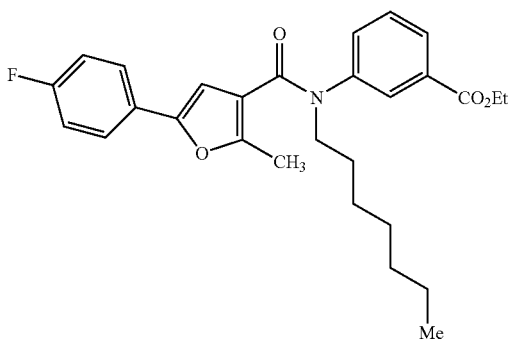

An oily matter; $^1$H-NMR (CDCl$_3$) δ 0.86 (3H, t), 1.22-1.35 (8H, m), 1.39 (3H, t), 1.53-1.66 (2H, m), 2.47 (3H, s), 3.87 (2H, t), 4.38 (2H, q), 5.63 (1H, s), 6.97 (2H, t), 7.27-7.34 (3H, m), 7.40 (1H, t), 7.87 (1H, t), 7.95 (1H, td).

Reference Example 16(3)

Ethyl 3-{N-benzyl-N-[5-(4-fluorophenyl)-2-methyl-3-furoyl]amino}benzoate

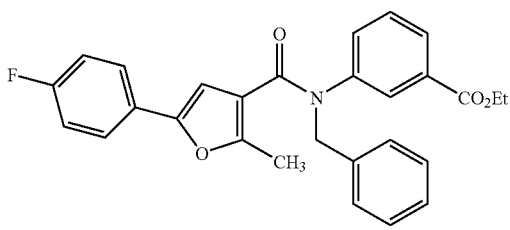

An oily matter; $^1$H-NMR (CDCl$_3$) δ 1.36 (3H, t), 2.52 (3H, s), 4.34 (2H, q), 5.11 (2H, s), 5.63 (1H, s), 6.97 (2H, t), 7.10-7.16 (1H, m), 7.23-7.37 (8H, m), 7.81 (1H, t), 7.90 (1H, td).

Reference Example 17

5-(4-(Fluorophenyl)-N-[3-(hydroxymethyl)phenyl]-2-methyl-3-furamide

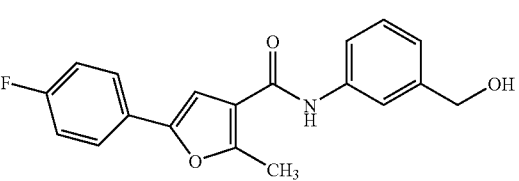

While ethyl 3-{[5-(4-fluorophenyl)-2-methyl-3-furoyl]amino}benzoate (1.01 g) and sodium borohydride (0.52 g) were stirred in tetrahydrofuran (30 ml), methanol (3 ml) was added at room temperature, and then the mixture was heated under reflux for 2 hours. After the reaction solution was cooled to room temperature, an aqueous ammonium chloride solution was added and the mixture was stirred as such for 1 hour. The mixture was twice extracted with ethyl acetate. The collected organic layer was dried over anhydrous magnesium sulfate, and the solvent was distilled off under reduced pressure. The obtained residue was purified by silica gel column chromatography (hexane:ethyl acetate=3:1 to 1:2), and crystallized from diisopropyl ether-hexane to obtain an objective product (0.72 g) as crystals.

Melting point 163-164° C.; $^1$H-NMR (CDCl$_3$-DMSO-d$_6$) δ 2.70 (3H, s), 3.51 (1H, t), 4.68 (2H, d), 7.01-7.14 (4H, m), 7.32 (1H, t), 7.60-7.69 (4H, m), 8.56 (1H, br s).

Reference Examples 17(1) to 17(5)

In the same manner as in Reference Example 17, the ester forms obtained in Reference Example 16, Reference Example 16(1) to Reference Example 16(3) and Reference Example 15(1) were reduced to obtain the below-described compounds.

Reference Example 17(1)

5-(4-Fluorophenyl)-N-[3-(hydroxymethyl)phenyl]-N,2-dimethyl-3-furamide

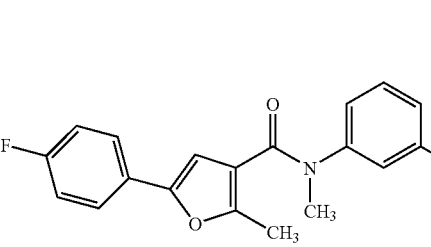

An oily matter; $^1$H-NMR (CDCl$_3$) δ 1.76 (1H, t), 2.49 (3H, s) 3.45 (3H, s), 4.69 (2H, d), 5.64 (1H, s), 6.97 (2H, t), 7.09 (1H, td), 7.21 (1H, s), 7.24-7.38 (4H, m).

Reference Example 17(2)

5-(4-Fluorophenyl)-N-[3-(hydroxymethyl)phenyl]-2-methyl-N-propyl-3-furamide

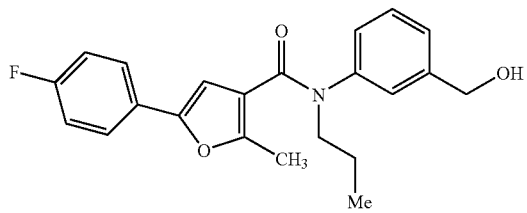

Melting point 116-117° C.; $^1$H-NMR (CDCl$_3$) δ 0.93 (3H, t), 1.56-1.77 (3H, m), 2.49 (3H, s), 3.82 (2H, t), 4.69 (2H, d), 5.58 (1H, s), 6.97 (2H, t), 7.08 (1H, td), 7.18 (1H, s), 7.26-7.38 (4H, m).

Reference Example 17(3)

5-(4-Fluorophenyl)-N-heptyl-N-[3-(hydroxymethyl)phenyl]-2-methyl-3-furamide

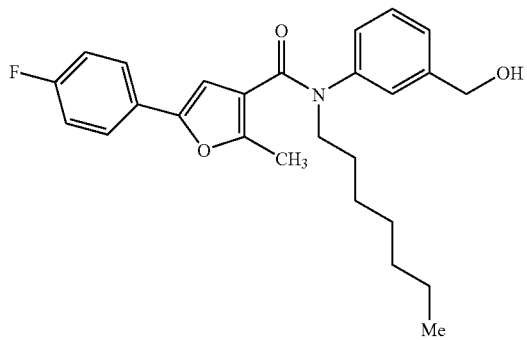

Melting point 89-91° C.; $^1$H-NMR (CDCl$_3$) δ 0.86 (3H, t), 1.21-1.33 (10H, m), 1.55-1.70 (3H, m), 2.49 (3H, s), 3.85 (2H, t), 4.69 (2H, d), 5.58 (1H, s), 6.97 (2H, t), 7.07 (1H, d), 7.18 (1H, s), 7.26-7.38 (4H, m).

Reference Example 17(4)

N-benzyl-5-(4-fluorophenyl)-N-[3-(hydroxymethyl)phenyl]-2-methyl-3-furamide

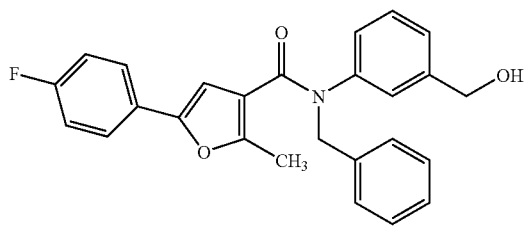

An oily matter; $^1$H-NMR (CDCl$_3$) δ 1.65 (1H, t), 2.53 (3H, s) 4.61 (2H, d), 5.08 (2H, s), 5.59 (1H, s), 6.92-7.02 (3H, m), 7.06 (1H, s), 7.23-7.34 (9H, m).

Reference Example 17(5)

N-[3-(hydroxymethyl)phenyl]-2-methyl-5-[4-(trifluoromethyl)phenyl]-3-furamide

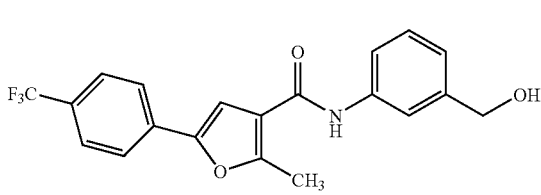

Melting point 173-174° C.; $^1$H-NMR (CDCl$_3$) δ 2.72 (3H, s) 4.71 (2H, d), 6.89 (1H, s), 7.14 (1H, d), 7.31-7.39 (1H, m), 7.50 (2H, d), 7.62-7.66 (3H, m), 7.75 (2H, d).

Reference Example 18

N-(3-formylphenyl)-2-methyl-5-[4-(trifluoromethyl)phenyl]-3-furamide

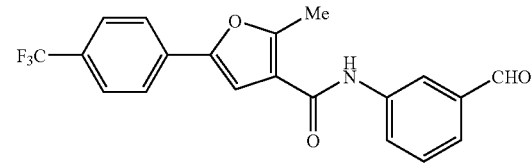

To a solution of N-[3-(hydroxymethyl)phenyl]-2-methyl-5-[4-(trifluoromethyl)phenyl]-3-furamide (0.98 g) in tetrahydrofuran (10 ml) was added manganese dioxide (3.0 g) and the mixture was stirred at room temperature for 2 hours. Manganese dioxide (1.0 g) was further added thereto and the mixture was stirred for 1 hour. Insolubles were filtered and then concentrated under reduced pressure. The residue was purified by recrystallization (hexane-ethyl acetate) to obtain an objective product (0.76 g) as crystals. Melting point 183-184° C.; $^1$H-NMR (CDCl$_3$) δ 2.75 (3H, s), 6.93 (1H, s), 7.50-7.68 (5H, m), 7.77 (2H, d), 7.98 (1H, d), 8.11 (1H, s), 10.02 (1H, s).

Reference Example 19 tert-Butyl 3-(hydroxymethyl)phenylcarbamate

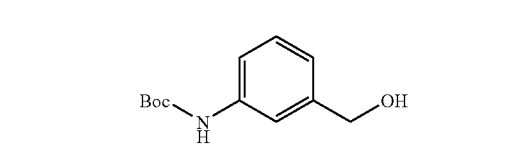

3-Aminobenzylalcohol (10.9 g), triethylamine (24.6 ml) and di-tert-butyl dicarbonate (21.2 g) were heated under reflux in tetrahydrofuran (100 ml) for 3 hours. The reaction solution was cooled to room temperature and then the solvent was distilled off under reduced pressure. The obtained residue was purified by silica gel column chromatography (hexane: ethyl acetate=6:1 to 3:1) to obtain an objective product (15.0 g) as an oily matter.

$^1$H-NMR (CDCl$_3$) δ 1.51 (9H, s), 1.96 (1H, br t), 4.65 (2H, d), 6.55 (1H, br s), 7.01-7.05 (1H, m), 7.18-7.31 (2H, m), 7.43 (1H, s).

Reference Example 20

Ethyl ({3-[(tert-butoxycarbonyl)amino)benzyl}thio)acetate

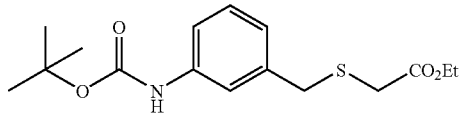

To a solution of tert-butyl 3-(hydroxymethyl)phenylcarbamate (4.94 g) and triethylamine (4.63 ml) in ethyl acetate (50 ml) was added dropwise a solution of methanesulfonyl chloride (3.04 g) in ethyl acetate (20 ml) with ice-cooling, and then the mixture was stirred as such for 0.5 hour. The produced precipitate was filtered and washed with ethyl acetate. The solvent of the obtained filtrate was distilled off under reduced pressure to obtain a crude product of methanesulfonic ester as an oily matter. The obtained oily matter was dissolved in tetrahydrofuran (30 ml). To the mixture was added at room temperature a solution obtained by stirring ethyl thioglycollate (2.93 g) and 1,8-diazabicyclo[5.4.0]-7-undecene (3.71 ml) in tetrahydrofuran (30 ml) for 0.5 hour. The mixture was stirred as such overnight. The reaction solution was diluted with ethyl acetate, washed with an aqueous sodium hydrogen carbonate solution twice, and then dried over anhydrous magnesium sulfate. The solvent was distilled off under reduced pressure. The obtained residue was purified by silica gel column chromatography (hexane ethyl acetate=15:1 to 6:1) to obtain an objective product (6.75 g) as a solid matter.

Melting point 75-76° C.; $^1$H-NMR (CDCl$_3$) δ 1.29 (3H, t), 1.51 (9H, s), 3.07 (2H, s), 3.79 (2H, s), 4.18 (2H, q), 6.47 (1H, br s), 6.97-7.03 (1H, m), 7.23-7.30 (2H, m), 7.36 (1H, s).

Reference Example 21

Ethyl [(3-aminobenzyl)thio]acetate.hydrochloride

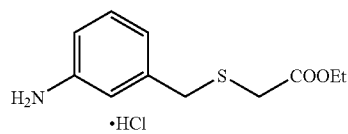

To a solution of ethyl ({3-[(tert-butoxycarbonyl)amino]benzyl}thio)acetate (6.57 g) in ethanol (30 ml) was added a 4 N solution (30 ml) of hydrogen chloride in ethyl acetate at room temperature and the mixture was stirred at 60° C. for 0.5 hour. The solvent of the mixture was distilled off under reduced pressure. The obtained residue was crystallized from diethyl ether to obtain an objective product (4.94 g) as crystals. Melting point 112-114° C.; $^1$H-NMR (CD$_3$OD) δ 1.27 (3H, t), 3.13 (2H, s), 3.90 (2H, s), 4.14 (2H, q), 7.28-7.34 (1H, m), 7.42-7.52 (3H, m).

Reference Example 22

3-(Methoxymethoxy)benzaldehyde

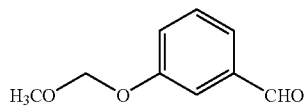

To a solution of 3-hydroxybenzaldehyde (13.0 g) in tetrahydrofuran (150 ml) was added a suspended matter (4.68 g) of 60% sodium hydride in liquid paraffin with ice-cooling and the mixture was stirred for 15 minutes. Chloromethylmethyl ether (10.3 g) was added thereto with ice-cooling, and the mixture was stirred at room temperature overnight. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=15:1 to 9:1) to obtain an objective product (16.4 g) as an oily matter.

$^1$H-NMR (CDCl$_3$) δ 3.49 (3H, s), 5.23 (2H, s), 7.27-7.31 (1H, m), 7.45 (1H, t), 7.50-7.54 (2H, m), 9.97 (1H, s).

Reference Example 23

3-(Methoxymethoxy)benzyl alcohol

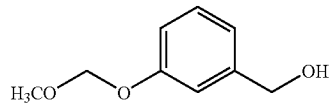

To a solution of 3-(methoxymethoxy)benzaldehyde (16.4 g) in methanol (100 ml) was slowly added sodium borohydride (3.74 g) and the mixture was stirred with ice-cooling at room temperature overnight. The reaction solution was concentrated under reduced pressure, poured into water and then extracted with ethyl acetate twice. The collected organic layer was dried over anhydrous magnesium sulfate and passed through silica gel. Then, the solvent was distilled off under reduced pressure to obtain an objective product (15.7 g) as an oily matter.

$^1$H-NMR (CDCl$_3$) δ 1.75 (1H, br s), 3.48 (3H, s), 4.67 (2H, s), 5.18 (2H, s), 6.94-7.06 (3H, m), 7.28 (1H, t).

Reference Example 24

Ethyl {[3-(methoxymethoxy)benzyl]thio}acetate

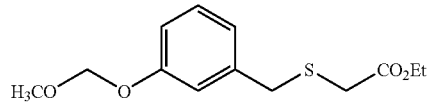

To a solution of 3-(methoxymethoxy)benzylalcohol (15.7 g) and triethylamine (19.5 ml) in ethyl acetate (150 ml) was added dropwise a solution of methanesulfonyl chloride (12.8 g) in ethyl acetate (50 ml) with ice-cooling and the mixture was stirred as such for 0.5 hour. The produced precipitate was filtered and washed with ethyl acetate. The solvent of the obtained filtrate was distilled off under reduced pressure to obtain a crude product of methanesulfonic ester as an oily matter. The obtained oily matter was dissolved in tetrahydrofuran (50 ml). To the mixture was added at room temperature a solution obtained by stirring ethyl thioglycollate (12.3 g) and 1,8-diazabicyclo[5.4.0]-7-undecene (15.3 ml) in tetrahydrofuran (30 ml) for 0.5 hour. The mixture was stirred as such overnight. The reaction solution was diluted with ethyl acetate and washed with an aqueous sodium hydrogen carbonate solution twice. The reaction solution was dried over anhydrous magnesium sulfate and passed through silica gel. Then, the solvent was distilled off under reduced pressure to obtain an objective product (25.3 g) as an oily matter.

$^1$H-NMR (CDCl$_3$) δ 1.29 (3H, t), 3.09 (2H, s), 3.48 (3H, s) 3.80 (2H, s), 4.19 (2H, q), 5.18 (2H, s), 6.91-7.02 (3H, m), 7.24 (1H, t).

Reference Example 25

Ethyl [(3-hydroxybenzyl)thio]acetate

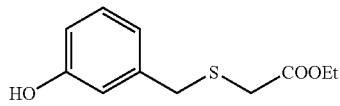

To a solution of ethyl {[3-(methoxymethoxy)thio]acetate (14.5 g) in ethanol (100 ml) was added concentrated hydrochloric acid (10 ml) at room temperature and the mixture stirred as such for 1 day. The solvent of the mixture was distilled off under reduced pressure to obtain a crude product which was purified by silica gel column chromatography (hexane:ethyl acetate=3:1) to obtain an objective product (12.3 g) as an oily matter.

$^1$H-NMR (CDCl$_3$) δ 1.29 (3H, t), 3.08 (2H, s), 3.78 (2H, s), 4.18 (2H, q), 5.12 (1H, br s), 6.74 (1H, dd), 6.84 (1H, s), 6.89 (1H, d), 7.19 (1H, t)

Reference Example 26

S-{3-[(Benzyloxy)methoxy]benzyl}thioacetate

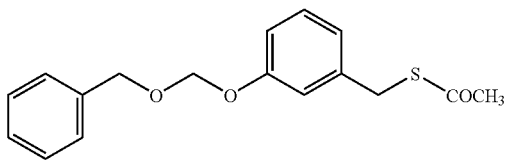

To a solution of 3-hydroxybenzylalcohol (23.8 g) in tetrahydrofuran (100 ml) was added 1,8-diazabicyclo[5.4.0]-7-undecene (29.2 g) with ice-cooling and the mixture was stirred for 0.5 hour. A solution of benzylchloromethyl ether (30.0 g) in tetrahydrofuran (50 ml) was added with ice-cooling and the mixture was stirred at room temperature overnight. The reaction solution was poured into dilute hydrochloric acid and twice extracted with ethyl acetate. The collected organic layer was dried over anhydrous magnesium sulfate, and the solvent was distilled off under reduced pressure to obtain an oily matter.

To a solution of the obtained oily matter and triethylamine (32.0 ml) in ethyl acetate (150 ml) was added dropwise a solution of methanesulfonyl chloride (24.1 g) in ethyl acetate (50 ml) with ice-cooling and the mixture was stirred as such for 0.5 hour. The produced precipitate was filtered and washed with ethyl acetate. The solvent of the obtained filtrate was distilled off under reduce pressure to obtain a crude product of methanesulfonic ester as an oily matter. The obtained oily matter was dissolved in N,N-dimethylformamide (100 ml) and potassium thioacetate (26.3 g) was added thereto at room temperature and the mixture was stirred as such overnight. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=15:1) to obtain an objective product (25.8 g) as an oily matter.

$^1$H-NMR (CDCl$_3$) δ 2.34 (3H, s), 4.10 (2H, s), 4.71 (2H, s), 5.28 (2H, s), 6.92-7.01 (3H, m), 7.22 (1H, t), 7.33 (5H, s).

Reference Example 27

Ethyl 2-({3-[(benzyloxy)methoxy]benzyl}thio)-2-methylpropionate

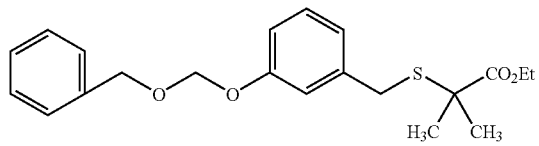

To a solution of S-{3-[(benzyloxy)methoxy]benzyl}thioacetate (6.46 g) in methanol (30 ml) was added at room temperature those obtained dissolving sodium hydroxide (0.85 g) in methanol (20 ml) and water (2 ml), and the mixture was stirred as such for 1 hour. The solvent of the mixture was distilled off under reduce pressure to obtain a solid matter. The obtained solid matter was dissolved in N,N-dimethylformamide (25 ml) and ethyl 2-bromo-2-methylpropionate (5.00 g) was added thereto at room temperature, and the mixture was stirred at 60° C. overnight. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=15:1) to obtain an objective product (7.67 g) as an oily matter.

$^1$H-NMR (CDCl$_3$) δ 1.27 (3H, t), 1.54 (6H, s), 3.82 (2H, s), 4.13 (2H, q), 4.71 (2H, s), 5.28 (2H, s), 6.94-7.05 (3H, m), 7.21 (1H, t), 7.33 (5H, s).

Reference Example 28

Ethyl 2-[(3-hydroxybenzyl)thio]-2-methylpropionate

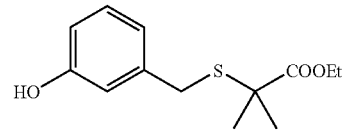

To a solution ethyl 2-({3-[(benzyloxy)methoxy]benzyl}thio)-2-methylpropionate (7.67 g) in ethanol (50 ml) was added concentrated hydrochloric acid (5 ml) at room temperature and the mixture was stirred at 60° C. for 2 hours. The solvent of the mixture was distilled off under reduced pressure. The obtained crude product was purified by silica gel column chromatography (hexane:ethyl acetate=6:1) to obtain an objective product (3.81 g) as an oily matter.

$^1$H-NMR (CDCl$_3$) δ 1.27 (3H, t), 1.53 (6H, s), 3.78 (2H, s), 4.11 (2H, q), 4.96 (1H, s), 6.69 (1H, dd), 6.79 (1H, t), 6.86 (1H, d), 7.14 (1H, t).

Reference Example 29

Ethyl {[3-(methoxymethoxy)benzyl]oxy}acetate

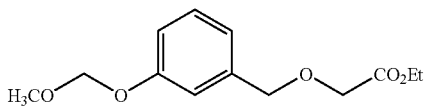

To a solution of 3-(methoxymethoxy)benzylalcohol (4.53 g) in 1,2-dimethoxyethane (150 ml) was added a suspended matter (1.29 g) of 60% sodium hydride in liquid paraffin with ice-cooling and the mixture was stirred for 0.5 hour. Ethyl bromoacetate (6.75 g) was added thereto with ice-cooling and the mixture was stirred at room temperature overnight. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=15:1 to 6:1) to obtain an objective product (4.62 g) as an oily matter.

$^1$H-NMR (CDCl$_3$) δ 1.29 (3H, t), 3.48 (3H, s), 4.10 (2H, s), 4.23 (2H, q), 4.61 (2H, s), 5.18 (2H, s), 6.96-7.05 (3H, m), 7.27 (1H, t).

Reference Example 30

Ethyl [(3-(hydroxybenzyl)oxy]acetate

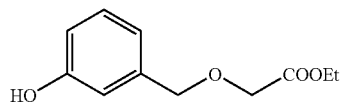

To a solution of ethyl {[3-(methoxymethoxy)benzyl]oxy}acetate (4.62 g) in ethanol (50 ml) was added concentrated hydrochloric acid (3 ml) at room temperature and the mixture was stirred at room temperature overnight. The solvent of the mixture was distilled off under reduced pressure. The obtained crude product was purified by silica gel column chromatography (hexane:ethyl acetate=3:1) to obtain an objective product (2.36 g) as an oily matter.

$^1$H-NMR (CDCl$_3$) δ 1.29 (3H, t), 4.10 (2H, s), 4.24 (2H, q) 4.59 (2H, s), 5.18 (1H, s), 6.75-6.81 (1H, m), 6.88-6.92 (2H, m), 7.22 (1H, t).

Reference Example 31

Methoxymethyl[3-(methoxymethoxy)phenyl]acetate

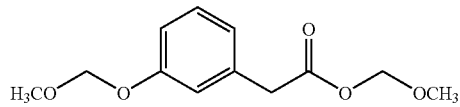

To a solution of (3-hydroxyphenyl)acetic acid (10.5 g) in tetrahydrofuran (150 ml) was added N-ethyldiisopropylamine (26.3 ml) with ice-cooling and the mixture was stirred for 0.5 hour. Chloromethylmethyl ether (13.8 g) was added with ice-cooling and the mixture was stirred at 60° C. overnight. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=6:1 to 3:1) to obtain an objective product (14.8 g) as an oily matter.

$^1$H-NMR (CDCl$_3$) δ 3.42 (3H, s), 3.47 (3H, s), 3.64 (2H, s), 5.17 (2H, s), 5.24 (2H, s), 6.92-6.98 (3H, m), 7.24 (1H, t).

Reference Example 32

[3-(Methoxymethoxy)phenyl]acetic acid

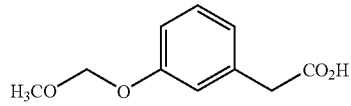

A mixture of methoxymethyl [3-(methoxymethoxy)phenyl]acetate (14.8 g), sodium hydroxide (4.93 g), methanol (50 ml), water (100 ml) and tetrahydrofuran (50 ml) was stirred at room temperature overnight. The reaction solution was concentrated and diluted with water. The reaction solution was acidified with dilute hydrochloric acid, and then extracted with ethyl acetate twice. The collected organic layer was dried over anhydrous sodium sulfate and the solvent was distilled off under reduced pressure. The obtained crude product was purified by silica gel column chromatography (hexane:ethyl acetate=3:1 to 1:1) to obtain an objective product (11.2 g) as an oily matter.

$^1$H-NMR (CDCl$_3$) δ 3.48 (3H, s), 3.63 (2H, s), 5.17 (2H, s), 6.91-6.99 (-3H, m), 7.26 (1H, t).

Reference Example 33

Ethyl 4-[3-(methoxymethoxy)phenyl]-3-oxobutanoate

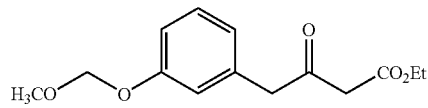

To a solution [3-(methoxymethoxy)phenyl]acetic acid (11.2 g) in tetrahydrofuran (150 ml) was added 1,1'-carbonyldiimidazole (10.2 g) at room temperature and the mixture was stirred as such for 3 hours. To the mixture was added a monopotassium salt of monoethyl malonate (10.7 g) and magnesium chloride (3.00 g) at room temperature and the mixture was stirred at 60° C. overnight. The reaction solution was diluted with ethyl acetate and water, and acidified with concentrated hydrochloric acid. Then, the ethyl acetate layer was separated and the aqueous layer was extracted with ethyl acetate. The collected organic layer was dried over anhydrous sodium sulfate and the solvent was distilled off under reduced pressure. The obtained crude product was purified by silica gel column chromatography (hexane:ethyl acetate 6:1 to 3:1) to obtain an objective product (10.7 g) as liquid.

$^1$H-NMR (CDCl$_3$) δ 1.27 (3H, t), 3.45 (2H, s), 3.47 (3H, s), 3.80 (2H, s), 4.17 (2H, q), 5.16 (2H, s), 6.83-6.98 (3H, m), 7.25 (1H, t).

Reference Example 34

Ethyl 4-[3-(methoxymethoxy)phenyl]butanoate

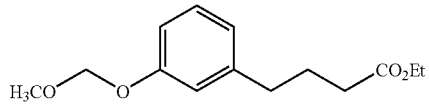

To a solution of ethyl 4-[3-(methoxymethoxy)phenyl]-3-oxobutanoate (6.28 g) in ethanol (40 ml) was slowly added sodium borohydride (0.89 g) with ice-cooling and the mixture was stirred as such for 0.5 hour. To the reaction solution was added an aqueous ammonium chloride solution was added and twice extracted with ethyl acetate. The collected organic layer was dried over anhydrous magnesium sulfate, and the solvent was distilled off under reduced pressure to obtain ethyl 3-hydroxy-4-[3-(methoxymethoxy)phenyl]butanoate as an oily matter.

To a solution of the obtained oily matter and triethylamine (4.93 ml) in ethyl acetate (100 ml) was added dropwise a solution of methanesulfonyl chloride (3.24 g) in ethyl acetate (30 ml) with ice-cooling and the mixture was stirred as such for 0.5 hour. The produced precipitate was filtered and washed with ethyl acetate. The solvent of the obtained filtrate was distilled off under reduced pressure to obtain a crude product of methanesulfonic ester as an oily matter. The obtained oily matter was dissolved in tetrahydrofuran (60 ml), 1,8-diazabicyclo[5.4.0]-7-undecene (3.95 g) was added at room temperature, and then the mixture was stirred as such for 1 hour. The solvent of the reaction solution was distilled off under reduced pressure and the obtained residue was subject to silica gel column chromatography (hexane:ethyl acetate=6:1) to obtain crude ethyl 4-[3-(methoxymethoxy) phenyl]-2-butenate as an oily matter.

A solution of the obtained oily matter in toluene (30 ml)-ethanol (5 ml) was hydrogenated at room temperature under normal pressure using a chlorotris(triphenylphosphine) rhodium (I) (0.65 g) as a catalyst overnight. The obtained crude product was purified by silica gel column chromatography (hexane:ethyl acetate=6:1) to obtain an objective product (3.67 g) as an oily matter.

$^1$H-NMR (CDCl$_3$) δ 1.26 (3H, t), 1.87-2.03 (2H, m), 2.32 (2H, t), 2.63 (2H, t), 3.48 (3H, s), 4.13 (2H, q), 5.17 (2H, s), 6.81-6.91 (3H, m), 7.20 (1H, dd).

Reference Example 35

Ethyl 4-(3-hydroxyphenyl)butanoate

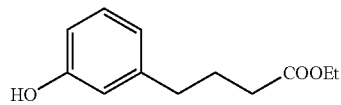

To a solution of ethyl 4-[3-(methoxymethoxy)phenyl]butanoate (3.67 g) in ethanol (50 ml) was added concentrated hydrochloric acid (3 ml) at room temperature and the mixture was stirred at room temperature overnight. The solvent of the mixture was distilled off under reduced pressure. The obtained crude product was purified by silica gel column chromatography (hexane:ethyl acetate=3:1) to obtain an objective product (2.72 g) as an oily matter.

$^1$H-NMR (CDCl$_3$) δ 1.26 (3H, t), 1.89-1.99 (2H, m), 2.32 (2H, t), 2.60 (2H, t), 4.12 (2H, q), 4.97 (1H, s), 6.65-6.68 (2H, m), 6.74 (1H, d), 7.14 (1H, dd).

Reference Example 36

Ethyl 3-(4-hydroxy-2-methylphenyl)propionate

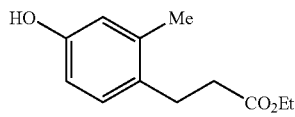

To a suspension of sodium hydride (1.33 g) in tetrahydrofuran (100 ml) was added dropwise ethyl diethylphosphonoacetate (4.16 ml) with ice-cooling and the mixture was stirred for 30 minutes. To the reaction solution was added dropwise a solution of 2-methyl 4-benzyloxy benzaldehyde (5.0 g) in tetrahydrofuran (25 ml) and the mixture was stirred at 0° C. for 2 hours and at room temperature for 1 hour. 1 N hydrochloric acid was added thereto and the mixture was diluted with ethyl acetate. Then, the organic layer was separated and then washed with a saturated sodium bicarbonate solution, water and saturated brine. The organic layer was dried over anhydrous magnesium sulfate, filtered and then concentrated under reduced pressure. The obtained residue was subject to silica gel column chromatography (hexane: ethyl acetate=3:1) and the obtained-compound was dissolved in ethanol (60 ml). After 10% palladium-carbon (2 g) was added under nitrogen gas stream, the atmosphere was substituted with a hydrogen atmosphere and the mixture was stirred at room temperature for 5 hours. Insolubles were filtered and the residue was purified by silica gel column chromatography (hexane:ethyl acetate=1:1) to obtain an objective product (4.43 g) as an oily matter.

$^1$H-NMR (CDCl$_3$) δ 1.24 (3H, t), 2.25 (3H, s), 2.50-2.56 (2H, m), 2.85 (2H, dd), 4.13 (2H, q), 5.21 (1H, d), 6.57 (1H, dd), 6.62 (1H, d), 6.97 (1H, d).

Reference Example 37

[4-(Benzyloxy)-2-methylphenyl]acetonitrile

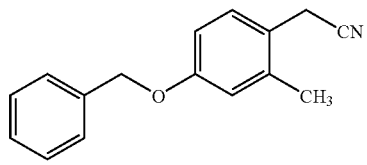

A suspension of potassium tert-butoxide (4.94 g) in dimethoxyethane (100 ml) was cooled to −78° C., toluenesulfonylmethyl isocyanide (4.73 g) was added thereto, and then the mixture was stirred for 5 minutes. Then, a solution of 2-methyl 4-benzyloxybenzaldehyde (4.99 g) in dimethoxyethane (50 ml) was added thereto and the mixture was stirred at −78° C. for 1 hour and at room temperature for 1 hour. Methanol was added thereto and the mixture was heated under reflux for 1 hour. After standing to cool, the reaction solution was poured into a saturated aqueous ammonium chloride solution and the aqueous layer was extracted with ethyl acetate. The organic layer was washed with saturated brine, dried over anhydrous magnesium sulfate, filtered and then concentrated under reduced pressure. The residue was purified by silica gel column chromatography (hexane:ethyl acetate=10:1 to 3:1) to obtain an objective product (3.04 g) as crystals.

Melting point 51-52° C.; $^1$H-NMR (CDCl$_3$) δ 2.30 (3H, s), 3.58 (2H, s), 5.04 (2H, s), 6.77-6.79 (1H, m), 6.83 (1H, s), 7.22 (1H, d), 7.31-7.43 (5H, m).

Reference Example 38

Methyl [4-(benzyloxy)-2-methylphenyl]acetate

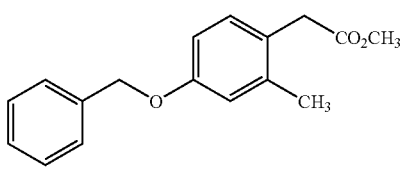

To a solution of [4-(benzyloxy)-2-methylphenyl]acetonitrile (2.97 g) in tetrahydrofuran (30 ml)-ethanol (30 ml) was added 8 N sodium hydroxide (30 ml) and the mixture was heated under reflux overnight. The mixture was acidified with 6 N hydrochloric acid, and then extracted with ethyl acetate. The organic layer was washed with saturated brine, dried over anhydrous magnesium sulfate, filtered, and then concentrated under reduced pressure. The residue was dissolved in N,N-dimethylformamide (50 ml), and potassium carbonate (3.46 g) and iodomethane (1.8 ml) were added thereto. The mixture was stirred at room temperature overnight and then diluted with ethyl acetate and washed with water and saturated brine. The mixture was dried over anhydrous magnesium sulfate, filtered, and then concentrated under reduced pressure. The residue was purified by silica gel column chromatography (hexane-ethyl acetate=5:1) to obtain an objective product (1.13 g) as an oily matter.

$^1$H-NMR (CDCl$_3$) δ 2.27 (3H, s), 3.57 (2H, s), 3.67 (3H, s), 5.03 (2H, s), 6.74-6.83 (2H, m), 7.10 (1H, d), 7.30-7.45 (5H, m).

Reference Example 39

Methyl (4-hydroxy-2-methylphenyl)acetate

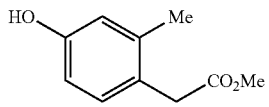

To a solution of methyl [4-(benzyloxy)-2-methylphenyl]acetate (1.13 g) in methanol (20 ml) was added 10% palladium-carbon (0.6 g) under nitrogen gas stream, the atmosphere was substituted with a hydrogen atmosphere and the mixture was stirred at room temperature for 2 days. Insolubles were filtered and the solvent was distilled off under reduced pressure to obtain an objective product (0.71 g) as an oily matter.

$^1$H-NMR (CDCl$_3$) δ 2.24 (3H, s), 3.56 (2H, s), 3.69 (3H, s) 6.61-6.62 (2H, m), 7.02 (1H, d).

Reference Example 40

[2-Methoxy-4-(methoxymethoxy)phenyl]acetonitrile

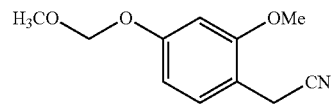

A suspension of potassium tert-butoxide (4.69 g) in dimethoxyethane (30 ml) was cooled to −78° C., toluenesulfonylmethyl isocyanide (4.49 g) was added thereto, and then the mixture was stirred for 5 minutes. Then, a solution of 2-methoxy-4-(methoxymethoxy)benzaldehyde (4.10 g) in dimethoxyethane (30 ml) was added, and the mixture was stirred at −78° C. for 1 hour and at room temperature for 1 hour. Methanol was added and heated under reflux for 1 hour. After standing to cool, the reaction solution was poured into a saturated aqueous ammonium chloride solution and the aqueous layer was extracted with ethyl acetate. The organic layer was washed with saturated brine, dried over anhydrous magnesium sulfate, filtered, and then concentrated under reduced pressure. The residue was purified by silica gel column chromatography (hexane:ethyl acetate=5:1 to 2:1) to obtain an objective product (2.13 g) as an oily matter.

¹H-NMR (CDCl₃) δ 3.48 (3H, s), 3.61 (2H, s), 3.84 (3H, s), 5.17 (2H, s), 6.58-6.66 (2H, m), 7.22 (1H, d).

Reference Example 41

Methyl (4-hydroxy-2-methoxyphenyl)acetate

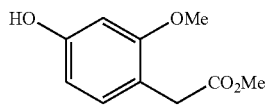

To a solution of [2-methoxy-4-(methoxymethoxy)phenyl]acetonitrile (2.13 g) in ethanol (10 ml) was added 8 N sodium hydroxide (10 ml) and the mixture was heated under reflux overnight. After completing the reaction, the mixture was acidified with 6 N hydrochloric acid and extracted with ethyl acetate. The organic layer was washed with saturated brine, dried over anhydrous magnesium sulfate, filtered, and then concentrated under reduced pressure. The residue was dissolved in N,N-dimethylformamide (50 ml). Potassium carbonate (2.14 g) and iodomethane (1.75 g) were added thereto, and the mixture was stirred at room temperature for 3 days. After diluting with ethyl acetate, the organic layer was washed with water and saturated brine. The organic layer was dried over anhydrous magnesium sulfate, filtered, and then concentrated under reduced pressure. The residue was dissolved in methanol (10 ml) and 1 ml of concentrated hydrochloric acid was added. The mixture was heated under reflux overnight. The reaction mixture was concentrated under reduced pressure and subjected to azeotropy with toluene to remove moisture. Then, the residue was purified by silica gel column chromatography (hexane ethyl acetate=5:1 to 2:1) to obtain an objective product (1.32 g) as an oily matter.

¹H-NMR (CDCl₃) δ 3.55 (2H, s), 3.70 (3H, s), 3.71 (3H, s), 5.95 (1H, br s), 6.24-6.32 (2H, m), 6.94 (1H, d).

Reference Example 42

Methyl (4-methyl-2-mercapto-1,3-thiazol-5-yl)acetate

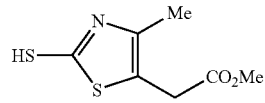

To a solution of (4-methyl-2-mercapto-1,3-thiazol-5-yl) acetic acid (10 g) in methanol (200 ml) was added concentrated sulfuric acid (0.5 ml) and the mixture was heated under reflux overnight. After methanol was distilled off under reduced pressure, the reaction mixture was diluted with ethyl acetate and washed with water and saturated brine. The organic layer was dried over anhydrous magnesium sulfate, filtered, and then concentrated under reduced pressure. The residue was purified by recrystallization (hexane-ethyl acetate) to obtain an objective product (7.18 g) as crystals. Melting point 139-140° C.; ¹H-NMR (CDCl₃) δ 2.18 (3H, s), 3.51 (2H, s), 3.74 (3H, s), 12.15 (1H, br s).

Reference Example 43

Benzyl 6-(benzyloxy)-2-naphthoate

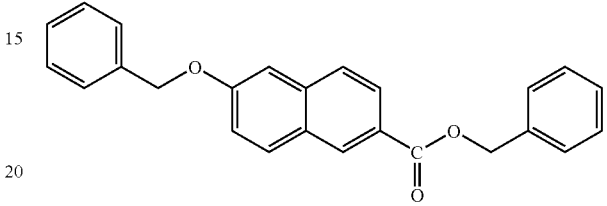

To a solution of 6-hydroxy-2-naphthoic acid (17.9 g) in N,N-dimethylformamide (200 ml) was added potassium carbonate (32.9 g) and benzyl bromide (22.6 ml) and the mixture was stirred at room temperature overnight. The reaction mixture was diluted with ethyl acetate and washed with water and saturated brine. The organic layer was dried over anhydrous magnesium sulfate, filtered, and then concentrated under reduced pressure. The residue was purified by recrystallization (hexane-ethyl acetate) to obtain an objective product (26.1 g) as crystals.

Melting point 97-98° C.; ¹H-NMR (CDCl₃) δ 5.18 (2H, s), 5.40 (2H, s), 7.21-7.27 (2H, m), 7.31-7.49 (10H, m), 7.72 (1H, d), 7.84 (1H, d), 8.04 (1H, dd), 8.54 (1H, s).

Reference Example 44

[6-(Benzyloxy)-2-naphthyl]methanol

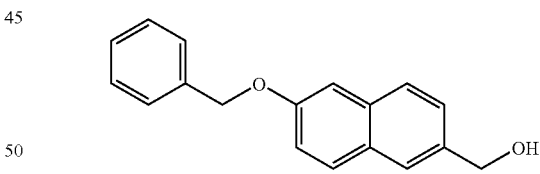

To a suspension of aluminum lithium hydride (2.32 g) in tetrahydrofuran (100 ml) was added dropwise a solution of benzyl 6-(benzyloxy)-2-naphthoate (15 g) in tetrahydrofuran (50 ml) with ice-cooling to and the mixture was stirred at 0° C. for 1 hour. Water (2.4 ml), 15% sodium hydroxide (2.4 ml) and water (7.2 ml) were added and the reaction was completed. The mixture was stirred at room temperature for 30 minutes. Insolubles were filtered and washed with tetrahydrofuran. The filtrate was concentrated under reduced pressure and the residue was purified by recrystallization (hexane-ethyl acetate) to obtain an objective product (10.1 g) as crystals.

Melting point 141-142° C.; $^1$H-NMR (CDCl$_3$) δ 4.79 (2H, s), 5.16 (2H, s), 7.21-25 (2H, m), 7.33-7.51 (6H, m), 7.69-7.75 (3H, m).

Reference Example 45

6-(Benzyloxy)-2-naphthaldehyde

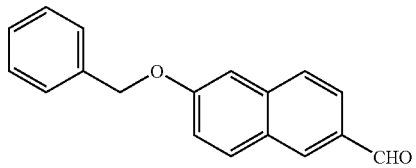

To a solution of [6-(benzyloxy)-2-naphthyl]methanol (5 g) in tetrahydrofuran (60 ml) was added manganese dioxide (15 g) and the mixture was stirred at room temperature overnight. Insolubles were filtered through Celite and washed with ethyl acetate. The filtrate was concentrated under reduced pressure and the residue was purified by recrystallization (hexane-ethyl acetate) to obtain an objective product (4.08 g) as crystals.

Melting point 107-108° C.; $^1$H-NMR (CDCl$_3$) δ 5.21 (2H, s) 7.24-7.50 (7H, m), 7.78 (1H, d), 7.88-7.92 (2H, m), 8.24 (1H, s), 10.08 (1H, s).

Reference Example 46

Ethyl (E)-3-[6-(benzyloxy)-2-naphthyl]acrylate

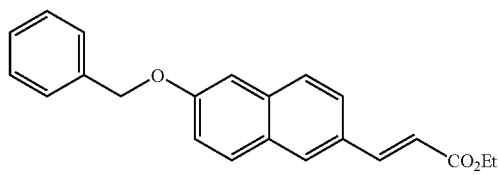

To a suspension of sodium hydride (0.46 g) in tetrahydrofuran (20 ml) was added dropwise ethyl diethylphosphonoacetate (4.16 ml) with ice-cooling and the mixture was stirred for 30 minutes. To the reaction solution was added dropwise a solution of 6-(benzyloxy)-2-naphthaldehyde (2.0 g) in tetrahydrofuran (15 ml) and the mixture was stirred at 0° C. for 2 hours. 1 N hydrochloric acid was added thereto and diluted in ethyl acetate. The organic layer was separated and washed with a saturated sodium bicarbonate solution, water and saturated brine. The organic layer was dried over anhydrous magnesium sulfate, filtered, and then concentrated under reduced pressure. The obtained residue was purified by recrystallization (hexane-ethyl acetate) to obtain an objective product (2.09 g) as crystals.

Melting point 110-112° C.; $^1$H-NMR (CDCl$_3$) δ 1.35 (3H, t) 4.28 (2H, q), 5.19 (2H, s), 6.48 (1H, d), 7.22-7.27 (2H, m), 7.34-7.50 (5H, m), 7.60-7.85 (5H, m).

Reference Example 47

Ethyl 3-(6-hydroxy-2-naphthyl)propionate

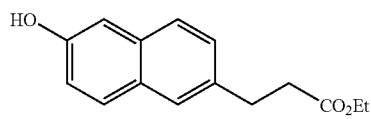

Ethyl (E)-3-[6-(benzyloxy)-2-naphthyl]acrylate (1.67 g) was dissolved in ethanol (15 ml) and 10% palladium-carbon (0.5 g) was added under nitrogen gas stream, the atmosphere was substituted with a hydrogen atmosphere and the mixture was stirred at room temperature overnight. Insolubles were filtered, and then the filtrate was purified by silica gel column chromatography (hexane:ethyl acetate=5:1 to 2:1) to obtain an objective product (0.86 g) as crystals.

Melting point 90-91° C.; $^1$H-NMR (CDCl$_3$) δ 1.32 (3H, t), 2.70 (2H, t), 3.07 (2H, t), 4.14 (2H, q), 5.54 (1H, s), 7.03-7.08 (2H, m), 7.24-7.29 (1H, m), 7.55-7.65 (3H, m).

Reference Example 48

2-[5-(4-Fluorophenyl)-2-methyl-3-furyl]pentanoic acid

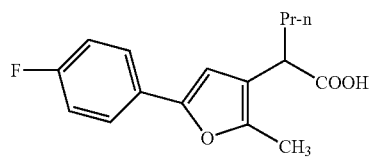

In the same manner as in Reference Example 12, an objective product was obtained from 1-[5-(4-fluorophenyl)-2-methyl-3-furyl]butan-1-ol obtained in Reference Example 14(1).

Melting point 96-97° C.; $^1$H-NMR (CDCl$_3$) δ 0.92 (3H, t), 1.23-1.42 (2H, m), 1.62-1.80 (1H, m), 1.89-2.07 (1H, m), 2.32 (3H, s), 3.45 (1H, t), 6.54 (1H, s), 7.03 (2H, t), 7.57 (2H, dd).

Reference Example 49

2-[5-(4-Fluorophenyl)-2-methyl-3-furyl]pentan-1-ol

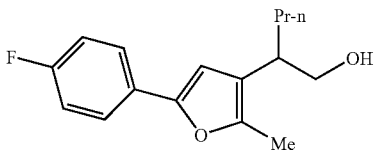

In the same manner as in Reference Example 13, an objective product was obtained from 2-[5-(4-fluorophenyl)-2-methyl-3-furyl]pentanoic acid obtained in Reference Example 12(2).

An oily matter; $^1$H-NMR (CDCl$_3$) δ 0.89 (3H, t), 1.19-1.62 (5H, m), 2.32 (3H, s), 2.66-2.76 (1H, m), 3.58 (1H, dd), 3.71 (1H, dd), 6.40 (1H, s), 7.04 (2H, t), 7.57 (2H, dd).

Reference Example 50

3-({2-Methyl-5-[4-(trifluoromethyl)phenyl]-3-furyl}methoxy)benzaldehyde

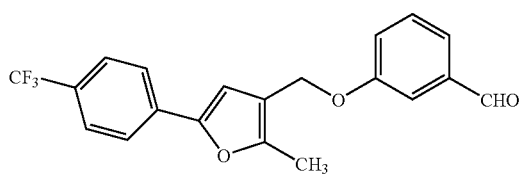

To a solution of {2-methyl-5-[4-(trifluoromethyl)phenyl]-3-furyl}methanol (4.12 g), 3-hydroxybenzaldehyde (2.4 g) and tributylphosphine (4.9 g) in tetrahydrofuran (250 ml) was added 1,1'-(azodicarbonyl)dipiperidine (6.1 g) at room temperature and the mixture was stirred overnight. The solvent of the reaction solution was distilled off under reduced pressure and diisopropyl ether was added. The precipitate was filtered off and washed with diisopropyl ether. The solvent of the filtrate was distilled off under reduced pressure. The obtained crude product was purified by silica gel column chromatography (hexane:ethyl acetate=15:1 to 9:1) to obtain an objective product (4.30 g) as a solid matter.

Melting point 85-86° C.; $^1$H-NMR (CDCl$_3$) δ 2.44 (3H, s), 4.95 (2H, s), 6.80 (1H, s), 7.22-7.28 (1H, m), 7.47-7.52 (3H, m), 7.60 (2H, d), 7.72 (2H, d), 10.00 (1H, s).

Reference Example 51

S-[3-({2-methyl-5-[4-(trifluoromethyl)phenyl]-3-furyl}methoxy)benzyl]thioacetate

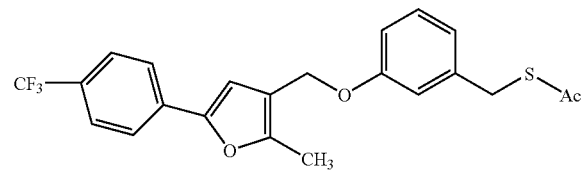

To a solution of 3-({2-methyl-5-[4-(trifluoromethyl)phenyl]-3-furyl}methoxy)benzaldehyde (2.52 g) in methanol (20 ml)-tetrahydrofuran (10 ml) was added sodium borohydride (0.26 g) with ice-cooling and the mixture was stirred for 0.5 hour at room temperature. The reaction solution was concentrated under reduced pressure, poured into water and then extracted with ethyl acetate twice. The collected organic layer was dried over anhydrous magnesium sulfate, passed through silica gel, and then the solvent was distilled off under reduced pressure to obtain an oily matter.

To a solution of the obtained oily matter and triethylamine (1.5 ml) in ethyl acetate (30 ml) was added dropwise methanesulfonyl chloride (0.65 ml) with ice-cooling and the mixture was stirred as such for 0.5 hour. The produced precipitate was filtered and washed with ethyl acetate. The solvent of the obtained filtrate was distilled off under reduced pressure to obtain an oily matter. The obtained oily matter was dissolved in N,N-dimethylformamide (20 ml) and potassium thioacetate (1.2 g) was added at room temperature. The mixture was stirred as such for 3 days. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=6:1) and crystallized from hexane to obtain an objective product (2.50 g) as crystals. Melting point 90-91° C.; $^1$H-NMR (CDCl$_3$) δ 2.35 (3H, s), 2.41 (3H, s), 4.10 (2H, s), 4.85 (2H, s), 6.78 (1H, s), 6.83-6.91 (3H, m), 7.22 (1H, t), 7.59 (2H, d), 7.70 (2H, d).

Reference Example 52

[4-Fluoro-3-(methoxymethoxy)phenyl]methanol

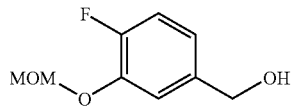

To a solution of 4-fluoro-3-hydroxybenzoic acid (9.81 g) in tetrahydrofuran (100 ml) was added N-ethyldiisopropylamine (17.9 g) at room temperature and the mixture was stirred for 0.5 hour. Chloromethylmethyl ether (12.6 g) was added thereto at room temperature and the mixture was stirred at 60° C. overnight. The reaction solution was poured into water and twice extracted with ethyl acetate. The collected organic layer was dried over anhydrous magnesium sulfate, and the solvent was distilled off under reduced pressure to obtain an oily matter.

To a suspension of aluminum lithium hydride (3.6 g) in tetrahydrofuran (100 ml) was added dropwise a solution of the obtained oily matter in tetrahydrofuran (100 ml) with ice-cooling and the mixture was stirred at room temperature overnight. The reaction solution was ice-cooled and water (3.5 ml), a 15% aqueous sodium hydroxide solution (3.5 ml) and water (9 ml) were sequentially added dropwise. Excess aluminum lithium hydride was decomposed and the resultant was stirred as such at room temperature for 2 hours. The produced precipitate was filtered off, and washed with ethyl acetate. The solvent of the collected filtrate was distilled off under reduced pressure. The obtained crude product was purified by silica gel column chromatography (ethyl acetate) to obtain an objective product (11.3 g) as an oily matter.

$^1$H-NMR (CDCl$_3$) δ 1.75 (1H, t), 3.53 (3H, s), 4.63 (2H, d), 5.22 (2H, s), 6.95 (1H, ddd), 7.06 (1H, dd), 7.20 (1H, dd).

Reference Example 53

Ethyl {[4-fluoro-3-(methoxymethoxy)benzyl]thio}acetate

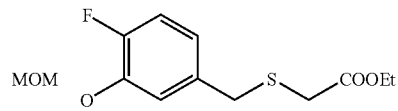

In the same manner as in Reference Example 24, an objective product was obtained from [4-fluoro-3-(methoxymethoxy)phenyl]methanol.

An oily matter; $^1$H-NMR (CDCl$_3$) δ 1.29 (3H, t), 3.07 (2H, s), 3.52 (3H, s), 3.78 (2H, s), 4.18 (2H, q), 5.21 (2H, s), 6.92 (1H, ddd), 7.02 (1H, dd), 7.18 (1H, dd).

Reference Example 54

Ethyl [(4-fluoro-3-hydroxybenzyl)thio]acetate

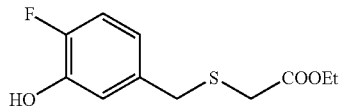

In the same manner as in Reference Example 25, an objective product was obtained from ethyl {[4-fluoro-3-(methoxymethoxy)benzyl]thio}acetate.

An oily matter; $^1$H-NMR (CDCl$_3$) δ 1.30 (3H, t), 3.06 (2H, s) 3.75 (2H, s), 4.18 (2H, q), 5.22 (1H, d), 6.81 (1H, ddd), 6.97-7.03 (2H, m).

Reference Example 55

(2-Fluoro-5-methoxyphenyl)methanol

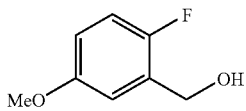

In the same manner as in Reference Example 23, an objective product was obtained from 2-fluoro-5-methoxybenzaldehyde.

An oily matter; $^1$H-NMR (CDCl$_3$) δ 1.83 (1H, t), 3.79 (3H, s), 4.73 (2H, d), 6.76 (1H, td), 6.93-6.99 (2H, m).

Reference Example 56

Ethyl [(2-fluoro-5-methoxybenzyl)thio]acetate

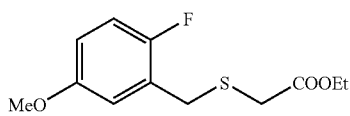

In the same manner as in Reference Example 24, an objective product was obtained from (2-fluoro-5-methoxyphenyl)methanol.

An oily matter; $^1$H-NMR (CDCl$_3$) δ 1.30 (3H, t), 3.16 (2H, s), 3.79 (3H, s), 3.83 (2H, s), 4.19 (2H, q), 6.71-6.79 (1H, m), 6.89 (1H, dd), 6.98 (1H, t).

Reference Example 57

Ethyl [(2-fluoro-5-hydroxybenzyl)thio]acetate

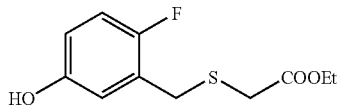

To a suspension of aluminum chloride (3.6 g) in toluene (20 ml) was added 1-octanethiol (12.7 g) at room temperature and the mixture was stirred for 0.5 hour. A solution of ethyl [(2-fluoro-5-methoxybenzyl)thio]acetate (2.81 g) in toluene (20 ml) was added thereto at room temperature, and the mixture was stirred at room temperature for 2 hours. The reaction solution was poured into iced water and twice extracted with ethyl acetate. The collected organic layer was dried over anhydrous magnesium sulfate, and the solvent was distilled off under reduced pressure. The obtained crude product was purified by silica gel column chromatography (hexane to hexane:ethyl acetate=3:1) to obtain an objective product (1.97 g) as an oily matter.

$^1$H-NMR (CDCl$_3$) δ 1.29 (3H, t), 3.15 (2H, s), 3.80 (2H, d), 4.18 (2H, q), 5.04 (1H, s), 6.69 (1H, td), 6.83 (1H, dd), 6.91 (1H, t).

Reference Example 58

1-{2-Methyl-5-[4-(trifluoromethyl)phenyl]-3-furyl}ethanone

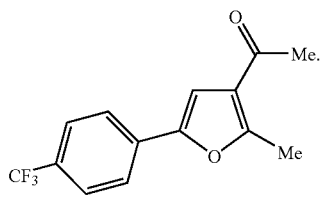

To a solution of 1,8-azabicyclo[5.4.0]-7-undecene (18.8 g) in toluene (50 ml) was added dropwise a solution of acetyl acetone (1.24 g) in toluene (30 ml) with ice-cooling. The reaction solution was stirred as such for 10 minutes, and then a solution of 2-bromo-4'-(trifluoromethyl)acetophenone (33.1 g) in toluene (80 ml) was added thereto with ice-cooling. The mixture was further stirred at room temperature for 2 hours. The produced precipitate was filtered and washed with toluene. The obtained toluene solution was passed through silica gel and the silica gel was washed with ethyl acetate-hexane (1:1). The collected solution was concentrated under reduced pressure, ethyl acetate-hexane was removed to obtain the toluene solution. To the toluene solution was added 4-toluenesulfonic acid.1 hydrate (2.4 g) and the mixture was stirred at 100° C. for 1.5 hours. The reaction solution was washed with an aqueous sodium hydrogen carbonate solution and the aqueous layer was extracted with ethyl acetate. The organic layer was collected and dried over magnesium sulfate and the solvent was distilled off under reduced pressure. The obtained crude product was purified by silica gel column chromatography (hexane:ethyl acetate=15:1) and crystallized from cold methanol to obtain an objective product (10.7 g) as crystals.

Melting point 87-88° C.; $^1$H-NMR (CDCl$_3$) δ 2.48 (3H, s), 2.69 (3H, s), 6.98 (1H, s), 7.64 (2H, d), 7.75 (2H, d).

Reference Example 59

[4-Fluoro-3-(methoxymethoxy)phenyl]acetonitrile

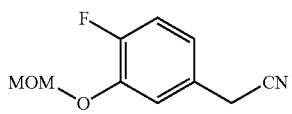

To a solution of [4-fluoro-3-(methoxymethoxy)phenyl]methanol (2.35 g), acetone cyanohydrin (1.61 g) and tributylphosphine (3.83 g) in tetrahydrofuran (70 ml) was added a solution (8.30 g) of 40% diethyl azodicarboxylate in toluene at room temperature and the mixture was stirred overnight. The solvent of the reaction solution was distilled off under reduced pressure and diisopropyl ether was added. The precipitate was filtered off and washed with diisopropyl ether. The solvent of the filtrate was distilled off under reduced pressure and the obtained crude product was purified by silica gel column chromatography (hexane:ethyl acetate=9:1 to 6:1) to obtain an objective product (2.27 g) as an oily matter.

$^1$H-NMR (CDCl$_3$) δ 3.53 (3H, s), 3.71 (2H, s), 5.23 (2H, s), 6.91-6.99 (1H, m), 7.05-7.18 (2H, m).

Reference Example 60

Ethyl (4-fluoro-3-hydroxyphenyl)acetate

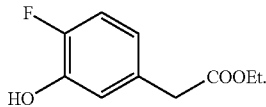

A mixture of [4-fluoro-3-(methoxymethoxy)phenyl]acetonitrile (2.27 g), sodium hydroxide (2.3 g), water (8 ml) and ethanol (30 ml) was stirred at 80° C. overnight. The solvent of the reaction solution was distilled off under reduced pressure and diluted with water. The reaction solution was acidified with dilute hydrochloric acid and twice extracted with ethyl acetate. The collected organic layer was dried over anhydrous sodium sulfate and the solvent was distilled off under reduced pressure to obtain an oily matter. The obtained oily matter was dissolved in ethanol (40 ml) and concentrated hydrochloric acid (0.5 ml) was added. The reaction mixture was stirred at 80° C. overnight. The reaction solution was diluted with water and twice extracted with ethyl acetate. The collected organic layer was dried over anhydrous sodium sulfate and the solvent was distilled off under reduced pressure. The obtained crude product was purified by silica gel column chromatography (hexane:ethyl acetate=6:1 to 3:1) to obtain an objective product (1.50 g) as an oily matter.

$^1$H-NMR (CDCl$_3$) δ 1.26 (3H, t), 3.53 (2H, s), 4.15 (2H, q), 5.17 (1H, d), 6.76 (1H, ddd), 6.94 (1H, dd), 7.01 (1H, dd).

Reference Example 61

(2-Fluoro-5-methoxyphenyl)acetonitrile

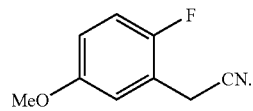

In the same manner as in Reference Example 59, an objective product was obtained from (2-fluoro-5-methoxyphenyl)methanol obtained in Reference Example 55. An oily matter; $^1$H-NMR (CDCl$_3$) δ 3.74 (2H, s), 3.80 (3H, s), 6.82 (1H, td), 6.94 (1H, dd), 7.01 (1H, t).

Reference Example 62

Ethyl (2-fluoro-5-hydroxyphenyl)acetate

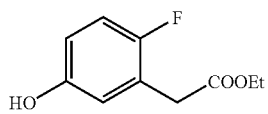

A mixture of (2-fluoro-5-methoxyphenyl)acetonitrile (1.91 g), sodium hydroxide (2.3 g), water (7 ml) and ethanol (30 ml) were stirred at 80° C. overnight. The solvent of the reaction solution was distilled off under reduced pressure and diluted with water. The reaction solution was acidified with dilute hydrochloric acid and twice extracted with ethyl acetate. The collected organic layer was dried over anhydrous sodium sulfate and the solvent was distilled off under reduced pressure to obtain an oily matter. The obtained oily matter was dissolved in ethanol (40 ml) and concentrated hydrochloric acid (0.5 ml) was added. The reaction mixture was stirred at 80° C. overnight. The reaction solution was diluted with water and twice extracted with ethyl acetate. The collected organic layer was dried over anhydrous sodium sulfate and the solvent was distilled off under reduced pressure to obtain an oily matter.

To a suspension of aluminum chloride (3.9 g) in toluene (30 ml) was added 1-octanethiol (13.5 g) at room temperature and the mixture was stirred for 0.5 hour. A solution of the obtained oily matter in toluene (20 ml) was added at room temperature and the mixture was stirred at room temperature for 2 hours. The reaction solution was poured into iced water and twice extracted with ethyl acetate. The collected organic layer was dried over anhydrous magnesium sulfate, and the solvent was distilled off under reduced pressure. The obtained crude product was purified by silica gel column chromatography (hexane to hexane:ethyl acetate=3:1) to obtain an objective product (1.84 g) as a solid matter. Melting point 85-87° C.;

$^1$H-NMR (CDCl$_3$) δ 1.27 (3H, t), 3.61 (2H, d), 4.19 (2H, q), 5.00 (1H, s), 6.65-6.73 (2H, m), 6.91 (1H, t).

Reference Example 63

[3-(Methoxymethoxy)-2-methylphenyl]methanol

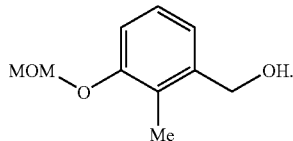

In the same manner as in Reference Example 52, an objective product was obtained from 3-hydroxy-2-methylbenzoic acid.

An oily matter; $^1$H-NMR (CDCl$_3$) δ 1.58 (1H, t), 2.26 (3H, s), 3.49 (3H, s), 4.69 (2H, d), 5.20 (2H, s), 7.03 (2H, d), 7.14 (1H, dd).

Reference Example 64

Ethyl [(3-hydroxy-2-methylbenzyl)thio]acetate

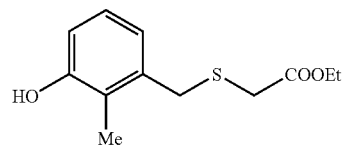

In the same manner as in Reference Example 24, ethyl {[3-(methoxymethoxy)-2-methylbenzyl]thio}acetate was obtained from [3-(methoxymethoxy)-2-methylphenyl]methanol, and the obtained matter was further processed by the method as described in Reference Example 25 to obtain an objective product.

An oily matter; $^1$H-NMR (CDCl$_3$) δ 1.31 (3H, t), 2.27 (3H, s) 3.12 (2H, s), 3.85 (2H, s), 4.20 (2H, q), 4.80 (1H, s), 6.71 (1H, d), 6.83 (1H, d), 7.00 (1H, t).

Reference Example 65

[2-Ethoxy-5-(tetrahydro-2H-pyran-2-yloxy)phenyl]methanol

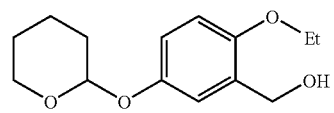

A suspended matter (2.98 g) of 60% sodium hydride in liquid paraffin was twice washed with hexane and then suspended in tetrahydrofuran (30 ml). A solution of methyl 2-hydroxy-5-(tetrahydro-2H-pyran-2-yloxy)benzoate (10.9 g) in tetrahydrofuran (80 ml) was added with ice-cooling and the mixture was stirred for 30 minutes. Ethyl iodide (4.16 ml) was added thereto with ice-cooling and the mixture was stirred at 60° C. for 2 days. The reaction solution was poured into water and twice extracted with ethyl acetate. The collected organic layer was dried over anhydrous magnesium sulfate, and the solvent was distilled off under reduced pressure to obtain an oily matter.

To a suspension of aluminum lithium hydride (2.5 g) in tetrahydrofuran (100 ml) was added dropwise a solution of the obtained oily matter in tetrahydrofuran (100 ml) with ice-cooling and the mixture was stirred at room temperature overnight. The reaction solution was ice-cooled, and water (2.5 ml), a 15% aqueous sodium hydroxide solution (2.5 ml) and water (6 ml) were sequentially added dropwise. Excess aluminum lithium hydride was decomposed and then the resulting mixture was stirred at room temperature for 2 hours. The obtained precipitate was filtered off and then washed with ethyl acetate. The solvent of the collected filtrate was distilled off under reduced pressure. The obtained crude product was purified by silica gel column chromatography (hexane:ethyl acetate=6:1 to 2:1) to obtain an objective product (6.64 g) as an oily matter.

$^1$H-NMR (CDCl$_3$) δ 1.42 (3H, t), 1.53-2.05 (6H, m), 2.49 (1H, t), 3.53-3.64 (1H, m), 3.87-4.00 (1H, m), 4.04 (2H, q), 4.65 (2H, d), 5.31 (1H, t), 6.78 (1H, d), 6.91-7.10 (2H, m).

Reference Example 66

Ethyl [(2-ethoxy-5-hydroxybenzyl)thio]acetate

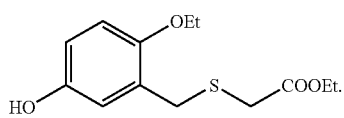

In the same manner as in Reference Example 24, ethyl {[2-ethoxy-5-(tetrahydro-2H-pyran-2-yloxy)benzyl]thio}acetate was obtained from [2-ethoxy-5-(tetrahydro-2H-pyran-2-yloxy)phenyl]methanol, and the obtained matter was further processed by the method as described in Reference Example 25 to obtain an objective product.

An oily matter; $^1$H-NMR (CDCl$_3$) δ 1.29 (3H, t), 1.40 (3H, t), 3.17 (2H, s), 3.80 (2H, s), 4.00 (2H, q), 4.19 (2H, q), 4.69 (1H, s), 6.66-6.81 (3H, m).

Reference Example 67

Ethyl (3-hydroxy-2-methylphenyl)acetate

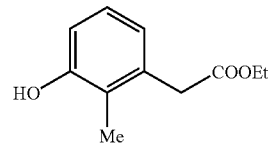

In the same manner as in Reference Example 59, [3-(methoxymethoxy))-2-methylphenyl]acetonitrile was obtained from [3-(methoxymethoxy)-2-methylphenyl]methanol, and the obtained matter was further processed by the method as described in Reference Example 60 to obtain an objective product.

An oily matter; $^1$H-NMR (CDCl$_3$) δ 1.25 (3H, t), 2.19 (3H, s), 3.64 (2H, s), 4.16 (2H, q), 4.85 (1H, s), 6.69 (1H, d), 6.79 (1H, d), 7.02 (1H, t).

Reference Example 68

[3-(Methoxymethoxy)-4-methylphenyl]methanol

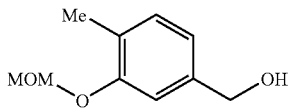

In the same manner as in Reference Example 52, an objective product was obtained from 3-hydroxy-4-methylbenzoic acid.

An oily matter; $^1$H-NMR (CDCl$_3$) δ 1.65 (1H, t), 2.24 (3H, s), 3.49 (3H, s), 4.64 (2H, d), 5.22 (2H, s), 6.91 (1H, dd), 7.06 (1H, s), 7.14 (1H, d).

Reference Example 69

Ethyl [(3-hydroxy-4-methylbenzyl)thio]acetate

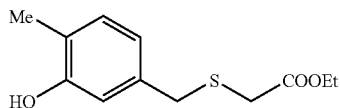

In the same manner as in Reference Example 24, ethyl {[3-(methoxymethoxy)-4-methylbenzyl]thio}acetate was obtained from [3-(methoxymethoxy)-4-methylphenyl] methanol, and the obtained matter was further processed by the method as described in Reference Example 25 to obtain an objective product.

An oily matter; $^1$H-NMR (CDCl$_3$) δ 1.29 (3H, t), 2.23 (3H, s), 3.07 (2H, s), 3.75 (2H, s), 4.18 (2H, q), 4.79 (1H, s), 6.78 (1H, s), 6.80 (1H, d), 7.06 (1H, d).

Reference Example 70

1-(3-Methoxyphenyl)butan-1-ol

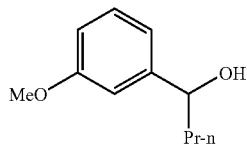

To a solution of 3-methoxybenzaldehyde (13.1 g) in tetrahydrofuran (100 ml) was added dropwise a 2 N solution (72 ml) of propylmagnesium bromide in tetrahydrofuran at −78° C. and the reaction solution was stirred at −50° C. for 1 hour. The reaction solution was poured into an aqueous ammonium chloride solution and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=6:1) to obtain an objective product (14.8 g) as an oily matter.

$^1$H-NMR (CDCl$_3$) δ 0.93 (3H, t), 1.21-1.53 (2H, m), 1.61-1.83 (2H, m), 1.82 (1H, d), 3.82 (3H, s), 4.62-4.71 (1H, m), 6.79-6.84 (1H, m), 6.91-6.94 (2H, m), 7.26 (1H, t).

Reference Example 71

S-[1-(3-methoxyphenyl)butyl]thioacetate

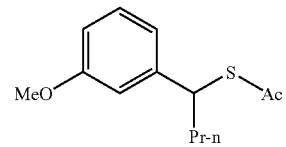

To a solution of 1-(3-methoxyphenyl)butan-1-ol (3.89 g) and triethylamine (4.5 ml) in ethyl acetate (30 ml) was added dropwise methanesulfonyl chloride (2.0 ml) with ice-cooling, and the mixture was stirred as such for 0.5 hour. The produced precipitate was filtered and washed with ethyl acetate. The solvent of the obtained filtrate was distilled off under reduced pressure to obtain an oily matter. The obtained oily matter was dissolved in N,N-dimethylformamide (15 ml) and potassium thioacetate (3.7 g) was added at room temperature. The reaction mixture was stirred at 50° C. overnight. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=15:1) to obtain an objective product (4.41 g) as an oily matter.

$^1$H-NMR (CDCl$_3$) δ 0.90 (3H, t), 1.17-1.46 (2H, m), 1.89 (2H, q), 2.29 (3H, s), 3.80 (3H, s), 4.55 (1H, t), 6.74-6.90 (3H, m), 7.22 (1H, t)

Reference Example 72

Ethyl {[1-(3-methoxyphenyl)butyl]thio}acetate

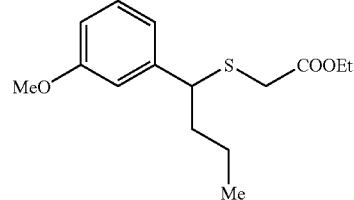

To a solution of S-[1-(3-methoxyphenyl)-butyl]thioacetate (1.89 g) in methanol (50 ml) was added sodium hydroxide (0.32 g) at room temperature and the mixture was stirred as such for 1 hour. The solvent of the mixture was distilled off under reduced pressure to obtain a solid matter. The obtained solid matter was dissolved in N,N-dimethylformamide (20 ml) and ethyl bromoacetate (1.1 ml) was added at room temperature. The reaction mixture was stirred at 60° C. for 1 hour. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=9:1) to obtain an objective product (1.60 g) as an oily matter.

$^1$H-NMR (CDCl$_3$) δ 0.88 (3H, t), 1.22-1.39 (2H, m), 1.26 (3H, t), 1.73-1.89 (2H, m), 2.90 (1H, d), 3.00 (1H, d), 3.81 (3H, s), 3.96 (1H, dd), 4.13 (2H, dq), 6.76-6.80 (1H, m), 6.87-6.90 (2H, m), 7.22 (1H, t).

Reference Example 73

Ethyl {[1-(3-hydroxyphenyl)butyl]thio}acetate

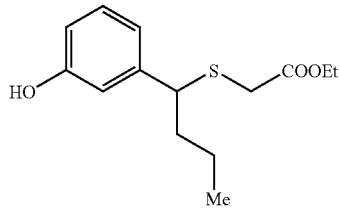

In the same manner as in Reference Example 57, an objective product was obtained from ethyl {[1-(3-methoxyphenyl)butyl]thio}acetate.

An oily matter; $^1$H-NMR (CDCl$_3$) δ 0.88 (3H, t), 1.21-1.40 (2H, m), 1.26 (3H, t), 1.75-1.88 (2H, m), 2.91 (1H, d), 3.02 (1H, d), 3.94 (1H, t), 4.13 (2H, q), 4.90 (1H, s), 6.69-6.75 (1H, m), 6.82 (1H, t), 6.87 (1H, d), 7.18 (1H, t).

Reference Example 74

4-Chloro-3-(methoxymethoxy)benzyl acetate

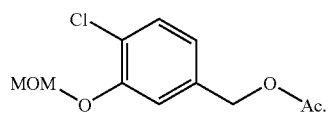

To a solution of 2-chloro-4-methylphenol (5.19 g) in tetrahydrofuran (50 ml) was added N-ethyldiisopropylamine (8.3 ml) at room temperature and the mixture was stirred for 0.5 hour.
Chloromethylmethyl ether (3.8 g) was added thereto at room temperature and the mixture was stirred at 60° C. overnight. The reaction solution was poured into water and twice extracted with ethyl acetate. The collected organic layer was dried over anhydrous magnesium sulfate and passed through silica gel. The solvent was distilled off under reduced pressure to obtain an oily matter.
A solution of the obtained oily matter, N-bromosuccinimide (6.5 g) and 2,2'-azobis(isobutyronitrile) (0.5 g) in tetrachloromethane (30 ml) was heated under reflux for 3 hours. After the reaction solution was cooled to room temperature, the precipitate was filtered off and then washed with diethyl ether. The solvent of the collected filtrate was distilled off under reduced pressure to obtain an oily matter. The obtained oily matter was dissolved in N,N-dimethylformamide (50 ml) and sodium acetate (6.0 g) was added at room temperature. The mixture was stirred at 60° C. overnight. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=9:1 to 6:1) to obtain an objective product (2.29 g) as an oily matter.

$^1$H-NMR (CDCl$_3$) δ 2.11 (3H, s), 3.53 (3H, s), 5.04 (2H, s), 5.26 (2H, s), 6.95 (1H, dd), 7.16 (1H, d), 7.35 (1H, d).

Reference Example 75

[4-Chloro-3-(methoxymethoxy)phenyl]methanol

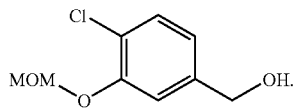

A mixture of 4-chloro-3-(methoxymethoxy)benzyl acetate (2.29 g), a 1 N aqueous sodium hydroxide solution (14 ml), methanol (20 ml) and tetrahydrofuran (20 ml) was stirred at room temperature overnight. The reaction solution was concentrated, diluted with water and twice extracted with ethyl acetate. The collected organic layer was dried over anhydrous sodium sulfate and passed through silica gel. The solvent was distilled off under reduced pressure to obtain an objective product (1.92 g) as an oily matter.

$^1$H-NMR (CDCl$_3$) δ 1.82 (1H, br t), 3.52 (3H, s), 4.65 (2H, d), 5.26 (2H, s), 6.95 (1H, tdd), 7.18 (1H, d), 7.34 (1H, d).

Reference Example 76

Ethyl [(4-chloro-3-hydroxybenzyl)thio]acetate

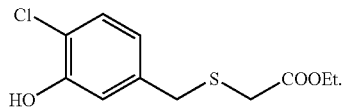

In the same manner as in Reference Example 24, ethyl {[4-chloro-3-(methoxymethoxy)benzyl]thio}acetate was obtained from [4-chloro-3-(methoxymethoxy)phenyl]methanol, and the obtained matter was further processed by the method as described in Reference Example 25 to obtain an objective product.

An oily matter; $^1$H-NMR (CDCl$_3$) δ 1.29 (3H, t), 3.06 (2H, s), 3.76 (2H, s), 4.18 (2H, q), 5.53 (1H, s), 6.85 (1H, dd), 7.01 (1H, d), 7.25 (1H, d).

Reference Example 77

3-(Acetyloxy)-5-methylbenzyl acetate

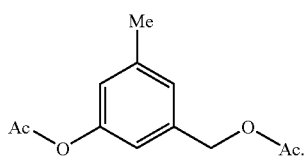

To a solution of 3,5-dimethylphenol (10.1 g) in pyridine (50 ml) was added acetyl chloride (7.8 g) with ice-cooling and the mixture was stirred at room temperature overnight. The reaction solution was poured into water and twice extracted with ethyl acetate. The collected organic layer was dried over anhydrous magnesium sulfate, and the solvent was distilled off under reduced pressure. The obtained residue was subject to silica gel column chromatography (hexane:ethyl acetate=6:1) to obtain an oily matter.

A solution of the obtained oily matter, N-bromosuccinimide (14.8 g) and 2,2'-azobis(isobutyronitrile) (0.3 g) in tetrachloromethane (50 ml) was heated under reflux for 1 hour. After the reaction solution was cooled to room temperature, the precipitate was filtered off and then washed with diethyl ether. The solvent of the collected filtrate was distilled off under reduced pressure to obtain an oily matter. The obtained oily matter was dissolved in N,N-dimethylformamide (50 ml) and sodium acetate (13.6 g) was added thereto at room temperature. The mixture was stirred at 60° C. for 6 hours. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=6:1 to 3:1) to obtain an objective product (9.87 g) as an oily matter.

$^1$H-NMR (CDCl$_3$) δ 2.10 (3H, s), 2.29 (3H, s), 2.36 (3H, s), 5.05 (2H, s), 6.86 (1H, s), 6.88 (1H, d), 7.02 (1H, d).

Reference Example 78

[3-(Methoxymethoxy)-5-methylphenyl]methanol

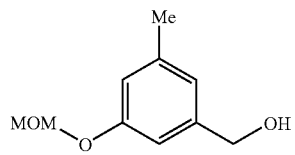

3-(Acetyloxy)-5-methylbenzyl acetate (9.87 g) was dissolved in methanol (20 ml) and tetrahydrofuran (30 ml).

A solution of a 0.5 N aqueous sodium hydroxide solution (89 ml) was added dropwise with ice-cooling and the mixture was stirred as such for 1 hour. The reaction solution was concentrated, diluted with water, and twice extracted with ethyl acetate. The collected organic layer was dried over anhydrous sodium sulfate and passed through silica gel. The solvent was distilled off under reduced pressure to obtain an oily matter.

To a solution of the obtained oily matter in tetrachloromethane (50 ml) was added N-ethyldiisopropylamine (4.4 ml) with ice-cooling and the mixture was stirred for 0.5 hour. Chloromethylmethyl ether (1.9 ml) was added thereto at 0° C. and the mixture was stirred at 60° C. overnight. The reaction solution was poured into water and twice extracted with ethyl acetate. The collected organic layer was dried over anhydrous magnesium sulfate and passed through silica gel. The solvent was distilled off under reduced pressure to obtain an oily matter. A mixture of the obtained oily matter, a 1 N aqueous sodium hydroxide solution (40 ml), methanol (30 ml) and tetrahydrofuran (30 ml) was stirred at room temperature overnight. The reaction solution was concentrated, diluted with water, and twice extracted with ethyl acetate. The collected organic layer was dried over anhydrous sodium sulfate and the solvent was distilled off under reduced pressure. The obtained crude product was purified by silica gel column chromatography (hexane:ethyl acetate=3:1 to 2:1) to obtain an objective product (2.11 g) as an oily matter.

$^1$H-NMR (CDCl$_3$) δ 1.64 (1H, t), 2.33 (3H, s), 3.47 (3H, s), 4.63 (2H, d), 5.16 (2H, s), 6.78 (1H, s), 6.83 (1H, s), 6.84 (1H, s).

Reference Example 79

Ethyl [3-(hydroxy)-5-methylbenzyl)thio]acetate

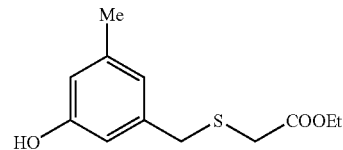

In the same manner as in Reference Example 24, ethyl {[3-(methoxymethoxy)-5-methylbenzyl]thio}acetate was obtained from [(3-(methoxymethoxy)-5-methylphenyl) methanol, and the obtained matter was further processed by the method as described in Reference Example 25 to obtain an objective product.

An oily matter; $^1$H-NMR (CDCl$_3$) δ 1.29 (3H, t), 2.29 (3H, s) 3.09 (2H, s), 3.73 (2H, s), 4.18 (2H, q), 4.79 (1H, s), 6.55 (1H, s), 6.62 (1H, s), 6.71 (1H, s).

Reference Example 80

Ethyl (3-hydroxy-5-methylphenyl)acetate

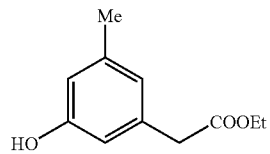

In the same manner as in Reference Example 59, [3-(methoxymethoxy))-5-methylphenyl]acetonitrile was obtained from [3-(methoxymethoxy)-5-methylphenyl]methanol, and the obtained matter was further processed by the method as described in Reference Example 60 to obtain an objective product.

An oily matter; $^1$H-NMR (CDCl$_3$) δ 1.26 (3H, t), 2.28 (3H, s), 3.51 (2H, s), 4.15 (2H, q), 4.88 (1H, s), 6.55-6.58 (2H, m), 6.65 (1H, s).

Reference Example 81

Ethyl (2E)-3-[2-ethyl-5-(3-methoxyphenyl)-3-furyl]acrylate

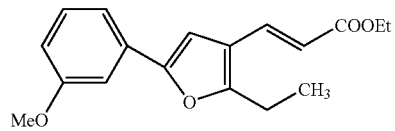

In the same manner as in Reference Example 7,2-ethyl-5-(3-methoxyphenyl)-3-furaldehyde was obtained from [2-ethyl-5-(3-methoxyphenyl)-3-furyl]methanol obtained in Reference Example 6(13), and the obtained matter was further processed by the method as described in Reference Example 8 to obtain an objective product.

An oily matter; $^1$H-NMR (CDCl$_3$) δ 1.32 (3H, t), 1.33 (3H, t), 2.84 (2H, q), 3.86 (3H s), 4.25 (2H, q), 6.13 (1H, d), 6.73 (1H, s), 6.83 (1H, ddd), 7.18-7.35 (3H, m), 7.58 (1H, d).

Reference Example 82

Ethyl 3-[2-ethyl-5-(3-methoxyphenyl)-3-furyl]propionate

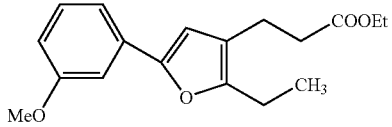

In the same manner as in Reference Example 9, an objective product was obtained from ethyl (2E)-3-[2-ethyl-5-(3-methoxyphenyl)-3-furyl]acrylate.

An oily matter; $^1$H-NMR (CDCl$_3$) δ 1.25 (3H, t), 1.25 (3H, t) 2.49-2.75 (6H, m), 3.85 (3H, s), 4.14 (2H, q), 6.46 (1H, s), 6.76 (1H, ddd), 7.14-7.30 (3H, m).

Reference Example 83

3-[2-Ethyl-5-(3-methoxyphenyl)-3-furyl]propan-1-ol

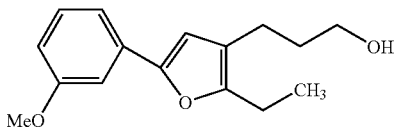

In the same manner as in Reference Example 11, an objective product was obtained from ethyl 3-[2-ethyl-5-(3-methoxyphenyl)-3-furyl]propionate.

An oily matter; $^1$H-NMR (CDCl$_3$) δ 1.26 (3H, t), 1.75-1.89 (2H, m), 2.47 (2H, t), 2.65 (2H, q), 3.69 (2H, q), 3.85 (3H, s), 6.48 (1H, S), 6.73-6.79 (1H, m), 7.15-7.30 (3H, m).

Reference Example 84

1-[3-(Methoxymethoxy)phenyl]ethanol

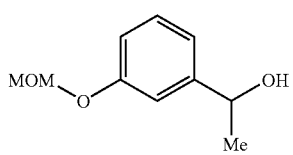

To a solution of 3-(methoxymethoxy)benzaldehyde (13.3 g) in tetrahydrofuran (100 ml) was added dropwise a 1 N solution (120 ml) of methylmagnesium bromide in tetrahydrofuran at −78° C. and the reaction solution was stirred at −78° C. for 1 hour. The reaction solution was poured into an aqueous ammonium chloride solution, and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=6:1 to 2:1) to obtain an objective product (11.4 g) as an oily matter.

$^1$H-NMR (CDCl$_3$) δ 1.49 (3H, d), 1.79 (1H, d), 3.49 (3H, s) 4.82-4.93 (1H, m), 5.19 (2H, s), 6.92-7.06 (3H, m), 7.27 (1H, t).

Reference Example 85

S-{1-[3-(methoxymethoxy)phenyl]ethyl}thioacetate

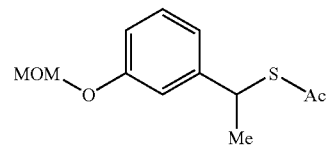

In the same manner as in Reference Example 71, an objective product was obtained from 1-[3-(methoxymethoxy)phenyl]ethanol.

An oily matter; $^1$H-NMR (CDCl$_3$) δ 1.64 (3H, d), 2.30 (3H, s), 3.48 (3H, S), 4.71 (1H, q), 5.17 (2H, S), 6.90-7.00 (3H, m), 7.23 (1H, t).

Reference Example 86

Ethyl 2-({1-[3-(methoxymethoxy)phenyl]ethyl}thio)-2-methylpropionate

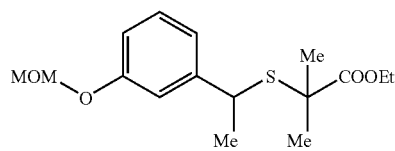

In the same manner as in Reference Example 27, an objective product was obtained from S-{1-[3-(methoxymethoxy)phenyl]ethyl}thioacetate.

An oily matter; $^1$H-NMR (CDCl$_3$) δ 1.20 (3H, t), 1.40 (3H, s) 1.52 (3H, S), 1.53 (3H, d), 3.48 (3H, S), 3.96 (1H, q), 3.97 (1H, q), 4.09 (1H, q), 5.17 (2H, s), 6.88 (1H, ddd), 6.97 (1H, d), 6.99 (1H, s), 7.20 (1H, t).

Reference Example 87

Ethyl 2-{[1-(3-hydroxyphenyl)ethyl]thio}-2-methylpropionate

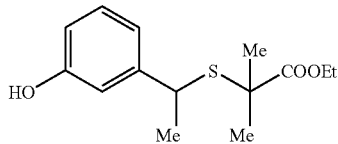

In the same manner as in Reference Example 28, an objective product was obtained from ethyl 2-({1-[3-(methoxymethoxy)phenyl]ethyl}thio)-2-methylpropionate. An oily matter; $^1$H-NMR (CDCl$_3$) δ 1.19 (3H, t), 1.40 (3H, s), 1.51 (3H, d), 1.52 (3H, s), 3.92 (1H, q), 3.93 (1H, q), 4.06 (1H, q), 4.90 (1H, s), 6.67 (1H, ddd), 6.82 (1H, t), 6.87 (1H, d), 7.14 (1H, t).

Reference Example 88

2-[3-(Methoxymethoxy)phenyl]propionitrile

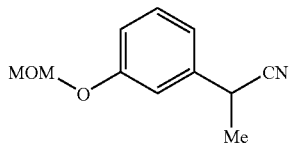

To a solution of 1-[3-(methoxymethoxy)phenyl]ethanol (1.59 g), acetone cyanohydrin (1.1 g) and tributylphosphine (3.3 ml) in tetrahydrofuran (70 ml) was added 1,1'-(azodicarbonyl)dipiperidine (3.3 g) at room temperature and the mixture was stirred overnight. The solvent of the reaction solution was distilled off under reduced pressure and diisopropyl ether was added. The precipitate was filtered off and washed with diisopropyl ether. The solvent of the filtrate was distilled off under reduced pressure and the obtained crude product was purified by silica gel column chromatography (hexane:ethyl acetate=15:1 to 6:1) to obtain an objective product (0.88 g) as an oily matter.

An oily matter; $^1$H-NMR (CDCl$_3$) δ 1.64 (3H, d), 3.49 (3H, s), 3.87 (1H, q), 5.19 (2H, s), 6.99-7.02 (3H, m), 7.30 (1H, t).

Reference Example 89

Ethyl 2-(3-hydroxyphenyl)propionate

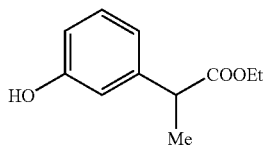

In the same manner as in Reference Example 60, an objective product was obtained from 2-[3-(methoxymethoxy)phenyl]propionitrile.

An oily matter; $^1$H-NMR (CDCl$_3$) δ 1.21 (3H, t), 1.47 (3H, d), 3.65 (1H, q), 4.06-4.38 (2H, m), 4.88 (1H, s), 6.72 (1H, ddd), 6.79 (1H, dd), 6.85 (1H, d), 7.17 (1H, t).

Reference Example 90

Ethyl 2-(2-fluoro-4-methoxyphenoxy)-2-methylpropionate

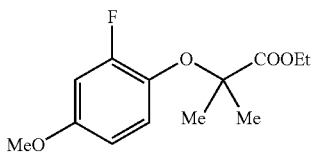

To a solution of 2-fluoro-4-methoxyphenol (5.29 g) and ethyl 2-bromo-2-methylpropionate (8.7 g) in N,N-dimethylformamide (30 ml) was added potassium carbonate (10.3 g) and the mixture was stirred at 90° C. overnight. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=15:1) to obtain an objective product (5.86 g) as an oily matter.

$^1$H-NMR (CDCl$_3$) δ 1.31 (3H, t), 1.53 (6H, s), 3.75 (3H, s), 4.24 (2H, q), 6.54 (1H, ddd), 6.63 (1H, dd), 6.98 (1H, t).

Reference Example 91

Ethyl 2-(2-fluoro-4-hydroxyphenoxy)-2-methylpropionate

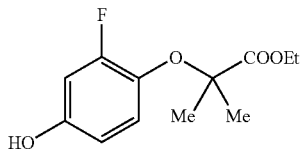

In the same manner as in Reference Example 57, an objective product was obtained from ethyl 2-(2-fluoro-4-methoxyphenoxy)-2-methylpropionate.

An oily matter; $^1$H-NMR (CDCl$_3$) δ 1.31 (3H, t), 1.52 (6H, d) 4.24 (2H, q), 4.89 (1H, s), 6.46 (1H, ddd), 6.58 (1H, dd), 6.92 (1H, t).

Reference Example 92

Ethyl 2-{[3-(methoxymethoxy)benzyl]oxy}-2-methylpropionate

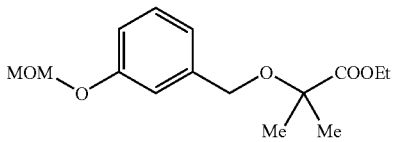

To a solution of 3-(methoxymethoxy)benzylalcohol (8.26 g) and triethylamine (10.6 ml) in ethyl acetate (100 ml) was added dropwise a solution of methanesulfonyl chloride (7.0 g) in ethyl acetate (30 ml) with ice-cooling and the mixture was stirred as such for 0.5 hour. The produced precipitate was filtered and washed with ethyl acetate. The solvent of the filtrate was distilled off under reduced pressure to obtain an oily matter.

To a solution of ethyl 2-hydroxyisobutyrate (13.4 g) in tetrahydrofuran (100 ml) was added a suspended matter (4.1 g) of 60% sodium hydride in liquid paraffin at room temperature and the mixture was stirred for 15 minutes. A solution of the obtained oily matter in tetrahydrofuran (50 ml) was added thereto at room temperature and the reaction mixture was stirred at 65° C. for 3 days. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=15:1) to obtain an objective product (5.55 g) as an oily matter.

$^1$H-NMR (CDCl$_3$) δ 1.31 (3H, t), 1.51 (6H, s), 3.48 (3H, s), 4.22 (2H, q), 4.44 (2H, s), 5.18 (2H, s), 6.92-6.97 (1H, m), 7.02-7.08 (2H, m), 7.25 (1H, t).

Reference Example 93

Ethyl 2-[(3-hydroxybenzyl)oxy]-2-methylpropionate

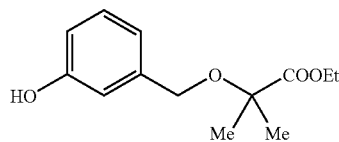

In the same manner as in Reference Example 25, an objective product was obtained from ethyl 2-{[3-(methoxymethoxy)benzyl]oxy}-2-methylpropionate.

An oily matter; $^1$H-NMR (CDCl$_3$) δ 1.30 (3H, t), 1.51 (6H, s), 4.22 (2H, q), 4.43 (2H, s), 4.86 (1H, s), 6.71-6.76 (1H, m), 6.90-6.93 (2H, m), 7.19 (1H, t).

Reference Example 94

Methyl 2-[(acetyloxy)methyl]-5-[4-(trifluoromethyl) phenyl]-3-furoate

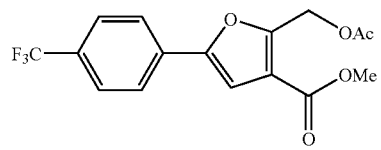

To a solution of methyl 2-methyl-5-[4-(trifluoromethyl) phenyl]-3-furoate (13.53 g) in ethyl acetate (300 ml) was added 2,2'-azobis(isobutyronitrile) (0.39 g) and N-bromosuccinimide (8.48 g) and the mixture was heated under reflux for 2 hours. The solvent was distilled off under reduced pressure to obtain a mixture of a solid matter and an oily matter. The obtained mixture was dissolved in N,N-dimethylformamide (100 ml) and sodium acetate (7.81 g) was added. The mixture was stirred at room temperature overnight. Water was added and the mixture was diluted with ethyl acetate. The organic layer was washed with water and saturated brine and dried over anhydrous magnesium sulfate and then the solvent was distilled off under reduced pressure. The residue was purified by silica gel column chromatography (hexane:ethyl acetate=5:1 to 2:1) to obtain an objective product (12.47 g) as a solid matter.

Melting point 60-61° C.; $^1$H-NMR (CDCl$_3$) δ 2.14 (3H, s), 3.89 (3H, s), 5.46 (2H, s), 7.08 (1H, s), 7.66 (2H, d), 7.78 (2H, d).

Reference Example 95

Ethyl 2-(ethoxymethyl)-5-[4-(trifluoromethyl)phenyl]-3-furoate

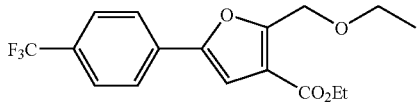

Methyl 2-[(acetyloxy)methyl]-5-[4-(trifluoromethyl)phenyl]-3-furoate (5.0 g) was dissolved in a mixed solvent of tetrahydrofuran (60 ml) and methanol (60 ml), and 1 N sodium hydroxide (32 ml) was added. The mixture was stirred at room temperature overnight. 1 N sodium hydroxide (20 ml) was further added thereto and then the mixture was stirred at room temperature for 5 hours. The mixture was acidified with concentrated hydrochloric acid and diluted with ethyl acetate. The organic layer was washed with water and saturated brine, and then dried over anhydrous magnesium sulfate. The solvent was distilled off under reduced pressure to obtain an oily matter. The obtained oily matter was dissolved in N,N-dimethylformamide (50 ml). Sodium hydride (1.76 g) and ethyl iodide (4.68 ml) were added with ice-cooling, and then the mixture was stirred for 3 hours. 1 N hydrochloric acid was added and diluted with ethyl acetate. The organic layer was washed with water and saturated brine, and then dried over anhydrous magnesium sulfate. The residue was purified by silica gel column chromatography (hexane:ethyl acetate=10:1 to 5:1) to obtain an objective product (3.65 g) as an oily matter.

$^1$H-NMR (CDCl$_3$) δ 1.26 (3H, t), 1.39 (3H, t), 3.63 (2H, q), 4.34 (2H, q), 4.85 (2H, s), 7.04 (1H, s), 7.64 (2H, d), 7.78 (2H, d).

Reference Example 96

{2-(Ethoxymethyl)-5-[4-(trifluoromethyl)phenyl]-3-furyl}methanol

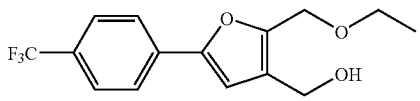

In the same manner as in Reference Example 6, an objective product was obtained from ethyl 2-(ethoxymethyl)-5-[4-(trifluoromethyl)phenyl]-3-furoate obtained in Reference Example 95.

Melting point 103-105° C.; $^1$H-NMR (CDCl$_3$) δ 1.26 (3H, dt) 3.60 (2H, dq), 4.57 (2H, s), 4.59 (2H, s), 6.77 (1H, s), 7.60 (2H, d), 7.73 (2H, d).

Reference Example 97

Ethyl 2-(4-hydroxy-2-methylbenzyl)butanoate

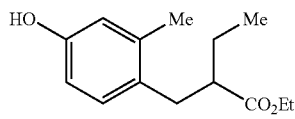

To a solution of ethyl 2-(diethoxyphosphoryl)butanoate (6.3 ml) in tetrahydrofuran (50 ml) was added a suspended matter (1.33 g) of 60% sodium hydride in liquid paraffin with ice-cooling and the mixture was stirred for 30 minutes.

A solution of 4-(benzyloxy)-2-methylbenzaldehyde (5.0 g) in tetrahydrofuran (30 ml) was added thereto and the mixture was stirred at room temperature overnight. 1 N hydrochloric acid was added to the reaction solution and the mixture was diluted with ethyl acetate. The organic layer was washed with water and saturated brine and then dried over anhydrous magnesium sulfate. The solvent was distilled off under reduced pressure. The obtained crude product was dissolved in ethanol (50 ml) and the atmosphere of the reaction vessel was substituted with a nitrogen atmosphere. 10% palladium-carbon (1.0 g) was added and the mixture was stirred overnight at room temperature under hydrogen atmosphere. A catalyst was filtered through Celite and the solvent was distilled off under reduced pressure. The obtained crude product was purified by silica gel column chromatography (hexane:ethyl acetate=10:1 to 2:1) to obtain an objective product (4.79 g) as an oily matter.

$^1$H-NMR (CDCl$_3$) δ 0.91 (3H, t), 1.19 (3H, t), 1.48-1.75 (2H, m), 2.25 (3H, s), 2.47-2.72 (2H, m), 2.84 (1H, dd), 4.07 (2H, q), 4.83-5.05 (1H, br), 6.52-6.62 (2H, m), 6.94 (1H, d).

Reference Example 97(1) to Reference Example 97(2)

In the same manner as in Reference Example 97, the below-described compounds were obtained from phosphonate corresponding to 4-(benzyloxy)-2-methylbenzaldehyde.

Reference Example 97(1)

Ethyl 3-(4-hydroxy-2-methylphenyl)-2-methylpropionate

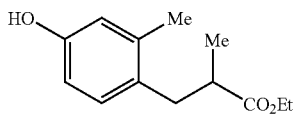

An oily matter; $^1$H-NMR (CDCl$_3$) δ 1.16 (3H, d), 1.19 (3H, t), 2.25 (3H, s), 2.53-2.72 (2H, m), 2.90-2.99 (1H, m), 4.19 (2H, q), 5.25 (1H, s), 6.54-6.63 (2H, m), 6.94 (1H, d).

Reference Example 97(2)

Ethyl 3-(4-hydroxy-2-methylphenyl)-2-methoxypropionate

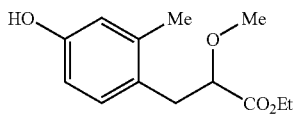

An oily matter; $^1$H-NMR (CDCl$_3$) δ 1.32 (3H, t), 2.28 (3H, s), 2.95 (2H, d), 3.32 (3H, s), 3.86-3.93 (1H, m), 4.18 (2H, q), 5.10 (1H, s), 6.56-6.64 (2H, m), 7.00 (1H, dd).

Reference Example 98

Ethyl 2-[(4-methoxyphenyl)thio]-2-methylpropionate

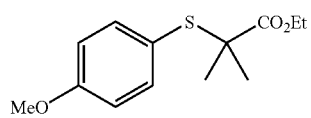

To a solution of 4-methoxybenzenethiol (3.7 ml) in N,N-dimethylformamide (100 ml) was added potassium carbonate (5.1 g) and ethyl 2-bromoisobutyrate (5.96 g), and then the mixture was stirred at 50° C. overnight. After standing to cool, the mixture was diluted with ethyl acetate and the organic layer was washed with water and saturated brine. Then, the organic layer was dried over anhydrous magnesium sulfate, and the solvent was distilled off under reduced pressure. The residue was purified by silica gel column chromatography (hexane:ethyl acetate=30:1 to 5:1) to obtain an objective product (7.11 g) as an oily matter. $^1$H-NMR (CDCl$_3$) δ 1.22 (3H, t), 1.45 (6H, s), 3.80 (3H, s), 4.10 (2H, q), 6.84 (2H, d), 7.38 (2H, d).

Reference Example 99

Ethyl 2-[(4-hydroxyphenyl)thio]-2-methylpropionate

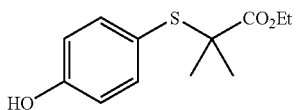

Aluminum chloride (0.88 g) was suspended in toluene (5 ml), octanethiol (3.5 ml) was added dropwise and the mixture was stirred until it was uniform. A solution of ethyl 2-[(4-methoxyphenyl)thio]-2-methylpropionate (7.06 g) in toluene (5 ml) was added and the mixture was stirred at room temperature for 3 hours. Water was added to the reaction mixture, and the mixture was diluted with ethyl acetate, washed with water and saturated brine and then dried over anhydrous magnesium sulfate. The solvent was distilled off under reduced pressure. The residue was purified by silica gel column chromatography (hexane:ethyl acetate=20:1 to 5:1) and further by recrystallization (hexane-diisopropyl ether) to obtain an objective product (6.23 g) as crystals.

Melting point 68-69° C.; $^1$H-NMR (CDCl$_3$) δ 1.26 (3H, t), 1.47 (6H, s), 4.14 (2H, q), 6.17 (1H, s), 6.68 (2H, d), 7.29 (2H, d).

Reference Example 100

Ethyl 3-(5-methoxy-1-benzofuran-2-yl)propionate
Ethyl 3-(5-methoxy-2,3-dihydro-1-benzofuran-2-yl)propionate

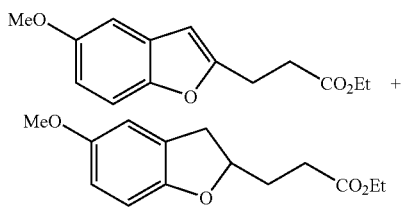

To a solution of ethyl (E)-3-(5-methoxy-1-benzofuran-2-yl)-2-propenoate (0.81 g) in ethyl acetate (10 ml) was added 10% palladium-carbon (0.20 g) under nitrogen gas stream, and the mixture was stirred under hydrogen atmosphere at room temperature for 1 hour. A catalyst was filtered through Celite and the solvent was distilled off under reduced pressure. The obtained crude product was purified by silica gel column chromatography (hexane:ethyl acetate 30:1 to 5:1) to obtain a mixture of ethyl 3-(5-methoxy-1-benzofuran-2-yl)propionate and ethyl 3-(5-methoxy-2,3-dihydro-1-benzofuran-2-yl)propionate (0.80 g) as an oily matter.

$^1$H-NMR (CDCl$_3$) δ 1.25, 1.26 (3H, t), 1.98-2.09 (0.86H, m), 2.47-2.55 (0.86H, m), 2.69-2.90 (1.58H, m), 3.08 (1.14H, t), 3.28 (0.42H, ddd), 3.74 (1.26H, s), 3.82 (1.74H, s), 4.09-4.21 (2H, m), 4.70-4.85 (0.42H, m), 6.35 (0.58H, d), 6.63-6.64 (0.86H, m), 6.73-6.74 (0.42H, m), 6.80 (0.58H, dd), 6.94 (0.58H, d), 7.27 (0.58H, d).

Reference Example 101

Ethyl 3-(5-hydroxy-1-benzofuran-2-yl)propionate
Ethyl 3-(5-hydroxy-2,3-dihydro-1-benzofuran-2-yl)propionate

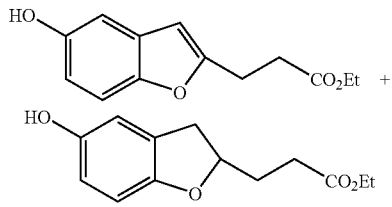

Aluminum chloride (0.88 g) was suspended in toluene (5 ml) and octanethiol (3.5 ml) was added dropwise. The mixture was stirred until it was uniform. A mixture of ethyl 3-(5-methoxy-1-benzofuran-2-yl)propionate and ethyl 3-(5-methoxy-2,3-dihydro-1-benzofuran-2-yl)propionate (0.80 g) in toluene (5 ml) was added and the mixture was stirred at room temperature for 3 hours. Water was added to the reaction mixture, and the mixture was diluted with ethyl acetate, washed with water and saturated brine and then dried over anhydrous magnesium sulfate. The solvent was distilled off under reduced pressure. The residue was purified by silica gel column chromatography (hexane:ethyl acetate=30:1 to 2:1) to obtain a mixture (0.56 g) of ethyl 3-(5-hydroxy-1-benzofuran-2-yl)propionate and ethyl 3-(5-hydroxy-2,3-dihydro-1-benzofuran-2-yl)propionate as an oily matter.

$^1$H-NMR (CDCl$_3$) δ 1.25, 1.26 (3H, t), 1.97-2.08 (0.84H, m), 2.47-2.55 (0.84H, m), 2.70-2.85 (1.56H, m), 3.07 (1.16H, t), 3.24 (0.42H, dd), 4.07-4.21 (2H, m), 4.69-4.83 (0.42H, m), 4.97 (0.42H, s), 5.23 (0.58H, s), 6.30 (0.58H, d), 6.57 (0.86H, s), 6.65-6.67 (0.42H, m), 6.72 (0.58H, dd), 6.88 (0.58H, d), 7.22 (0.58H, d).

Reference Example 102

Ethyl (5-methoxy-1-benzofuran-2-yl)acetate

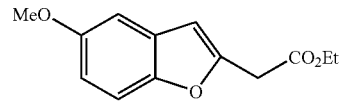

To a solution of (5-methoxy-1-benzofuran-2-yl)methanol (2.40 g) in tetrahydrofuran (100 ml) was sequentially added acetone cyanohydrin (1.85 ml), tributylphosphine (6.71 ml) and 1,1'-(azodicarbonyl)dipiperidine (26.80 g) and the mixture was stirred at 0° C. for 2 hours and at room temperature for 2 hours. The solvent of the reaction solution was distilled off under reduced pressure and diisopropyl ether was added. The precipitate was filtered off and washed with diisopropyl ether. The solvent of the filtrate was distilled off under reduced pressure of filtrate, and the obtained crude product was subject to silica gel column chromatography (hexane:ethyl acetate=30:1 to 10:1) to obtain an oily matter. The obtained oily matter was dissolved in ethanol (10 ml). An 8 N aqueous sodium hydroxide solution (10 ml) was added, and the mixture was heated under reflux overnight. The mixture was diluted with water and the aqueous layer was washed with ether. Then, the mixture was acidified with concentrated hydrochloric acid and extracted with ethyl acetate. The organic layer was combined, washed with water and saturated brine and then dried over anhydrous magnesium sulfate and the solvent was distilled off under reduced pressure to obtain a crude product. The crude product was dissolved in ethanol (10 ml) and concentrated sulfuric acid (0.1 ml) was added. The mixture was heated under reflux overnight. After standing to cool, the mixture was diluted with ethyl acetate and the organic layer was washed with water, a saturated sodium bicarbonate solution and saturated brine and then dried over anhydrous magnesium sulfate, and the solvent was distilled off under reduced pressure. The obtained crude product was purified by silica gel column chromatography (hexane:ethyl acetate=20:1 to 5:1) to obtain an objective product (0.46 g) as an oily matter.

$^1$H-NMR (CDCl$_3$) δ 1.28 (3H, t), 3.79 (2H, s), 3.82 (3H, s), 4.20 (2H, q), 6.55-6.56 (1H, m), 6.83 (1H, dd), 6.97 (1H, d), 7.31 (1H, dd).

Reference Example 103

Ethyl (5-hydroxy-1-benzofuran-2-yl)acetate

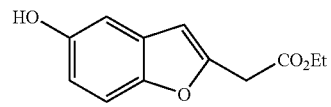

Aluminum chloride (0.53 g) was suspended in toluene (4 ml) and octanethiol (1.65 ml) was added dropwise. The mixture was stirred until it was uniform. A solution of ethyl (5-methoxy-1-benzofuran-2-yl)acetate (0.37 g) in toluene (4 ml) was added, and then the mixture was stirred at room temperature for 3 hours. Water was added to the reaction mixture, and the mixture was diluted with ethyl acetate, washed with water and saturated brine and then dried over anhydrous magnesium sulfate. The solvent was distilled off under reduced pressure. The residue was purified by silica gel column chromatography (hexane:ethyl acetate=20:1 to 5:1) to obtain an objective product (0.29 g) as an oily matter.

$^1$H-NMR (CDCl$_3$) δ 1.28 (3H, t), 3.78 (2H, s), 4.21 (2H, q), 5.10 (1H, s), 6.48 (1H, d), 6.73 (1H, dd), 6.88 (1H, d), 7.24 (1H, d).

Reference Example 104

2-Formyl-5-methoxyphenyl trifluoromethanesulfonate

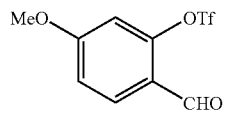

2-Hydroxy-4-methoxybenzaldehyde (10.0 g) was dissolved in tetrahydrofuran (200 ml), pyridine (39 ml) and trifluoromethanesulfonic anhydride (12.2 ml) were sequentially added with ice-cooling, and the mixture was stirred at room temperature overnight. A saturated sodium bicarbonate solution was added, and then the mixture was diluted with ethyl acetate, washed with 1 N hydrochloric acid, water and saturated brine, and then dried over anhydrous magnesium sulfate. The solvent was distilled off under reduced pressure. The residue was purified by silica gel column chromatography (hexane:ethyl acetate=20:1 to 5:1) to obtain an objective product (13.07 g) as an oily matter.

$^1$H-NMR (CDCl$_3$) δ 3.92 (3H, s), 6.87 (1H, d), 7.03 (1H, dd), 7.94 (1H, d), 10.12 (1H, s).

Reference Example 105

Ethyl (E)-3-(4-methoxy-2{([(trifluoromethyl)sulfonyl]oxy}phenyl)-2-propenoate

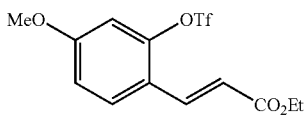

To a solution of ethyl diethylphosphonoacetate (6.1 ml) in tetrahydrofuran (100 ml) was added a suspended matter (2.2 g) of 60% sodium hydride in liquid paraffin with ice-cooling and then the mixture was stirred for 0.5 hour. A solution of 2-formyl-5-methoxyphenyl trifluoromethanesulfonate (10.0 g) in tetrahydrofuran (50 ml), and then the mixture was stirred at 0° C. for 2 hours. 1 N hydrochloric acid was added to the reaction solution and then diluted with ethyl acetate. The organic layer was washed with water and saturated brine, dried over anhydrous magnesium sulfate, and then the solvent was distilled off under reduced pressure. The obtained crude product was purified by silica gel column chromatography (hexane:ethyl acetate=20:1 to 10:1) to obtain an objective product (9.07 g) as an oily matter.

$^1$H-NMR (CDCl$_3$) δ 1.33 (3H, t), 3.86 (3H, s), 4.27 (2H, q), 6.38 (1H, d), 6.86 (1H, d), 6.95 (1H, dd), 7.63 (1H, d), 7.80 (1H, d).

Reference Example 106

Ethyl (E)-3-(2-allyl-4-methoxyphenyl)-2-propenoate

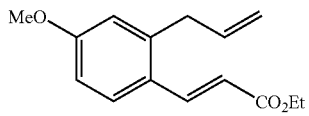

A solution of ethyl (E)-3-(4-methoxy-2-{[(trifluoromethyl)sulfonyl]oxy}phenyl)-2-propenoate (8.92 g) in N,N-dimethylformamide (100 ml) was added allyltributyl tin (9.2 ml) and tetrakis(triphenylphosphine) palladium (1.46 g) under nitrogen atmosphere, and the mixture was stirred at 80° C. overnight. The mixture was diluted with ethyl acetate, washed with a saturated sodium bicarbonate solution, water and saturated brine and then dried over anhydrous magnesium sulfate. The solvent was distilled off under reduced pressure. The obtained crude product was purified by silica gel column chromatography (hexane:ethyl acetate=30:1 to 20:1 to 10:1) to obtain an objective product (5.84 g) as an oily matter.

$^1$H-NMR (CDCl$_3$) δ 1.32 (3H, t), 3.50 (2H, d), 3.81 (3H, s), 4.24 (2H, q), 4.98-5.11 (2H, m), 5.87-6.00 (1H, m), 6.25 (1H, d), 6.73-6.79 (2H, m), 7.55 (1H, d), 7.91 (1H, d).

Reference Example 107

Ethyl 3-(4-methoxy-2-propylphenyl)propionate

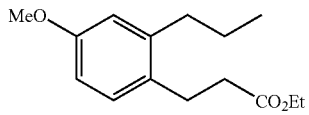

To a solution of ethyl (E)-3-(2-allyl-4-methoxyphenyl)-2-propenoate (5.23 g) in ethyl acetate (50 ml) was added 10% palladium-carbon (1.0 g) and the mixture was stirred at room temperature overnight. A catalyst was filtered and the solvent was distilled off under reduced pressure. The obtained crude product was purified by silica gel column chromatography (hexane:ethyl acetate=30:1 to 5:1) to obtain an objective product (5.35 g) as an oily matter. $^1$H-NMR (CDCl$_3$) δ 0.98

(3H, t), 1.25 (3H, t), 1.57-1.65 (2H, m), 2.51-2.58 (4H, m), 2.86-2.91 (2H, m), 3.77 (3H, m), 4.13 (2H, q), 6.65-6.70 (2H, m), 7.04 (1H, d).

Reference Example 108

Ethyl 3-(4-hydroxy-2-propylphenyl)propionate

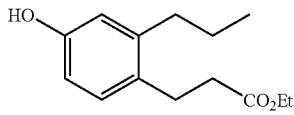

Aluminum chloride (4.02 g) was suspended in toluene (30 ml) and octanethiol (13 ml) was added dropwise. The mixture was stirred until it was uniform. Then, a solution of ethyl 3-(4-methoxy-2-propylphenyl)propionate (3.02 g) in toluene (10 ml) was added thereto and the mixture was stirred at room temperature for 3 hours. Water was added to the reaction mixture, and the mixture was diluted with ethyl acetate, washed with water and saturated brine and then dried over anhydrous magnesium sulfate. The solvent was distilled off under reduced pressure. The residue was purified by silica gel column chromatography (hexane:ethyl acetate=20:1 to 2:1) to obtain an objective product (2.52 g) as an oily matter.

$^{1}$H-NMR (CDCl$_{3}$) δ 0.97 (3H, t), 1.24 (3H, t), 1.52-1.65 (2H, m), 2.50-2.56 (4H, m), 2.85-2.90 (2H, m), 4.13 (2H, q), 6.59 (1H, dd), 6.63 (1H, d), 6.97 (1H, d).

Reference Example 109

Ethyl 2-(2-chloro-4-methoxyphenoxy)-2-methylpropionate

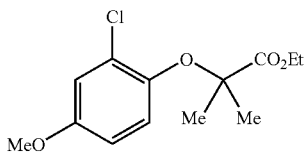

To a solution of 4-methoxy-2-chlorophenol (2.0 g) in N,N-dimethylformamide (10 ml) was added ethyl 2-bromoisobutyrate (2.0 ml) and a suspended matter (0.66 g) of 60% sodium hydride in liquid paraffin was added to the mixture with ice-cooling. The mixture was stirred at room temperature overnight. A suspended matter (0.30 g) of 60% sodium hydride in liquid paraffin was added thereto and the mixture was stirred at room temperature for 5 hours. Water was added thereto with ice-cooling and then the mixture was diluted with ethyl acetate. The organic layer was washed with water and saturated brine and then dried over anhydrous magnesium sulfate, and the solvent was distilled off under reduced pressure. The residue was purified by silica gel column chromatography (hexane:ethyl acetate=5:1) to obtain an objective product (1.01 g) as an oily matter.

$^{1}$H-NMR (CDCl$_{3}$) δ 1.31 (3H, t), 1.56 (6H, s), 3.76 (3H, s), 4.26 (2H, q), 6.68 (1H, dd), 6.92 (1H, d), 6.95 (1H, d).

Reference Example 110

Ethyl 2-(2-chloro-4-hydroxyphenoxy)-2-methylpropionate

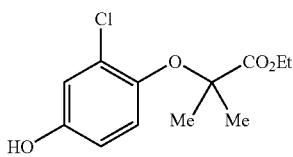

In the same manner as in Reference Example 108, an objective product was obtained from ethyl 2-(2-chloro-4-methoxyphenoxy)-2-methylpropionate obtained in Reference Example 109.

An oily matter; $^{1}$H-NMR (CDCl$_{3}$) δ 1.30 (3H, t), 1.56 (6H, s) 4.26 (2H, q), 4.84 (1H, s), 6.61 (1H, dd), 6.88 (1H, d), 6.90 (1H, d).

Reference Example 111

S-[4-fluoro-3-(methoxymethoxy)benzyl]ethylthioacetate

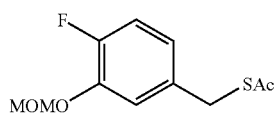

To a solution of [4-fluoro-3-(methoxymethoxy)phenyl]methanol (5.28 g) in ethyl acetate (60 ml) was added dropwise triethylamine (4.8 ml) and methanesulphonyl chloride (2.31 ml) with ice-cooling, and the mixture was stirred for 30 minutes. Insolubles were filtered through Celite and the solvent was distilled off under reduced pressure to obtain an oily matter. The obtained oily matter was dissolved in N,N-dimethylformamide (100 ml) and potassium thioacetate (3.90 g) was added. The reaction mixture was stirred at room temperature for 2 hours. The mixture was diluted with ethyl acetate, was washed with water and saturated brine and then dried over anhydrous magnesium sulfate, and the solvent was distilled off under reduced pressure. The residue was purified by silica gel column chromatography (hexane:ethyl acetate=10:1 to 5:1) to obtain an objective product (5.60 g) as an oily matter.

$^{1}$H-NMR (CDCl$_{3}$) δ 2.34 (3H, s), 3.52 (3H, s), 4.05 (2H, s), 5.19 (2H, s), 6.85-7.04 (2H, m), 7.12 (1H, dd).

Reference Example 112

Ethyl 2-{[4-fluoro-3-(methoxymethoxy)benzyl]thio}-2-methylpropionate

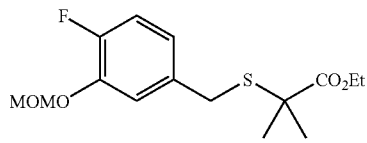

To a solution of S-[4-fluoro-3-(methoxymethoxy)benzyl]ethanethioate (2.50 g) in ethanol (20 ml) was added 1 N sodium hydroxide (11 ml) and the mixture was stirred at room temperature overnight. The mixture was acidified with 1 N hydrochloric acid and diluted with ethyl acetate. Then, the mixture was washed with water and saturated brine and dried over anhydrous magnesium sulfate and the solvent was distilled off under reduced pressure to obtain an oily matter. The obtained oily matter was dissolved in N,N-dimethylformamide (30 ml) and potassium carbonate (2.11 g) and ethyl 2-bromoisobutyrate (1.80 ml) were added. The mixture was stirred at room temperature overnight. The mixture was diluted with ethyl acetate and then washed with water and saturated brine. The mixture was dried over anhydrous magnesium sulfate, and the solvent was distilled off under reduced pressure to obtain an oily matter. The residue was purified by silica gel column chromatography (hexane:ethyl acetate=30:1 to 10:1) to obtain an objective product (1.95 g) as an oily matter.

$^1$H-NMR (CDCl$_3$) δ 1.27 (3H, t), 1.52 (6H, s), 3.51 (3H, s), 3.78 (2H, s), 4.13 (2H, q), 5.20 (2H, s), 6.86-7.04 (2H, m), 7.12 (1H, dd).

Reference Example 113

Ethyl 2-[(4-fluoro-3-(hydroxybenzyl)thio]-2-methylpropionate

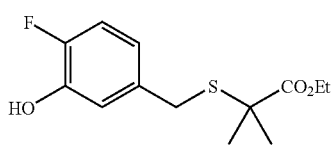

To a solution of ethyl 2-{[4-fluoro-3-(methoxymethoxy)benzyl]thio}-2-methylpropionate (1.0 g) in ethanol (10 ml) was added concentrated hydrochloric acid (0.5 ml) and the mixture was stirred at 50 to 60° C. for 1 hour. The mixture was diluted with ethyl acetate and then washed with water and saturated brine. The mixture was dried over anhydrous magnesium sulfate, and the solvent was distilled off under reduced pressure to obtain an oily matter. The residue was purified by silica gel column chromatography (hexane:ethyl acetate=10:1 to 2:1) to obtain an objective product (0.86 g) as an oily matter.

$^1$H-NMR (CDCl$_3$) δ 1.27 (3H, t), 1.53 (6H, s), 3.75 (2H, s), 4.13 (2H, q), 5.25 (1H, br), 6.74-6.79 (1H, m), 6.93-7.00 (2H, m).

Reference Example 114

S-(2-Fluoro-5-methoxybenzyl)ethanethioate

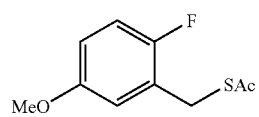

In the same manner as in Reference Example 111, an objective product was obtained from (2-fluoro-5-methoxybenzyl)methanol obtained in Reference Example 55. An oily matter; $^1$H-NMR (CDCl$_3$) δ 2.35 (3H, s), 3.76 (3H, s), 4.11 (2H, s), 6.68-6.76 (1H, m), 6.85-6.98 (2H, m).

Reference Example 115

Ethyl 2-[(2-fluoro-5-methoxybenzyl)thio]-2-methylpropionate

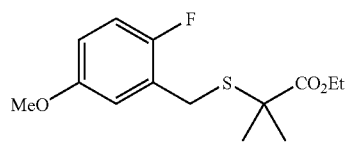

In the same manner as in Reference Example 112, an objective product was obtained S-(2-fluoro-5-methoxybenzyl)ethanethioate obtained in Reference Example 114.

An oily matter; $^1$H-NMR (CDCl$_3$) δ 1.27 (3H, t), 1.55 (6H, s) 3.76 (3H, s), 3.84 (2H, s), 4.11 (2H, q), 6.67-6.77 (1H, m), 6.85 (1H, dd), 6.92 (1H, t).

Reference Example 116

Ethyl 2-[(2-fluoro-5-hydroxybenzyl)thio]-2-methylpropionate

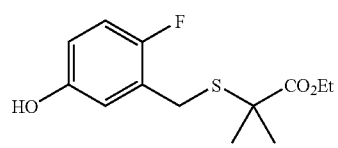

In the same manner as in Reference Example 108, an objective product was obtained from ethyl 2-[(2-fluoro-5-methoxybenzyl)thio]-2-methylpropionate obtained in Reference Example 115.

An oily matter; ¹H-NMR (CDCl₃) δ 1.25 (3H, t), 1.55 (6H, s) 3.81 (2H, s), 4.10 (2H, q), 5.40 (1H, s), 6.64-6.69 (1H, m), 6.80-6.93 (2H, m).

Reference Example 117

(2-Fluoro-3-methoxyphenyl)methanol

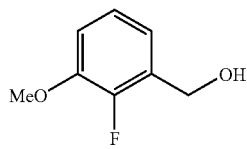

In the same manner as in Reference Example 6, an objective product was obtained from 2-fluoro-3-methoxybenzoic acid.
Melting point 59-60° C.; ¹H-NMR (CDCl₃) δ 1.87 (1H, t), 3.88 (3H, s), 4.75 (2H, d), 6.88-7.09 (3H, m).

Reference Example 118

S-(2-fluoro-3-methoxybenzyl)ethanethioate

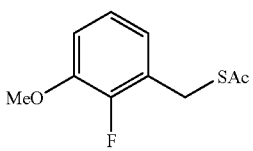

In the same manner as in Reference Example 111, an objective product was obtained from (2-fluoro-3-methoxyphenyl)methanol obtained in Reference Example 117. An oily matter; ¹H-NMR (CDCl₃) δ 2.38 (3H, s), 3.86 (3H, s), 4.16 (2H, d), 6.82-7.01 (3H, m).

Reference Example 119

Ethyl 2-[(2-fluoro-3-methoxybenzyl)thio]-2-methyl-propionate

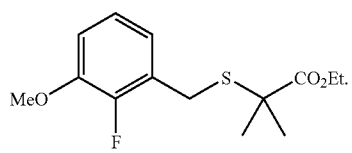

In the same manner as in Reference Example 112, an objective product was obtained from S-(2-fluoro-3-methoxybenzyl)ethanethioate obtained in Reference Example 118.
An oily matter; ¹H-NMR (CDCl₃) δ 1.28 (3H, t), 1.55 (6H, s), 3.86 (2H, s), 3.88 (3H, s), 4.14 (2H, q), 6.81-7.02 (3H, m).

Reference Example 120

Ethyl 2-[(2-fluoro-3-hydroxyphenyl)thio]-2-methyl-propionate

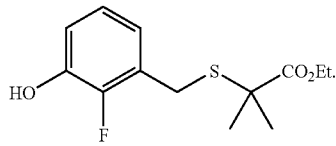

In the same manner as in Reference Example 108, an objective product was obtained from ethyl 2-[(2-fluoro-3-methoxybenzyl)thio]-2-methylpropionate obtained in Reference Example 119.
An oily matter; ¹H-NMR (CDCl₃) δ 1.27 (3H, t), 1.55 (6H, s), 3.86 (2H, s), 4.13 (2H, q), 5.29 (1H, d), 6.80-6.99 (3H, m).

Reference Example 121

(2-Fluoro-3-methoxyphenyl)acetonitrile

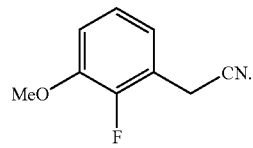

In the same manner as in Reference Example 88, an objective product was obtained from (2-fluoro-3-methoxyphenyl)methanol obtained in Reference Example 117. An oily matter; ¹H-NMR (CDCl₃) δ 3.76 (2H, s), 3.89 (3H, s), 6.91-7.15 (3H, m).

Reference Example 122

Ethyl (2-fluoro-3-methoxyphenyl)acetate

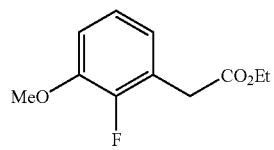

A mixture of (2-fluoro-3-methoxyphenyl)acetonitrile (0.77 g), 8 N sodium hydroxide (10 ml) and ethanol (10 ml) was heated under reflux overnight. The solvent of the reaction solution was distilled off under reduced pressure, and the reaction solution was acidified with concentrated hydrochloric acid and twice extracted with ethyl acetate. The collected organic layer was washed with saturated brine and dried over anhydrous magnesium sulfate. The solvent was distilled off under reduced pressure to obtain an oily matter. The obtained oily matter was dissolved in ethanol (10 ml), concentrated sulfuric acid (0.1 ml) was added, and then the mixture was heated under reflux overnight. The reaction solution was diluted with ethyl acetate and washed with water, a saturated sodium bicarbonate solution and saturated brine. The organic layer was dried over anhydrous sodium sulfate and the solvent was distilled off under reduced pressure. The obtained crude product was purified by silica gel column chromatography (hexane:ethyl acetate=10:1) to obtain an objective product (0.79 g) as an oily matter.

$^1$H-NMR (CDCl$_3$) δ 1.25 (3H, t), 3.65 (3H, s), 3.87 (2H, s) 4.16 (2H, q), 6.79-6.90 (2H, m), 6.98-7.04 (1H, m).

Reference Example 123

Ethyl (2-fluoro-3-hydroxyphenyl)acetate

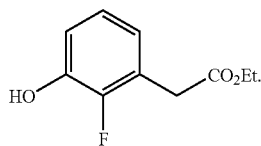

In the same manner as in Reference Example 108, an objective product was obtained from ethyl (2-fluoro-3-methoxyphenyl)acetate obtained in Reference Example 122. An oily matter; $^1$H-NMR (CDCl$_3$) δ 1.26 (3H, t), 3.65 (2H, s), 4.17 (2H, q), 5.51 (1H, s), 6.73-6.86 (1H, m), 6.88-6.98 (2H, m).

Reference Example 124

Methoxymethyl 4-chloro-3-(methoxymethoxy)benzoate

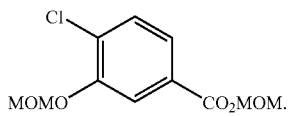

To a solution of 4-chloro-3-hydroxybenzoic acid (3.11 g) in tetrahydrofuran (50 ml) was added N-ethyldiisopropylamine (9.4 ml) and chloromethylmethyl ether (3.5 ml) and the mixture was heated under reflux overnight. The mixture was diluted with ethyl acetate and then washed with water and saturated brine. The mixture was dried over anhydrous magnesium sulfate, and the solvent was distilled off under reduced pressure to obtain an oily matter. The residue was purified by silica gel column chromatography (hexane:ethyl acetate=30:1 to 5:1) to obtain an objective product (4.39 g) as an oily matter.

$^1$H-NMR (CDCl$_3$) δ 3.53 (3H, s), 3.54 (3H, s), 5.31 (2H, s), 5.47 (2H, s), 7.45 (1H, d), 7.68 (1H, dd), 7.84 (1H, d).

Reference Example 125

[4-Chloro-3-(methoxymethoxy)phenyl]methanol

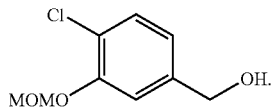

In the same manner as in Reference Example 6, an objective product was obtained from methoxymethyl 4-chloro-3-(methoxymethoxy)benzoate obtained in Reference Example 124. An oily matter; $^1$H-NMR (CDCl$_3$) δ 3.52 (3H, s), 4.64 (2H, d) 5.25 (2H, s), 6.91-6.96 (1H, m), 7.17 (1H, d), 7.34 (1H, d).

Reference Example 126

Methyl (4-chloro-3-hydroxyphenyl)acetate

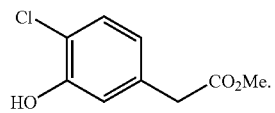

To a solution of [4-chloro-3-(methoxymethoxy)phenyl]methanol (2.01 g), acetone cyanohydrin (1.4 ml) and tributylphosphine (5.0 ml) in tetrahydrofuran (100 ml) was added 1,1'-(azodicarbonyl)dipiperidine (5.05 g) at room temperature, and the mixture was stirred overnight. The solvent of the reaction solution was distilled off under reduced pressure and diisopropyl ether was added. The precipitate was filtered off and washed with diisopropyl ether. The solvent of the filtrate was distilled off under reduced pressure and the obtained crude product was purified by silica gel column chromatography (hexane:ethyl acetate=30:1 to 5:1) to obtain an oily matter. The obtained oily matter was dissolved in ethanol (10 ml) and 8 N sodium hydroxide (5 ml) was added. The mixture was heated under reflux overnight. The solvent of the reaction solution was distilled off under reduced pressure. The reaction solution was acidified with concentrated hydrochloric acid and twice extracted with ethyl acetate. The collected organic layer was washed with saturated brine and dried over anhydrous magnesium sulfate and the solvent was distilled off under reduced pressure to obtain an oily matter. The obtained oily matter was dissolved in 10% hydrochloric acid-methanol (10 ml) and the mixture was stirred at room temperature overnight. The solvent was distilled off under reduced pressure and purified by silica gel column chromatography (hexane:ethyl acetate=20:1 to 5:1) to obtain an objective product (0.55 g) as an oily matter.

$^1$H-NMR (CDCl$_3$) δ 3.56 (2H, s), 3.69 (3H, s), 5.68 (1H, s), 6.79 (1H, dd), 6.94 (1H, d), 7.25 (1H, d).

Reference Example 127

S-[4-chloro-3-(methoxymethoxy)benzyl]ethanethioate

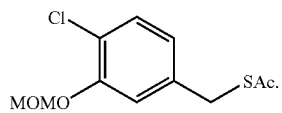

In the same manner as in Reference Example 111, an objective product was obtained from [4-chloro-3-(methoxymethoxy)phenyl]methanol obtained in Reference Example 125.

An oily matter; $^1$H-NMR (CDCl$_3$) δ 2.34 (3H, s), 3.52 (3H, s), 4.05 (2H, s), 5.23 (2H, s), 6.88 (1H, dd), 7.09 (1H, d), 7.27 (1H, d).

Reference Example 128

Ethyl 2-[(4-chloro-3-hydroxybenzyl)thio]-2-methyl-propionate

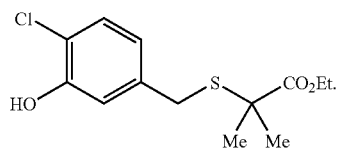

To a solution of S-[4-chloro-3-(methoxymethoxy)benzyl]ethanethioate (1.72 g) in ethanol-tetrahydrofuran (10 ml-10 ml) was added 1 N sodium hydroxide (10 ml) and the mixture was stirred at room temperature for 3 days. The mixture was acidified with 1 N hydrochloric acid, diluted with ethyl acetate and then washed with water and saturated brine. The mixture was dried over anhydrous magnesium sulfate, and the solvent was distilled off under reduced pressure to obtain an oily matter. The obtained oily matter was dissolved in N,N-dimethylformamide (30 ml). Potassium carbonate (1.37 g) and ethyl 2-bromoisobutyrate (1.2 ml) were added and the mixture was stirred at 50° C. overnight. The mixture was diluted with ethyl acetate and then washed with water and saturated brine. The mixture was dried over anhydrous magnesium sulfate, and the solvent was distilled off under reduced pressure to obtain an oily matter. The residue was purified by silica gel column chromatography (hexane:ethyl acetate=30:1 to 10:1) to obtain an oily matter. The obtained oily matter was dissolved in ethanol (10 ml) and concentrated hydrochloric acid (0.1 ml) was added. The mixture was stirred at 60° C. overnight. The solvent was distilled off under reduced pressure. The resultant was diluted with ethyl acetate, washed with water and saturated brine and then dried over anhydrous magnesium sulfate, and the solvent was distilled off under reduced pressure. The residue was purified by silica gel column chromatography (hexane:ethyl acetate=20:1 to 5:1) to obtain an objective product (0.45 g) as an oily matter.

$^1$H-NMR (CDCl$_3$) δ 1.27 (3H, t), 1.52 (6H, s), 3.76 (2H, s) 4.12 (2H, q), 5.58 (1H, s), 6.82 (1H, dd), 6.98 (1H, d), 7.22 (1H, d).

Reference Example 129

Ethyl (3-hydroxy-1H-indazol-1-yl)acetate

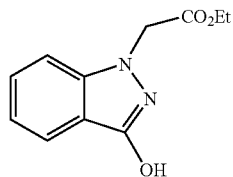

To a solution of 3-indazolinone (5.0 g) in N,N-dimethylformamide (150 ml) was added to potassium carbonate (5.14 g) and ethyl bromoacetate (4.13 ml) and the mixture was stirred at room temperature overnight. The mixture was diluted with ethyl acetate and then washed with water and saturated brine. The mixture was dried over anhydrous magnesium sulfate, and the solvent was distilled off under reduced pressure to obtain an oily matter. The residue was purified by recrystallization (hexane-ethyl acetate) to obtain an objective product (1.47 g) as crystals.

Melting point 181-182° C.; $^1$H-NMR (CDCl$_3$) δ 1.25 (3H, t) 4.22 (2H, q), 4.84 (2H, s), 7.09-7.20 (2H, m), 7.41-7.49 (1H, m), 7.77 (1H, d).

Reference Example 130

5-(Methoxymethoxy)-2-nitrobenzaldehyde

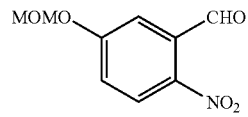

To a solution of 5-hydroxy-2-nitrobenzaldehyde (25 g) in N,N-dimethylformamide (300 ml) was added chloromethyl-methyl ether (13.7 ml) and a suspended matter (7.2 g) of 60% sodium hydride in liquid paraffin was added to the mixture with ice-cooling. The mixture was stirred at room temperature overnight. 1 N hydrochloric acid was added dropwise with ice-cooling, and the mixture was diluted with ethyl acetate and then washed with water and saturated brine. The mixture was dried over anhydrous magnesium sulfate, and the solvent was distilled off under reduced pressure to obtain crude crystals. The residue was purified by recrystallization (hexane-ethyl acetate) to obtain an objective product (23.37 g) as crystals.

Melting point 68-69° C.; $^1$H-NMR (CDCl$_3$) δ 3.49 (3H, s), 5.29 (2H, s), 7.29 (1H, dd), 7.46 (1H, d), 8.15 (1H, d), 10.45 (1H, 5).

Reference Example 131

Ethyl 5-(methoxymethoxy)-1-benzothiophene-2-carboxylate

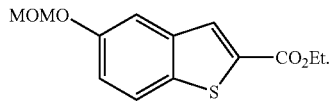

To a solution of 5-(methoxymethoxy)-2-nitrobenzaldehyde (20 g) in N,N-dimethylformamide (300 ml) was added ethyl thioglycollate (12.5 ml) and potassium carbonate (16.36 g) and the mixture was stirred at 60° C. overnight. Water was added thereto and the mixture was extracted with ethyl acetate. The combined organic layer was washed with water and saturated brine. The organic layer was dried over anhydrous magnesium sulfate, and the solvent was distilled off under reduced pressure to obtain an oily matter. The residue was purified by silica gel column chromatography (hexane:ethyl acetate=30:1 to 5:1) to obtain an objective product (6.60 g) as an oily matter.

¹H-NMR (CDCl₃) δ 1.40 (3H, t), 3.50 (3H, s), 4.39 (2H, q), 5.22 (2H, s), 7.18 (1H, dd), 7.49 (1H, d), 7.72 (1H, d), 7.95 (1H, s).

Reference Example 132

[5-(Methoxymethoxy)-1-benzothien-2-yl]methanol

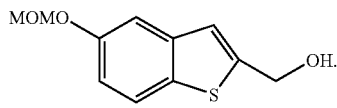

In the same manner as in Reference Example 6, an objective product was obtained from ethyl 5-(methoxymethoxy)-1-benzothiophen-2-carboxylate obtained in Reference Example 131.

Melting point 74-75° C.; ¹H-NMR (CDCl₃) δ 2.03 (1H, t), 3.50 (3H, s), 4.89 (2H, d), 5.21 (2H, s), 7.05 (1H, dd), 7.12 (1H, d), 7.38 (1H, d), 7.67 (1H, d)

Reference Example 133

[5-(Methoxymethoxy)-1-benzothien-2-yl]acetonitrile

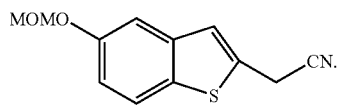

In the same manner as in Reference Example 88, an objective product was obtained from [5-(methoxymethoxy)-1-benzothien-2-yl]methanol obtained in Reference Example 132. An oily matter; ¹H-NMR (CDCl₃) δ 3.51 (3H, s), 3.97 (2H, d) 5.22 (2H, s), 7.08 (1H, dd), 7.23 (1H, s), 7.40 (1H, d), 7.65 (1H, d).

Reference Example 134

Methyl (5-hydroxy-1-benzothien-2-yl)acetate

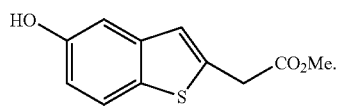

[5-(Methoxymethoxy)-1-benzothien-2-yl]acetonitrile (1.03 g) was dissolved in ethanol (10 ml) and 8 N sodium hydroxide (10 ml) was added. The mixture was heated under reflux overnight. The solvent of the reaction solution was distilled off under reduced pressure, and the reaction solution was acidified with concentrated hydrochloric acid and then extracted with ethyl acetate twice. The collected organic layer was washed with saturated brine and then dried over anhydrous magnesium sulfate and the solvent was distilled off under reduced pressure to obtain an oily matter. The obtained oily matter was dissolved in 10% hydrochloric acid-methanol (10 ml) and the mixture was stirred at room temperature overnight. The solvent was distilled off under reduced pressure and the residue was purified by silica gel column chromatography (hexane:ethyl acetate=4:1 to 2:1) to obtain an objective product (0.43 g) as an oily matter.

Melting point 136-137° C.; ¹H-NMR (CDCl₃) δ 3.75 (3H, s), 3.89 (2H, s), 5.09 (1H, s), 6.86 (1H, dd), 7.03 (1H, s), 7.10 (1H, d), 7.59 (1H, d).

Reference Example 135

5-(Methoxymethoxy)-1-benzothiophene-2-carbaldehyde

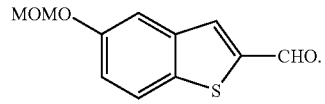

In the same manner as in Reference Example 7, an objective product was obtained from [5-(methoxymethoxy)-1-benzothien-2-yl]methanol obtained in Reference Example 132. ¹H-NMR (CDCl₃) δ 3.51 (3H, s), 5.25 (2H, s), 7.25 (1H, dd), 7.58 (1H, d), 7.78 (1H, d), 7.94 (1H, s), 10.07 (1H, s).

Reference Example 136

Ethyl (E)-3-[5-(methoxymethoxy)-1-benzothien-2-yl]-2-propenoate

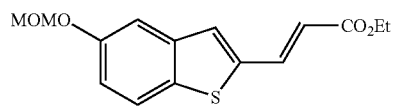

In the same manner as in Reference Example 8, an objective product was obtained from 5-(methoxymethoxy)-1-benzothiophene-2-carbaldehyde obtained in Reference Example 135.

Melting point 81-82° C.; ¹H-NMR (CDCl₃) δ 1.34 (3H, t), 3.50 (3H, s), 4.27 (2H, q), 5.22 (2H, s), 6.27 (1H, d), 7.11 (1H, dd), 7.37 (1H, s), 7.41 (1H, d), 7.66 (1H, d), 7.84 (1H, d).

Reference Example 137

Ethyl 3-[5-(methoxymethoxy)-1-benzothien-2-yl]propionate

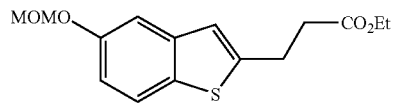

To a solution of ethyl (E)-3-[5-(methoxymethoxy)-1-benzothien-2-yl]-2-propenoate (1.46 g) in ethyl acetate (20 ml) was added 10% palladium-carbon (1.0 g) and the mixture was stirred under hydrogen atmosphere at room temperature overnight. A catalyst was filtered through Celite and the filtrate was distilled off under reduced pressure. The obtained crude product was purified by silica gel column chromatography (hexane:ethyl acetate=20:1 to 5:1) to obtain an objective product (1.20 g) as an oily matter.

¹H-NMR (CDCl₃) δ 1.25 (3H, t), 2.73 (2H, t), 3.21 (2H, t), 3.50 (3H, s), 4.16 (2H, q), 5.20 (2H, s), 6.96 (1H, s), 7.00 (1H, dd), 7.33 (1H, d), 7.62 (1H, d).

Reference Example 138

Ethyl 3-(5-hydroxy-1-benzothien-2-yl)propionate

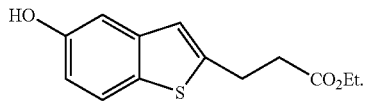

Ethyl 3-[5-(methoxymethoxy)-1-benzothien-2-yl]propionate (1.20 g) was diluted with ethanol (20 ml) and concentrated hydrochloric acid (1 ml) was added. The mixture was stirred at 60° C. for 3 hours. The solvent was distilled off under reduced pressure and the mixture was diluted with ethyl acetate, washed with water and saturated brine and then dried over anhydrous magnesium sulfate. The solvent was distilled off under reduced pressure to obtain an oily matter. The residue was purified by silica gel column chromatography (hexane:ethyl acetate=5:1 to 1:1) to obtain an objective product (0.87 g) as crystals. Melting point 111-113° C.; ¹H-NMR (CDCl₃) δ 1.25 (3H, t), 2.73 (2H, t), 3.20 (2H, t), 4.16 (2H, q), 5.19 (1H, s), 6.82 (1H, dd), 6.89 (1H, s), 7.06 (1H, d), 7.56 (1H, d).

Reference Example 139

(E)-4-{2-methyl-5-[4-(trifluoromethyl)phenyl]-3-furyl}-3-buten-1-ol

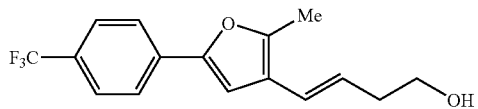

To a suspension of (3-hydroxypropyl)triphenylphosphonium bromide (12.41 g) in tetrahydrofuran (60 ml) was added dropwise n-butyllithium (a 1.6 M hexane solution, 36 ml) with ice-cooling and the mixture was stirred for 30 minutes. Then, a solution of 2-methyl-5-[4-(trifluoromethyl)phenyl]-3-furaldehyde (6.41 g) in tetrahydrofuran (50 ml) was added dropwise and the mixture was stirred for 1.5 hours with ice-cooling. 1 N hydrochloric acid was added and the mixture was diluted with ethyl acetate. The organic layer was washed with water and saturated brine and then dried over anhydrous magnesium sulfate and the solvent was distilled off under reduced pressure to obtain an oily matter. The residue was purified by silica gel column chromatography (hexane:ethyl acetate=10:1 to 1:1) to obtain an objective product (4.77 g) as an oily matter.

¹H-NMR (CDCl₃) δ 2.37 (3H, s), 2.47 (2H, q), 3.75 (2H, t), 5.90 (1H, dt), 6.30 (1H, d), 6.82 (1H, s), 7.60 (2H, d), 7.70 (2H, d).

Reference Example 140

4-{2-Methyl-5-[4-(trifluoromethyl)phenyl]-3-furyl}-1-butanol

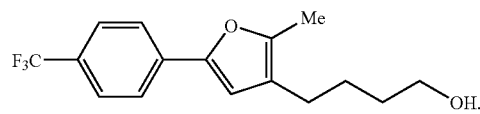

In the same manner as in Reference Example 9, an objective product was obtained from (E)-4-{2-methyl-5-[4-(trifluoromethyl)phenyl]-3-furyl}-3-buten-1-ol obtained in Reference Example 139.

An oily matter; ¹H-NMR (CDCl₃) δ 1.59-1.65 (5H, m), 2.29 (3H, s), 2.36-2.43 (2H, m), 3.64-3.70 (2H, m), 6.58 (1H, s), 7.57 (2H, d), 7.67 (2H, d).

Reference Example 141

S-{[5-(methoxymethoxy)-1-benzothien-2-yl]methyl}ethanethioate

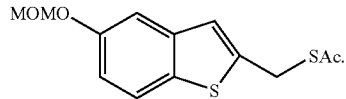

In the same manner as in Reference Example 111, an objective product was obtained from [5-(methoxymethoxy)-1-benzothien-2-yl]methanol obtained in Reference Example 132. An oily matter; ¹H-NMR (CDCl₃) δ 2.37 (3H, s), 3.49 (3H, s) 4.35 (2H, s), 5.20 (2H, s), 7.02 (1H, dd), 7.11 (1H, d), 7.34 (1H, d), 7.60-7.63 (1H, m).

Reference Example 142

Ethyl 2-({[5-(methoxymethoxy)-1-benzothien-2-yl)methyl}thio)-2-methylpropionate

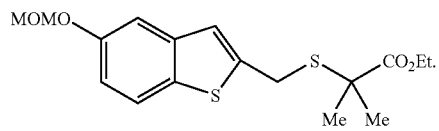

In the same manner as in Reference Example 112, an objective product was obtained from S-{[5-(methoxymethoxy)-1-benzothien-2-yl]methyl}ethanethioate obtained in Reference Example 141.

¹H-NMR (CDCl₃) δ 1.26 (3H, t), 1.55 (6H, s), 3.49 (3H, s), 4.10 (2H, s), 4.11 (2H, q), 5.20 (2H, s), 7.00 (1H, dd), 7.08 (1H, s), 7.32 (1H, d), 7.60 (1H, d).

Reference Example 143

Ethyl 2-{[(5-hydroxy-1-benzothien-2-yl)methyl]thio}-2-methylpropionate

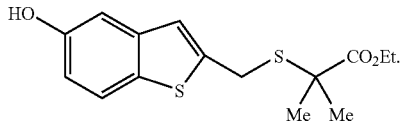

In the same manner as in Reference Example 138, an objective product was obtained from ethyl 2-({[5-(methoxymethoxy)-1-benzothien-2-yl]methyl}thio)-2-methylpropionate obtained in Reference Example 142.

An oily matter; $^1$H-NMR (CDCl$_3$) δ 1.25 (3H, t), 1.56 (6H, s), 4.05-4.16 (4H, m), 4.93 (1H, s), 6.85 (1H, dd), 7.04 (1H, d), 7.08 (1H, d), 7.57 (1H, d).

Reference Example 144 tert-Butyl(dimethyl)[(2-methyl-3-furyl)methoxy]silane

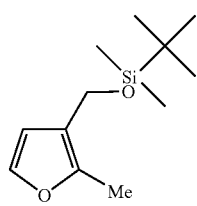

To a suspension of aluminum lithium hydride (9.2 g) in tetrahydrofuran (200 ml) was added dropwise a solution of ethyl 2-methyl-3-furoate (31.1 g) in tetrahydrofuran (100 ml) with ice-cooling and the mixture was stirred at 0° C. for 1 hour. The reaction solution was ice-cooled and water (9 ml), a 15% aqueous sodium hydroxide solution (9 ml) and water (23 ml) were sequentially added dropwise thereto. Excess aluminum lithium hydride was decomposed and then the resulting mixture was stirred as such at room temperature for 2 hours. The obtained precipitate was filtered off and washed with ethyl acetate. The solvent of the collected filtrate was distilled off under reduced pressure to obtain an oily matter.

To a solution of the obtained oily matter, 4-N,N-dimethylaminopyridine (1.2 g) and triethylamine (33.8 ml) in tetrahydrofuran (250 ml) was added tert-butyl chlorodimethylsilane (33.5 g) at room temperature and the mixture was stirred as such overnight. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=15:1) to obtain an objective product (38.2 g) as an oily matter.

$^1$H-NMR (CDCl$_3$) δ 0.08 (6H, s), 0.91 (9H, s), 2.26 (3H, s), 4.51 (2H, s), 6.31 (1H, d), 7.22 (1H, d).

Reference Example 145 tert-Butyl {[5-(5,5-dimethyl-1,3,2-dioxaborinan-2-yl)-2-methyl-3-furyl]methoxy}dimethylsilane

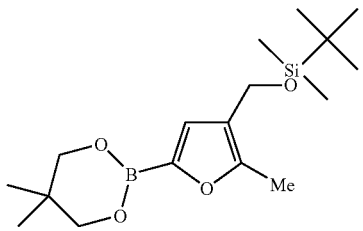

To a solution of 2,2,6,6-tetramethylpiperidine (27.9 ml) in tetrahydrofuran (150 ml) was added dropwise a 1.6 N solution (100 ml) of n-butyllithium in hexane with ice-cooling and the mixture was stirred for 10 minutes. The reaction mixture was cooled to −78° C., and then triisopropyl borate (40.2 g) and tert-butyl(dimethyl)[(2-methyl-3-furyl)methoxy]silane (24.2 g) was added. After the mixture was stirred at −78° C. for 2 hours, the temperature was slowly elevated to room temperature over 4 hours, and then the mixture was stirred at room temperature overnight. The reaction solution was poured into an aqueous ammonium chloride solution and 3 times extracted with ethyl acetate. The collected organic layer was dried over anhydrous magnesium sulfate, and the solvent was distilled off under reduced pressure to obtain an oily matter.

A solution of the obtained oily matter and 2,2-dimethyl-1,3-propanediol (13.3 g) in toluene (200 ml) was stirred at room temperature overnight. The reaction solution was washed with water and the aqueous layer extracted with ethyl acetate. The collected organic layer was dried over anhydrous magnesium sulfate, and the solvent was distilled off under reduced pressure. The obtained crude product was purified by silica gel column chromatography (hexane:ethyl acetate=30:1 to 9:1) to obtain an objective product (12.9 g) as an oily matter.

$^1$H-NMR (CDCl$_3$) δ 0.07 (6H, s), 0.90 (9H, s), 1.01 (6H, s), 2.31 (3H, s), 3.74 (4H, s), 4.50 (2H, s), 6.91 (1H, s).

Reference Example 146

[5-(4-Methoxyphenyl)-2-methyl-3-furyl]methanol

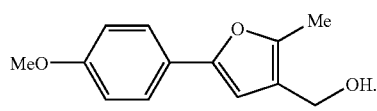

To a solution of tert-butyl {[5-(5,5-dimethyl-1,3,2-dioxaborinan-2-yl)-2-methyl-3-furyl]methoxy}dimethylsilane (4.06 g) in a mixed solvent of toluene-water (30 ml-30 ml) was added sodium carbonate (2.54 g) and 4-bromoanisole (1.8 ml) and the atmosphere of the reaction vessel was substituted with a nitrogen atmosphere. Then, tetrakis(triphenylphosphine) palladium (0.70 g) was added thereto and the mixture was stirred at 80° C. overnight. The mixture was diluted with ethyl acetate and the organic layer was washed with water and saturated brine and dried over anhydrous magnesium sulfate, and the solvent was distilled off under reduced pressure to obtain an oily matter. The residue was purified by silica gel column chromatography (hexane:ethyl acetate=40:1 to 10:1) to obtain an oily matter. The obtained oily matter was dissolved in tetrahydrofuran (20 ml) and tetra-n-butylammonium fluoride (a 1 M tetrahydrofuran solution, 15 ml) was added dropwise thereto and the mixture was stirred at room temperature for 1 hour. The mixture was diluted with ethyl acetate and the organic layer was washed with water and saturated brine and dried over anhydrous magnesium sulfate, and the solvent was distilled off under reduced pressure to obtain an oily matter. The residue was purified by silica gel column chromatography (hexane:ethyl acetate=10:1 to 1:1) to obtain an objective product (0.78 g) as crystals.

Melting point 62-64° C.; $^1$H-NMR (CDCl$_3$) δ 2.34 (3H, s), 3.82 (3H, s), 4.49 (2H, s), 6.49 (1H, s), 6.90 (2H, d), 7.55 (2H, d).

Reference Example 146(1) to Reference Example 146(4)

In the same manner as in Reference Example 146, the below-described compounds were obtained from aryl halide corresponding to tert-butyl {[5-(5,5-dimethyl-1,3,2-dioxaborinan-2-yl)-2-methyl-3-furyl]methoxy}dimethylsilane obtained in Reference Example 145.

Reference Example 146(1)

[5-(3-Fluorophenyl)-2-methyl-3-furyl]methanol

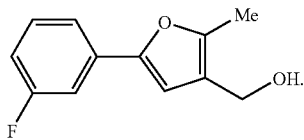

An oily matter; $^1$H-NMR (CDCl$_3$) δ 2.36 (3H, s), 4.50 (2H, s), 6.65 (1H, s), 6.85-6.96 (1H, m), 7.25-7.40 (3H, m).

Reference Example 146(2)

{2-Methyl-5-[2-(trifluoromethyl)phenyl]-3-furyl}methanol

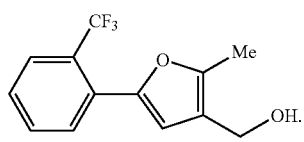

An oily matter; $^1$H-NMR (CDCl$_3$) δ 2.37 (3H, s), 4.52 (2H, s), 6.69 (1H, s), 7.34-7.39 (1H, m), 7.51-7.56 (1H, m), 7.70-7.73 (2H, m).

Reference Example 146(3)

(2-Methyl-5-phenyl-3-furyl)methanol

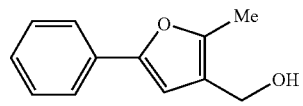

an oily matter; $^1$H-NMR (CDCl$_3$) δ 2.35 (3H, s), 4.49 (2H, s), 6.61 (1H, s), 7.18-7.24 (1H, m), 7.31-7.37 (2H, m), 7.60 (2H, d).

Reference Example 146(4)

[2-Methyl-5-(4-methylphenyl)-3-furyl]methanol

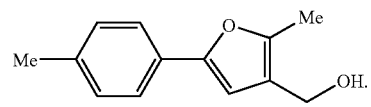

Melting point 79-80° C.; $^1$H-NMR (CDCl$_3$) δ 2.34 (6H, s), 4.49 (2H, s), 6.55 (1H, s), 7.14 (2H, dd), 7.49 (2H, dd).

Reference Example 147

Ethyl 2-[(3-methoxyphenyl)thio]-2-methylpropionate

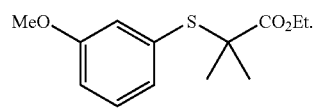

In the same manner as in Reference Example 98, an objective product was obtained from 3-methoxybenzenethiol. An oily matter; $^1$H-NMR (CDCl$_3$) δ 1.21 (3H, t), 1.49 (6H, s) 3.78 (3H, s), 4.11 (2H, q), 6.88-6.91 (1H, m), 7.00-7.05 (2H, m), 7.18-7.25 (1H, m).

Reference Example 148

Ethyl 2-[(3-hydroxyphenyl)thio]-2-methylpropionate

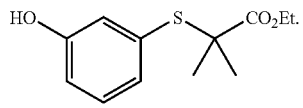

In the same manner as in Reference Example 99, an objective product was obtained from ethyl 2-[(3-methoxyphenyl)thio]-2-methylpropionate obtained in Reference Example 147.

An oily matter; $^1$H-NMR (CDCl$_3$) δ 1.21 (3H, t), 1.49 (6H, s) 4.12 (2H, q), 5.87 (1H, s), 6.81-6.85 (1H, m), 6.95-7.02 (2H, m), 7.13-7.18 (1H, m).

Reference Example 149

Ethyl 4-[(3-{2-methyl-5-[4-(trifluoromethyl)phenyl]-3-furyl}propanoyl)amino]-3-oxobutanoate

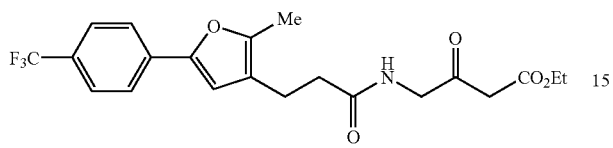

To a solution of 3-{2-methyl-5-[4-(trifluoromethyl)phenyl]-3-furyl}propionic acid (0.80 g) in acetonitrile (20 ml) was added dropwise triethylamine (0.23 ml) and pivaloyl chloride (0.21 g) with ice-cooling and the mixture was stirred for 30 minutes. Then, ethyl 4-amino-3-oxobutanoate hydrochloride (0.33 g) and triethylamine (0.23 ml) were sequentially added thereto and the mixture was stirred at room temperature for 1.5 hours. After diluting with ethyl acetate, the organic layer was washed with water and saturated brine and dried over anhydrous magnesium sulfate, and the solvent was distilled off under reduced pressure to obtain an oily matter. The residue was purified by silica gel column chromatography (hexane:ethyl acetate=3:1 to 1:1) to obtain an objective product (0.41 g) as crystals.

Melting point 131-133° C.; $^1$H-NMR (CDCl$_3$) δ 1.26 (3H, t), 2.31 (3H, s), 2.48 (2H, t), 2.73 (2H, t), 3.47 (2H, s), 4.18 (2H, q), 4.26 (2H, d), 6.15 (1H, s), 6.58 (1H, s), 7.57 (2H, d), 7.66 (2H, d).

Reference Example 149(1) AND REFERENCE EXAMPLE 149(2)

In the same manner as in Reference Example 149, the below-described compounds were obtained from the ketoamino form corresponding to 3-{2-methyl-5-[4-(trifluoromethyl)phenyl]-3-furyl}propionic acid.

Reference Example 149(1)

Ethyl 4-[(3-{2-methyl-5-[4-(trifluoromethyl)phenyl]-3-furyl}propanoyl)amino]-3-oxopentanoate

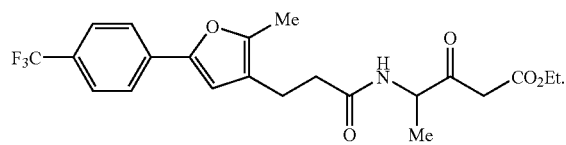

Melting point 133-136° C.; $^1$H-NMR (CDCl$_3$) δ 1.24 (3H, t), 1.34 (3H, d), 2.30 (3H, s), 2.44 (2H, t), 2.72 (2H, t), 3.50 (2H, s), 4.15 (2H, q), 4.68 (1H, quintet), 6.17 (1H, d), 6.57 (1H, s), 7.57 (2H, d), 7.66 (2H, d).

Reference Example 149(2)

Ethyl 5-methyl-4-[(3-{2-methyl-5-[4-(trifluoromethyl)phenyl]-3-furyl}propanoyl)amino]oxohexanoate

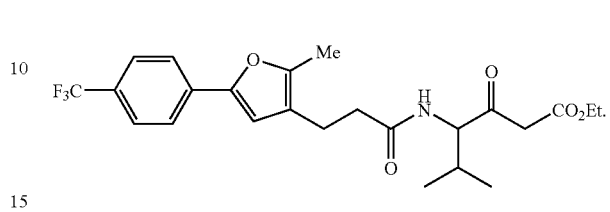

An oily matter; $^1$H-NMR (CDCl$_3$) δ 0.72 (3H, d), 0.92 (3H, d) 1.24 (3H, t), 2.17-2.27 (1H, m), 2.31 (3H, s), 2.49 (2H, t), 2.74 (2H, t), 3.50 (2H, s), 4.16 (2H, q), 4.73 (1H, dd), 6.10 (1H, d), 6.60 (1H, s), 7.57 (2H, d), 7.67 (2H, d).

Reference Example 150

4-{2-Methyl-5-[4-(trifluoromethyl)phenyl]-3-furyl}butanoic acid

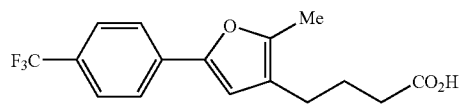

To a solution of 4-{2-methyl-5-[4-(trifluoromethyl)phenyl]-3-furyl}butanol (1.18 g) in dichloromethane (20 ml) was added triethylamine (2.21 ml) and a solution of a sulfur trioxide pyridine complex (2.53 g) in dimethylsulfoxide (20 ml) was added with ice-cooling. The mixture was stirred at room temperature for 30 minutes and diluted with diethyl ether. The organic layer was washed with hydrochloric acid, water and saturated brine and then dried over anhydrous magnesium sulfate, and the solvent was distilled off under reduced pressure to obtain an oily matter. The obtained oily matter was dissolved in tert-butanol (32 ml), and water (8 ml), sodium dihydrogenphosphate (0.72 g) and 2-methyl-2-butene (2.1 ml) were added. Sodium chlorite (0.54 g) was finally added thereto and the mixture was stirred at room temperature for 1 hour and was diluted with ethyl acetate. Then, the organic layer was washed with hydrochloric acid, water and saturated brine and then dried over anhydrous magnesium sulfate, and the solvent was distilled off under reduced pressure to obtain an oily matter. The residue was purified by silica gel column chromatography (hexane:ethyl acetate=5:1 to 2:1, 1:1) to obtain an objective product (0.36 g) as an oily matter.

$^1$H-NMR (CDCl$_3$) δ 1.87-1.94 (2H, m), 2.29 (3H, s), 2.38 (2H, t), 2.43 (2H, t), 6.57 (1H, s), 7.57 (2H, d), 7.66 (2H, d).

Reference Example 151

Ethyl 4-[(4-{2-methyl-5-[4-(trifluoromethyl)phenyl]-3-furyl}butanoyl)amino]-3-oxopentanoate

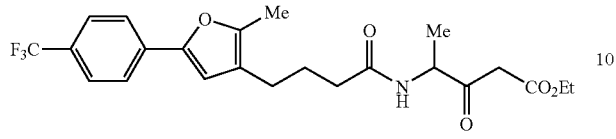

In the same manner as in Reference Example 149, an objective product was obtained from 4-{2-methyl-5-[4-(trifluoromethyl)phenyl]-3-furyl}butanoic acid obtained in Reference Example 150.

Amorphous; $^1$H-NMR (CDCl$_3$) δ 1.27 (3H, t), 1.38 (3H, d), 1.85-1.94 (2H, m), 2.24 (2H, t), 2.29 (3H, s), 2.41 (2H, d), 3.55 (2H, s), 4.19 (2H, q), 4.70 (1H, quintet), 6.17 (1H, d), 6.58 (1H, s), 7.57 (2H, d), 7.67 (2H, d).

Reference Example 152

2-(Trimethylsilyl)ethyl 2-methyl-5-[(4-trifluoromethyl)phenyl]-3-furoate

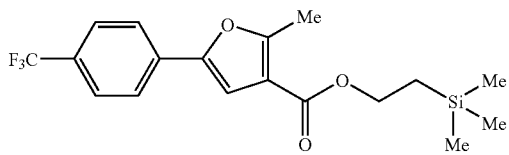

To a solution of methyl 2-methyl-5-[4-(trifluoromethyl)phenyl]-3-furoate (4.86 g) in a mixed solvent of tetrahydrofuran-methanol (50 ml-50 ml) was added 1 N sodium hydroxide (26 ml) and the mixture was stirred at 60° C. for 4 hours. After standing to cool, the mixture was acidified with 1 N hydrochloric acid and diluted with ethyl acetate. The organic layer was washed with water and saturated brine and dried over anhydrous magnesium sulfate, and the solvent was distilled off under reduced pressure to obtain an oily matter. The obtained oily matter was dissolved in tetrahydrofuran (100 ml), and 4-dimethylaminopyridine (0.21 g), 1-ethyl-3-(3-dimethylaminopropyl)carbodiimide.hydrochloride (4.92 g) and 2-(trimethylsilyl)ethanol (2.95 ml) were sequentially added. The mixture was stirred at room temperature overnight and diluted with ethyl acetate. Then, the organic layer was washed with water and saturated brine and dried over anhydrous magnesium sulfate, and the solvent was distilled off under reduced pressure to obtain an oily matter. The residue was purified by silica gel column chromatography (hexane:ethyl acetate=20:1 to 10:1) to obtain an objective product (4.52 g) as crystals. Melting point 80-81° C.; $^1$H-NMR (CDCl$_3$) δ 0.086 (9H, s), 1.07-1.16 (2H, m), 2.67 (3H, s), 4.31-4.40 (2H, m), 6.99 (1H, s), 7.62 (2H, d), 7.72 (2H, d).

Reference Example 153

Ethyl 2-methyl-2-(4-methylphenoxy)propionate

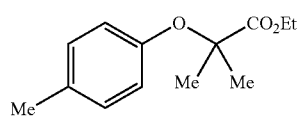

In the same manner as in Reference Example 98, an objective product was obtained from p-cresol. An oily matter; $^1$H-NMR (CDCl$_3$) δ 1.25 (3H, t), 1.56 (6H, s) 2.27 (3H, s), 4.23 (2H, q), 6.73 (2H, d), 7.01 (2H, d).

Reference Example 154

Ethyl 2-[4-(bromomethyl)phenoxy]-2-methylpropionate

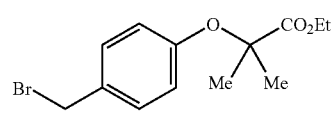

To a solution of ethyl 2-methyl-2-(4-methylphenoxy)propionate (8.89 g) in ethyl acetate (100 ml) was added 2,2'-azobis(isobutyronitrile) (0.33 g) in N-bromosuccinimide (7.12 g) and the mixture was heated under reflux overnight. The solvent was distilled off under reduced pressure and the residue was diluted with hexane. Insolubles were filtered through Celite and washed with hexane. The filtrate was distilled off under reduced pressure to an objective product (12.13 g) as an oily matter. An oily matter; $^1$H-NMR (CDCl$_3$) δ 1.23 (3H, t), 1.60 (6H, s), 4.22 (2H, q), 4.46 (2H, s), 6.78 (2H, d), 7.26 (2H, d).

Reference Example 155

[4-(2-Ethoxy-1,1-dimethyl-2-oxoethoxy)benzyl](triphenyl)phosphonium bromide

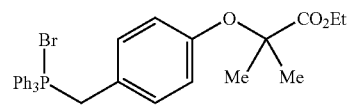

To a solution of ethyl 2-[4-(bromomethyl)phenoxy]-2-methylpropionate (12.13 g) in toluene (100 ml) was added triphenylphosphine (10.5 g) and the mixture was heated under reflux overnight. The solvent was distilled off under reduced pressure. Diisopropyl ether was added to the residue for crystallization, and the resultant was washed with toluene to obtain an objective product (17.37 g) as a solid matter.

Melting point 185-186° C.; ¹H-NMR (CDCl₃) δ 1.07 (3H, t), 1.48 (6H, s), 4.10 (2H, q), 5.10 (2H, d), 6.62 (2H, d), 6.85 (2H, dd), 7.60-7.76 (12H, m), 7.87-7.92 (3H, m).

Reference Example 156

Ethyl 3-{2-ethyl-5-[4-(trifluoromethyl)phenyl]-3-furyl}-3-oxopropionate

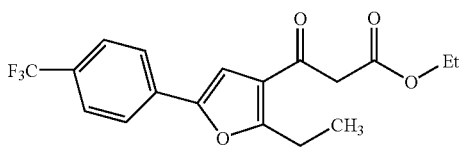

To a solution of 2-ethyl-5-[4-(trifluoromethyl)phenyl]-3-furoate (13.0 g) in tetrahydrofuran (150 ml) was added 1,1'-carbonyldiimidazole (8.2 g) at room temperature and the mixture was stirred as such for 2 hours. To the mixture was added a monopotassium salt of monoethyl malonate (8.6 g) and magnesium chloride (2.4 g) at room temperature and the mixture was stirred at 60° C. overnight. The reaction solution was diluted with water and twice extracted with ethyl acetate. The collected organic layer was dried over anhydrous sodium sulfate and the solvent was distilled off under reduced pressure. The obtained crude product was purified by silica gel column chromatography (hexane:ethyl acetate=15:1 to 6:1) to obtain an objective product (13.3 g) as an oily matter.

¹H-NMR (CDCl₃) δ 1.26-1.36 (6H, m), 3.05 (0.4H, q), 3.11 (1.6H, q), 3.79 (1.6H, s), 4.23 (2H, q), 5.34 (0.2H, s), 6.81 (0.2H, s), 6.95 (0.8H, s), 7.62 (0.4H, d), 7.64 (1.6H, d), 7.72 (0.4H, d), 7.74 (1.6H, d).

Reference Example 157

3-{[tert-Butyl(dimethyl)silyl]oxy}-1-{2-ethyl-5-[4-(trifluoromethyl)phenyl]-3-furyl}propan-1-ol

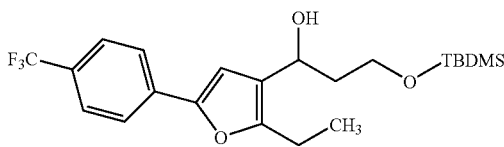

To a suspension of aluminum lithium hydride (1.1 g) in tetrahydrofuran (100 ml) was added dropwise a solution of ethyl 3-{2-ethyl-5-[4-(trifluoromethyl)phenyl]-3-furyl}-3-oxopropionate (7.13 g) in tetrahydrofuran (50 ml) with ice-cooling and the mixture was stirred at 0° C. for 1 hour. After the reaction solution was ice-cooled, water (1 ml), a 15% aqueous sodium hydroxide solution (1 ml) and water (2.5 ml) were sequentially added dropwise thereto, and excess aluminum lithium hydride was decomposed. The mixture was stirred as such at room temperature for 2 hours. The produced precipitate was filtered off and washed with ethyl acetate. The solvent of the collected filtrate was distilled off under reduced pressure to obtain an oily matter.

To a solution of the obtained oily matter, 4-N,N-dimethylaminopyridine (0.25 g) and triethylamine (3.4 ml) in tetrahydrofuran (100 ml) was added tert-butyl chlorodimethylsilane (3.0 g) at room temperature and the mixture was stirred as such overnight. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=15:1 to 9:1) to obtain an objective product (4.44 g) as an oily matter.

¹H-NMR (CDCl₃) δ 0.11 (6H, s), 0.93 (9H, s), 1.29 (3H, t), 1.76-1.86 (1H, m), 1.98-2.12 (1H, m), 2.74 (2H, q), 3.44 (1H, d), 3.80-3.96 (2H, m), 4.89-4.96 (1H, m), 6.77 (1H, s), 7.59 (2H, d), 7.70 (2H, d).

Reference Example 158 tert-Butyl (3-{2-ethyl-5-[4-(trifluoromethyl)phenyl]-3-furyl}-3-methoxypropoxy)dimethylsilane

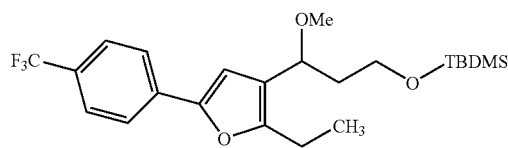

3-{[tert-Butyl(dimethyl)silyl]oxy}-1-{2-ethyl-5-[4-(trifluoromethyl)phenyl]-3-furyl}propan-1-ol (1.31 g) was dissolved in 1,2-dimethoxyethane (40 ml), a suspended matter (0.15 g) of 60% sodium hydride in liquid paraffin was added at room temperature and the mixture was stirred as such for 0.5 hour. To the mixture was added methyl iodide (0.57 ml) at room temperature and the mixture was stirred at room temperature overnight and at 60° C. for 8 hours. The reaction solution was poured into water and twice extracted with ethyl acetate. The collected organic layer was dried over anhydrous magnesium sulfate, and the solvent was distilled off under reduced pressure. The obtained residue was purified by silica gel column chromatography (hexane to hexane:ethyl acetate=15:1) to obtain an objective product (0.87 g) as an oily matter.

¹H-NMR (CDCl₃) δ 0.04 (3H, s), 0.06 (3H, s), 0.90 (9H, s), 1.29 (3H, t), 1.74-1.83 (1H, m), 2.01-2.12 (1H, m), 2.72 (2H, dq), 3.21 (3H, s), 3.54-3.61 (1H, m), 3.71-3.78 (1H, m), 4.33 (1H, dd), 6.66 (1H, s), 7.59 (2H, d), 7.70 (2H, d).

Reference Example 159

3-{2-Ethyl-5-[4-(trifluoromethyl)phenyl]-3-furyl}-3-methoxy-1-propanol

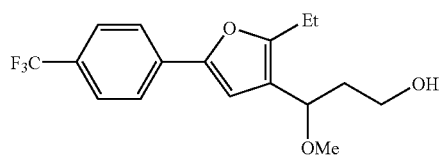

To a solution of tert-butyl (3-{2-ethyl-5-[4-(trifluoromethyl)phenyl]-3-furyl}-3-methoxypropoxy)dimethylsilane (0.86 g) in tetrahydrofuran (5 ml) was added dropwise tetra-n-butylammonium fluoride (a 1 M tetrahydrofuran solution, 3 ml). and the mixture was stirred at room temperature for 1 hour was diluted with ethyl acetate. Then, the organic layer was washed with water and saturated brine and dried over anhydrous magnesium sulfate, and the solvent was distilled off under reduced pressure to obtain an oily matter. The residue was purified by silica gel column chromatography (hexane:ethyl acetate=5:1 to 1:1) to obtain an objective product (0.54 g) as an oily matter.

$^1$H-NMR (CDCl$_3$) δ 1.29 (3H, t), 1.79-1.91 (1H, m), 2.07-2.22 (1H, m), 2.46 (1H, br), 2.73 (2H, q), 3.24 (3H, s), 3.79-3.81 (2H, m), 4.39 (1H, dd), 6.70 (1H, s), 7.60 (2H, d), 7.72 (2H, d).

Reference Example 160

Di(4-hydroxyphenyl)disulfide

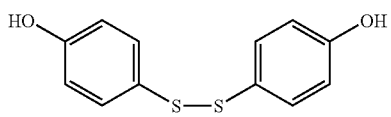

4-Hydroxythiophenol (5 g) was dissolved in acetone (50 ml), copper (II) nitrate trihydrate (1.9 g) was added thereto and the mixture was stirred at room temperature for 30 minutes. The solvent was distilled off, ethyl acetate was added and insolubles were filtered off. The solvent of the filtrate was distilled off and the residue was purified by silica gel column chromatography (ethyl acetate:hexane) to obtain an objective product (3.7 g) as amorphous.

$^1$H-NMR (CDCl$_3$) δ 4.98 (2H, s), 6.75 (4H, d), 7.35 (4H, d).

Reference Example 161

Di(4-(1-(ethoxycarbonyl)-1-methylethoxy)phenyl) disulfide

Di(4-hydroxyphenyl)disulfide (3.7 g), ethyl 2-bromoisobutyrate (6.5 ml) and potassium carbonate (12.2 g) were heated in N,N-dimethylformamide (50 ml) at 50° C. overnight. Ethyl 2-bromoisobutyrate (3 ml) was added thereto and the mixture was further heated overnight. The mixture was poured into water and extracted with ethyl acetate. The organic layer was washed with water and brine and dried over magnesium sulfate, and the solvent was distilled off under reduced pressure. The residue was purified by silica gel column chromatography (ethyl acetate:hexane) to obtain an objective product (4.4 g) as an oily matter.

$^1$H-NMR (CDCl$_3$) δ 1.23 (6H, t), 1.59 (12H, s), 4.22 (4H, q), 6.75 (4H, d), 7.33 (4H, d).

Reference Example 162

N-(3-hydroxybenzyl)-N-methylglycine methyl ester

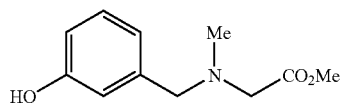

3-Hydroxybenzaldehyde (2.5 g), N-methylsarcosine methyl ester hydrochloride (2.9 g), triethylamine (3.5 ml) and sodium triacetoxy borohydride (8.7 g) were stirred in 1,2-dichloroethane (100 ml) at room temperature for 6 hours. The solvent was distilled off, an aqueous sodium hydrogen carbonate solution was added thereto and the mixture was extracted with ethyl acetate. The organic layer was washed with water and brine and dried over magnesium sulfate, and the solvent was distilled off to obtain an objective product (4.3 g) as an oily matter.

$^1$H-NMR (CDCl$_3$) δ 2.39 (3H, s), 3.27 (2H, s), 3.62 (2H, s), 3.71 (3H, s), 6.72-6.77 (1H, m), 6.84-6.87 (2H, m), 7.14-7.22 (1H, m).

Reference Example 163

Ethyl 3'-(benzyloxy)-1,1'-biphenyl-3-carboxylate

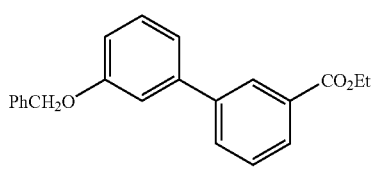

Ethyl 3-bromobenzoate (0.5 g), 3-benzyloxyphenyl boric acid (0.5 g), a 1 M aqueous potassium carbonate solution (6 ml) and ethanol (6 ml) was added to toluene (50 ml) and the mixture was stirred at room temperature under argon atmosphere for 30 minutes. Tetrakistriphenylphosphine palladium (80 mg) was added thereto and the mixture was refluxed for 4 hours. The mixture was extracted with ethyl acetate, the organic layer was washed with water and brine and dried over magnesium sulfate, and the solvent was distilled off. The residue was purified by silica gel column chromatography (ethyl acetate/hexane) to obtain an objective product (0.65 g) as an oily matter.

¹H-NMR (CDCl₃) δ 1.41 (3H, t), 4.40 (2H, q), 5.13 (2H, s), 6.97-7.01 (1H, m), 7.20-7.25 (1H, m), 7.33-7.51 (1H, m), 7.73-7.77 (1H, m), 8.00-8.03 (1H, m), 8.25-8.26 (1H, m).

Reference Example 164

Ethyl 3'-hydroxy-1,1'-biphenyl-3-carboxylate

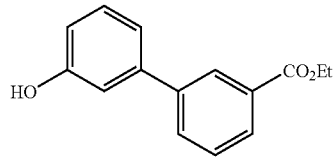

Ethyl 3'-(benzyloxy)-1,1'-biphenyl-3-carboxylate (0.65 g) was dissolved in ethanol (50 ml) and the solution was catalytically reduced using 10% palladium-carbon (50% water content, 0.1 g) overnight. A catalyst was filtered off and the solvent of the filtrate was distilled off to obtain an objective product (0.4 g) as an oily matter.

¹H-NMR (CDCl₃) δ 1.42 (3H, t), 4.41 (2H, q), 5.00 (1H, br), 6.85 (1H, dd), 7.09-7.11 (1H, m), 7.17-7.22 (1H, m), 7.30-7.38 (1H,m), 7.46-7.54 (1H, m), 7.73-7.79 (1H, m), 8.00-8.06 (1H, m), 8.25-8.26 (1H, m).

Reference Example 165

Methyl [3'-(benzyloxy)-1,1'-biphenyl-3-yl]acetate

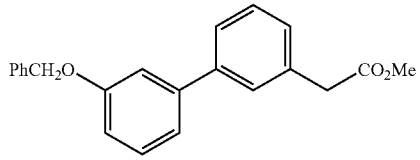

Methyl m-hydroxyphenyl acetate (1.7 g) and triethylamine (2.9 ml) was dissolved in dichloromethane (50 ml), and trifluoromethanesulfonic anhydride (1.8 ml) was added dropwise thereto with ice-cooling. The mixture was stirred for 15 minutes, the reaction solution was washed with water and dried and the solvent was distilled off. A half amount of the residue was dissolved in toluene (50 ml,) and 3-benzyloxyphenyl boric acid (0.5 g), a 1 M aqueous potassium carbonate solution (6 ml) and ethanol (6 ml) was added thereto. The mixture was stirred at room temperature under argon atmosphere for 30 minutes.

Tetrakistriphenylphosphine palladium (100 mg) was added thereto and the mixture was refluxed overnight. The mixture was extracted with ethyl acetate, the organic layer was washed with water and brine and dried over magnesium sulfate, and the solvent was distilled off. The residue was purified by silica gel column chromatography (ethyl acetate/hexane) to obtain an objective product (0.69 g) as an oily matter.

¹H-NMR (CDCl₃) δ 3.67-3.71 (5H, m), 5.12 (2H, s), 6.94-6.98 (1H, m), 7.16-7.49 (12H, m).

Reference Example 166

Methyl (3'-hydroxy-1,1'-biphenyl-3-yl)acetate

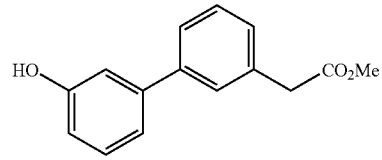

Methyl 3'-(benzyloxy)-1,1'-biphenyl-3-yl]acetate (0.69 g) was dissolved in ethanol (50 ml) and ethyl acetate (10 ml), and the mixture was catalytically reduced using 10% palladium-carbon (50% water content, 0.8 g) for 6 hours. A catalyst was filtered off and the solvent of the filtrate was distilled off. The residue was purified by silica gel column chromatography (ethyl acetate/hexane) to obtain an objective product (0.27 g) as an oily matter.

¹H-NMR (CDCl₃) δ 3.69-3.71 (5H, m), 4.81 (1H, s), 6.81 (1H, d), 7.04 (1H, s), 7.15 (1H, d), 7.25-7.32 (2H, m), 7.35-7.41 (1H, m), 7.45-7.48 (2H, m).

Reference Example 167

Methyl 2-methyl-2-[(4-nitrobenzyl)thio]propionate

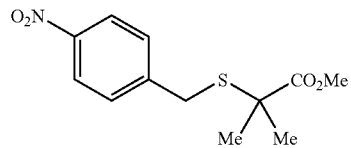

4-Nitrobenzyl bromide (1.8 g), methyl 2-mercaptoisobutyrate (1.16 g) and potassium carbonate (2.4 g) were stirred in DMF (10 ml) at room temperature for 1 hour. The mixture was poured into water and extracted with ethyl acetate. The organic layer was washed with water and brine and dried over magnesium sulfate, and the solvent was distilled off to obtain an objective product (2.2 g) as an oily matter.

¹H-NMR (CDCl₃) δ 1.54 (6H, s), 3.63 (3H, s), 3.90 (2H, s), 7.48 (2H, d), 8.15 (2H, d).

Reference Example 168

Methyl 2-[(4-aminobenzyl)thio]-2-methylpropionate

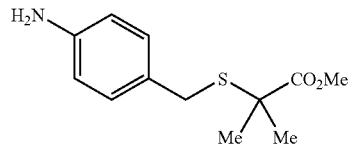

Methyl 2-methyl-2-[(4-nitrobenzyl)thio]propionate (2.2 g) and reduced iron (2.3 g) were stirred at room temperature in acetic acid (50 ml) overnight. The solvent was distilled off and ethyl acetate was added. Insolubles were filtered through Celite, the filtrate was washed with an aqueous sodium hydrogen carbonate solution, water and brine and then dried over magnesium sulfate, and the solvent was distilled off. The residue was purified by silica gel column chromatography (ethyl acetate/hexane) to obtain an objective product (1.4 g) as an oily matter.

$^1$H-NMR (CDCl$_3$) δ 1.53 (6H, s), 3.63 (2H, br), 3.67 (3H, s), 3.73 (2H, s), 6.60 (2H, d), 7.07 (2H, d).

Example 1

[(3{[5-(4-Fluorophenyl)-2-methyl-3-furoyl]amino}benzyl)thio]acetic acid

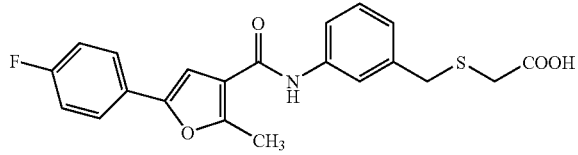

To a solution of 5-(4-fluorophenyl)-N-[3-(hydroxymethyl)phenyl]-2-methyl-3-furancarboxamide (0.26 g) and triethylamine (0.33 ml) in tetrahydrofuran (10 ml) was added dropwise methanesulfonyl chloride (68 μl) at room temperature and the mixture was stirred as such for 0.5 hour. To the obtained mixture was added ethyl thioglycollate (0.10 ml) was added at room temperature and the mixture was stirred as such overnight. The solvent of the reaction solution was distilled off under reduced pressure and the obtained crude product was purified by silica gel column chromatography (hexane:ethyl acetate=9:1 to 3:1) to obtain a solid matter. The obtained solid matter was dissolved in methanol (3 ml) and tetrahydrofuran (5 ml). A 1 N aqueous sodium hydroxide solution (1.6 ml) was added and then the mixture was stirred at room temperature overnight. The reaction solution was concentrated and diluted with water. The reaction solution was acidified with hydrochloric acid and twice extracted with ethyl acetate. The collected organic layer was dried over anhydrous sodium sulfate and the solvent was distilled off under reduced pressure. The obtained crude product was crystallized from hexane to obtain an objective product (0.11 g) as powders. Melting point 198-199° C.; $^1$H-NMR (CDCl$_3$-CD$_3$OD) δ 2.70 (3H, s), 3.11 (2H, s), 3.85 (2H, s), 7.06-7.14 (4H, m), 7.29 (1H, t), 7.61-7.70 (4H, m), 8.88 (1H, s).

Example 1(1) to Example 1(5)

In the same manner as in Example 1, the below-described compounds were obtained from the compounds obtained in Reference Example 17(1) to Reference Example 17(5).

Example 1(1)

[(3{[5-(4-Fluorophenyl)-2-methyl-3-furoyl](methyl)amino}benzyl)thio]acetic acid

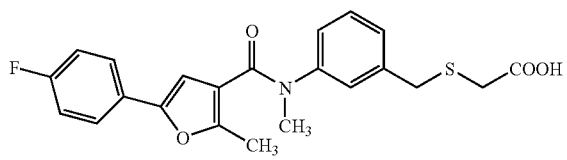

Melting point 155-156° C.; $^1$H-NMR (CDCl$_3$) δ 2.49 (3H, s) 2.81 (2H, s), 3.45 (3H, s), 3.78 (2H, s), 5.68 (1H, s), 6.97 (2H, t), 7.12-7.15 (2H, m), 7.22-7.39 (4H, m).

Example 1(2)

[(3{[5-(4-Fluorophenyl)-2-methyl-3-furoyl](propyl)amino}benzyl)thio]acetic acid

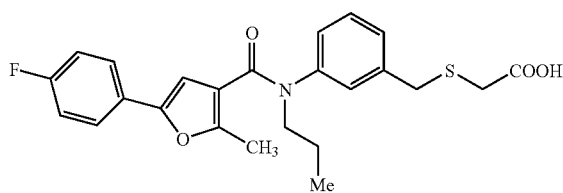

Melting point 140-141° C.; $^1$H-NMR (CDCl$_3$) δ 0.94 (3H, t) 1.55-1.74 (2H, m), 2.49 (3H, s), 2.78 (2H, s), 3.78 (2H, s), 3.83 (2H, t), 5.63 (1H, s), 6.96 (2H, t), 7.10-7.25 (2H, m), 7.23-7.39 (4H, m).

Example 1(3)

[(3{[5-(4-Fluorophenyl)-2-methyl-3-furoyl](heptyl)amino}benzyl)thio]acetic acid

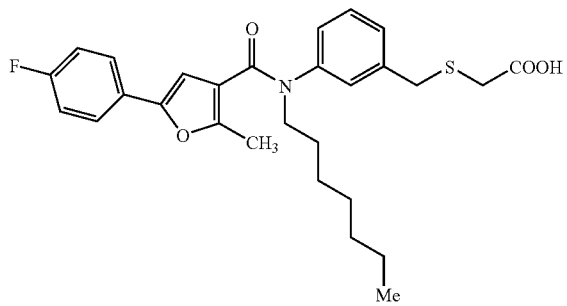

Melting point 94-96° C.; $^1$H-NMR (CDCl$_3$) δ 0.86 (3H, t), 1.25-1.34 (10H, m), 1.56-1.65 (2H, m), 2.48 (3H, s), 2.78 (2H, s), 3.77 (2H, s), 3.84 (2H, t), 5.62 (1H, s), 6.96 (2H, t), 7.08-7.13 (2H, m), 7.23-7.36 (4H, m).

Example 1(4)

[(3{Benzyl[5-(4-fluorophenyl)-2-methyl-3-furoyl]amino}benzyl)thio]acetic acid

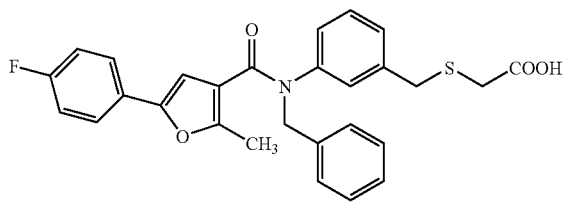

An oily matter; $^1$H-NMR (CD$_3$OD) δ 2.53 (3H, s), 2.69 (2H, s), 3.69 (2H, s), 5.08 (2H,'s), 5.63 (1H, s), 6.91-7.03 (4H, m), 7.17-7.31 (9H, m).

Example 1(5)

{[3-({2-Methyl-5-[4-(trifluoromethyl)phenyl]-3-furoyl}amino)benzyl]thio}acetic acid

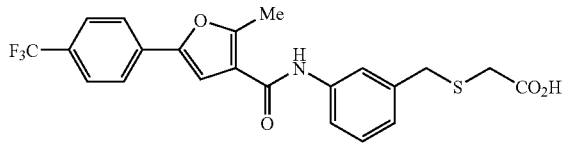

Melting point 188-189° C.; $^1$H-NMR (CDCl$_3$) δ 2.72 (3H, s) 3.10 (2H, s), 3.85 (2H, s), 7.08-7.18 (2H, m), 7.26-7.34 (1H, m), 7.59-7,70 (3H, m), 7.77 (2H, d), 8.42 (1H, s).

Example 2

{[3-({2-Ethyl-5-[4-(trifluoromethyl)phenyl]-3-furoyl}amino)benzyl]thio}acetic acid

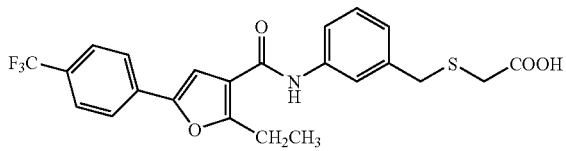

Ethyl [(3-aminobenzyl)thio]acetate.hydrochloride (0.41 g) was dissolved in water and the solution was alkalified with potassium carbonate and twice extracted with ethyl acetate. The collected organic layer was dried over anhydrous magnesium sulfate, and the solvent was distilled off under reduced pressure to obtain ethyl [(3-aminobenzyl)thio]acetate as an oily matter.

To a solution of 2-ethyl-5-[4-(trifluoromethyl)phenyl]-3-furancarboxylate (0.45 g) and N,N-dimethylformamide (1 drop) in tetrahydrofuran (10 ml) was added dropwise oxalyl chloride (0.28 ml) at room temperature and the mixture was stirred for 0.5 hour. The solvent of the reaction solution was distilled off under reduced pressure to obtain a crude product of acid chloride as a solid matter. The above obtained ethyl [(3-aminobenzyl)thio]acetate and sodium hydrogen carbonate (0.27 g) were stirred in tetrahydrofuran (20 ml) and the obtained acid chloride was dissolved in tetrahydrofuran (10 ml). The mixture was added dropwise at room temperature and stirred as such overnight. The reaction solution was diluted with ethyl acetate, washed with water and dried over anhydrous magnesium sulfate, and then the solvent was distilled off under reduced pressure to obtain an oily matter. The obtained oily matter was dissolved in methanol (5 ml) and tetrahydrofuran (5 ml) and a 1 N aqueous sodium hydroxide solution (3 ml) was added thereto. The mixture was stirred at room temperature overnight. The reaction solution was concentrated and diluted with water. The reaction solution was acidified with hydrochloric acid and twice extracted with ethyl acetate. The collected organic layer was dried over anhydrous sodium sulfate and the solvent was distilled off under reduced pressure. The obtained crude product was crystallized from diisopropyl ether-hexane to obtain an objective product (0.62 g) as crystals.

Melting point 199-200° C.; $^1$H-NMR (CDCl$_3$-DMSO-d$_6$) δ 1.36 (3H, t), 3.10 (2H, s), 3.16 (2H, q), 3.85 (2H, s), 7.10 (1H, d), 7.15 (1H, s), 7.29 (1H, t), 7.58 (1H, s), 7.64 (2H, d), 7.67 (1H, d), 7.77 (2H, d), 8.33 (1H, s).

Example 2(1) to Example 2(5)

In the same manner as in Example 2, ethyl [(3-aminobenzyl)thio]acetate.hydrochloride was condensed with the corresponding carboxylic acid (as synthesized in Reference Example, or as commercially available) and hydrolyzed to obtain the below-described compounds.

Example 2(1)

{[3-({2-Isopropyl-5-[4-(trifluoromethyl)phenyl]-3-furoyl}amino)benzyl]thio}acetic acid

Melting point 173-174° C.; $^1$H-NMR (CDCl$_3$-DMSO-d$_6$) δ 1.38 (6H, d), 3.10 (2H, s), 3.85 (2H, s), 3.89-3.98 (1H, m), 7.10 (1H, d), 7.11 (1H, s), 7.29 (1H, t), 7.58 (1H, s), 7.64 (2H, d), 7.67 (1H, d), 7.76 (2H, d), 8.26 (1H, s).

Example 2(2)

{[3-({2-Butyl-5-[4-(trifluoromethyl)phenyl]-3-furoyl}amino)benzyl]thio}acetic acid

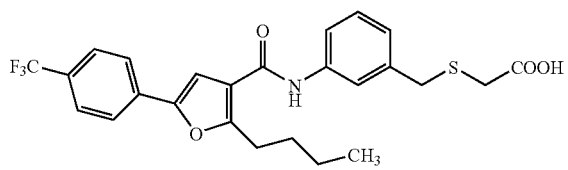

Melting point 195-196° C.; $^1$H-NMR (CDCl$_3$-DMSO-d$_6$) δ 0.96 (3H, t), 1.38-1.50 (2H, m), 1.72-1.82 (2H, m), 3.10 (2H, s), 3.14 (2H, t), 3.85 (2H, s), 7.09-7.17 (2H, m), 7.29 (1H, t), 7.56 (1H, s), 7.64 (2H, d), 7.67 (1H, d), 7.76 (2H, d), 8.31 (1H, s).

Example 2(3)

[(3-{[5-(4-Chlorophenyl)-2-furoyl]amino}benzyl)thio]acetic acid

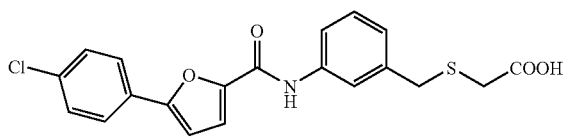

Melting point 173-174° C.; $^1$H-NMR (CDCl$_3$-DMSO-d$_6$) δ 3.11 (2H, s), 3.86 (2H, s), 6.79 (1H, d), 7.12 (1H, d), 7.29-7.34 (2H, m), 7.42 (2H, d), 7.61 (1H, t), 7.73-7.78 (3H, m), 8.65 (1H, s).

Example 2(4)

({3-[(3-{2-Methyl-5-[4-(trifluoromethyl)phenyl]-3-furyl}propionyl) amino)benzyl}thio) acetic acid

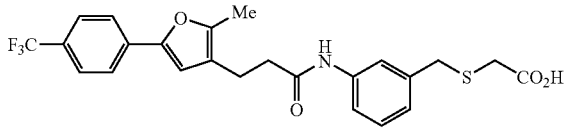

$^1$H-NMR (CDCl$_3$) δ 2.33 (3H, s), 2.59 (2H, t), 2.80 (2H, t), 3.07 (2H, s), 3.80 (2H, s), 6.65 (1H, s), 7.04 (1H, d), 7.24 (1H, t), 7.46 (1H, s), 7.56 (3H, m), 7.67 (2H, d), 8.57 (1H, br s).

Example 2(5)

({3-[(3-{2-Butyl-5-[4-(trifluoromethyl)phenyl]-3-furyl}propionyl) amino) benzyl}thio) acetic acid

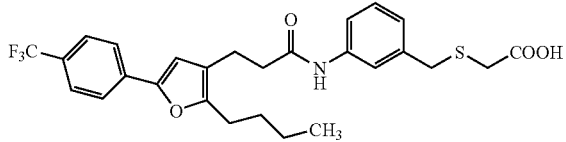

Melting point 137-138° C.; $^1$H-NMR (CDCl$_3$-DMSO-d$_6$) δ 0.93 (3H, t), 1.32-1.42 (2H, m), 1.59-1.69 (2H, m), 2.59 (2H, t), 2.66 (2H, t), 2.81 (2H, t), 3.07 (2H, s), 3.80 (2H, s), 6.65 (1H, s), 7.04 (2H, d), 7.24 (1H, t), 7.44 (1H, s), 7.56 (3H, d), 7.66 (2H, d), 8.39 (1H, s).

Example 3

[(3-{[5-Phenyl-2-(trifluoromethyl)-3-furoyl]amino}benzyl)thio]acetic acid

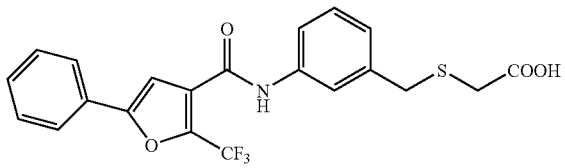

While ethyl [(3-aminobenzyl)thio]acetate hydrochloride (0.21 g), 5-phenyl-2-(trifluoromethyl)-3-furancarboxylic acid (0.21 g) and triethylamine (0.28 ml) were stirred in tetrahydrofuran (10 ml) and N,N-dimethylformamide (2 ml), diethyl phosphorocyanidate (0.14 ml) was added dropwise thereto at room temperature and the mixture was stirred as such overnight. The reaction solution was poured into an aqueous sodium hydrogen carbonate solution and twice extracted with ethyl acetate. The collected organic layer was dried over anhydrous sodium sulfate and the solvent was distilled off under reduced pressure. The obtained crude product was purified by silica gel column chromatography (hexane:ethyl acetate=3:1 to 1:1) to obtain an oily matter. The obtained oily matter was dissolved in methanol (3 ml) and tetrahydrofuran (3 ml), a 1 N aqueous sodium hydroxide solution (1 ml) was added thereto and the mixture was stirred at room temperature overnight. The reaction solution was concentrated and diluted with water. The reaction solution was acidified with hydrochloric acid and twice extracted with ethyl acetate. The collected organic layer was dried over anhydrous sodium sulfate and the solvent was distilled off under reduced pressure. The obtained crude product was crystallized from diisopropyl ether-hexane to obtain an objective product (60 mg) as powders.

Melting point 178-182° C.; $^1$H-NMR (CDCl$_3$-DMSO-d$_6$) δ 3.10 (2H, s), 3.85 (2H, s), 7.12 (1H, d), 7.21 (1H, s), 7.30 (1H, t), 7.39-7.51 (3H, m), 7.67-7.77 (4H, m), 9.50 (1H, s).

Example 4

({3-[(3-{2-Ethyl-5-[4-(trifluoromethyl)phenyl]-3-furyl}propanoyl)amino]benzyl}thio)acetic acid

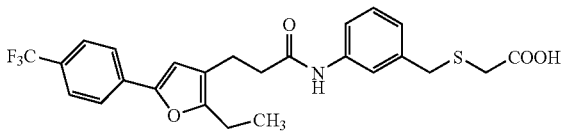

While ethyl [(3-aminobenzyl)thio]acetate. hydrochloride (0.20 g), 3-{2-ethyl-5-[4-(trifluoromethyl)phenyl]-3-furyl}propionic acid (0.24 g), 1-hydroxybenzotriazole hydrate (0.14 g) and triethylamine (0.16 ml) was stirred in N,N-dimethylformamide (5 ml), 1-ethyl-3-(3-dimethylaminopropyl)carbodiimide.hydrochloride (0.18 g) was added thereto at room temperature, and then the mixture was stirred as such overnight. The reaction solution was poured into an aqueous sodium hydrogen carbonate solution and twice extracted with ethyl acetate. The collected organic layer was dried over anhydrous sodium sulfate and the solvent was distilled off under reduced pressure. The obtained residue was dissolved in methanol (3 ml) and tetrahydrofuran (3 ml), a 1 N aqueous sodium hydroxide solution (2 ml) was added and then the mixture was stirred at room temperature overnight. The reaction solution was concentrated and diluted with water. The reaction solution was acidified with dilute hydrochloric acid and twice extracted with ethyl acetate. The collected organic layer was dried over anhydrous sodium sulfate and the solvent was distilled off under reduced pressure. The obtained crude product was crystallized from diisopropyl ether to obtain an objective product (0.12 g) as powders. Melting point 139-141° C.; $^1$H-NMR (CDCl$_3$-DMSO-d$_6$) δ 1.26 (3H, t), 2.58 (2H, t), 2.70 (2H, q), 2.82 (2H, t), 3.07 (2H, s), 3.80 (2H, s), 6.64 (1H, s), 7.07 (1H, d), 7.26 (1H, t), 7.41 (1H, s), 7.53 (1H, d), 7.57 (2H, d), 7.68 (2H, d), 7.90 (1H, s).

Example 4(1) and Example 4(2)

In the same manner as in Example 4, ethyl [(3-aminobenzyl)thio]acetate.hydrochloride was condensed with the corresponding carboxylic acid (as synthesized in Reference Example) and hydrolyzed to obtain the below-described compounds.

Example 4(1)

({3-[({2-Methyl-5-[4-(trifluoromethyl)phenyl]-3-furyl}acetyl)amino]benzyl}thio)acetic acid

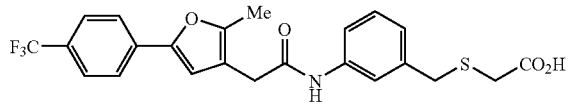

Melting point 173-174° C.; $^1$H-NMR (CDCl$_3$) δ 2.40 (3H, s), 3.07 (2H, s), 3.49 (2H, s), 3.80 (2H, s), 6.78 (1H, s), 7.06 (1H, d), 7.24 (1H, t), 7.45 (1H, s), 7.54-7.61 (3H, m), 7.71 (2H, d), 8.50 (1H, s).

Example 4(2)

({3-[({2-Methyl-5-[4-(trifluoromethyl)phenyl]-3-furoyl}amino)benzyl]thio}acetic acid

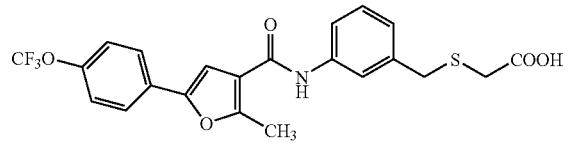

Melting point 200-202° C.; $^1$H-NMR (CDCl$_3$-DMSO-d$_6$) δ 2.71 (3H, s), 3.10 (2H, s), 3.85 (2H, s), 7.97-7.10 (1H, m), 7.19-7.31 (4H, m), 7.64-7.72 (4H, m), 8.94 (1H, s).

Example 5

[(3-{[4-(4-Fluorophenyl)-2,5-dimethyl-3-furyl]methoxy}benzyl)thio]acetic acid

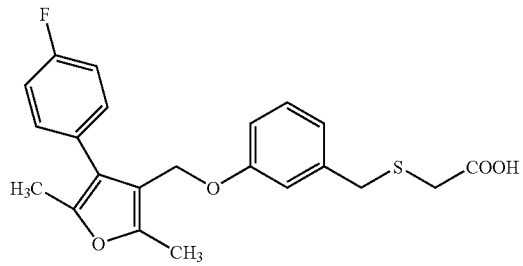

To a solution of [4-(4-fluorophenyl)-2,5-dimethyl-3-furyl]methanol (0.29 g), ethyl [(3-hydroxybenzyl)thio]acetate (0.32 g) and tributylphosphine (0.39 ml) in tetrahydrofuran (20 ml) was added a solution of diethyl azodicarboxylate in 40% toluene (0.68 g) at room temperature and the mixture was stirred overnight. The solvent of the reaction solution was distilled off under reduced pressure and the obtained crude product was purified by silica gel column chromatography (hexane:ethyl acetate=20:1 to 6:1) to obtain an oily matter. The obtained oily matter was dissolved in methanol (3 ml) and tetrahydrofuran (3 ml), a 1 N aqueous sodium hydroxide solution (1.3 ml) was added thereto, and then the mixture was stirred at room temperature overnight. The reaction solution was concentrated and diluted with water. The reaction solution was acidified with dilute hydrochloric acid and twice extracted with ethyl acetate. The collected organic layer was dried over anhydrous sodium sulfate and the solvent was distilled off under reduced pressure. The obtained crude product was purified by silica gel column chromatography (hexane:ethyl acetate=1:1 to ethyl acetate) to obtain an objective product (66 mg) as an oily matter.

$^1$H-NMR (CDCl$_3$) δ 2.28 (3H, s), 2.33 (3H, s), 3.12 (2H, s), 3.81 (2H, s), 4.69 (2H, s), 6.79-6.95 (3H, m), 7.03 (2H, t), 7.23 (1H, t), 7.30 (2H, dd).

Example 5(1) to Example 5(12)

In the same manner as in Example 5, the corresponding furanalkanol (as synthesized in Reference Example) was condensed with the corresponding phenol (the compound synthesized in Reference Example or the already known compound) and hydrolyzed to obtain the below-described compounds.

Example 5(1)

[(3-{[4-(4-Fluorophenyl)-2-isopropyl-5-methyl-3-furyl]methoxy}benzyl)thio]acetic acid

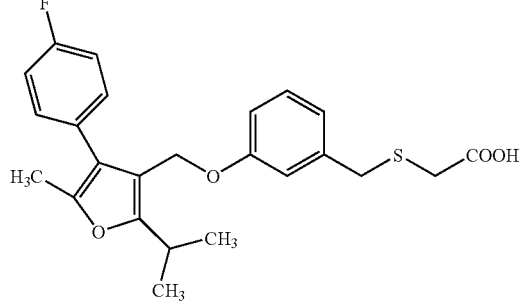

An oily matter; $^1$H-NMR (CDCl$_3$) δ 1.29 (6H, d), 2.29 (3H, s) 3.04-3.18 (1H, m), 3.12 (2H, s), 3.81 (2H, s), 4.70 (2H, s), 6.79-6.94 (3H, m), 7.03 (2H, t), 7.22 (1H, t), 7.31 (2H, dd).

Example 5(2)

[(3-{[2-Dichlorohexyl-4-(4-fluorophenyl)-5-methyl-3-furyl]methoxy}benzyl)thio]acetic acid

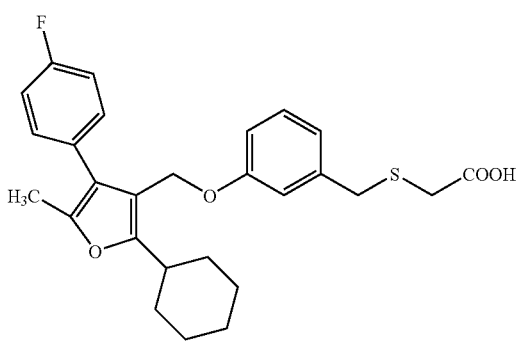

An oily matter; ¹H-NMR (CDCl₃) δ 1.20-1.45 (2H, m), 1.55-1.85 (8H, m), 2.28 (3H, s), 2.65-2.80 (1H, m), 3.13 (2H, s), 3.81 (2H, s), 4.70 (2H, s), 6.80-6.95 (3H, m), 7.02 (2H, t), 7.23 (1H, t), 7.31 (2H, dd).

Example 5(3)

[(3-{[4-(4-Fluorophenyl)-5-methyl-2-phenyl-3-furyl]methoxy}benzyl)thio]acetic acid

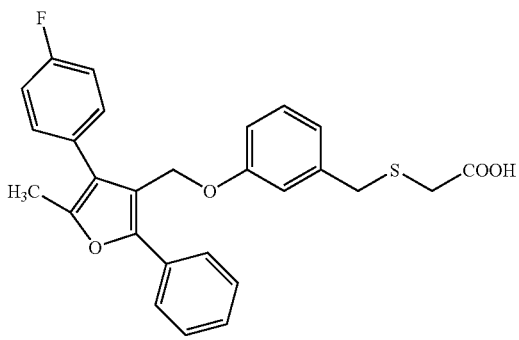

An oily matter; ¹H-NMR (CDCl₃) δ 2.41 (3H, s), 3.14 (2H, s), 3.82 (2H, s), 4.80 (2H, s), 6.86-6.98 (3H, m), 7.06 (2H, t), 7.22-7.44 (6H, m), 7.66-7.70 (2H, m).

Example 5(4)

[(3-{[5-Phenyl-2-(trifluoromethyl)-3-furyl]methoxy}benzyl)thio]acetic acid

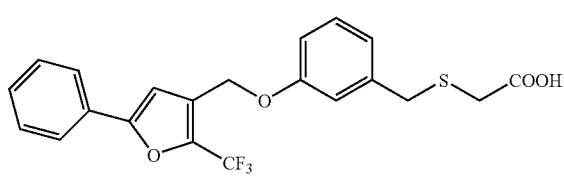

Melting point 84-85° C.; ¹H-NMR (CDCl₃) δ 3.11 (2H, s), 3.84 (2H, s), 5.09 (2H, s), 6.85 (1H, s), 6.87-6.99 (3H, m), 7.27 (1H, t), 7.34-7.46 (3H, m), 7.67-7.73 (2H, m).

Example 5(5)

{[3-(2-Ethyl-5-[4-(trifluoromethyl)phenyl]-3-furyl)methoxy)benzyl]thio}acetic acid

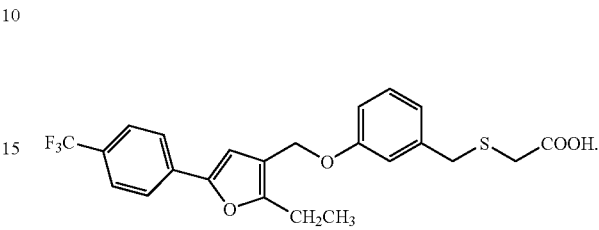

Melting point 93-94° C.; ¹H-NMR (CDCl₃) δ 1.31 (3H, t), 2.77 (2H, q), 3.12 (2H, s), 3.83 (2H, s), 4.88 (2H, s), 6.78 (1H, s), 6.86-6.97 (3H, m), 7.25 (1H, t), 7.59 (2H, d), 7.70 (2H, d).

Example 5(6)

{[3-(2-Isopropyl-5-[4-(trifluoromethyl)phenyl]-3-furyl)methoxy)benzyl]thio}acetic acid

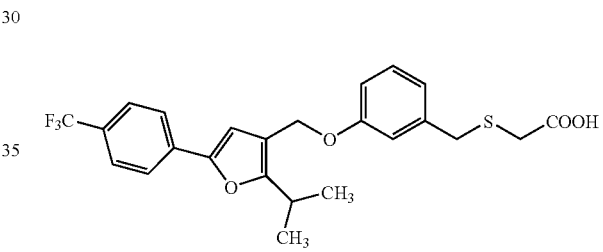

Melting point 84-85° C.; ¹H-NMR (CDCl₃) δ 1.34 (6H, d), 3.12 (2H, s), 3.12-3.21 (1H, m), 3.83 (2H, s), 4.89 (2H, s), 6.77 (1H, s), 6.88 (1H, dd), 6.93-6.97 (2H, m), 7.25 (1H, t), 7.59 (2H, d), 7.70 (2H, d)

Example 5(7)

{[3-(2-Butyl-5-[4-(trifluoromethyl)phenyl]-3-furyl)methoxy)benzyl]thio}acetic acid

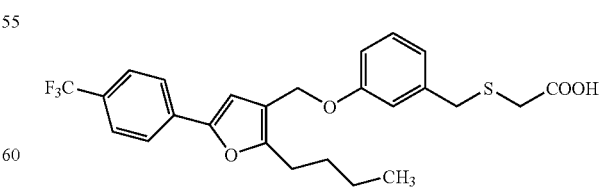

Melting point 77-78° C.; ¹H-NMR (CDCl₃) δ 0.94 (3H, t), 1.34-1.46 (2H, m), 1.64-1.74 (2H, m), 2.73 (2H, t), 3.12 (2H, s), 3.83 (2H, s), 4.87 (2H, s), 6.79 (1H, s), 6.87-6.97 (3H, m), 7.26 (1H, t), 7.59 (2H, d), 7.70 (2H, d).

Example 5(8)

3-(4-{[5-(4-Fluorophenyl)-2-methyl-3-furyl]methoxy}-2-methylphenyl)propionic acid

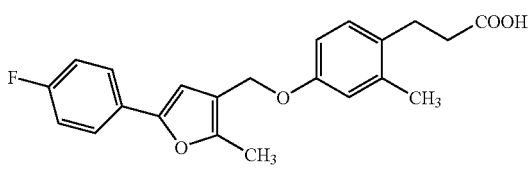

Melting point 123-125° C.; $^1$H-NMR (CDCl$_3$) δ 2.31 (3H, s) 2.37 (3H, s), 2.62 (2H, t), 2.91 (2H, t), 4.82 (2H, s), 6.58 (1H, s), 6.74-6.80 (2H, m), 7.04 (2H, t), 7.07 (1H, d), 7.57 (2H, dd).

Example 5(9)

3-[4-({2-Ethyl-5-[4-(trifluoromethyl)phenyl]-3-furyl}methoxy)-2-methylphenyl]propionic acid

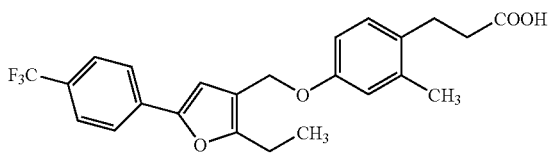

Melting point 95-97° C.; $^1$H-NMR (CDCl$_3$) δ 1.30 (3H, t), 2.31 (3H, s), 2.62 (2H, t), 2.76 (2H, q), 2.91 (2H, t), 4.84 (2H, s), 6.74-6.79 (3H, m), 7.08 (1H, d), 7.59 (2H, d), 7.70 (2H, d).

Example 5(10)

3-[4-({2-Isopropyl-5-[4-(trifluoromethyl)phenyl]-3-furyl}methoxy)-2-methylphenyl]propionic acid

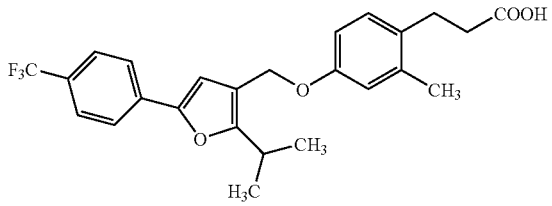

Melting point 108-109° C.; $^1$H-NMR (CDCl$_3$) δ 1.33 (6H, d), 2.31 (3H, s), 2.62 (2H, t), 2.91 (2H, t), 3.10-3.20 (1H, m), 4.85 (2H, s), 6.74-6.79 (3H, m), 7.08 (1H, d), 7.59 (2H, d), 7.70 (2H, d).

Example 5(11)

3-[4-({2-Butyl-5-[4-(trifluoromethyl)phenyl]-3-furyl}methoxy)-2-methylphenyl]propionic acid

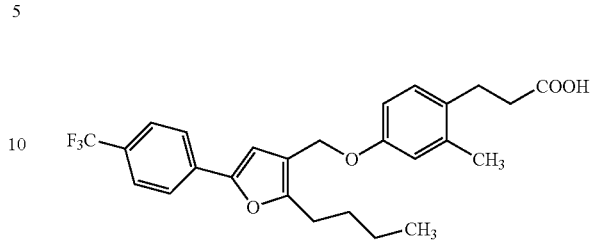

Melting point 118-119° C.; $^1$H-NMR (CDCl$_3$) δ 0.94 (3H, t), 1.36-1.45 (2H, m), 1.63-1.73 (2H, m), 2.31 (3H, s), 2.62 (2H, t), 2.72 (2H, t), 2.91 (2H, t), 4.83 (2H, s), 6.74-6.79 (3H, m), 7.08 (1H, d), 7.59 (2H, d), 7.70 (2H, d).

Example 5(12)

3-(2-Methyl-4-{[5-phenyl-2-(trifluoromethyl)-3-furyl]methoxy}phenyl)propionic acid

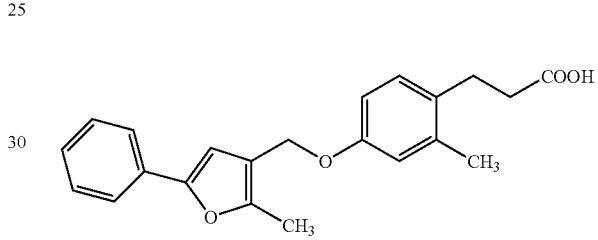

Melting point 151-152° C.; $^1$H-NMR (CDCl$_3$) δ 2.31 (3H, s), 2.61 (2H, t), 2.90 (2H, t), 5.05 (2H, s), 6.73-6.82 (3H, m), 7.08 (1H, d), 7.31-7.44 (3H, m), 7.68-7.71 (2H, m).

Example 6

2-[(3-{[5-(4-Fluorophenyl)-2-methyl-3-furyl]methoxy}benzyl)thio]-2-methylpropionic acid

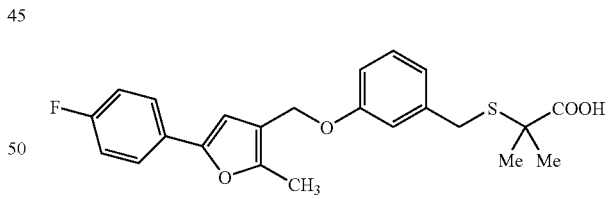

To a solution of [5-(4-fluorophenyl)-2-methyl-3-furyl]methanol (1.05 g), ethyl 2-[(3-hydroxybenzyl)thio]-2-methylpropionate (1.29 g) and tributylphosphine (2.05 g) in tetrahydrofuran (100 ml) was added 1,1'-(azodicarbonyl)dipiperidine (2.56 g) at room temperature and the mixture was stirred overnight. The solvent of the reaction solution was distilled off under reduced pressure and diisopropyl ether was added thereto. The precipitate was filtered off and washed with diisopropyl ether. The solvent of the filtrate was distilled off under reduced pressure and the obtained crude product was purified by silica gel column chromatography (hexane:ethyl acetate=30:1 to 9:1) to obtain an oily matter. The obtained oily matter was dissolved in methanol (30 ml) and tetrahydrofuran (30 ml), a 1 N aqueous sodium hydroxide solution (10 ml) was added thereto and the mixture was stirred at room temperature overnight. The reaction solution was concentrate and diluted with water. The reaction solution was acidified with dilute hydrochloric acid and twice extracted with ethyl acetate. The collected organic layer was dried over anhydrous sodium sulfate and the solvent was distilled off under reduced pressure. The obtained crude product was crystallized from diisopropyl ether-hexane to obtain an objective product (1.49 g) as crystals.

Melting point 134-135° C.; $^1$H-NMR (CDCl$_3$) δ 1.56 (6H, s), 2.37 (3H, s), 3.88 (2H, s), 4.84 (2H, s), 6.58 (1H, s), 6.84 (1H, dd), 6.91-6.96 (2H, m), 7.04 (2H, t), 7.21 (1H, t), 7.58 (2H, dd).

Example 6(1) to Example 6(126)

In the same manner as in Example 6, the corresponding furanalkanol (as synthesized in Reference Example) was condensed with the corresponding phenol (the compound synthesized in Reference Example or the already known compound) and hydrolyzed to obtain the below-described compounds.

Example 6(1)

[(3-{[5-(4-Fluorophenyl)-2-methyl-3-furyl]methoxy}benzyl)thio]acetic acid

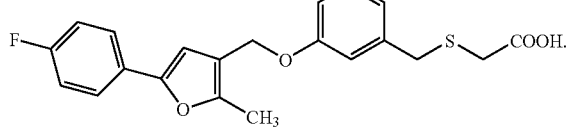

Melting point 120-122° C.; $^1$H-NMR (CDCl$_3$) δ 2.39 (3H, s) 3.12 (2H, s), 3.84 (2H, s), 4.87 (2H, s), 6.60 (1H, s), 6.86-6.97 (3H, m), 7.05 (2H, t), 7.26 (1H, t), 7.59 (2H, dd).

Example 6(2)

{[3-({2-Methyl-5-[4-(trifluoromethyl)phenyl]-3-furyl}methoxy)benzyl]thio}acetic acid

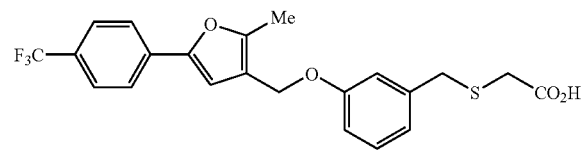

Amorphous; $^1$H-NMR (CDCl$_3$) δ 2.41 (3H, s), 3.11 (2H, s), 3.83 (2H, s), 4.97 (2H, s), 6.78 (1H, s), 6.86-6.89 (1H, m), 6.93-6.97 (2H, m), 7.22-7.27 (1H, m), 7.58 (2H, d), 7.69 (2H, d).

Example 6(3)

[2-Methyl-4-({2-methyl-5-[4-(trifluoromethyl)phenyl]-3-furyl}methoxy)phenyl]acetic acid

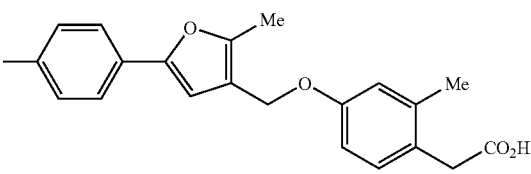

Melting point 147-149° C.; $^1$H-NMR (CDCl$_3$) δ 2.30 (3H, s) 2.39 (3H, s), 3.61 (2H, s), 4.83 (2H, s), 6.76-6.82 (3H, m), 7.12 (1H, d), 7.59 (2H, d), 7.70 (2H, d).

Example 6(4)

3-[2-Methyl-4-({2-methyl-5-[4-(trifluoromethyl)phenyl]-3-furyl}methoxy)phenyl]propionic acid

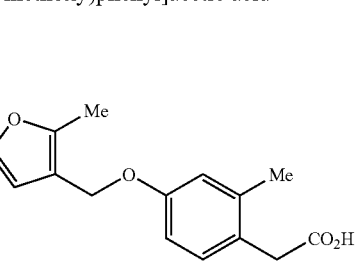

Melting point 140-141° C.; $^1$H-NMR (CDCl$_3$) δ 2.31 (3H, s) 2.40 (3H, s), 2.61 (2H, t), 2.90 (2H, t), 4.83 (2H, s), 6.73-6.79 (3H, m), 7.08 (1H, d), 7.58 (2H, d), 7.69 (2H, d).

Example 6(5)

2-Methyl-2-[4-({2-methyl-5-[4-(trifluoromethyl)phenyl]-3-furyl}methoxy)phenoxy]propionic acid

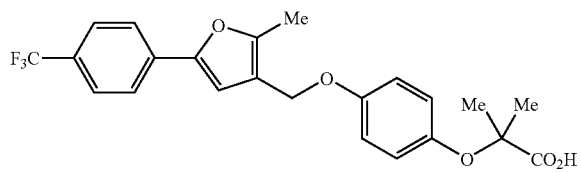

Melting point 134-135° C.; $^1$H-NMR (CDCl$_3$) δ 1.54 (6H, s), 2.39 (3H, s), 4.83 (2H, s), 6.76 (1H, s), 6.86-6.95 (4H, m), 7.59 (2H, d) 7.70 (2H, d).

Example 6(6)

3-[2-Methoxy-4-({2-methyl-5-[4-(trifluoromethyl)phenyl]-3-furyl}methoxy)phenyl]propionic acid

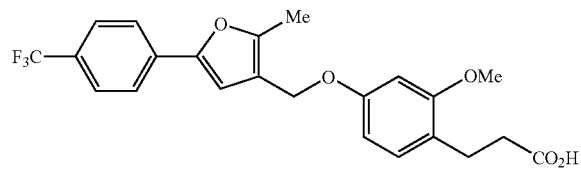

Melting point 159-160° C.; $^1$H-NMR (CDCl$_3$) δ 2.40 (3H, s), 2.63 (2H, t), 2.88 (2H, t), 3.78 (3H, s), 4.83 (2H, s), 6.46-6.49 (2H, m), 6.77 (1H, s), 7.07 (1H, d), 7.59 (2H, d), 7.70 (2H, d).

Example 6(7)

[4-({2-Methyl-5-[4-(trifluoromethyl)phenyl]-3-furyl}methoxy)phenoxy]acetic acid

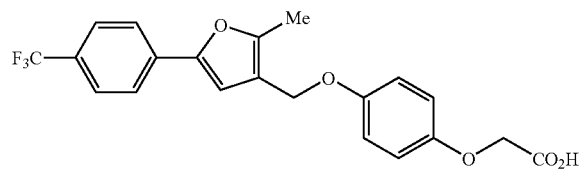

Melting point 168-169° C.; $^1$H-NMR (CDCl$_3$) δ 2.38 (3H, s) 4.55 (2H, s), 4.81 (2H, s), 6.77 (1H, s) 6.88 (4H, s), 7.59 (2H, d), 7.70 (2H, d).

Example 6(8)

[4-(3-{2-Methyl-5-[4-(trifluoromethyl)phenyl]-3-furyl}propoxy)phenyl]acetic acid

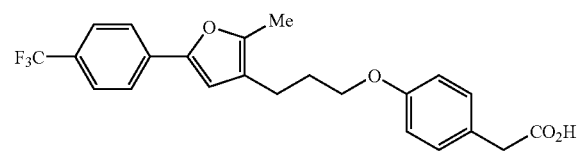

Melting point 113-114° C.; $^1$H-NMR (CDCl$_3$) δ 1.98-2.05 (2H, m), 2.27 (3H, s), 2.57 (2H, t), 3.59 (2H, s), 3.94 (2H, t), 6.59 (1H, s), 6.86 (2H, d), 7.19 (2H, d), 7.57 (2H, t), 7.67 (2H, d).

Example 6(9)

[4-({2-Methyl-5-[4-(trifluoromethyl)phenyl]-3-furyl}methoxy)phenyl]acetic acid

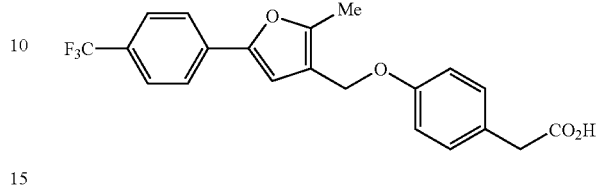

Melting point 147-149° C.; $^1$H-NMR (CDCl$_3$) δ 2.39 (3H, s) 3.60 (2H, s), 4.85 (2H, s), 6.77 (1H, s), 6.92 (2H, d), 7.20 (2H, d), 7.59 (2H, d), 7.70 (2H, d).

Example 6(10)

[2-Methoxy-4-({2-methyl-5-[4-(trifluoromethyl)phenyl]-3-furyl}methoxy)phenyl]acetic acid

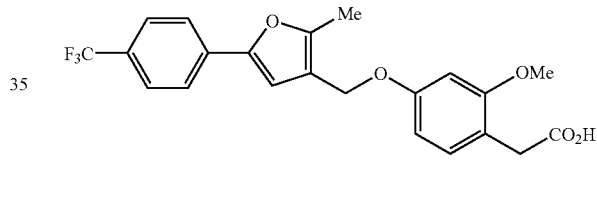

Melting point 168-169° C.; $^1$H-NMR (CDCl$_3$) δ 2.41 (3H, s) 3.61 (2H, s), 3.80 (3H, s), 4.85 (2H, s), 6.53-6.55 (2H, m), 6.79 (1H, s), 7.11 (1H, d), 7.60 (2H, d), 7.71 (2H, d).

Example 6(11)

[(3-{[5-(4-Fluorophenyl)-2-methyl-3-furyl]methoxy}benzyl)oxy]acetic acid

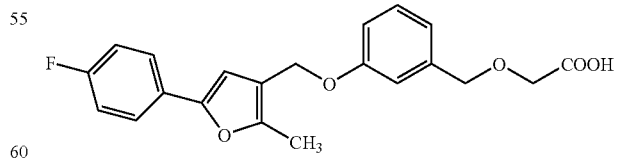

Melting point 109-110° C.; $^1$H-NMR (CDCl$_3$) δ 2.38 (3H, s), 4.14 (2H, s), 4.64 (2H, s), 4.86 (2H, s), 6.59 (1H, s), 6.92-6.98 (3H, m), 7.04 (2H, t), 7.30 (1H, t), 7.58 (2H, dd).

Example 6(12)

{[3-(3-{2-Butyl-5-[4-(trifluoromethyl)phenyl]-3-furyl}propoxy)benzyl]thio}acetic acid

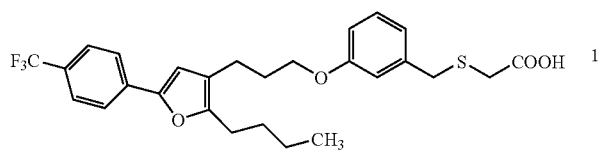

Melting point 106-107° C.; $^1$H-NMR (CDCl$_3$) δ 0.89 (3H, t), 1.27-1.39 (2H, m), 1.56-1.66 (2H, m), 1.98-2.07 (2H, m), 2.58 (2H, t), 2.61 (2H, t), 3.11 (2H, s), 3.81 (2H, s), 3.96 (2H, t), 6.60 (1H, s), 6.79-6.82 (1H, m), 6.89-6.91 (2H, m), 7.22 (1H, t), 7.57 (2H, d), 7.66 (2H, d).

Example 6(13)

[4-(2-{2-Methyl-5-[4-(trifluoromethyl)phenyl]-3-furyl}ethoxy)phenyl]acetic acid

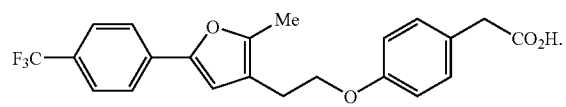

Melting point 115-116° C.; $^1$H-NMR (CDCl$_3$) δ 2.34 (3H, s) 2.84 (2H, t), 3.58 (2H, s), 4.08 (2H, t), 6.66 (1H, s), 6.86 (2H, d), 7.18 (2H, d), 7.57 (2H, d), 7.68 (2H, d).

Example 6(14)

{4-Methyl-2-[({2-methyl-5-[4-(trifluoromethyl)phenyl]-3-furyl}methyl)thio]-1,3-thiazol-5-yl}acetic acid

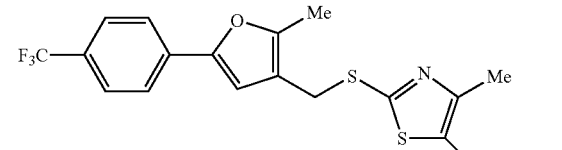

Melting point 175-176° C.; $^1$H-NMR (CDCl$_3$) δ 2.32 (3H, s) 2.34 (3H, s), 3.67 (2H, s), 4.15 (2H, s), 6.70 (1H, s), 7.57 (2H, d), 7.67 (2H, d).

Example 6(15)

[3-(3-{2-Butyl-5-[4-(trifluoromethyl)phenyl]-3-furyl}propoxy)phenyl]acetic acid

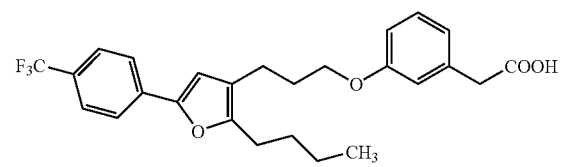

Melting point 80-82° C.; $^1$H-NMR (CDCl$_3$) δ 0.89 (3H, t), 1.26-1.39 (2H, m), 1.56-1.66 (2H, m), 1.97-2.06 (2H, m), 2.57 (2H, t), 2.60 (2H, t), 3.61 (2H, s), 3.95 (2H, t), 6.59 (1H, s), 6.79-6.87 (3H, m), 7.23 (1H, t), 7.56 (2H, d), 7.66 (2H, d).

Example 6(16)

[4-(3-{2-Butyl-5-[4-(trifluoromethyl)phenyl]-3-furyl}propoxy)phenyl]acetic acid

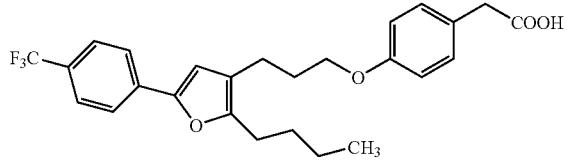

Melting point 96-97° C.; $^1$H-NMR (CDCl$_3$) δ 0.89 (3H, t), 1.27-1.39 (2H, m), 1.56-1.66 (2H, m), 1.97-2.06 (2H, m), 2.57 (2H, t), 2.60 (2H, t), 3.59 (2H, s), 3.94 (2H, t), 6.59 (1H, s), 6.85 (2H, d), 7.18 (2H, d), 7.57 (2H, d), 7.66 (2H, d)

Example 6(17)

{2-[(3-{2-Butyl-5-[4-(trifluoromethyl)phenyl]-3-furyl}propyl)thio]-4-methyl-1,3-thiazol-5-yl}acetic acid

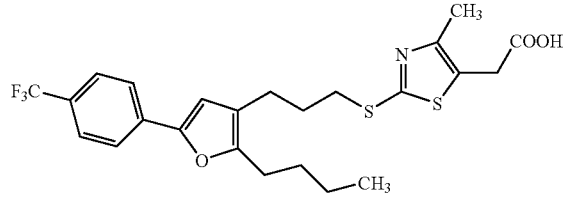

Melting point 93-94° C.; $^1$H-NMR (CDCl$_3$) δ 0.93 (3H, t), 1.31-1.43 (2H, m), 1.59-1.69 (2H, m), 1.95-2.04 (2H, m), 2.32 (3H, s), 2.53 (2H, t), 2.62 (2H, t), 3.14 (2H, t), 3.73 (2H, s), 6.57 (1H, s), 7.57 (2H, d), 7.66 (2H, d).

Example 6(18)

[2-({[5-(4-Fluorophenyl)-2-methyl-3-furyl]methyl}thio)-4-methyl-1,3-thiazol-5-yl]acetic acid

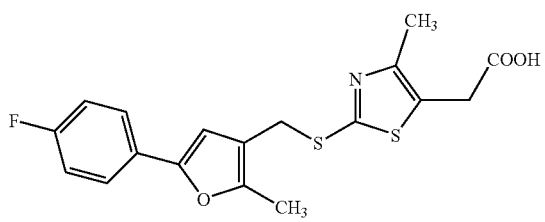

Melting point 202-205° C.; $^1$H-NMR (CDCl$_3$-DMSO-d$_6$) δ 2.30 (3H, s), 2.34 (3H, s), 3.67 (2H, s), 4.15 (2H, s), 6.52 (1H, s), 7.03 (2H, t), 7.55 (2H, dd).

Example 6(19)

4-(3-{[5-(4-Fluorophenyl)-2-methyl-3-furyl]methoxy}phenyl)butanoic acid

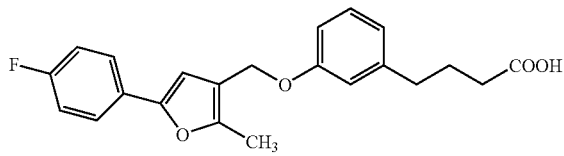

Melting point 98-99° C.; $^1$H-NMR (CDCl$_3$) δ 1.89-2.04 (2H, m), 2.38 (2H, t), 2.66 (2H, t), 4.84 (2H, s), 6.60 (1H, s), 6.79-6.84 (3H, m), 7.05 (2H, t), 7.22 (1H, t), 7.59 (2H, dd).

Example 6(20)

{[3-(3-{2-Ethyl-5-[4-(trifluoromethyl)phenyl]-3-furyl}propoxy)benzyl]thio}acetic acid

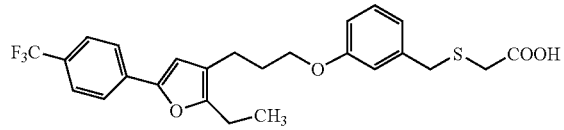

Melting point 106-107° C.; $^1$H-NMR (CDCl$_3$) δ 1.22 (3H, t) 1.98-2.07 (2H, m), 2.58 (2H, t), 2.64 (2H, q), 3.11 (2H, s), 3.81 (2H, s), 3.96 (2H, t), 6.59 (1H, s), 6.78-6.81 (1H, m), 6.89 (1H, s), 6.90 (1H, d), 7.22 (1H, t), 7.57 (2H, d), 7.67 (2H, d).

Example 6(21)

{[3-({2-Methyl-5-[4-(trifluoromethoxy)phenyl]-3-furyl}methoxy)benzyl]thio}acetic acid

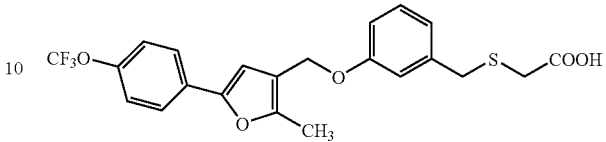

Melting point 84-85° C.; $^1$H-NMR (CDCl$_3$) δ 2.39 (3H, s), 3.11 (2H, s), 3.83 (2H, s), 4.86 (2H, s), 6.66 (1H, s), 6.86-6.97 (3H, m), 7.19 (2H, d), 7.25 (1H, t), 7.62 (2H, d).

Example 6(22)

3-[2-Methyl-4-(2-{2-methyl-5-[4-(trifluoromethyl)phenyl]-3-furyl}ethoxy)phenyl]propionic acid

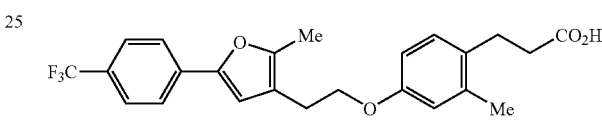

Melting point 118-120° C.; $^1$H-NMR (CDCl$_3$) δ 2.28 (3H, s), 2.34 (3H, s), 2.59 (2H, t), 2.81-2.90 (4H, m), 4.06 (2H, t), 6.61-6.71 (3H, m), 7.04 (1H, d), 7.57 (2H, d), 7.67 (2H, d).

Example 6(23)

[4-(2-{2-Methyl-5-[4-(trifluoromethyl)phenyl]-3-furyl}ethoxy)phenoxy]acetic acid

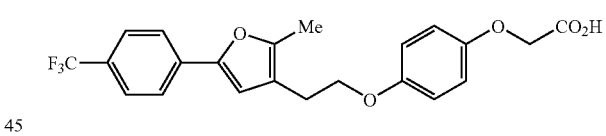

Melting point 132-133° C.; $^1$H-NMR (CDCl$_3$) δ 2.34 (3H, s), 2.83 (2H, d), 4.05 (2H, d), 4.62 (2H, s), 6.65 (1H, s), 6.81-6.85 (4H, m), 7.57 (2H, d), 7.67 (2H, d).

Example 6(24)

3-[2-Methyl-4-(3-{2-methyl-5-[4-(trifluoromethyl)phenyl]-3-furyl}propoxy)phenyl]propionic acid

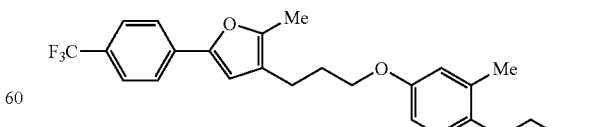

Melting point 125-126° C.; $^1$H-NMR (CDCl$_3$) δ 1.95-2.04 (2H, m), 2.27 (3H, s), 2.28 (3H, m), 2.53-2.63 (4H, m), 2.88 (2H, t), 3.92 (2H, d), 6.59 (1H, s), 6.48-6.71 (2H, m), 7.02 (1H, d), 7.56 (2H, d), 7.66 (2H, d).

Example 6(25)

[4-(3-{2-Methyl-5-[4-(trifluoromethyl)phenyl]-3-furyl}propoxy)phenoxy]acetic acid

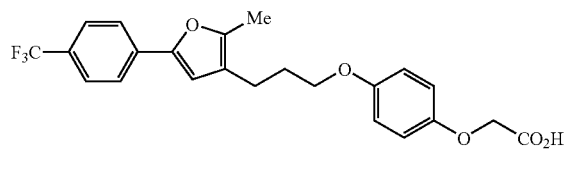

Melting point 134-135° C.; $^1$H-NMR (CDCl$_3$) δ 1.98-2.04 (2H, m), 2.26 (3H, s), 2.56 (2H, t), 3.90 (2H, t), 4.62 (2H, s), 6.58 (1H, s), 6.81-6.88 (4H, m), 7.56 (2H, d), 7.66 (2H, d).

Example 6(26)

[3-(3-{2-Ethyl-5-[4-(trifluoromethyl)phenyl]-3-furyl}propoxy)phenyl]acetic acid

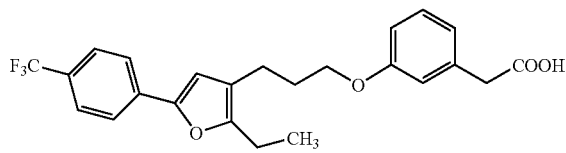

Melting point 113-114° C.; $^1$H-NMR (CDCl$_3$) δ 1.22 (3H, t) 1.97-2.06 (2H, m), 2.58 (2H, t), 2.64 (2H, q), 3.61 (2H, s), 3.96 (2H, t), 6.59 (1H, s), 6.79-6.86 (3H, m), 7.23 (1H, t), 7.57 (2H, d), 7.66 (2H, d).

Example 6(27)

[4-(3-{2-Ethyl-5-[4-(trifluoromethyl)phenyl]-3-furyl}propoxy)phenyl]acetic acid

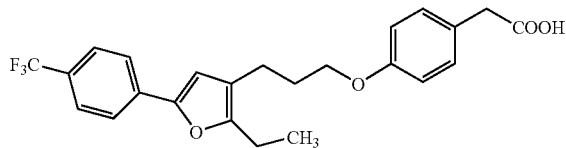

Melting point 121-122° C.; $^1$H-NMR (CDCl$_3$) δ 1.22 (3H, t), 1.97-2.06 (2H, m), 2.57 (2H, t), 2.64 (2H, q), 3.59 (2H, s), 3.95 (2H, t), 6.59 (1H, s), 6.85 (2H, d), 7.18 (2H, d), 7.57 (2H, d), 7.66 (2H, d).

Example 6(28)

{2-[(3-{2-Ethyl-5-[4-(trifluoromethyl)phenyl]-3-furyl}propyl)thio]-4-methyl-1,3-thiazol-5-yl}acetic acid

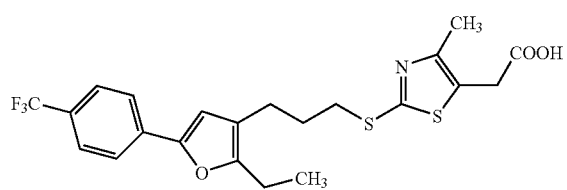

Melting point 99-100° C.; $^1$H-NMR (CDCl$_3$) δ 1.25 (3H, t) 1.94-2.05 (2H, m), 2.31 (3H, s), 2.53 (2H, t), 2.66 (2H, q), 3.14 (2H, t), 3.73 (2H, s), 6.57 (1H, s), 7.57 (2H, d), 7.67 (2H, d)

Example 6(29)

[(3-{1-[5-(4-Fluorophenyl)-2-methyl-3-furyl]ethoxy}benzyl)thio]acetic acid

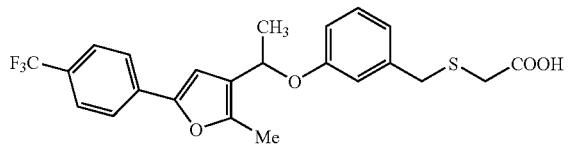

Amorphous powders; $^1$H-NMR (CDCl$_3$) δ 1.62 (3H, d), 2.34 (3H, s), 3.02 (2H, s), 3.78 (2H, s), 5.26 (1H, q), 6.55 (1H, s), 6.77-6.90 (3H, m), 7.02 (2H, t), 7.19 (1H, t), 7.55 (2H, dd).

Example 6(30)

[(3-{1-[5-(4-Fluorophenyl)-2-methyl-3-furyl]butoxy}benzyl)thio]acetic acid

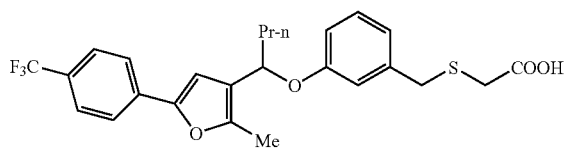

An oily matter; $^1$H-NMR (CDCl$_3$) δ 0.96 (3H, t), 1.33-1.58 (2H, m), 1.70-1.87 (1H, m), 1.94-2.09 (1H, m), 2.34 (3H, s), 3.00 (2H, s), 3.77 (2H, s), 5.04 (1H, t), 6.51 (1H, s), 6.75-6.88 (3H, m), 7.02 (2H, t), 7.17 (1H, t), 7.54 (2H, dd).

Example 6(31)

2-Methyl-2-[4-(3-{2-methyl-5-[4-(trifluoromethyl)phenyl]-3-furyl}propoxy)phenoxy]propionic acid

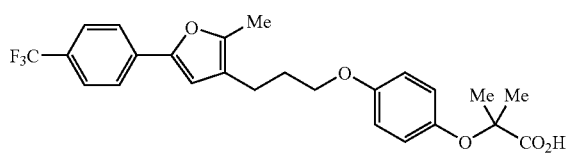

Melting point 123-124° C.; $^1$H-NMR (CDCl$_3$) δ 1.54 (6H, s) 1.97-2.04 (2H, m), 2.26 (3H, s), 2.57 (2H, t), 3.92 (2H, t), 6.59 (1H, s), 6.76-6.94 (4H, m), 7.57 (2H, d), 7.66 (2H, d).

Example 6(32)

{4-Methyl-2-[(2-{2-methyl-5-[4-(trifluoromethyl)phenyl]-3-furyl}ethyl)thio]-1,3-thiazol-5-yl}acetic acid

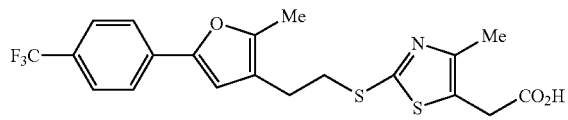

Melting point 130-132° C.; $^1$H-NMR (CDCl$_3$) δ 2.31, 2.32 (6H, each s), 2.81 (2H, t), 3.31 (2H, t), 3.71 (2H, s), 6.60 (1H, s), 7.57 (2H, t), 7.66 (2H, d).

Example 6(33)

{4-Methyl-2-[(3-{2-methyl-5-[4-(trifluoromethyl)phenyl]-3-furyl}propyl)thio]-1,3-thiazol-5-yl}acetic acid

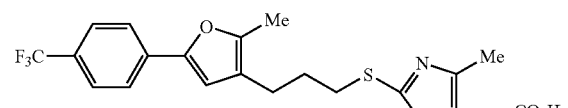

Melting point 110-112° C.; $^1$H-NMR (CDCl$_3$) δ 1.82-1.95 (2H, m) 2.24 (6H, s), 2.41-2.45 (2H, m), 3.07 (2H, t), 3.59 (2H, s) 6.53 (1H, s), 7.53 (2H, d), 7.62 (2H, d).

Example 6(34)

3-[6-({2-Methyl-5-[4-(trifluoromethyl)phenyl]-3-furyl}methoxy)-2-naphthyl]propionic acid

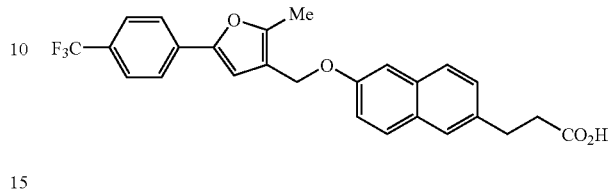

Melting point 191-192° C.; $^1$H-NMR (CDCl$_3$) δ 2.44 (3H, s) 2.76 (2H, t), 3.09 (2H, t), 4.97 (2H, s), 6.82 (1H, s), 7.15-7.20 (2H, m), 7.31 (1H, dd) 7.57-7.60 (3H, m), 7.66-7.72 (4H, m).

Example 6(35)

2-[(3-{2-[5-(4-Fluorophenyl)-2-methyl-3-furyl]ethoxy}benzyl)thio]-2-methylpropionic acid

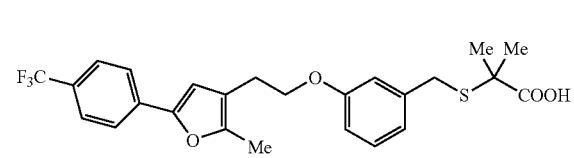

Melting point 78-81° C.; $^1$H-NMR (CDCl$_3$) δ 1.55 (6H, s), 3.31 (3H, s), 2.82 (2H, t), 3.86 (2H, s), 4.07 (2H, t), 6.46 (1H, s), 6.76 (1H, dd), 6.87 (1H, s), 6.90 (1H, d), 7.02 (2H, t), 7.18 (1H, t), 7.55 (2H, dd).

Example 6(36)

{4-Methyl-2-[({2-methyl-5-[4-(trifluoromethoxy)phenyl]-3-furyl}methyl)thio]-1,3-thiazol-5-yl}acetic acid

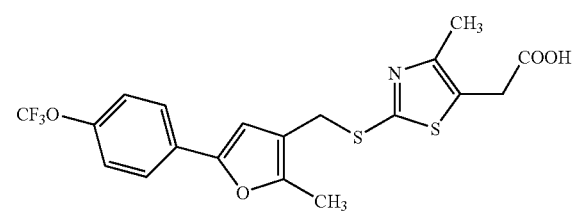

Melting point 163-165° C.; $^1$H-NMR (CDCl$_3$-DMSO-d$_6$) δ 2.31 (3H, s), 2.34 (3H, s), 3,67 (2H, s), 4.15 (2H, s), 6.58 (1H, s), 7.18 (2H, d), 7.59 (2H, d).

Example 6(37)

2-{[3-({2-[5-(4-Fluorophenyl)-2-methyl-3-furyl]pentyl}oxy)benzyl]thio}-2-methylpropionic acid

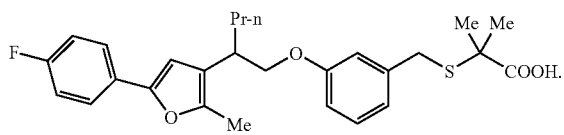

An oily matter; $^1$H-NMR (CDCl$_3$) δ 0.90 (3H, t), 1.19-1.62 (3H, m), 1.56 (6H, s), 1.71-1.88 (1H, m), 2.31 (3H, s), 2.89-3.00 (1H, m), 3.85 (2H, s), 3.95 (2H, d), 6.45 (1H, s), 6.73-6.77 (1H, m), 6.86 (1H, s), 6.89 (1H, d), 7.03 (2H, t), 7.18 (1H, t), 7.57 (2H, dd).

Example 6(38)

[2-({2-[5-(4-Fluorophenyl)-2-methyl-3-furyl]ethyl}thio)-4-methyl-1,3-thiazol-5-yl]acetic acid

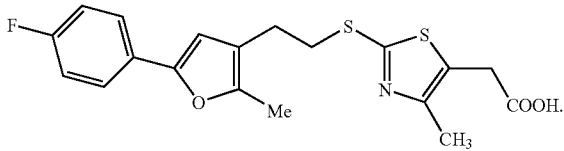

Melting point 124-126° C.; $^1$H-NMR (CDCl$_3$) δ 2.29 (3H, s) 2.32 (3H, s), 2.80 (2H, t), 3.31 (2H, t), 3.72 (2H, s), 6.42 (1H, s), 7.03 (2H, t), 7.55 (2H, dd).

Example 6(39)

[5-(3-{2-Ethyl-5-[4-(trifluoromethyl)phenyl]-3-furyl}propoxy)-2-methoxyphenyl]acetic acid

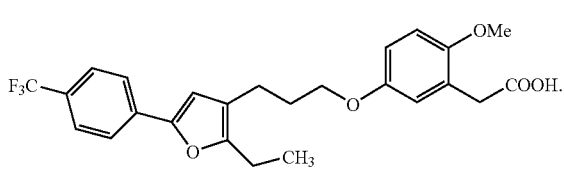

Melting point 138-139° C.; $^1$H-NMR (CDCl$_3$) δ 1.22 (3H, t), 1.95-2.05 (2H, m), 2.56 (2H, t), 2.64 (2H, q), 3.64 (2H, s), 3.79 (3H, s), 3.91 (2H, t), 6.59 (1H, s), 6.78 (3H, m), 7.57 (2H, d), 7.67 (2H, d).

Example 6(40)

[3-(3-{2-Ethyl-5-[4-(trifluoromethyl)phenyl]-3-furyl}propoxy)-4-methoxyphenyl]acetic acid

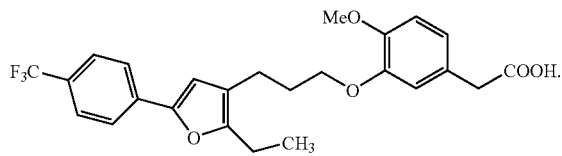

Melting point 137-138° C.; $^1$H-NMR (CDCl$_3$) δ 1.22 (3H, t) 2.03-2.12 (2H, m), 2.58 (2H, t), 2.64 (2H, q), 3.55 (2H, s), 3.85 (3H, s), 4.01 (2H, t), 6.60 (1H, s), 6.78-6.82 (3H, m), 7.56 (2H, d), 7.66 (2H, d).

Example 6(41)

2-[(3-{[5-(3-Methoxyphenyl)-2-methyl-3-furyl]methoxy}benzyl)thio]-2-methylpropionic acid

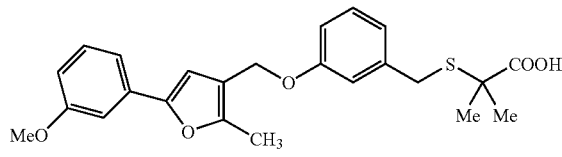

An oily matter; $^1$H-NMR (CDCl$_3$) δ 1.56 (6H, s), 2.38 (3H, s), 3.84 (3H, s), 3.88 (2H, s), 4.83 (2H, s), 6.65 (1H, s), 6.77 (1H, ddd), 6.82-6.85 (1H, m), 6.91-6.97 (2H, m), 7.15-7.28 (4H, m)

Example 6(42)

{[4-Fluoro-3-({2-methyl-5-[4-(trifluoromethyl)phenyl]-3-furyl}methoxy)benzyl]thio}acetic acid

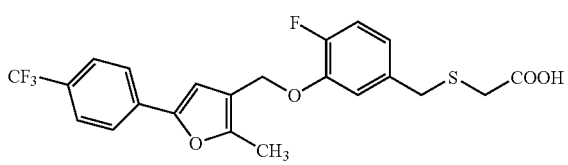

Melting point 110-111° C.; $^1$H-NMR (CDCl$_3$) δ 2.41 (3H, s) 3.08 (2H, s), 3.80 (2H, s), 4.96 (2H, s), 6.80 (1H, s), 6.86-6.92 (1H, m), 6.99-7.08 (2H, m), 7.59 (2H, d), 7.70 (2H, d).

Example 6(43)

{[2-Fluoro-5-({2-methyl-5-[4-(trifluoromethyl)phenyl]-3-furyl}methoxy)benzyl]thio}acetic acid

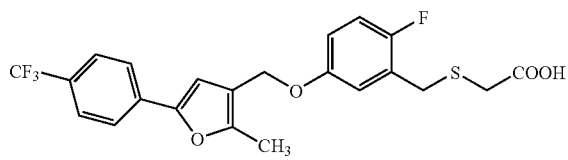

Melting point 105-106° C.; $^1$H-NMR (CDCl$_3$) δ 2.40 (3H, s), 3.19 (2H, s), 3.86 (2H, s), 4.84 (2H, s), 6.78 (1H, s), 6.82-6.88 (1H, m), 6.92-7.05 (2H, m), 7.60 (2H, d), 7.71 (2H, d).

Example 6(44)

2-[4-(3-{2-Ethyl-5-[4-(trifluoromethyl)phenyl]-3-furyl}propoxy)phenyl]-2-methylpropionic acid

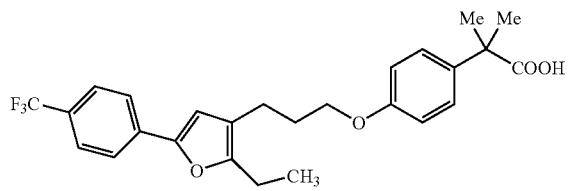

Melting point 102-103° C.; $^1$H-NMR (CDCl$_3$) δ 1.22 (3H, t) 1.58 (6H, s), 1.97-2.06 (1H, m), 2.57 (2H, t), 2.64 (2H, q), 3.95 (2H, t), 6.59 (1H, s), 6.85 (2H, d), 7.30 (2H, d), 7.57 (2H, d), 7.66 (2H, d).

Example 6(45)

2-[3-(3-{2-Ethyl-5-[4-(trifluoromethyl)phenyl]-3-furyl}propoxy)phenyl]-2-methylpropionic acid

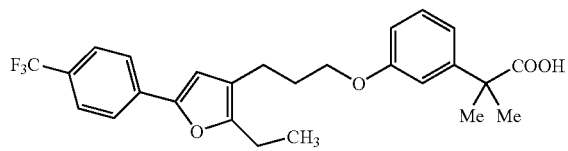

Melting point 94-95° C.; $^1$H-NMR (CDCl$_3$) δ 1.22 (3H, t), 1.58 (6H, s), 1.98-2.07 (1H, m), 2.58 (2H, t), 2.64 (2H, q), 3.96 (2H, t), 6.59 (1H, s), 6.77 (1H, ddd), 6.94-6.98 (2H, m), 7.24 (1H, t), 7.57 (2H, d), 7.66 (2H, d).

Example 6(46)

[3-(3-{2-Ethyl-5-[4-(trifluoromethyl)phenyl]-3-furyl}propoxy)-4-fluorophenyl]acetic acid

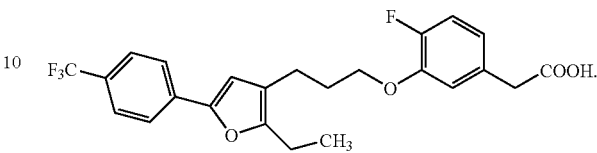

Melting point 91-93° C.; $^1$H-NMR (CDCl$_3$) δ 1.21 (3H, t), 2.01-2.10 (2H, m), 2.60 (2H, t), 2.64 (2H, q), 3.57 (2H, s), 4.02 (2H, t), 6.60 (1H, s), 6.78 (1H, ddd), 6.85 (1H, dd), 7.02 (1H, dd), 7.57 (2H, d), 7.67 (2H, d).

Example 6(47)

[5-(3-{2-Ethyl-5-[4-(trifluoromethyl)phenyl]-3-furyl}propoxy)-2-fluorophenyl]acetic acid

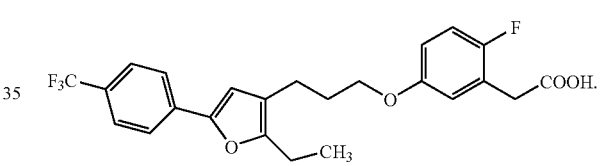

Melting point 128-129° C.; $^1$H-NMR (CDCl$_3$) δ 1.22 (3H, t), 1.96-2.05 (2H, m), 2.57 (2H, t), 2.63 (2H, q), 3.67 (2H, d), 3.91 (2H, t), 6.58 (1H, s), 6.73-6.78 (2H, m), 6.97 (1H, t), 7.57 (2H, d), 7.67 (2H, d).

Example 6(48)

{[2-Methyl-3-({2-methyl-5-[4-(trifluoromethyl)phenyl]-3-furyl}methoxy)benzyl]thio}acetic acid

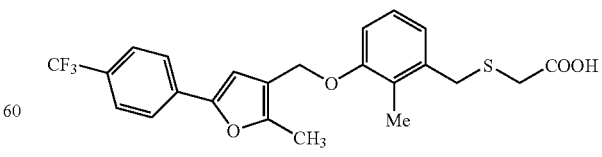

Melting point 151-152° C.; $^1$H-NMR (CDCl$_3$) δ 2.27 (3H, s) 2.40 (3H, s), 3.16 (2H, s), 3.88 (2H, s), 4.86 (2H, s), 6.78 (1H, s), 6.88 (1H, d), 6.89 (1H, d), 7.12 (1H, t), 7.59 (2H, d), 7.71 (2H, d).

Example 6(49)

{[2-Ethoxy-5-({2-methyl-5-[4-(trifluoromethyl)phenyl]-3-furyl}methoxy)benzyl]thio}acetic acid

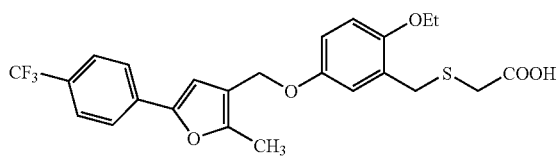

Melting point 85-87° C.; $^1$H-NMR (CDCl$_3$) δ 1.41 (3H, t), 2.39 (3H, s), 3.21 (2H, s), 3.84 (2H, s), 4.02 (2H, q), 4.82 (2H, s), 6.78 (1H, s), 6.82 (1H, s), 6.82 (1H, d), 6.91 (1H, d), 7.58 (2H, d), 7.69 (2H, d).

Example 6(50)

[3-(3-{2-Ethyl-5-[4-(trifluoromethyl)phenyl]-3-furyl}propoxy)-2-methylphenyl]acetic acid

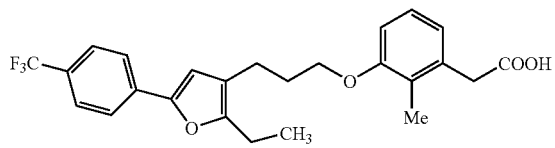

Melting point 109-110° C.; $^1$H-NMR (CDCl$_3$) δ 1.22 (3H, t) 2.00-2.09 (2H, m), 2.22 (3H, s), 2.60 (2H, t), 2.63 (2H, q), 3.69 (2H, s), 3.96 (2H, t), 6.59 (1H, s), 6.75 (1H, d), 6.81 (1H, d), 7.10 (1H, t), 7.57 (2H, d), 7.66 (2H, d).

Example 6(51)

{[4-Methyl-3-({2-methyl-5-[4-(trifluoromethyl)phenyl]-3-furyl}methoxy)benzyl]thio}acetic acid

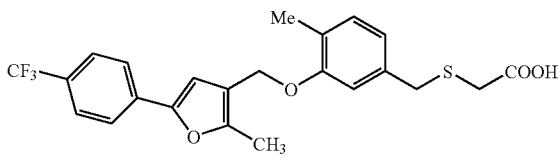

Melting point 120-121° C.; $^1$H-NMR (CDCl$_3$) δ 2.21 (3H, s) 2.42 (3H, s), 3.11 (2H, s), 3.83 (2H, s), 4.89 (2H, s), 6.78 (1H, s), 6.83 (1H, dd), 6.91 (1H, d), 7.09 (1H, d), 7.59 (2H, d), 7.70 (2H, d).

Example 6(52)

({1-[3-({2-Methyl-5-[4-(trifluoromethyl)phenyl]-3-furyl}methoxy)phenyl]butyl}thio)acetic acid

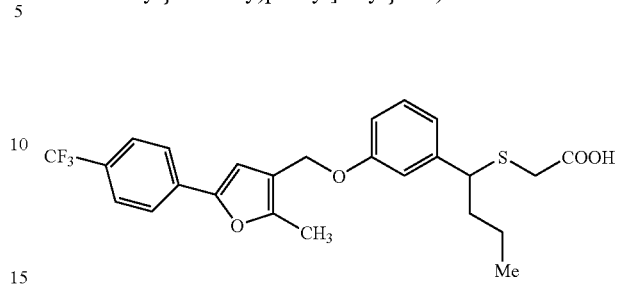

An oily matter; $^1$H-NMR (CDCl$_3$) δ 0.88 (3H, t), 1.21-1.42 (2H, m), 1.77-1.91 (2H, m), 2.41 (3H, s), 2.93 (1H, d), 3.04 (1H, d), 3.97 (1H, dd), 4.87 (2H, s), 6.79 (1H, s), 6.85-6.95 (3H, m), 7.24 (1H, t), 7.59 (2H, d), 7.70 (2H, d).

Example 6(53)

[2-({[5-(3-Methoxyphenyl)-2-methyl-3-furyl]methyl}thio)-4-methyl-1,3-thiazol-5-yl]acetic acid

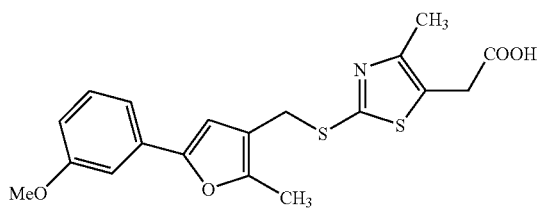

Melting point 174-176° C.; $^1$H-NMR (CDCl$_3$-DMSO-d$_6$) δ 2.31 (3H, s), 2.34 (3H, s), 3.67 (2H, s), 3.84 (3H, s), 4.15 (2H, s), 6.60 (1H, s), 6.75-6.79 (1H, m), 7.13 (1H, s), 7.18 (1H, d), 7.26 (1H, t).

Example 6(54)

{[4-Chloro-3-({2-methyl-5-[4-(trifluoromethyl)phenyl]-3-furyl}methoxy)benzyl]thio}acetic acid

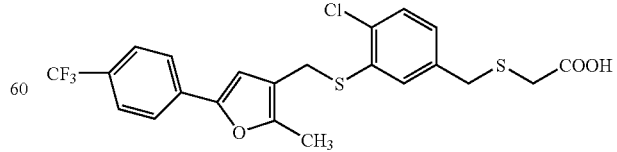

Melting point 99-101° C.; $^1$H-NMR (CDCl$_3$) δ 2.43 (3H, s), 3.08 (2H, s), 3.82 (2H, s), 4.98 (2H, s), 6.82 (1H, s), 6.89 (1H, dd), 7.03 (1H, d), 7.32 (1H, d), 7.60 (2H, d), 7.71 (2H, d).

Example 6(55)

{[3-Methyl-5-({2-methyl-5-[4-(trifluoromethyl)phenyl]-3-furyl}methoxy)benzyl]thio}acetic acid

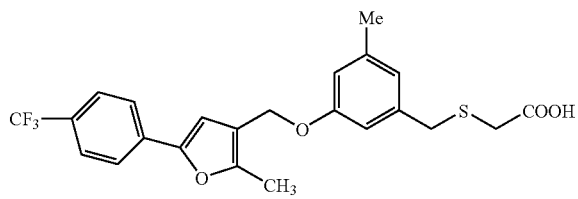

Melting point 123-124° C.; $^1$H-NMR (CDCl$_3$) δ 2.32 (3H, s) 2.41 (3H, s), 3.13 (2H, s), 3.79 (2H, s), 4.85 (2H, s), 6.70 (1H, s), 6.76 (2H, s), 6.77 (1H, s), 7.58 (2H, d), 7.69 (2H, d).

Example 6(56)

[3-(3-{2-Ethyl-5-[4-(trifluoromethyl)phenyl]-3-furyl}propoxy)-5-methylphenyl]acetic acid

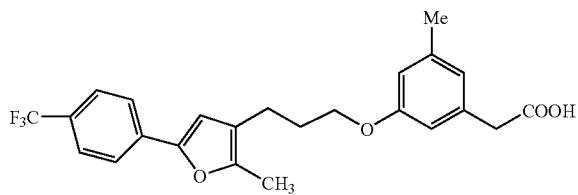

Melting point 100-101° C.; $^1$H-NMR (CDCl$_3$) δ 1.22 (3H, t) 1.96-2.04 (2H, m), 2.30 (3H, s), 2.57 (2H, t), 2.64 (2H, q), 3.56 (2H, s), 3.94 (2H, t), 6.59 (1H, s), 6.63 (2H, s), 6.67 (1H, s), 7.56 (2H, d), 7.66 (2H, d).

Example 6(57)

2-[4-(3-{2-Ethyl-5-[4-(trifluoromethyl)phenyl]-3-furyl}propoxy)phenoxy]-2-methylpropionic acid

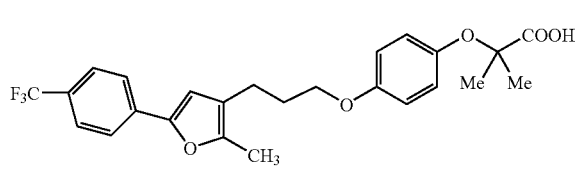

Melting point 70-71° C.; $^1$H-NMR (CDCl$_3$) δ 1.22 (3H, t), 1.53 (6H, s), 1.95-2.09 (2H, m), 2.58 (2H, t), 2.64 (2H, q), 3.93 (2H, t), 6.60 (1H, s), 6.81 (2H, d), 6.92 (2H, d), 7.58 (2H, d), 7.68 (2H, d).

Example 6(58)

2-[2-Chloro-4-(3-{2-ethyl-5-[4-(trifluoromethyl)phenyl]-3-furyl}propoxy)phenoxy]-2-methylpropionic acid

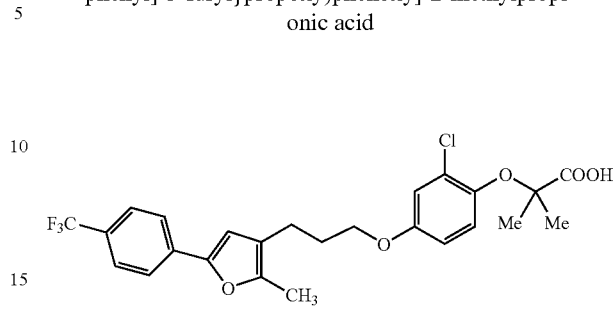

An oily matter; $^1$H-NMR (CDCl$_3$) δ 1.22 (3H, t), 1.58 (6H, s), 1.97-2.06 (2H, m), 2.57 (2H, t), 2.63 (2H, q), 3.92 (2H, t), 6.58 (1H, s), 6.73 (1H, dd), 6.94 (1H, d), 7.04 (1H, d), 7.57 (2H, d), 7.67 (2H, d).

Example 6(59)

2-Methyl-2-{[3-({2-methyl-5-[3-(trifluoromethyl)phenyl]-3-furyl}methoxy)benzyl]thio}propionic acid

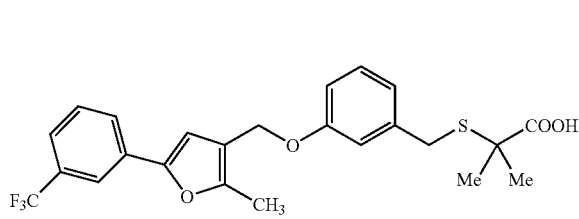

Melting point 81-82° C.; $^1$H-NMR (CDCl$_3$) δ 1.57 (6H, s), 2.40 (3H, s), 3.88 (2H, s), 4.86 (2H, s), 6.75 (1H, s), 6.82-6.87 (1H, m), 6.92-6.96 (2H, m), 7.22 (1H, t), 7.46 (2H, d), 7.75-7.79 (1H, m), 7.86 (1H, s).

Example 6(60)

2-(4-{[5-(3-Methoxyphenyl)-2-methyl-3-furyl]methoxy}phenoxy)-2-methylpropionic acid

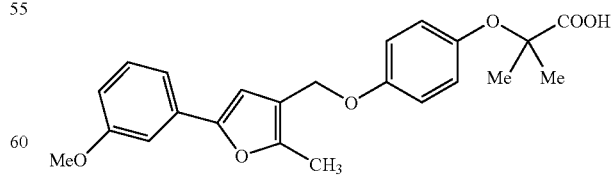

Melting point 111-112° C.; $^1$H-NMR (CDCl$_3$) δ 1.54 (6H, s), 2.38 (3H, s), 3.84 (3H, s), 4.82 (2H, s), 6.64 (1H, s), 6.76-6.80 (1H, m), 6.88 (2H, d), 6.93 (2H, d), 7.15-7.29 (3H, m).

Example 6(61)

(3-{3-[2-Ethyl-5-(3-methoxyphenyl)-3-furyl]propoxy}phenyl)acetic acid

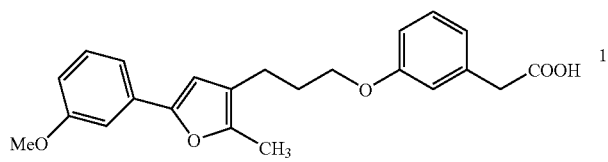

An oily matter; $^1$H-NMR (CDCl$_3$) δ 1.21 (3H, t), 1.96-2.05 (2H, m), 2.56 (2H, t), 2.62 (2H, q), 3.61 (2H, s), 3.84 (3H, s), 3.95 (2H, t), 6.47 (1H, s), 6.73-6.76 (1H, m), 6.79-6.86 (3H, m), 7.13-7.27 (4H, m).

Example 6(62)

2-(4-{3-[2-Ethyl-5-(3-methoxyphenyl)-3-furyl]propoxy}phenoxy)-2-methylpropionic acid

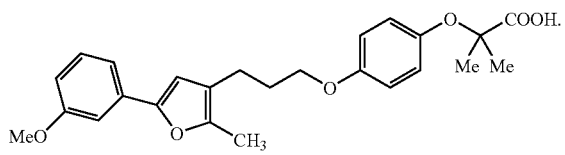

An oily matter; $^1$H-NMR (CDCl$_3$) δ 1.20 (3H, t), 1.53 (6H, s), 1.96-2.05 (2H, m), 2.56 (2H, t), 2.61 (2H, q), 3.84 (3H, s), 3.92 (2H, t), 6.46 (1H, s), 6.72-6.77 (1H, m), 6.79 (2H, d), 6.90 (2H, d), 7.12-7.27 (3H, m).

Example 6(63)

2-Methyl-2-[4-({2-methyl-5-[3-(trifluoromethyl)phenyl]-3-furyl}methoxy)phenoxy]propionic acid

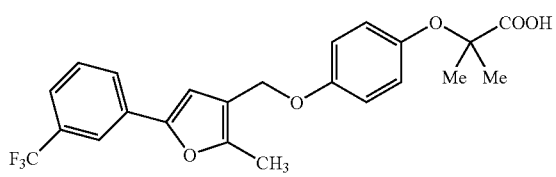

Melting point 83-84° C.; $^1$H-NMR (CDCl$_3$) δ 1.55 (6H, s), 2.40 (3H, s), 4.84 (2H, s), 6.75 (1H, s), 6.86-6.97 (4H, m), 7.47 (2H, d), 7.75-7.79 (1H, m), 7.86 (1H, s).

Example 6(64)

{4-Methyl-2-[({2-methyl-5-[3-(trifluoromethyl)phenyl]-3-furyl}methyl)thio]-1,3-thiazol-5-yl}acetic acid

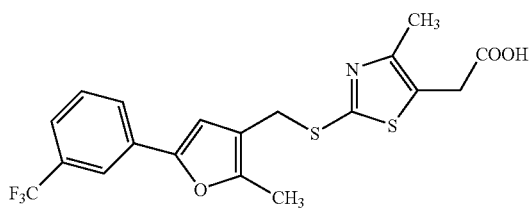

Melting point 193-194° C.; $^1$H-NMR (CDCl$_3$-DMSO-d$_6$) δ 2.33 (3H, s), 2.34 (3H, s), 3.67 (2H, s), 4.16 (2H, s), 6.70 (1H, s), 7.45-7.48 (2H, m), 7.72-7.77 (1H, m), 7.83 (1H, s).

Example 6(65)

2-{[1-(3-{[5-(4-Fluorophenyl)-2-methyl-3-furyl]methoxy}phenyl)ethyl]thio}-2-methylpropionic acid

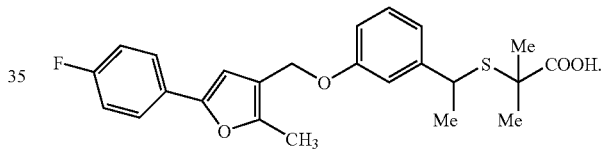

Melting point 89-90° C.; $^1$H-NMR (CDCl$_3$) δ 1.39 (3H, s), 1.53 (3H, s), 1.56 (3H, d), 2.38 (3H, s), 4.13 (1H, q), 4.85 (2H, s), 6.59 (1H, s), 6.81 (1H, dd), 6.93 (1H, d), 6.97 (1H, t), 7.04 (2H, t), 7.20 (1H, t), 7.57 (2H, dd).

Example 6(66)

2-Methyl-2-({1-[3-({2-methyl-5-[4-(trifluoromethyl)phenyl]-3-furyl}methoxy)phenyl]ethyl}thio)propionic acid

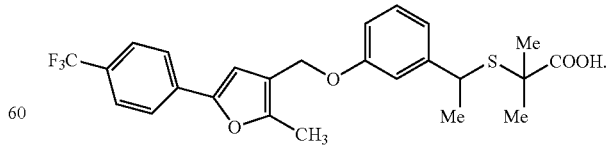

Melting point 75-77° C.; $^1$H-NMR (CDCl$_3$) δ 1.40 (3H, s), 1.53 (3H, s), 1.56 (3H, d), 2.42 (3H, s), 4.14 (1H, q), 4.87 (2H, s), 6.79 (1H, s), 6.79-6.84 (1H, m), 6.92-6.99 (2H, m), 7.21 (1H, t), 7.59 (2H, d), 7.71 (2H, d).

Example 6(67)

2-[3-(3-{2-Ethyl-5-[4-(trifluoromethyl)phenyl]-3-furyl}propoxy)phenyl]propionic acid

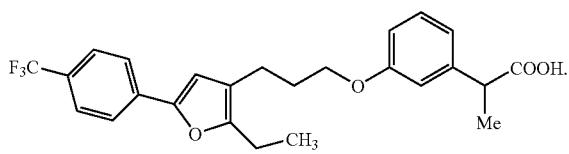

An oily matter; ¹H-NMR (CDCl₃) δ 1.22 (3H, t), 1.50 (3H, d) 1.97-2.06 (2H, m), 2.58 (2H, t), 2.64 (2H, q), 3.71 (1H, q), 3.96 (2H, t), 6.59 (1H, s), 6.79 (1H, ddd), 6.86-6.91 (2H, m), 7.23 (1H, t), 7.56 (2H, d), 7.66 (2H, d).

Example 6(68)

2-[2-Fluoro-4-({2-methyl-5-[4-(trifluoromethyl)phenyl]-3-furyl}methoxy)phenoxy]-2-methylpropionic acid

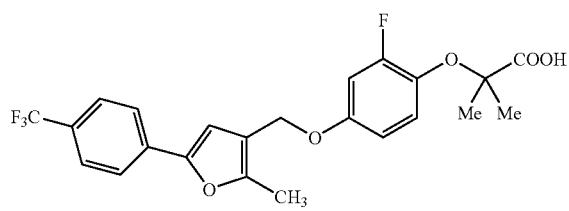

Melting point 82-83° C.; ¹H-NMR (CDCl₃) δ 1.55 (6H, d), 2.41 (3H, s), 4.83 (2H, s), 6.65-6.80 (2H, m), 6.77 (1H, s), 7.05 (1H, t), 7.60 (2H, d), 7.71 (2H, d).

Example 6(69)

2-[4-(3-{2-Ethyl-5-[4-(trifluoromethyl)phenyl]-3-furyl}propoxy)-2-fluorophenoxy]-2-methylpropionic acid

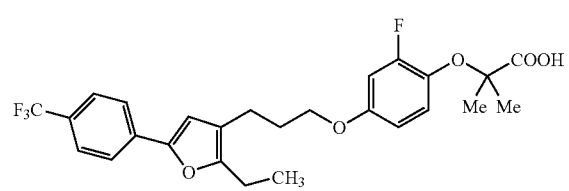

An oily matter; ¹H-NMR (CDCl₃) δ 1.22 (3H, t), 1.54 (6H, s) 1.95-2.09 (2H, m), 2.54-2.69 (4H, m), 3.92 (2H, t), 6.56-6.71 (2H, m), 6.59 (1H, s), 7.03 (1H, t), 7.58 (2H, d), 7.68 (2H, d).

Example 6(70)

2-Methyl-2-{[3-({2-methyl-5-[4-(trifluoromethyl)phenyl]-3-furyl}methoxy)benzyl]oxy}propionic acid

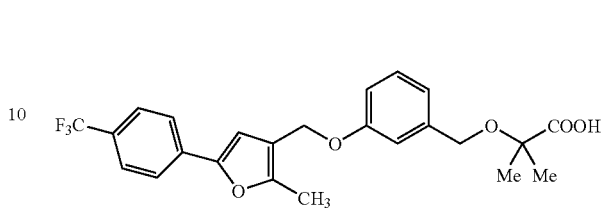

Melting point 95-96° C.; ¹H-NMR (CDCl₃) δ 1.57 (6H, s), 2.42 (3H, s), 4.52 (2H, s), 4.89 (2H, s), 6.79 (1H, s), 6.89-7.01 (3H, m), 7.30 (1H, t), 7.60 (2H, d), 7.71 (2H, d).

Example 6(71)

2-[(3-{[5-(4-Fluorophenyl)-2-methyl-3-furyl]methoxy}benzyl)oxy]-2-methylpropionic acid

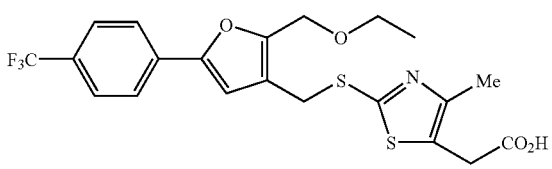

Amorphous powders; ¹H-NMR (CDCl₃) δ 1.57 (6H, s), 2.39 (3H, s), 4.52 (2H, s), 4.87 (2H, s), 6.60 (1H, s), 6.90-7.09 (5H, m), 7.29 (1H, t), 7.59 (2H, dd).

Example 6(72)

{2-[({2-(Ethoxymethyl)-5-[4-(trifluoromethyl)phenyl]-3-furyl}methyl)thio]-4-methyl-1,3-thiazol-5-yl}acetic acid Melting point 104-106° C.; ¹H-NMR (CDCl₃) δ 1.23 (3H, t), 2.34 (3H, s), 3.56 (2H, q), 3.73 (2H, s), 4.26 (2H, s), 4.51 (2H, s), 6.75 (1H, s), 7.59 (2H, d), 7.72 (2H, d).

Example 6(73)

{2-[({2-Butyl-5-[4-(trifluoromethyl)phenyl]-3-furyl}methyl)thio]-4-methyl-1,3-thiazol-5-yl}acetic acid

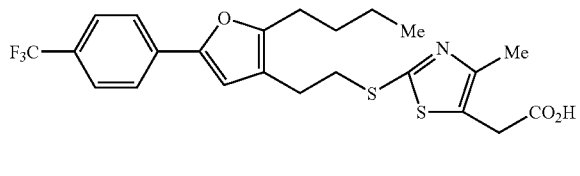

An oily matter; $^1$H-NMR (CDCl$_3$) δ 0.92 (3H, t), 1.32-1.39 (2H, m), 1.59-1.66 (2H, m), 2.30 (3H, s), 2.62 (2H, t), 2.80 (2H, t), 3.28 (2H, t), 3.67 (2H, s), 6.60 (1H, s), 7.56 (2H, d), 7.65 (2H, d).

Example 6(74)

2-{[3-({2-(Ethoxymethyl)-5-[4-(trifluoromethyl)phenyl]-3-furyl}methoxy)benzyl]thio}-2-methylpropionic acid

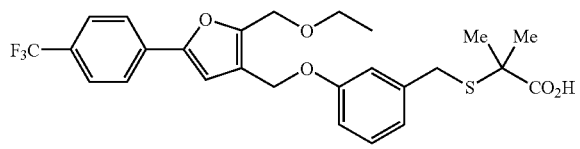

An oily matter; $^1$H-NMR (CDCl$_3$) δ 1.23 (3H, t), 1.55 (6H, s) 3.60 (2H, q), 3.88 (2H, s), 4.58 (2H, s), 4.97 (2H, s), 6.83-6.87 (2H, m), 6.92-6.98 (2H, m), 7.19 (1H, d), 7.60 (2H, d), 7.75 (2H, d).

Example 6(75)

2-[2-Methyl-4-({2-methyl-5-[4-(trifluoromethyl)phenyl]-3-furyl}methoxy)benzyl]butanoic acid

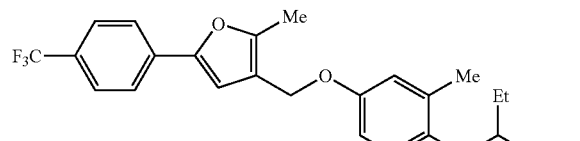

Melting point 118-119° C.; $^1$H-NMR (CDCl$_3$) δ 0.97 (3H, t), 1.58-1.72 (2H, m), 2.30 (3H, s), 2.39 (3H, s), 2.54-2.58 (1H, m), 2.72 (1H, dd), 2.92 (1H, dd), 4.82 (2H, s), 6.71-6.79 (3H, m), 7.06 (1H, d), 7.58 (2H, d), 7.70 (2H, d).

Example 6(76)

2-Methyl-3-[2-methyl-4-({2-methyl-5-[4-(trifluoromethyl)phenyl]-3-furyl}methoxy)phenyl]propionic acid

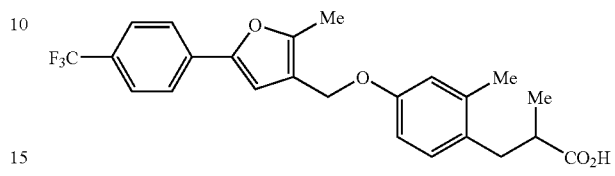

Melting point 96-97° C.; $^1$H-NMR (CDCl$_3$) δ 1.20 (3H, d), 2.30 (3H, s), 2.39 (3H, s), 2.57-2.75 (2H, m), 3.04 (1H, dd), 4.82 (2H, s), 6.72-6.78 (3H, m), 7.04 (1H, d), 7.57 (2H, d), 7.69 (2H, d).

Example 6(77)

2-Methoxy-3-[2-methyl-4-({2-methyl-5-[4-(trifluoromethyl)phenyl]-3-furyl}methoxy)phenyl]propionic acid

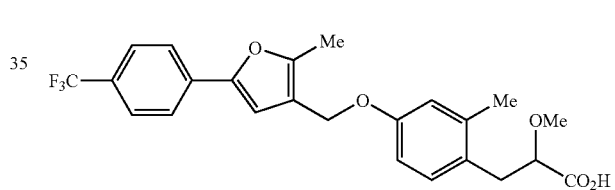

Melting point 125-126° C.; $^1$H-NMR (CDCl$_3$) δ 2.34 (3H, s) 2.40 (3H, s), 2.97 (1H, dd), 3.13 (1H, dd), 3.35 (3H, s), 3.95 (1H, dd), 4.83 (2H, s), 6.74-6.79 (3H, m), 7.12 (1H, d), 7.58 (2H, d), 7.69 (2H, d).

Example 6(78)

2,2-Dimethyl-3-[4-({2-methyl-5-[4-(trifluoromethyl)phenyl]-3-furyl}methoxy)phenyl]propionic acid

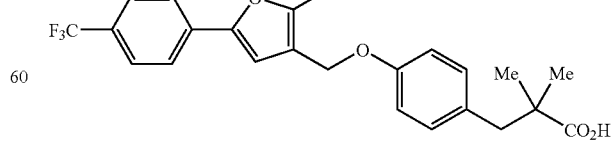

Melting point 125-127° C.; $^1$H-NMR (CDCl$_3$) δ 1.20 (6H, s) 2.38 (3H, s), 2.48 (2H, s), 4.82 (2H, s), 6.75 (1H, s), 6.88 (2H, d), 7.10 (2H, d), 7.57 (2H, d), 7.68 (2H, d).

Example 6(79)

2,2-Dimethyl-3-[4-(2-{2-methyl-5-[4-(trifluoromethyl)phenyl]-3-furyl}ethoxy)phenyl]propionic acid

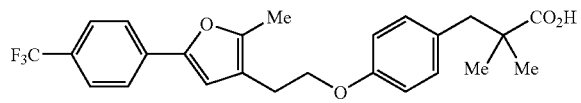

An oily matter; $^1$H-NMR (CDCl$_3$) δ 1.18 (6H, s), 2.33 (3H, s) 2.78-2.86 (4H, m), 4.06 (2H, t), 6.65 (1H, s), 6.81 (2H, d), 7.07 (2H, d), 7.56 (2H, d), 7.66 (2H, d).

Example 6(80)

2,2-Dimethyl-3-[4-(3-{2-methyl-5-[4-(trifluoromethyl)phenyl]-3-furyl}propoxy)phenyl]propionic acid

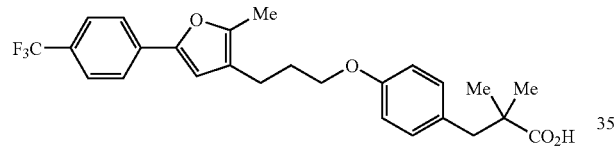

Amorphous powders; $^1$H-NMR (CDCl$_3$) δ 1.18 (6H, s), 2.00 (2H, t), 2.26 (3H, s), 2.56 (2H, t), 2.82 (2H, s), 3.93 (2H, t), 6.59 (1H, s), 6.80 (2H, d), 7.07 (2H, d), 7.56 (2H, d), 7.65 (2H, d)

Example 6(81)

[3-Methoxy-4-({2-methyl-5-[4-(trifluoromethyl)phenyl]-3-furyl}methoxy)phenyl]acetic acid

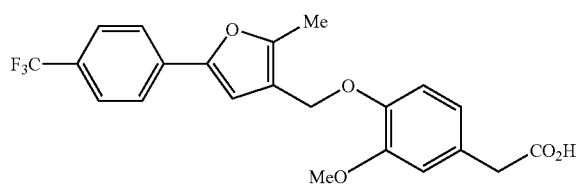

Melting point 139-140° C.; $^1$H-NMR (CDCl$_3$) δ 2.38 (3H, s) 3.59 (2H, s), 3.86 (3H, s), 4.91 (2H, s), 6.78-6.82 (3H, m), 7.58 (2H, d), 7.69 (2H, d).

Example 6(82)

3-[4-Methoxy-3-({2-methyl-5-[4-(trifluoromethyl)phenyl]-3-furyl}methoxy)phenyl]propionic acid

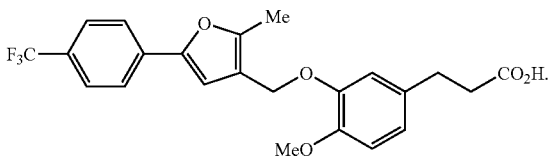

Melting point 128-129° C.; $^1$H-NMR (CDCl$_3$) δ 2.38 (3H, s) 2.60-2.68 (2H, m), 2.89 (2H, t), 3.84 (3H, s), 4.91 (2H, s), 6.81 (4H, s), 7.58 (2H, d), 7.69 (2H, d).

Example 6(83)

[3-(2-{2-Methyl-5-[4-(trifluoromethyl)phenyl]-3-furyl}ethoxy)phenyl]acetic acid

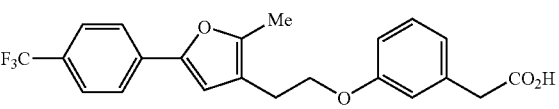

Melting point 92-94° C.; $^1$H-NMR (CDCl$_3$) δ 2.34 (3H, s), 2.84 (2H, t), 3.61 (2H, s), 4.08 (2H, t), 6.66 (1H, s), 6.81-6.88 (3H, m), 7.19-7.27 (1H, m), 7.57 (2H, d), 7.68 (2H, d).

Example 6(84)

[3-(3-{2-Methyl-5-[4-(trifluoromethyl)phenyl]-3-furyl}propoxy)phenyl]acetic acid

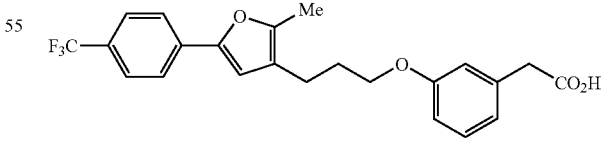

Melting point 111-113° C.; $^1$H-NMR (CDCl$_3$) δ 2.01 (2H, t), 2.26 (3H, s), 2.56 (2H, t), 3.61 (2H, s), 3.95 (2H, t), 6.59 (1H, s), 6.80-6.87 (3H, m), 7.19-7.27 (1H, m), 7.56 (2H, d), 7.66 (2H, d).

Example 6(85)

2-Methyl-2-[3-({2-methyl-5-[4-(trifluoromethyl)phenyl]-3-furyl}methoxy)phenyl]propionic acid

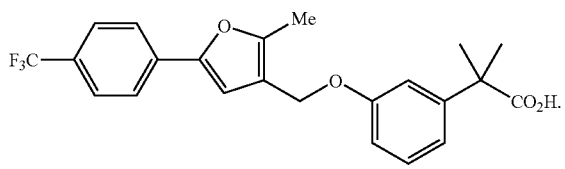

Melting point 127-128° C.; $^1$H-NMR (CDCl$_3$) δ 1.59 (6H, s), 2.40 (3H, s), 4.85 (2H, s), 6.78 (1H, s), 6.85-6.89 (1H, m), 7.00-7.02 (2H, m), 7.24-7.30 (1H, m), 7.59 (2H, d), 7.70 (2H, d).

Example 6(86)

2-Methyl-2-[4-({2-methyl-5-[4-(trifluoromethyl)phenyl]-3-furyl}methoxy)phenyl]propionic acid

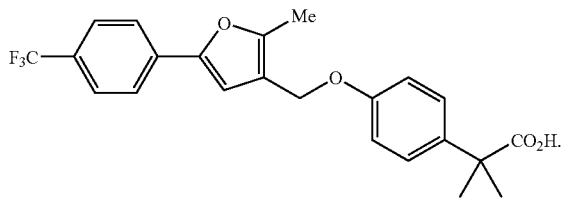

Melting point 105-107° C.; $^1$H-NMR (CDCl$_3$) δ 1.58 (6H, s), 2.39 (3H, s), 4.85 (2H, s), 6.76 (1H, s), 6.94 (2H, d), 7.34 (2H, d), 7.59 (2H, d), 7.70 (2H, d).

Example 6(87)

[3-({2-Methyl-5-[4-(trifluoromethyl)phenyl]-3-furyl}methoxy)phenoxy]acetic acid

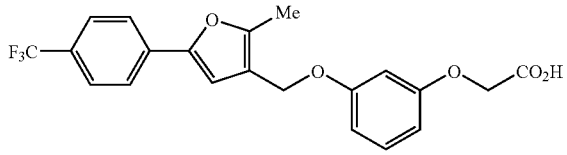

Melting point 118-119° C.; $^1$H-NMR (CDCl$_3$) δ 2.40 (3H, s), 4.66 (2H, s), 4.84 (2H, s), 6.51-6.54 (1H, m), 6.56-6.58 (1H, m), 6.62-6.66 (1H, m), 6.77 (1H, s), 7.11 (1H, d), 7.59 (2H, d), 7.69 (2H, d).

Example 6(88)

2-Methyl-2-{[4-({2-methyl-5-[4-(trifluoromethyl)phenyl]-3-furyl}methoxy)phenyl]thio}propionic acid

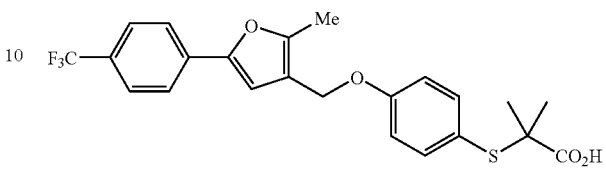

Melting point 128-129° C.; $^1$H-NMR (CDCl$_3$) δ 1.48 (6H, s), 2.38 (3H, s), 4.84 (2H, s), 6.73 (1H, s), 6.93 (2H, d), 7.46 (2H, d), 7.58 (2H, d), 7.68 (2H, d).

Example 6(89)

3-[5-({2-Methyl-5-[4-(trifluoromethyl)phenyl]-3-furyl}methoxy)-1-benzofuran-2-yl]propionic acid

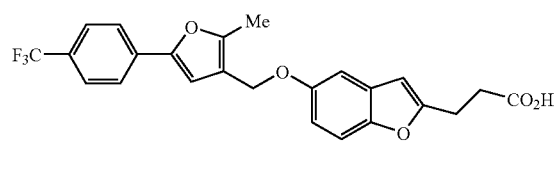

Melting point 156-157° C.; $^1$H-NMR (CDCl$_3$) δ 2.39 (3H, s), 2.82 (2H, t), 3.10 (2H, t), 4.88 (2H, s), 6.39 (1H, s), 6.80 (1H, s), 6.88 (1H, dd), 7.04 (1H, d), 7.30 (1H, d), 7.59 (2H, d), 7.70 (2H, d).

Example 6(90)

[5-({2-Methyl-5-[4-(trifluoromethyl)phenyl]-3-furyl}methoxy)-1-benzofuran-2-yl]acetic acid

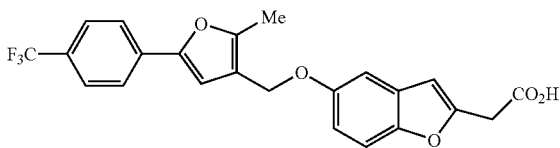

Melting point 140-142° C.; $^1$H-NMR (CDCl$_3$) δ 2.34 (3H, s), 3.75 (2H, s), 4.80 (2H, s), 6.51 (1H, s), 6.74 (1H, s), 6.86 (1H, d), 7.00 (1H, s), 7.25 (1H, s), 7.55 (2H, d), 7.65 (2H, d).

Example 6(91)

3-[4-({2-Methyl-5-[4-(trifluoromethyl)phenyl]-3-furyl}methoxy)-2-propylphenyl]propionic acid

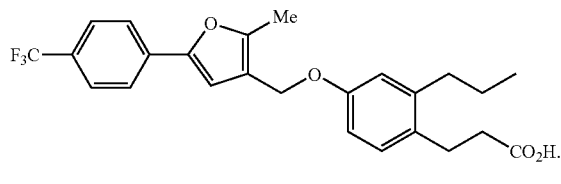

Melting point 129-131° C.; $^1$H-NMR (CDCl$_3$) δ 0.99 (3H, t), 1.57-1.68 (2H, m), 2.40 (3H, s), 2.54-2.66 (4H, m), 2.93 (2H, t), 4.84 (2H, s), 6.73-6.79 (3H, m), 7.09 (1H, d), 7.59 (2H, d), 7.70 (2H, d).

Example 6(92)

2-[2-Chloro-4-({2-methyl-5-[4-(trifluoromethyl)phenyl]-3-furyl}methoxy)phenoxy]-2-methylpropionic acid

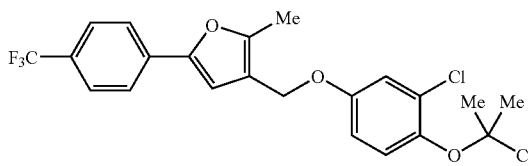

Melting point 92-93° C.; $^1$H-NMR (CDCl$_3$) δ 1.59 (6H, s), 2.40 (3H, s), 4.82 (2H, s), 6.75 (1H, s), 6.81 (1H, dd), 7.02 (1H, d), 7.07 (1H, d), 7.59 (2H, d), 7.70 (2H, d).

Example 6(93)

[3-Chloro-4-(3-{2-ethyl-5-[4-(trifluoromethyl)phenyl]-3-furyl}propoxy)phenyl]acetic acid

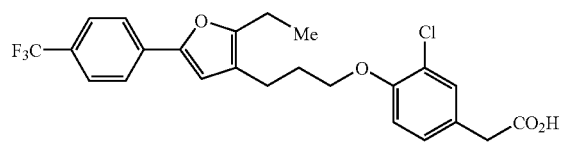

Melting point 112-113° C.; $^1$H-NMR (CDCl$_3$) δ 1.20 (3H, t), 2.04-2.08 (2H, m), 2.64-2.68 (4H, m), 3.57 (2H, s), 4.00 (2H, t), 6.59 (1H, s), 6.82 (1H, d), 7.08 (1H, dd), 7.30 (1H, d), 7.57 (2H, d), 7.66 (2H, d).

Example 6(94)

2-{[4-Fluoro-3-({2-methyl-5-[4-(trifluoromethyl)phenyl]-3-furyl}methoxy)benzyl]thio}-2-methylpropionic acid

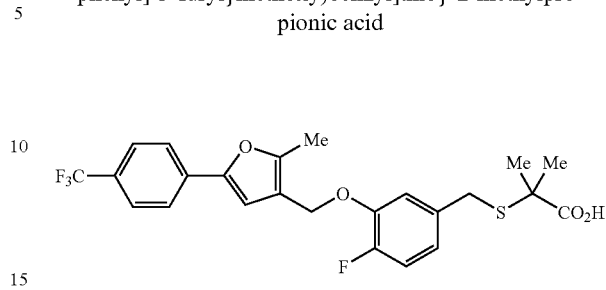

Melting point 120-123° C.; $^1$H-NMR (CDCl$_3$) δ 1.54 (6H, s), 2.40 (3H, s), 3.83 (2H, s), 4.93 (2H, s), 6.78 (1H, s), 6.88-6.89 (1H, m), 6.93-7.06 (2H, m), 7.58 (2H, d), 7.68 (2H, d).

Example 6(95)

2-{[2-Fluoro-5-({2-methyl-5-[4-(trifluoromethyl)phenyl]-3-furyl}methoxy)benzyl]thio}-2-methylpropionic acid

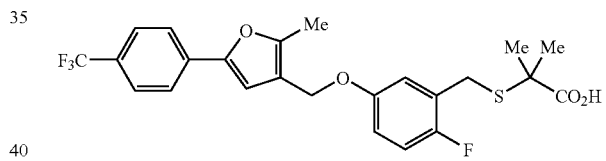

Melting point 131-132° C.; $^1$H-NMR (CDCl$_3$) δ 1.57 (6H, s), 2.39 (3H, s), 3.90 (2H, s), 4.81 (2H, s), 6.76-6.82 (2H, m), 6.90-6.99 (2H, m), 7.58 (2H, d), 7.69 (2H, d).

Example 6(96)

2-{[2-Fluoro-3-({2-methyl-5-[4-(trifluoromethyl)phenyl]-3-furyl}methoxy)benzyl]thio}-2-methylpropionic acid

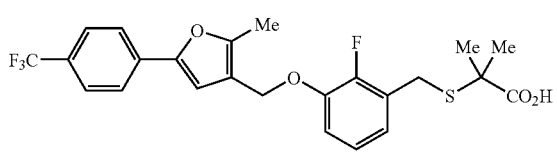

Melting point 106-108° C.; $^1$H-NMR (CDCl$_3$) δ 1.57 (6H, s), 2.38 (3H, s), 3.93 (2H, s), 4.91 (2H, s), 6.77 (1H, s), 6.90-6.99 (3H, m), 7.58 (2H, d), 7.68 (2H, d).

Example 6(97)

[3-(3-{2-Ethyl-5-[4-(trifluoromethyl)phenyl]-3-furyl}propoxy)-2-fluorophenyl]acetic acid

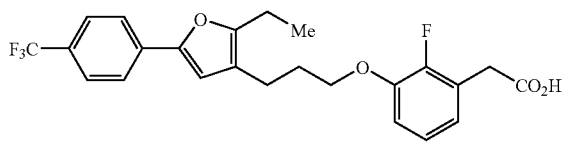

Melting point 92-93° C.; $^1$H-NMR (CDCl$_3$) δ 1.21 (3H, t), 1.98-2.12 (2H, m), 2.57-2.70 (4H, m), 3.72 (2H, d), 4.02 (2H, t), 6.60 (1H, s), 6.78-7.04 (3H, m), 7.57 (2H, d), 7.67 (2H, d).

Example 6(98)

[4-Chloro-3-(3-{2-ethyl-5-[4-(trifluoromethyl)phenyl]-3-furyl}propoxy)phenyl]acetic acid

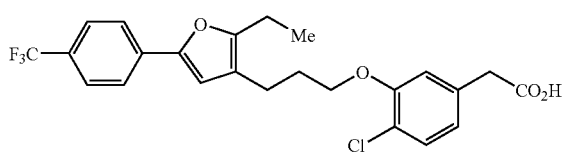

Melting point 104-105° C.; $^1$H-NMR (CDCl$_3$) δ 1.20 (3H, t), 2.03-2.10 (2H, m), 2.59-2.70 (4H, m), 3.58 (2H, s), 4.02 (2H, t), 6.60 (1H, s), 6.78-6.81 (2H, m), 7.31 (1H, d), 7.57 (2H, d), 7.67 (2H, d).

Example 6(99)

2-{[4-Chloro-3-({2-methyl-5-[4-(trifluoromethyl)phenyl]-3-furyl}methoxy)benzyl]thio}-2-methylpropionic acid

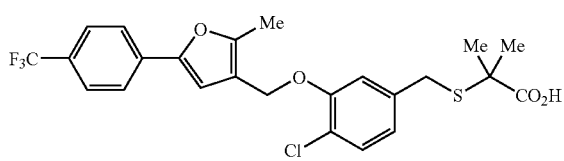

Melting point 140-142° C.; $^1$H-NMR (CDCl$_3$) δ 1.53 (6H, s), 2.41 (3H, s), 3.84 (2H, s), 4.93 (2H, s), 6.79 (1H, s), 6.86 (1H, dd), 6.99 (1H, d), 7.24 (1H, s), 7.58 (2H, d), 7.69 (2H, d).

Example 6(100)

[3-(3-{2-Ethyl-5-[4-(trifluoromethyl)phenyl]-3-furyl}propoxy)-1H-indazol-1-yl]acetic acid

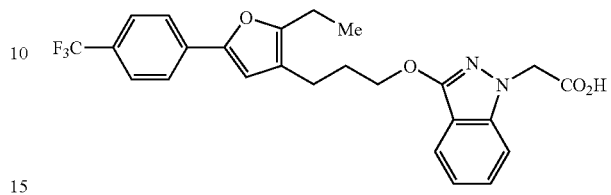

Melting point 139-140° C.; $^1$H-NMR (CDCl$_3$) δ 1.22 (3H, t), 2.07-2.12 (2H, m), 2.57-2.68 (4H, m), 4.37 (2H, t), 4.92 (2H, s), 6.61 (1H, s), 7.06-7.11 (1H, m), 7.16 (1H, d), 7.37-7.42 (1H, m), 7.56 (2H, d), 7.64-7.69 (3H, m).

Example 6(101)

[5-({2-Methyl-5-[4-(trifluoromethyl)phenyl]-3-furyl}methoxy)-1-benzothien-2-yl]acetic acid

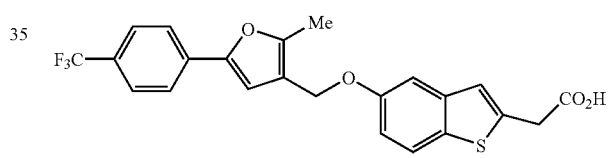

Melting point 153-154° C.; $^1$H-NMR (CDCl$_3$) δ 2.41 (3H, s), 3.94 (2H, d), 4.91 (2H, s), 6.79 (1H, s), 7.00 (1H, dd), 7.12 (1H, s), 7.24-7.25 (1H, m), 7.59 (2H, d), 7.65 (1H, d), 7.70 (2H, d).

Example 6(102)

[5-(3-{2-Ethyl-5-[4-(trifluoromethyl)phenyl]-3-furyl}propoxy)-1-benzothien-2-yl]acetic acid

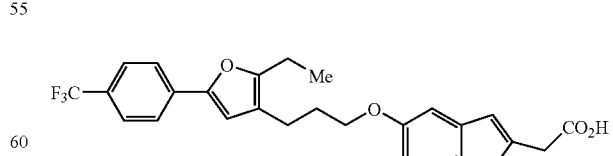

Melting point 111-112° C.; $^1$H-NMR (CDCl$_3$) δ 1.21 (3H, t), 2.04 (2H, t), 2.57-2.67 (4H, m), 3.92 (2H, s), 3.99 (2H, t), 6.59 (1H, s), 6.93-6.96 (1H, m), 7.08 (1H, s), 7.13 (1H, s), 7.55 (2H, d), 7.60 (1H, s), 7.66 (2H, d).

Example 6(103)

3-[5-({2-Methyl-5-[4-(trifluoromethyl)phenyl]-3-furyl}methoxy)-1-benzothien-2-yl]propionic acid

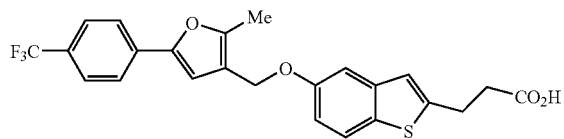

Melting point 187-188° C.; $^1$H-NMR (CDCl$_3$) δ 2.41 (3H, s), 2.73 (2H, t), 3.21 (2H, t), 4.91 (2H, s), 6.81 (1H, s), 6.93-6.98 (2H, m), 7.21 (1H, d), 7.59 (2H, d), 7.62 (1H, s), 7.71 (2H, d).

Example 6(104)

2-Methyl-2-[4-(4-{2-methyl-5-[4-(trifluoromethyl)phenyl]-3-furyl}butoxy)phenoxy]propionic acid

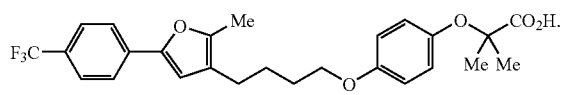

Melting point 67-69° C.; $^1$H-NMR (CDCl$_3$) δ 1.53 (6H, s), 1.70-1.83 (4H, m), 2.29 (3H, s), 2.38-2.45 (2H, m), 3.93 (2H, t), 6.58 (1H, s), 6.79 (2H, d), 6.90 (2H, d), 7.56 (2H, d), 7.66 (2H, d).

Example 6(105)

2-Methyl-2-{4-[((E)-4-{2-methyl-5-[4-(trifluoromethyl)phenyl]-3-furyl}-3-butenyl)oxy]phenoxy}propionic acid

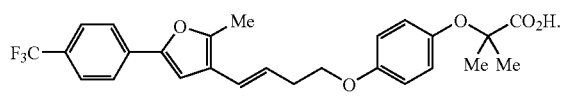

An oily matter; $^1$H-NMR (CDCl$_3$) δ 1.54 (6H, s), 2.37 (3H, s), 2.63-2.69 (2H, m), 4.02 (2H, t), 5.97 (1H, dt), 6.30 (1H, d), 6.81-6.87 (3H, m), 6.88-6.95 (2H, m), 7.58 (2H, d), 7.69 (2H, d).

Example 6(106)

2-Methyl-2-{[4-(4-{2-methyl-5-[4-(trifluoromethyl)phenyl]-3-furyl}butoxy)phenyl]thio}propionic acid

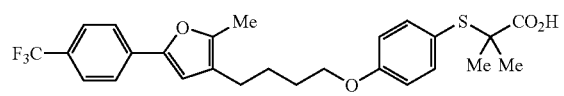

Melting point 155-156° C.; $^1$H-NMR (CDCl$_3$) δ 1.46 (6H, s), 1.68-1.83 (4H, m), 2.29 (3H, m), 2.36-2.44 (2H, m), 3.95 (2H, t), 6.58 (1H, s), 6.82 (2H, d), 7.40 (2H, d), 7.56 (2H, d), 7.66 (2H, d).

Example 6(107)

2-Methyl-2-({[5-({2-methyl-5-[4-(trifluoromethyl)phenyl]-3-furyl}methoxy)-1-benzothien-2-yl]methyl}thio)propionic acid

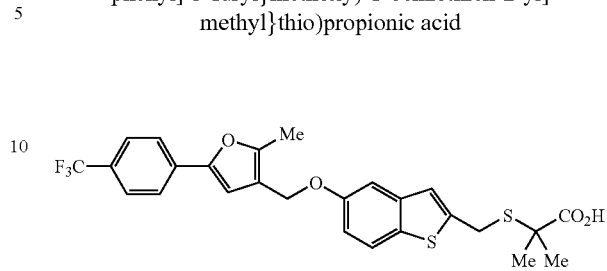

Melting point 158-159° C.; $^1$H-NMR (CDCl$_3$) δ 1.57 (6H, s), 2.40 (3H, s), 4.16 (2H, d), 4.89 (2H, s), 6.78 (1H, s), 6.98 (1H, dd), 7.12 (1H, s), 7.21 (1H, d), 7.59 (2H, d), 7.62 (1H, d), 7.70 (2H, d).

Example 6(108)

2-Methyl-2-{[4-({2-methyl-5-[3-(trifluoromethyl)phenyl]-3-furyl}methoxy)phenyl]thio}propionic acid

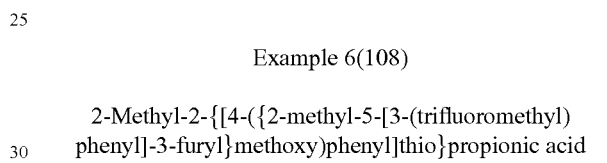

Melting point 108-109° C.; $^1$H-NMR (CDCl$_3$) δ 1.48 (6H, s), 2.38 (3H, s), 4.85 (2H, s), 6.71 (1H, s), 6.94 (2H, d), 7.44-7.48 (4H, m), 7.72-7.76 (1H, m), 7.84 (1H, s).

Example 6(109)

2-Methyl-2-{[3-({2-methyl-5-[4-(trifluoromethyl)phenyl]-3-furyl}methoxy)benzyl]thio}propionic acid

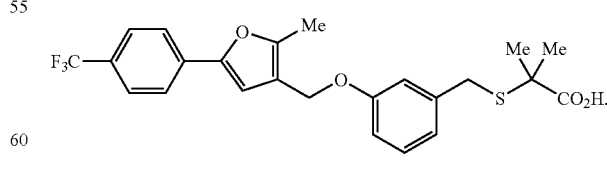

Melting point 148-149° C.; $^1$H-NMR (CDCl$_3$) δ 1.56 (6H, s), 2.40 (3H, s), 3.88 (2H, s), 4.85 (2H, s), 6.77 (1H, s), 6.81-6.97 (3H, m), 7.20 (1H, d), 7.59 (2H, d), 7.70 (2H, d).

Example 6(110)

2-[(3-{[5-(4-Methoxyphenyl)-2-methyl-3-furyl]methoxy}benzyl)thio]-2-methylpropionic acid

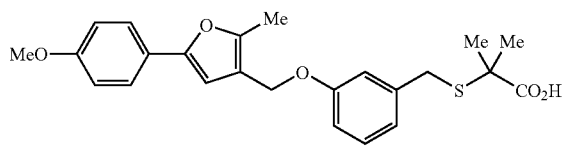

Melting point 96-97° C.; $^1$H-NMR (CDCl$_3$) δ 1.56 (6H, s), 2.36 (3H, s), 3.82 (3H, s), 3.87 (2H, s), 4.83 (2H, s), 6.52 (1H, s), 6.81-6.97 (4H, m), 7.19 (1H, d), 7.55 (2H, d).

Example 6(111)

2-[(3-{[5-(4-Chlorophenyl)-2-methyl-3-furyl]methoxy}benzyl)thio]-2-methylpropionic acid

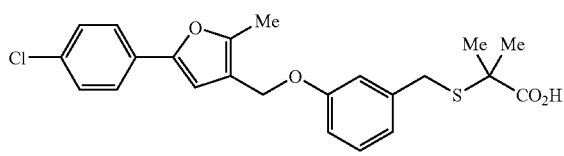

Melting point 143-144° C.; $^1$H-NMR (CDCl$_3$) δ 1.56 (6H, s), 2.37 (3H, s), 3.87 (2H, s), 4.83 (2H, s), 6.64 (1H, s), 6.80-6.95 (3H, m), 7.19 (1H, d), 7.31 (2H, d), 7.54 (2H, d).

Example 6(112)

2-[(3-{[5-(3-Fluorophenyl)-2-methyl-3-furyl]methoxy}benzyl)thio]-2-methylpropionic acid

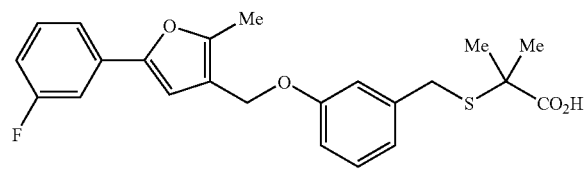

Melting point 116-117° C.; $^1$H-NMR (CDCl$_3$) δ 1.56 (6H, s) 2.38 (3H, s), 3.88 (2H, s), 4.84 (2H, s), 6.68 (1H, s), 6.82-6.97 (4H, m), 7.18-7.39 (4H, m).

Example 6(113)

2-[(4-{[5-(4-Methoxyphenyl)-2-methyl-3-furyl]methoxy}phenyl)thio]-2-methylpropionic acid

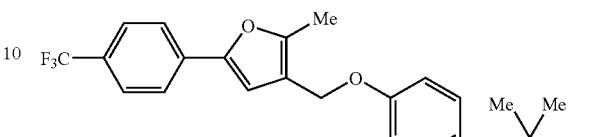

Melting point 145-146° C.; $^1$H-NMR (CDCl$_3$) δ 1.48 (6H, s), 2.34 (3H, s), 3.81 (3H, s), 4.82 (2H, s), 6.48 (1H, s), 6.86-6.95 (4H, m), 7.45 (2H, d), 7.53 (2H, d).

Example 6(114)

2-[(4-{[5-(4-Chlorophenyl)-2-methyl-3-furyl]methoxy}phenyl)thio]-2-methylpropionic acid

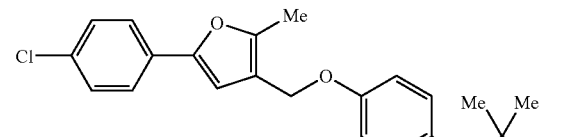

Melting point 130-131° C.; $^1$H-NMR (CDCl$_3$) δ 1.48 (6H, s), 2.36 (3H, s), 4.83 (2H, s), 6.61 (1H, s), 6.93 (2H, d), 7.31 (2H, d), 7.46 (2H, d), 7.53 (2H, d).

Example 6(115)

2-[(4-{[5-(3-Fluorophenyl)-2-methyl-3-furyl]methoxy}phenyl)thio]-2-methylpropionic acid

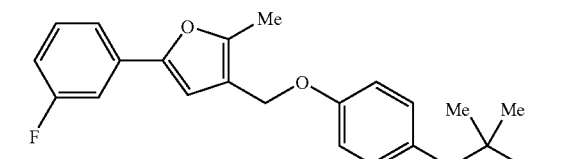

Melting point 146-147° C.; $^1$H-NMR (CDCl$_3$) δ 1.48 (6H, s), 2.37 (3H, s), 4.84 (2H, s), 6.65 (1H, s), 6.92-6.95 (3H, m), 7.26-7.38 (3H, m), 7.46 (2H, d).

Example 6(116)

2-Methyl-2-{[3-({2-methyl-5-[2-(trifluoromethyl)phenyl]-3-furyl}methoxy)benzyl]thio}propionic acid

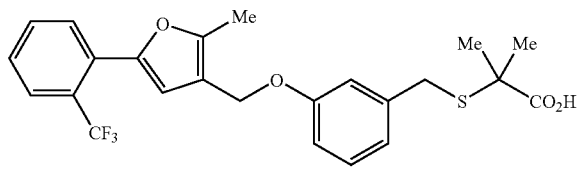

An oily matter; $^1$H-NMR (CDCl$_3$) δ 1.55 (6H, s), 2.38 (3H, s), 3.86 (2H, s), 4.85 (2H, s), 6.71 (1H, s), 6.79-6.96 (3H, m), 7.16-7.24 (1H, m), 7.36 (1H, t), 7.53 (1H, t), 7.69-7.74 (2H, m).

Example 6(117)

2-Methyl-2-{[4-({2-methyl-5-[2-(trifluoromethyl)phenyl]-3-furyl}methoxy)phenyl]thio}propionic acid

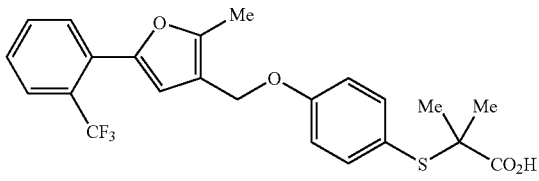

Melting point 115-116° C.; $^1$H-NMR (CDCl$_3$) δ 1.48 (6H, s), 2.37 (3H, s), 4.86 (2H, s), 6.70 (1H, s), 6.93 (2H, d), 7.36-7.39 (1H, m), 7.45 (2H, d), 7.53 (1H, t), 7.70-7.73 (2H, m).

Example 6(118)

2-Methyl-2-{[3-({2-methyl-5-[4-(trifluoromethyl)phenyl]-3-furyl}methoxy)phenyl]thio}propionic acid

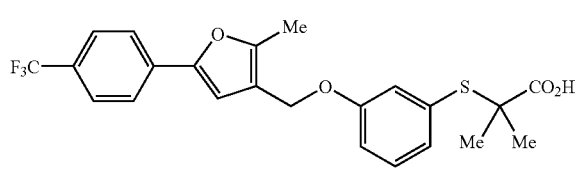

Melting point 127-128° C.; $^1$H-NMR (CDCl$_3$) δ 1.49 (6H, s), 2.38 (3H, s), 4.83 (2H, s), 6.75 (1H, s), 6.95-6.99 (1H, m), 7.10-7.13 (2H, m), 7.21-7.27 (1H, m), 7.58 (2H, d), 7.68 (2H, d).

Example 6(119)

2-Methyl-2-({3-[(2-methyl-5-phenyl-3-furyl)methoxy]benzyl}thio)propionic acid

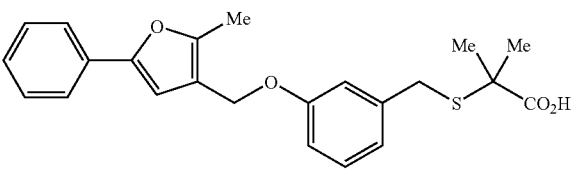

Melting point 113-114° C.; $^1$H-NMR (CDCl$_3$) δ 1.55 (6H, s), 2.37 (3H, s), 3.87 (2H, s), 4.84 (2H, s), 6.64 (1H, s), 6.81-6.85 (1H, m), 6.91-6.97 (2H, m), 7.17-7.24 (2H, m), 7.33-7.36 (2H, m), 7.59-7.62 (2H, m).

Example 6(120)

2-Methyl-2-[(3-{[2-methyl-5-(4-methylphenyl)-3-furyl]methoxy}benzyl)thio]propionic acid

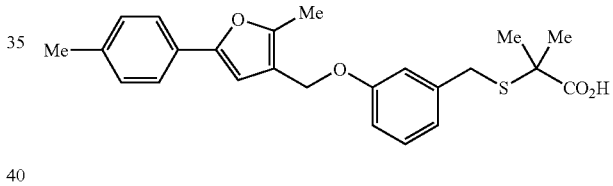

Melting point 121-122° C.; $^1$H-NMR (CDCl$_3$) δ 1.55 (6H, s), 2.34 (3H, s), 2.36 (3H, s), 3.87 (2H, s), 4.83 (2H, s), 6.58 (1H, s), 6.81-6.85 (1H, m), 6.90-6.96 (2H, m), 7.13-7.24 (3H, m), 7.50 (2H, d).

Example 6(121)

[3-(3-{2-Ethyl-5-[4-(trifluoromethyl)phenyl]-3-furyl}-3-methoxypropoxy)phenyl]acetic acid

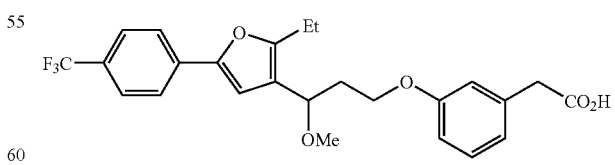

An oily matter; $^1$H-NMR (CDCl$_3$) δ 1.23 (3H, t), 2.00-2.06 (1H, m), 2.32-2.38 (1H, m), 2.64-2.73 (2H, m), 3.23 (3H, s), 3.60 (2H, s), 3.88-3.93 (1H, m), 4.06-4.13 (1H, m), 4.43 (1H, t), 6.69 (1H, s), 6.77-6.87 (3H, m), 7.19-7.25 (1H, m), 7.60 (2H, d), 7.70 (2H, d).

Example 6(122)

2-Methyl-2-{[4-(3-{2-methyl-5-[4-(trifluoromethyl)phenyl]-3-furyl}propoxy)phenyl]thio}propionic acid

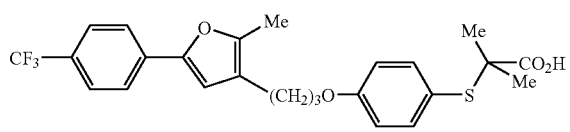

Melting point 127-128° C.; $^1$H-NMR (CDCl$_3$) δ 1.48 (6H, s), 1.98-2.05 (2H, m), 2.26 (3H, s), 2.57 (2H, t), 3.95 (2H, t), 6.58 (1H, s), 6.85 (2H, d), 7.43 (2H, d), 7.57 (2H, d), 7.67 (2H, d).

Example 6(123)

3-[4-({2-Methyl-5-[4-(trifluoromethyl)phenyl]-3-furyl}methoxy)phenyl]propionic acid

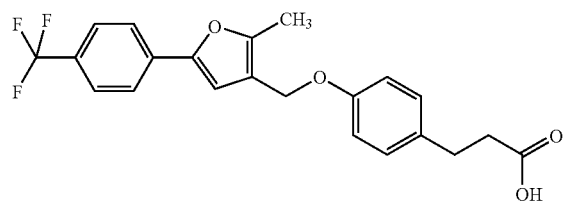

Melting point 182-183° C.; $^1$H-NMR (CDCl$_3$) δ 2.40 (3H, s), 2.66 (2H, t), 2.92 (2H, t), 4.85 (2H, s), 6.78 (1H, s), 6.91 (2H, d), 7.15 (2H, d), 7.60 (2H, d), 7.71 (2H, d).

Example 6(124)

N-methyl-N-[3-({2-methyl-5-[4-(trifluoromethyl)phenyl]-3-furyl}methoxy)benzyl]glycine

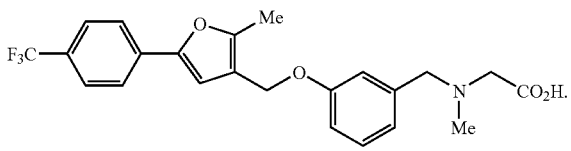

Amorphous; $^1$H-NMR (DMSO-d$_6$) δ 2.34 (3H, s), 2.42 (3H, s), 3.19 (2H, s), 3.75 (2H, s), 4.94 (2H, s), 6.93-6.97 (2H, m), 7.04 (1H, s), 7.20 (1H, s), 7.28 (1H, t), 7.74 (2H, d), 7.86 (2H, d).

Example 6(125)

3'-({2-Methyl-5-[4-(trifluoromethyl)phenyl]-3-furyl}methoxy)-1,1'-biphenyl-3-carboxylic acid

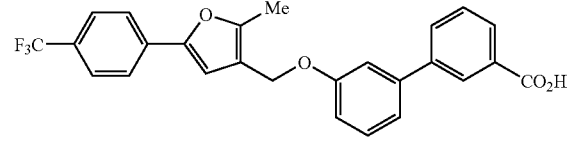

Melting point 178-179° C.; $^1$H-NMR (CDCl$_3$) δ 2.44 (3H, s), 4.96 (2H, s), 6.82 (1H, s), 6.99-7.03 (1H, m), 7.24-7.27 (2H, m), 7.41 (1H, t), 7.52-7.61 (3H, m), 7.72 (2H, d), 7.82-7.85 (1H, m), 8.08-8.12 (1H, m), 8.34-8.36 (1H, m).

Example 6(126)

[3'-({2-Methyl-5-[4-(trifluoromethyl)phenyl]-3-furyl}methoxy)-1,1'-biphenyl-3-yl]acetic acid

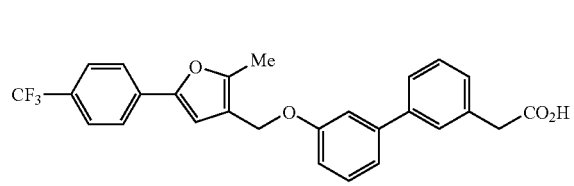

Melting point 128-129° C.; $^1$H-NMR (CDCl$_3$) δ 2.41 (3H, s), 3.70 (2H, s), 4.92 (2H, s), 6.81 (1H, s), 6.93-6.99 (1H, m), 7.18-7.43 (5H, m), 7.48-7.52 (2H, m), 7.59 (2H, d), 7.71 (2H, d).

Example 7

Ethyl 3-[3-({2-methyl-5-[4-(trifluoromethyl)phenyl]-3-furoyl}amino)phenyl]propionate

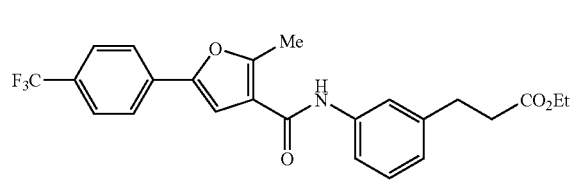

To a suspension (5 ml) of 3 sodium hydride (81 mg) in tetrahydrofuran was added dropwise ethyl diethylphosphonoacetate (0.26 ml) with ice-cooling and the mixture was stirred for 30 minutes. To the reaction solution was added dropwise a solution of N-(3-formylphenyl)-2-methyl-5-[4-(trifluoromethyl)phenyl]-3-furamide (0.50 g) in tetrahydrofuran (5 ml) and the mixture was stirred at 0° C. for 2 hours. 1 N hydrochloric acid was added thereto and the mixture was diluted with ethyl acetate. The organic layer was separated and washed with a saturated sodium bicarbonate solution, water and saturated brine. The organic layer was dried over anhydrous magnesium sulfate, filtered and concentrated under reduced pressure. The obtained residue was dissolved in a solution of ethanol-tetrahydrofuran (5 ml-5 ml) and 10% palladium-carbon was added thereto under nitrogen gas stream, the atmosphere was substituted with a hydrogen atmosphere and the mixture was stirred at room temperature for 3 hours. Insolubles were filtered and purified by silica gel column chromatography (hexane:ethyl acetate=8:1 to 5:1) to obtain an objective product (0.38 g) as crystals.

Melting point 134-135° C.; $^1$H-NMR (CDCl$_3$) δ 1.24 (3H, t), 2.63 (2H, t), 2.72 (3H, s), 2.96 (2H, t), 4.13 (2H, q), 6.89 (1H, s), 6.99 (1H, d), 7.23-7.31 (1H, m), 7.41-7.50 (3H, m), 7.64 (2H, d), 7.75 (2H, d).

Example 8

3-[3-({2-Methyl-5-[4-(trifluoromethyl)phenyl]-3-furoyl}amino)phenyl]propionic acid

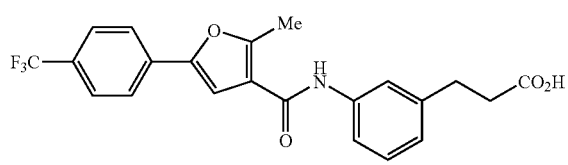

To a solution of ethyl 3-[3-({2-methyl-5-[4-(trifluoromethyl)phenyl]-3-furoyl}amino)phenyl]propionate (0.33 g) in tetrahydrofuran-ethanol (3 ml-3 ml) was added dropwise a 1 N aqueous sodium hydroxide solution (1.5 ml) and the mixture was stirred at room temperature for 1 hour. The mixture was acidified with 1 N hydrochloric acid and diluted with ethyl acetate. The organic layer was separated and washed with saturated brine. The organic layer was dried over anhydrous magnesium sulfate, filtered and concentrated under reduced pressure. The obtained residue was purified by recrystallization (hexane-ethyl acetate) to obtain an objective product (245 mg) as crystals.

Melting point 200-201° C.; $^1$H-NMR (CDCl$_3$) δ 2.62 (2H, t), 2.73 (3H, s), 2.95 (2H, t), 6.97 (1H, d), 7.24 (1H, t), 7.34 (1H, s), 7.54-7.59 (2H, m), 7.64 (2H, d), 7.77 (2H, d), 9.01 (1H, s).

Example 9

2-{[3-({2-Methyl-5-[4-(trifluoromethyl)phenyl]-3-furyl}methoxy)benzyl]thio}butanoic acid

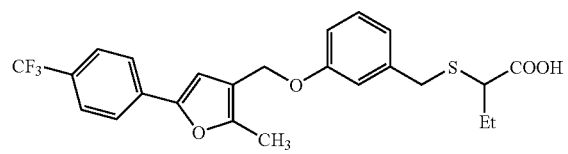

To a solution of S-[3-({2-methyl-5-[4-(trifluoromethyl)phenyl]-3-furyl}methoxy)benzyl]thioacetate (0.50 g) in methanol (10 ml) was added a 1 N aqueous sodium hydroxide solution (1.2 ml) at room temperature and the mixture was stirred as such for 1 hour. The solvent of the mixture was distilled off under reduced pressure to obtain a solid matter. The obtained solid matter was dissolved in N,N-dimethylformamide (10 ml), and ethyl 2-bromobutyrate (0.28 g) was added thereto at room temperature. The mixture was stirred at 60° C. overnight. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=15:1 to 9:1) to obtain an oily matter.

The obtained oily matter was dissolved in methanol (5 ml) and tetrahydrofuran (5 ml), a 1 N aqueous sodium hydroxide solution (3 ml) was added thereto and the mixture was stirred at room temperature overnight. The reaction solution was concentrated and diluted with water. The reaction solution was acidified with dilute hydrochloric acid and twice extracted with ethyl acetate. The collected organic layer was dried over anhydrous sodium sulfate and passed through silica gel. The obtained crude product was crystallized from diethyl ether-hexane to obtain an objective product (0.24) as crystals.

Melting point 78-80° C.; $^1$H-NMR (CDCl$_3$) δ 0.96 (3H, t), 1.59-1.95 (2H, m), 2.42 (3H, s), 3.10 (1H, t), 3.79 (1H, d), 3.88 (1H, d), 4.88 (2H, s), 6.80 (1H, s), 6.85-6.98 (3H, m), 7.25 (1H, t), 7.60 (2H, d), 7.71 (2H, d).

Example 9(1) to Example 9(4)

In the same manner as in Example 9, S-[3-({2-methyl-5-[4-(trifluoromethyl)phenyl]-3-furyl}methoxy)benzyl]thioacetate was condensed with the corresponding α-haloester and hydrolyzed to obtain the below-described compounds.

Example 9(1)

2-{[3-({2-Methyl-5-[4-(trifluoromethyl)phenyl]-3-furyl}methoxy)-benzyl]thio}propionic acid

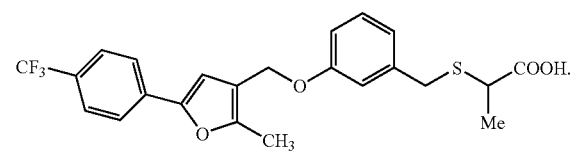

Melting point 82-83° C.; $^1$H-NMR (CDCl$_3$) δ 1.40 (3H, d), 2.41 (3H, s), 3.31 (1H, q), 3.80 (1H, d), 3.90 (1H, d), 4.87 (2H, s), 6.79 (1H, s), 6.85-6.89 (1H, m), 6.95-6.99 (2H, m), 7.24 (1H, t), 7.59 (2H, d), 7.70 (2H, d).

Example 9(2)

Difluoro{[3-({2-methyl-5-[4-(trifluoromethyl)phenyl]-3-furyl}methoxy)-benzyl]thio}acetic acid

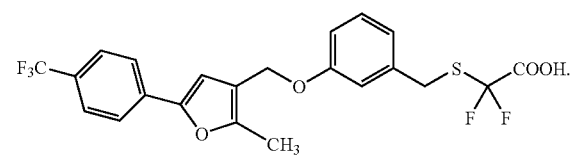

Amorphous powders; $^1$H-NMR (CDCl$_3$-DMSO-d$_6$) δ 2.36 (3H, s), 4.02 (2H, s), 4.80 (2H, s), 6.74 (1H, s), 6.80 (1H, dd), 6.90 (1H, d), 6.95 (1H, s), 7.16 (1H, t), 7.56 (2H, d), 7.66 (2H, d).

Example 9(3)

1-{[3-({2-Methyl-5-[4-(trifluoromethyl)phenyl]-3-furyl}methoxy)benzyl]thio}cyclobutanecarboxylic acid

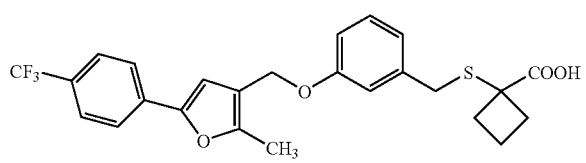

Melting point 121-122° C.; $^1$H-NMR (CDCl$_3$) δ 1.87-1.99 (1H, m), 2.11-2.25 (3H, m), 2.41 (3H, s), 2.63-2.73 (2H, m), 3.78 (2H, s), 4.86 (2H, s), 6.78 (1H, s), 6.83-6.86 (1H, m), 6.92-6.96 (2H, m), 7.22 (1H, t), 7.58 (2H, d), 7.69 (2H, d).

Example 9(4)

2-{[3-({2-Methyl-5-[4-(trifluoromethyl)phenyl]-3-furyl}methoxy)benzyl]thio}pentanoic acid

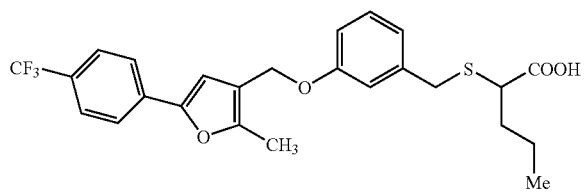

Melting point 61-62° C.; $^1$H-NMR (CDCl$_3$) δ 0.83 (3H, t), 1.26-1.45 (2H, m), 1.55-1.66 (1H, m), 1.76-1.88 (1H, m), 2.41 (3H, s), 3.18 (1H, t), 3.80 (1H, d), 3.87 (1H, d), 4.88 (2H, s), 6.79 (1H, s), 6.87 (1H, dd), 6.97 (1H, d), 6.99 (1H, s), 7.25 (1H, t), 7.60 (2H, d), 7.71 (2H, d).

Example 10

{2-[(2-{2-Methyl-5-[4-(trifluoromethyl)phenyl]-3-furyl}-2-oxoethyl)thio]-4-methyl-1,3-thiazol-5-yl}acetic acid

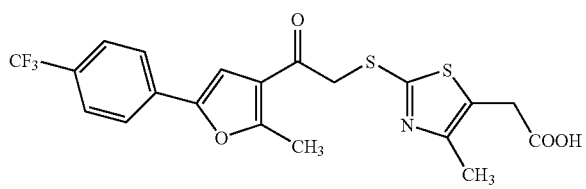

To a solution of 1-{2-methyl-5-[4-(trifluoromethyl)phenyl]-3-furyl}ethanone (0.48 g), 47% hydrobromic acid (1 drop) and acetic acid (2 ml) in diethyl ether (20 ml) was added at 0° C. a solution of bromine (91 μl) in diethyl ether (5 ml) and the mixture was stirred as such for 15 minutes. The reaction solution was diluted with ethyl acetate, washed with water, dried over anhydrous sodium sulfate and the solvent was distilled off under reduced pressure to obtain a solid matter. To a solution of methyl (2-mercapto-4-methyl-1,3-thiazol-5-yl)acetate (0.43 g) in tetrahydrofuran (2 ml) was added 1,8-diazabicyclo[5.4.0]-7-undecene (0.32 ml) at room temperature and the mixture was stirred for 10 minutes. The obtained mixture was added to a solution of the obtained solid matter in tetrahydrofuran (20 ml) at room temperature and the mixture was stirred as such overnight. The reaction solution was poured into water and twice extracted with ethyl acetate. The collected organic layer was dried over anhydrous magnesium sulfate, and the solvent was distilled off under reduced pressure. The obtained crude product was purified by silica gel column chromatography (hexane:ethyl acetate=3:1 to 1:1) to obtain a solid matter.

The obtained solid matter was dissolved in methanol (5 ml) and tetrahydrofuran (5 ml), a 1 N aqueous sodium hydroxide solution (2 ml) was added thereto, and then the mixture was stirred at room temperature overnight. The reaction solution was concentrated and diluted with water. The reaction solution was acidified with dilute hydrochloric acid and twice extracted with ethyl acetate. The collected organic layer was dried over anhydrous sodium sulfate and the solvent was distilled off under reduced pressure. The obtained crude product was purified by silica gel column chromatography (hexane:ethyl acetate=1:1 to ethyl acetate) and crystallized from hexane to obtain an objective product (54 mg) as powders.

Melting point 140-143° C.; $^1$H-NMR (CDCl$_3$-DMSO-d$_6$) δ 2.31 (3H, s), 2.70 (3H, s), 3.66 (2H, s), 4.46 (2H, s), 7.10 (1H, s), 7.64 (2H, d), 7.75 (2H, d).

Example 11

Ethyl [2-(2-{2-methyl-5-[4-(trifluoromethyl)phenyl]-3-furyl}ethyl)-1,3-thiazol-5-yl]acetate

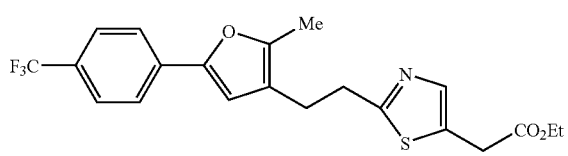

To a solution of ethyl 4-[(3-{2-methyl-5-[4-(trifluoromethyl)phenyl]-3-furyl}propanoyl)amino]-3-oxobutanoate (0.46 g) in tetrahydrofuran (10 ml) was added Lawson's reagent (0.66 g) and the mixture was stirred at 70° C. for 1 hour. The solvent was distilled off under reduced pressure and the obtained crude product was purified by silica gel column chromatography (hexane:ethyl acetate=6:1 to 2:1) to obtain an objective product (0.41 g) as an oily matter.

$^1$H-NMR (CDCl$_3$) δ 1.26 (3H, t), 2.24 (3H, s), 2.85 (2H, t), 3.20 (2H, t), 3.79 (2H, s), 4.18 (2H, q), 6.58 (1H, s), 7.48 (1H, s), 7.57 (2H, d), 7.67 (2H, d).

Example 11(1) to Example 11(3)

In the same manner as in Example 11, cyclization was performed to obtain the below-described compounds from the ketoamide forms and Lawson's reagents.

Example 11(1)

Ethyl 4-methyl-2-(2-{2-methyl-5-[4-(trifluoromethyl)phenyl]-3-furyl}ethyl)-1,3-thiazol-5-yl]acetate

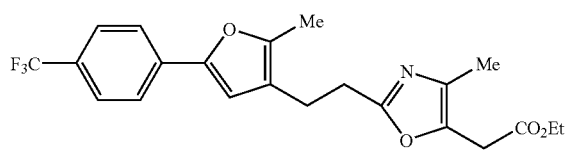

An oily matter; $^1$H-NMR (CDCl$_3$) δ 1.26 (3H, t), 2.24 (3H, s), 2.34 (3H, s), 2.82 (2H, t), 3.15 (2H, t), 3.69 (2H, s), 4.17 (2H, q), 6.59 (1H, s), 7.58 (2H, d), 7.66 (2H, d).

Example 11(2)

Ethyl [4-isopropyl-2-(2-{2-methyl-5-[4-(trifluoromethyl)phenyl]-3-furyl}ethyl)-1,3-thiazol-5-yl]acetate

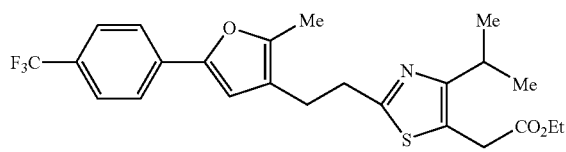

An oily matter; $^1$H-NMR (CDCl$_3$) δ 1.21-1.28 (9H, m), 2.21 (2H, s), 2.83 (2H, t), 2.98-3.05 (1H, m), 3.20 (2H, d), 3.70 (2H, s), 4.16 (2H, q), 6.58 (1H, s), 7.57 (2H, d), 7.66 (2H, d).

Example 11(3)

Ethyl [4-methyl-2-(3-{2-methyl-5-[4-(trifluoromethyl)phenyl]-3-furyl}propyl)-1,3-thiazol-5-yl]acetate

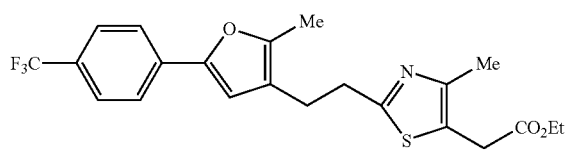

An oily matter; $^1$H-NMR (CDCl$_3$) δ 1.27 (3H, t), 1.98-2.09 (2H, m), 2.28 (3H, s), 2.33 (3H, s), 2.46 (2H, t), 2.94 (2H, t), 3.69 (2H, s), 4.18 (2H, q), 6.59 (1H, s), 7.57 (2H, d), 7.67 (2H, d).

Example 12

Ethyl [2-(2-{2-methyl-5-[4-(trifluoromethyl)phenyl]-3-furyl}ethyl)-1,3-oxazol-5-yl]acetate

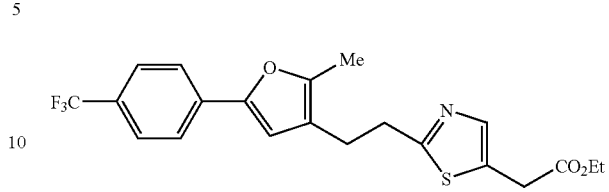

To a solution of ethyl 4[(3-{2-methyl-5-[4-(trifluoromethyl)phenyl]-3-furyl}propanoyl)amino]-3-oxobutanoate (0.40 g) in N,N-dimethylformamide (5 ml) was added phosphorus oxychloride (0.13 ml) and the mixture was stirred at 70° C. for 1 hour. After standing to cool, a saturated sodium bicarbonate solution was added thereto, the mixture was diluted with ethyl acetate and washed with water and saturated brine. The mixture was dried over anhydrous magnesium sulfate, and the solvent was distilled off under reduced pressure. The residue was purified by silica gel column chromatography (hexane:ethyl acetate=5:1 to 2:1) to obtain an objective product (0.30 g) as an oily matter.

$^1$H-NMR (CDCl$_3$) δ 1.26 (3H, t), 2.27 (3H, m), 2.83 (2H, t), 2.97 (2H, t), 3.67 (2H, s), 4.16 (2H, q), 6.54 (1H, s), 6.85 (1H, s), 7.56 (2H, d), 7.65 (2H, d).

Example 12(1) to Example 12(2)

In the same manner as in Example 12, cyclization was performed to obtain the below-described compounds from the ketoamide forms and phosphorus oxychloride.

Example 12(1)

Ethyl [4-methyl-2-(2-{2-methyl-5-[4-(trifluoromethyl)phenyl]-3-furyl}ethyl)-1,3-oxazol-5-yl]acetate

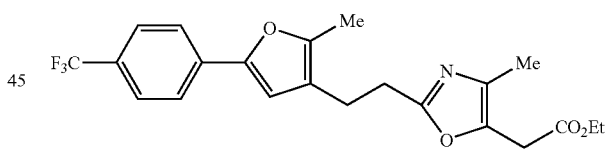

An oily matter; $^1$H-NMR (CDCl$_3$) δ 1.25 (3H, t), 2.10 (3H, s), 2.27 (3H, s), 2.79-2.84 (2H, m), 2.89-2.95 (2H, m), 3.60 (2H, s), 4.16 (2H, q), 6.54 (1H, s), 7.56 (2H, d), 7.66 (2H, d).

Example 12(2)

Ethyl [4-isopropyl-2-(2-{2-methyl-5-[4-(trifluoromethyl)phenyl]-3-furyl}ethyl)-1,3-oxazol-5-yl]acetate

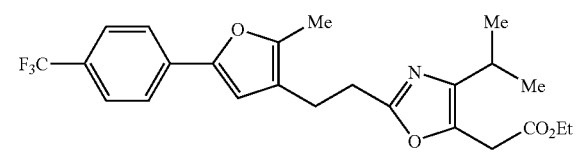

An oily matter; $^1$H-NMR (CDCl$_3$) δ 1.20-1.27 (9H, m), 2.25 (3H, s), 2.74-2.84 (3H, m), 2.88-2.98 (2H, m), 3.61 (2H, s), 4.15 (2H, q), 6.51 (1H, s), 7.56 (2H, d), 7.65 (2H, d).

Example 13(1) to Example 13(7)

In the same manner as in Example 8, the ester forms obtained in Example 11 and Example 12 were hydrolyzed to obtain the below-described compounds.

Example 13(1)

[2-(2-{2-Methyl-5-[4-(trifluoromethyl)phenyl]-3-furyl}ethyl)-1,3-thiazol-5-yl]acetic acid

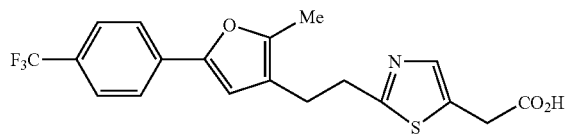

Melting point 143-145° C.; $^1$H-NMR (CDCl$_3$) δ 2.22 (3H, s), 2.83 (2H, t), 3.21 (2H, t), 3.83 (2H, s), 6.55 (1H, s), 7.52 (1H, s), 7.56 (2H, d), 7.65 (2H, d).

Example 13(2)

[4-Methyl-2-(2-{2-methyl-5-[4-(trifluoromethyl)phenyl]-3-furyl}ethyl)-1,3-thiazol-5-yl]acetic acid

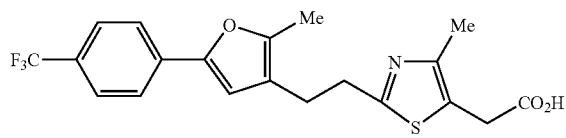

Melting point 168-169° C.; $^1$H-NMR (CDCl$_3$) δ 2.22 (3H, s), 2.34 (3H, s), 2.79 (2H, t), 3.16 (2H, t), 3.72 (2H, s), 6.55 (1H, s), 7.54 (2H, d), 7.64 (2H, d).

Example 13(3)

[4-Isopropyl-2-(2-{2-methyl-5-[4-(trifluoromethyl)phenyl]-3-furyl}ethyl)-1,3-thiazol-5-yl]acetic acid

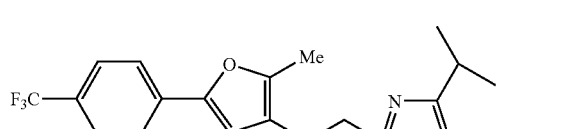

Melting point 176-177° C.; $^1$H-NMR (CDCl$_3$) δ 1.24 (3H, s), 1.26 (3H, s), 2.20 (3H, s), 2.81 (2H, t), 2.99 (1H, quintet), 3.16 (2H, t), 3.75 (2H, s), 6.53 (1H, s), 7.56 (2H, d), 7.63 (2H, d).

Example 13(4)

[4-Methyl-2-(3-{2-methyl-5-[4-(trifluoromethyl)phenyl]-3-furyl}propyl)-1,3-thiazol-5-yl]acetic acid

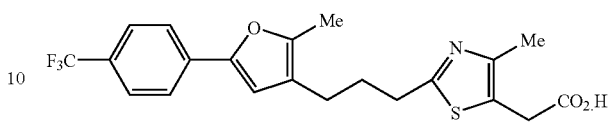

Melting point 162-163° C.; $^1$H-NMR (CDCl$_3$) δ 1.96-2.07 (2H, m), 2.27 (3H, s), 2.33 (3H, s), 2.45 (2H, t), 2.97 (2H, t), 3.72 (2H, s), 6.58 (1H, s), 7.56 (2H, d), 7.66 (2H, d).

Example 13(5)

[2-(2-{2-Methyl-5-[4-(trifluoromethyl)phenyl]-3-furyl}ethyl)-1,3-oxazol-5-yl]acetic acid

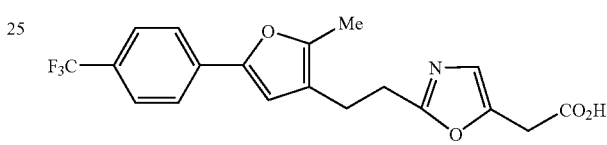

Melting point 143-144° C.; $^1$H-NMR (CDCl$_3$) δ 2.24 (3H, s), 2.81 (2H, t), 2.99 (2H, t), 3.71 (2H, d), 6.52 (1H, s), 6.90 (1H, s), 7.54 (2H, d), 7.62 (2H, d).

Example 13(6)

[4-Methyl-2-(2-{2-methyl-5-[4-(trifluoromethyl)phenyl]-3-furyl}ethyl)-1,3-oxazol-5-yl]acetic acid

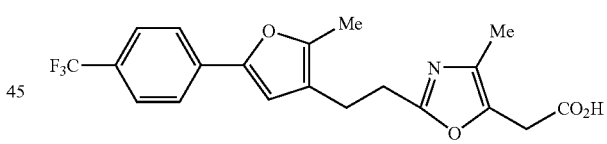

Melting point 120-121° C.; $^1$H-NMR (CDCl$_3$) δ 2.09 (3H, s), 2.24 (3H, s), 2.79 (2H, t), 2.93 (2H, t), 3.63 (2H, s), 6.51 (1H, s), 7.54 (2H, d), 7.62 (2H, d).

Example 13(7)

[4-Isopropyl-2-(2-{2-methyl-5-[4-(trifluoromethyl)phenyl]-3-furyl}ethyl)-1,3-oxazol-5-yl]acetic acid

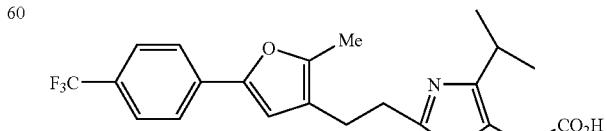

Melting point 126-128° C.; $^1$H-NMR (CDCl$_3$) δ 1.18 (3H, s), 1.21 (3H, s), 2.26 (3H, s), 2.75-2.82 (3H, m), 2.95 (2H, t), 3.65 (2H, s), 6.47 (1H, s), 7.52 (2H, d), 7.61 (2H, d).

Example 14

2-(Trimethylsilyl)ethyl 2-{[4-(3-methoxy-2-dimethyl-3-oxopropyl)phenoxy]methyl}-5-[4-(trifluoromethyl)phenyl]-3-furoate

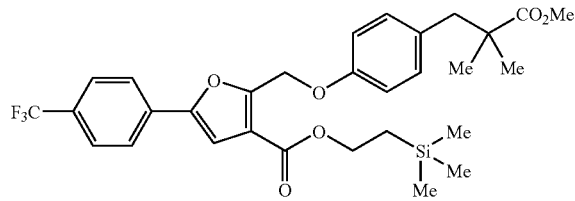

To a solution of 2-(trimethylsilyl)ethyl 2-methyl-5-[4-(trifluoromethyl)phenyl]-3-furoate (2.5 g) in ethyl acetate (50 ml) was added 2,2'-azobis(isobutyronitrile) (0.11 g) and N-bromosuccinimide (1.20 g), and the mixture was heated under reflux for 5 hours. The solvent was distilled off under reduced pressure and the resultant material was washed with toluene. Insolubles were filtered through Celite and washed with toluene. The solvent of the filtrate was distilled off under reduced pressure to obtain an oily matter. The obtained oily matter was dissolved in N,N-dimethylformamide (50 ml). Potassium carbonate (1.40 g) and methyl 3-(4-hydroxyphenyl)-2,2-dimethylpropanoate (1.55 g) were added and the mixture was stirred at room temperature for 2 hours and at 50° C. for 1 hour. The mixture was diluted with ethyl acetate, washed with water and saturated brine and dried over anhydrous magnesium sulfate and the solvent was distilled off under reduced pressure. The residue was purified by silica gel column chromatography (hexane:ethyl acetate=20:1 to 10:1) to obtain an objective product (2.68 g) as an oily matter.

$^1$H-NMR (CDCl$_3$) δ 0.07 (9H, s), 1.07-1.11 (2H, m), 1.16 (6H, s), 2.79 (2H, s), 3.64 (3H, s), 4.34-4.40 (2H, m), 5.39 (2H, s), 6.92 (2H, d), 7.00-7.05 (3H, s), 7.63 (2H, d), 7.75 (2H, d).

Example 14(1)

2-(Trimethylsilyl)ethyl 2-{[4-(2-ethoxy-1,1-dimethyl-2-oxoethoxy)phenoxy]methyl}-5-[4-(trifluoromethyl)phenyl]-3-furoate

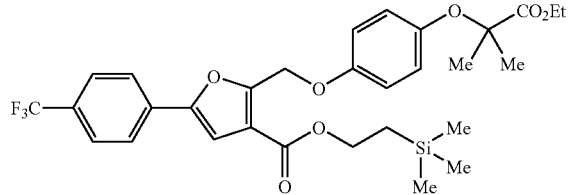

In the same manner as in Example 14, an objective product was obtained from 2-(trimethylsilyl)ethyl 2-methyl-5-[4-(trifluoromethyl)phenyl]-3-furoate and ethyl 2-(4-hydroxyphenoxy)-2-methylpropionate.

An oily matter $^1$H-NMR (CDCl$_3$) δ 0.07 (9H, s), 1.05-1.14 (2H, m), 1.26 (3H, dt), 1.54 (6H, s), 4.23 (2H, q), 4.33-4.42 (2H, m), 5.37 (2H, s), 6.81-6.95 (4H, m), 7.05 (1H, s), 7.64 (2H, d), 7.76 (2H, d).

Example 15

2-{[4-(3-Methoxy-2,2-dimethyl-3-oxopropyl)phenoxy]methyl}-5-[4-(trifluoromethyl)phenyl]-3-furoic acid

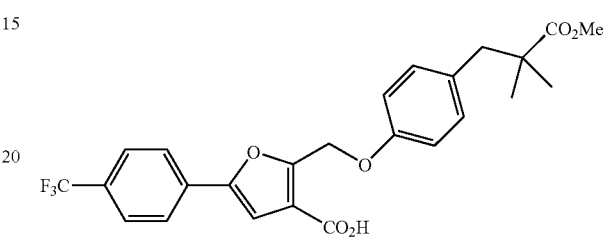

To a solution of 2-(trimethylsilyl)ethyl 2-{[4-(3-ethoxy-2,2-dimethyl-3-oxopropyl)phenoxy]methyl}-5-[4-(trifluoromethyl)phenyl]-3-furoate (2.65 g) in tetrahydrofuran (50 ml) was added tetra-n-butylammonium chloride (a tetrahydrofuran solution (1 M), 5.7 ml) and the mixture was stirred at room temperature overnight. The reactant was diluted with ethyl acetate, washed with water and saturated brine and dried over anhydrous magnesium sulfate and the solvent was distilled off under reduced pressure. The residue was purified by recrystallization (hexane-ethyl acetate) to obtain an objective product (1.76 g) as crystals.

Melting point 153-155° C.; $^1$H-NMR (CDCl$_3$) δ 1.17 (6H, s), 2.80 (2H, s), 3.65 (3H, s), 5.41 (1H, s), 6.94 (2H, d), 7.05 (2H, d), 7.11 (1H, s), 7.65 (2H, d), 7.77 (2H, d).

Example 15(1)

2-{[4-(2-Ethoxy-1,1-dimethyl-2-oxoethoxy)phenoxy]methyl}-5-[4-(trifluoromethyl)phenyl]-3-furoic acid

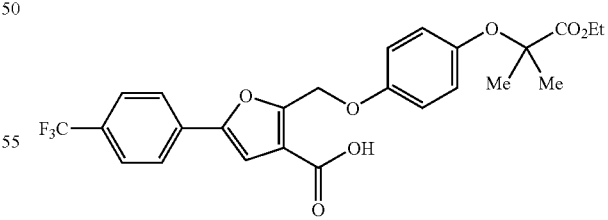

In the same manner as in Example 15, an objective product was obtained from 2-(trimethylsilyl)ethyl 2-{[4-(2-ethoxy-1,1-dimethyl-2-oxoethoxy)phenoxy]methyl}-5-[4-(trifluoromethyl)phenyl]-3-furoate obtained in Example 14(1).

Melting point 87-88° C.; $^1$H-NMR (CDCl$_3$) δ 1.26 (3H, t), 1.54 (6H, s), 4.22 (2H, q), 5.38 (2H, s), 6.85 (2H, d), 6.92 (2H, d), 7.09 (1H, s), 7.65 (2H, d), 7.77 (2H, d).

Example 16

Methyl 3-[4-({3-(hydroxymethyl)-5-[4-(trifluoromethyl)phenyl]-2-furyl}methoxy)phenyl]-2,2-dimethylpropanoate

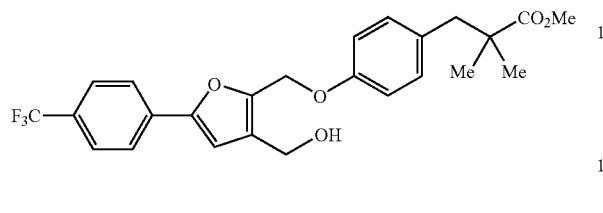

To a solution of 2-{[4-(3-methoxy-2,2-dimethyl-3-oxopropyl)phenoxy]methyl}-5-[4-(trifluoromethyl)phenyl]-3-furoic acid (1.60 g) in tetrahydrofuran (40 ml) was sequentially added dropwise triethylamine (0.58 ml) and ethyl chlorocarbonate (0.37 ml) with ice-cooling, and then the mixture was stirred at room temperature for 30 minutes. After cooling to −20° C., sodium borohydride (0.33 g) was added, and then methanol (20 ml) was added dropwise. The mixture was stirred for 2 hours. The reaction was completed in 1 N hydrochloric acid and diluted with ethyl acetate. Then, the reactant was washed with water and saturated brine and dried over anhydrous magnesium sulfate, and the solvent was distilled off under reduced pressure. The residue was purified by silica gel column chromatography (hexane:ethyl acetate=5:1 to 2:1) to obtain an objective product (1.16 g) as an oily matter.

$^1$H-NMR (CDCl$_3$) δ 1.17 (6H, s), 2.80 (2H, s), 3.63 (3H, s), 4.60 (2H, s), 5.08 (2H, s), 6.82 (1H, s), 6.89 (2H, d), 7.04 (2H, d), 7.62 (2H, d), 7.75 (2H, d).

Example 16(1)

Ethyl 2-[4-({3-(hydroxymethyl)-5-[4-(trifluoromethyl)phenyl]-2-furyl}methoxy)phenoxy]-2-methylpropionate

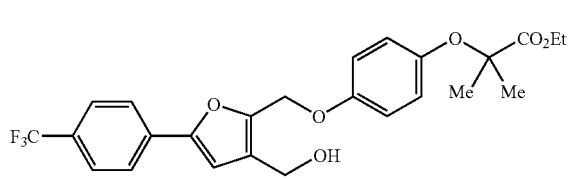

In the same manner shown to Example 16, an objective product was obtained from 2-{[4-(2-ethoxy-1,1-dimethyl-2-oxoethoxy)phenoxy]methyl}-5-[4-(trifluoromethyl)phenyl]-3-furoic acid.

An oily matter; $^1$H-NMR (CDCl$_3$) δ 1.27 (3H, t), 1.54 (6H, s), 4.24 (2H, q), 4.59 (2H, d), 5.05 (2H, s), 6.81 (1H, s), 6.86 (4H, d), 7.62 (2H, d), 7.75 (2H, d).

Example 17

3-[4-({3-(Hydroxymethyl)-5-[4-(trifluoromethyl)phenyl]-2-furyl}methoxy)phenyl]-2,2-dimethylpropanoic acid

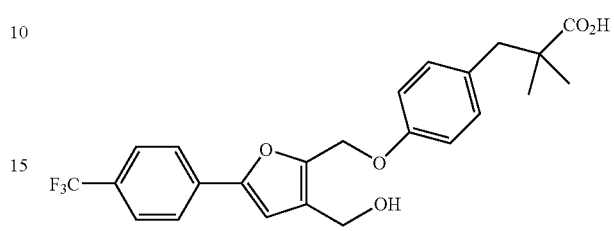

In the same manner as in Example 8, the ester form obtained in Example 16 was used to obtain an objective product.

Melting point 91-92° C.; $^1$H-NMR (CDCl$_3$) δ 1.20 (6H, s), 2.82 (2H, s), 4.56 (2H, s), 5.05 (2H, s), 6.76 (1H, s), 6.89 (2H, d), 7.10 (2H, d), 7.59 (2H, d), 7.70 (2H, d).

Example 18

Methyl 2,2-dimethyl-3-[4-({3-{[(phenoxycarbothioyl)oxy]methyl}-5-[4-(trifluoromethyl)phenyl]-2-furyl}methoxy)phenyl]propionate

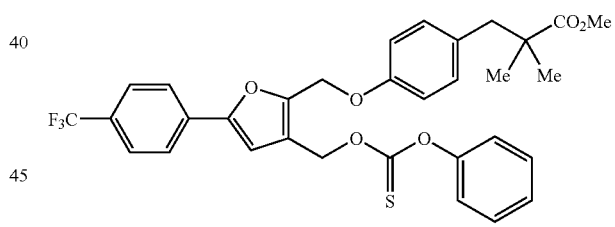

To a solution of methyl 3-[4-({3-{[(hydroxymethyl)-5-[4-(trifluoromethyl)phenyl]-2-furyl}methoxy)phenyl]-2,2-dimethylpropionate (0.40 g) in acetonitrile (5 ml) was added 4-(dimethylamino)pyridine (0.211 g), and phenyl chlorothionoformate (0.132 ml) was added dropwise thereto with ice-cooling. The mixture was stirred with ice-cooling for 30 minutes and at room temperature for 30 minutes. The reaction solution was diluted with ethyl acetate, washed with water, saturated brine and dried over anhydrous magnesium sulfate and the solvent was distilled off under reduced pressure. The residue was purified by silica gel column chromatography (hexane:ethyl acetate=30:1 to 5:1) to obtain an objective product (0.40 g) as an oily matter.

$^1$H-NMR (CDCl$_3$) δ 1.17 (6H, s), 2.80 (2H, s), 3.64 (3H, s), 5.13 (2H, s), 5.52 (2H, s), 6.89-6.92 (3H, m), 7.02-7.10 (3H, m), 7.19-7.33 (2H, m), 7.37-7.47 (2H, m), 7.62 (2H, d), 7.76 (2H, d).

Example 18(1)

Ethyl 2-methyl-2-[4-({3-{[(phenoxycarbothioyl)oxy]methyl}-5-[4-(trifluoromethyl)phenyl]-2-furyl}methoxy)phenoxy]propionate

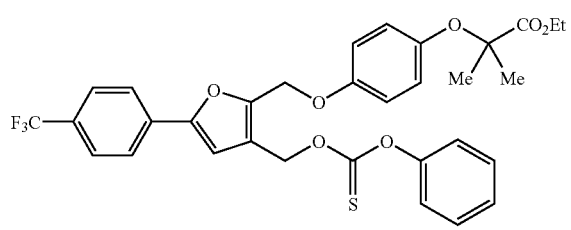

In the same manner as in Example 18, an objective product was obtained from ethyl 2-[4-({3-(hydroxymethyl)-5-[4-(trifluoromethyl)phenyl]-2-furyl}methoxy)phenoxy]-2-methylpropionate.

An oily matter; $^1$H-NMR (CDCl$_3$) δ 1.26 (3H, t), 1.54 (6H, s), 4.23 (2H, q), 5.11 (2H, s), 5.51 (2H, s), 6.87-6.91 (5H, m), 7.09 (2H, d), 7.31 (1H, d), 7.38-7.45 (2H, m), 7.64 (2H, d), 7.77 (2H, d).

Example 19

Ethyl 2,2-dimethyl-3-[4-({3-methyl-5-[4-(trifluoromethyl)phenyl]-2-furyl}methoxy)phenyl]propionate

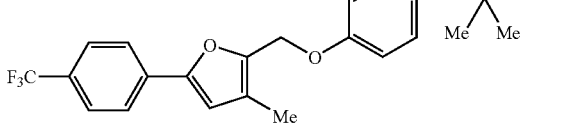

To a solution of methyl 2,2-dimethyl-3-[4-({3-{[(phenoxycarbothioyl)oxy]methyl}-5-[4-(trifluoromethyl)phenyl]-2-furyl}methoxy)phenyl]propionate (0.40 g) in toluene (5 ml) was added 2,2'-azobis(isobutyronitrile) (0.022 g) and tributyltin hydride (0.27 ml) and the mixture was heated under reflux for 2 hours. The solvent was distilled off under reduced pressure and the residue was purified by silica gel column chromatography (hexane:ethyl acetate=30:1 to 4:1) to obtain an objective product (0.17 g) as an oily matter.

$^1$H-NMR (CDCl$_3$) δ 1.17 (6H, s), 2.11 (3H, s), 2.80 (2H, s), 3.65 (3H, s), 4.98 (2H, s), 6.62 (1H, s), 6.90 (2H, d), 7.04 (2H, d), 7.59 (2H, d), 7.53 (2H, d).

Example 19(1)

Ethyl 2-methyl-2-[4-({3-methyl-5-[4-(trifluoromethyl)phenyl]-2-furyl}methoxy)phenyl]propionate

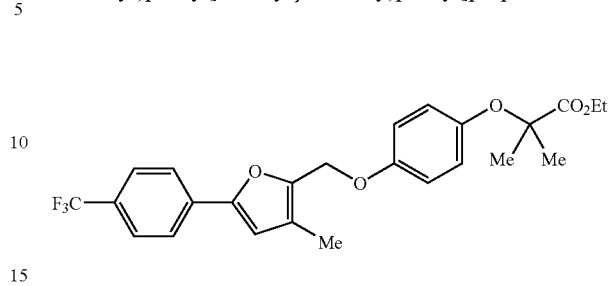

In the same manner as in Example 19, an objective product was obtained from 2-methyl-2-[4-({3-{[(phenoxycarbothioyl)oxy]methyl}-5-[4-(trifluoromethyl)phenyl]-2-furyl}methoxy)phenoxy]propionate.

An oily matter; $^1$H-NMR (CDCl$_3$) δ 1.27 (3H, t), 1.54 (6H, s), 2.09 (3H, s), 4.23 (2H, q), 4.95 (2H, s), 6.62 (1H, s), 6.86 (4H, d), 7.60 (2H, d), 7.73 (2H, d).

Example 20(1) and Example 20(2)

In the same manner as in Example 8, the ester forms obtained in Example 19 and Example 19(1) were hydrolyzed to obtain the below-described compounds.

Example 20(1)

2,2-Dimethyl-3-[4-({3-methyl-5-[4-(trifluoromethyl)phenyl]-2-furyl}methoxy)phenyl]propionic acid

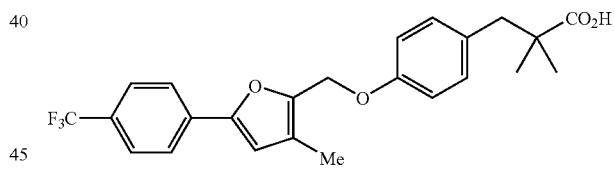

Melting point 124-126° C.; $^1$H-NMR (CDCl$_3$) δ 1.20 (6H, s), 2.09 (3H, s), 2.84 (2H, s), 4.97 (2H, s), 6.60 (1H, s), 6.91 (2H, d), 7.10 (2H, d), 7.58 (2H, d), 7.71 (2H, d).

Example 20(2)

2-Methyl-2-[4-({3-methyl-5-[4-(trifluoromethyl)phenyl]-2-furyl}methoxy)phenoxy]propionic acid

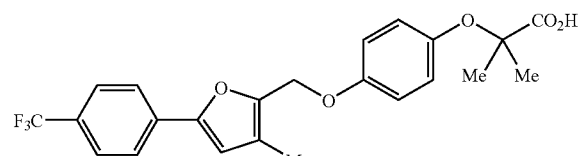

Melting point 116-117° C.; $^1$H-NMR (CDCl$_3$) δ 1.55 (6H, s), 2.10 (3H, s), 4.97 (2H, s), 6.61 (1H, s), 6.92 (4H, s), 7.59 (2H, d), 7.72 (2H, d).

Example 21-a

Ethyl 2-methyl-2-[4-((E)-2-{2-methyl-5-[4-(trifluoromethyl)phenyl]-3-furyl}ethenyl)phenoxy]propionate

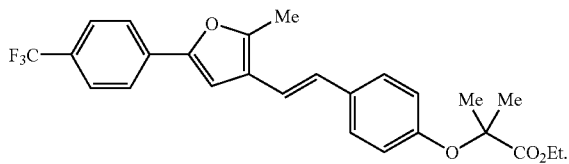

Example 21-b

Ethyl 2-methyl-2-[4-((Z)-2-{2-methyl-5-[4-(trifluoromethyl)phenyl]-3-furyl}ethenyl)phenoxy]propionate

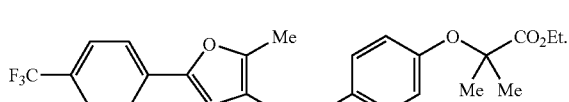

To a solution of 2-methyl-5-[4-(trifluoromethyl)phenyl]-3-furaldehyde (1.0 g) in N,N-dimethylformamide (20 ml) was added [4-(2-ethoxy-1,1-dimethyl-2-oxoethoxy)benzyl](triphenyl)phosphonium bromide (2.66 g) and potassium carbonate (0.82 g) and the mixture was stirred at room temperature overnight. The reaction solution was diluted with ethyl acetate, washed with water and saturated brine and dried over anhydrous magnesium sulfate and the solvent was distilled off under reduced pressure. The residue was purified by silica gel column chromatography (hexane:ethyl acetate=30:1 to 10:1) to obtain an objective product (E-isomer; 0.53 g, Z-isomer; 0.54 g) as a solid matter, respectively.

Ethyl 2-methyl-2-[4-((E)-2-{2-methyl-5-[4-(trifluoromethyl)phenyl]-3-furyl}ethenyl)phenoxy]propionate:

Melting point 99-100° C.; $^1$H-NMR (CDCl$_3$) δ 1.26 (3H, t), 1.61 (6H, s), 2.45 (3H, s), 4.24 (2H, q), 6.73 (2H, ABq), 6.82 (2H, d), 6.92 (1H, s), 7.34 (2H, d), 7.60 (2H, d), 7.72 (2H, d).

Ethyl 2-methyl-2-[4-((Z)-2-{2-methyl-5-[4-(trifluoromethyl)phenyl]-3-furyl}ethenyl)phenoxy]propionate:

Melting point 84-85° C.; $^1$H-NMR (CDCl$_3$) δ 1.24 (3H, t), 1.61 (6H, s), 2.28 (3H, s), 4.22 (2H, q), 6.23 (1H, d), 6.42 (1H, s), 6.48 (1H, d), 6.78 (2H, d), 7.20 (2H, d), 7.551 (2H, s), 7.558 (2H, s).

Example 22(1) and Example 22(2)

In the same manner as in Example 8, the ester forms obtained in Example 21-a and Example 21-b were hydrolyzed to obtain the below-described compounds.

Example 22(1)

2-Methyl-2-[4-((E)-2-{2-methyl-5-[4-(trifluoromethyl)phenyl]-3-furyl}ethenyl)phenoxy]propionic acid

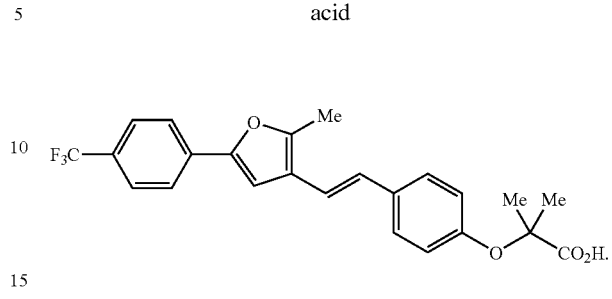

Melting point 140-141° C.; $^1$H-NMR (CDCl$_3$) δ 1.63 (6H, s), 2.45 (3H, s), 6.77 (2H, ABq), 6.92 (1H, s), 6.93 (2H, d), 7.39 (2H, d), 7.60 (2H, d), 7.72 (2H, d).

Example 22(2)

2-Methyl-2-[4-((Z)-2-{2-methyl-5-[4-(trifluoromethyl)phenyl]-3-furyl}ethenyl)phenoxy]propionic acid

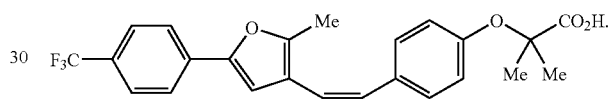

Melting point 117-118° C.; $^1$H-NMR (CDCl$_3$) δ 1.61 (6H, s), 2.28 (3H, s), 6.27 (1H, d), 6.41 (1H, s), 6.49 (1H, d), 7.87 (2H, d), 7.25 (2H, d), 7.55 (4H, s).

Example 23

Ethyl 2-methyl-2-[4-(2-{2-methyl-5-[4-(trifluoromethyl)phenyl]-3-furyl}ethyl)phenoxy]propionate

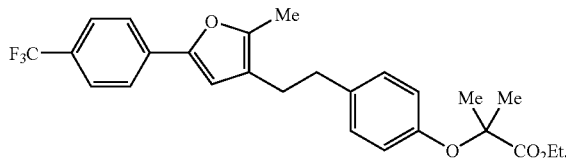

To a solution of ethyl 2-methyl-2-[4-((E)-2-{2-methyl-5-[4-(trifluoromethyl)phenyl]-3-furyl}ethenyl)phenoxy]propionate (0.34 g) in a mixed solvent of toluene-ethanol (4 ml-1 ml) was added chlorotris(triphenylphosphine) rhodium (I) (0.69 mg) and the mixture was stirred at 60° C. under hydrogen atmosphere overnight. The solvent was distilled off under reduced pressure and diluted with diisopropyl ether. Insolubles were filtered and the filtrate was distilled off under reduced pressure. The residue was purified by silica gel column chromatography (hexane:ethyl acetate=20:1 to 5:1) to obtain an objective product (0.18 g) as a solid matter.

Melting point 99-100° C.; $^1$H-NMR (CDCl$_3$) δ 1.25 (3H, t), 1.58 (6H, s), 2.09 (3H, s), 2.62 (2H, t), 2.77 (2H, t), 4.23 (2H, q), 6.51 (1H, s), 6.77 (2H, d), 7.00 (2H, d), 7.57 (2H, d), 7.66 (2H, d).

Example 24

2-Methyl-2-[4-(2-{2-methyl-5-[4-(trifluoromethyl)phenyl]-3-furyl}ethyl)phenoxy]propionic acid

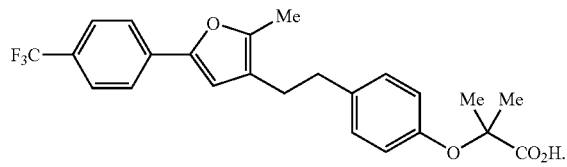

In the same manner shown to Example 8, an objective product was obtained from ethyl 2-methyl-2-[4-(2-{2-methyl-5-[4-(trifluoromethyl)phenyl]-3-furyl}ethyl)phenoxy]propionate.

Melting point 87-88° C.; $^1$H-NMR (CDCl$_3$) δ 1.51 (6H, s), 2.09 (3H, s), 2.60 (2H, t), 2.76 (2H, t), 6.50 (1H, s), 6.84 (2H, d), 7.02 (2H, d), 7.55 (2H, d), 7.62 (2H, d).

Example 25

2-Methyl-2-{4-({2-methyl-5-[4-(trifluoromethyl)phenyl]-3-furyl}methyl)thio]phenoxy}propionic acid

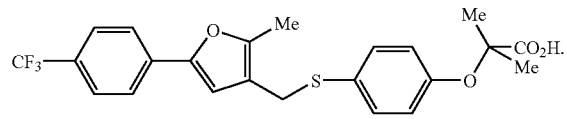

{2-Methyl-5-[4-(trifluoromethyl)phenyl]-3-furyl}methanol (0.35 g) and di(4-(1-(ethoxycarbonyl)-1-methylethoxy)phenyl)disulfide (1.3 g) were dissolved in tetrahydrofuran (20 ml), tributylphosphine (1 ml) was added thereto and the mixture was stirred at room temperature overnight. The solvent was distilled off and the residue was purified by basic silica gel column chromatography (ethyl acetate:hexane) and silica gel column chromatography (ethyl acetate: hexane) to obtain oil (0.49 g). The obtained oil was dissolved in ethanol (100 ml), a 1 N aqueous sodium hydroxide solution (10 ml) was added and then the mixture was stirred at room temperature overnight. After concentration, 1 N hydrochloric acid was added and extracted with ethyl acetate. The organic layer was washed with water and brine and dried over magnesium sulfate, and the solvent was distilled off to obtain crude crystals. The obtained crystals were recrystallized from ethyl acetate-hexane to obtain an objective product as crystals.

Melting point 112-113° C.; $^1$H-NMR (CDCl$_3$) δ 1.60 (6H, s), 2.07 (3H, s), 3.80 (2H, s), 6.64 (1H, s), 6.85 (2H, d), 7.28 (2H, d), 7.58 (2H, d), 7.67 (2H, d).

Example 26

2-Methyl-2-{4-[(3-{2-methyl-5-[4-(trifluoromethyl)phenyl]-3-furyl}propyl)thio]phenoxy}propionic acid

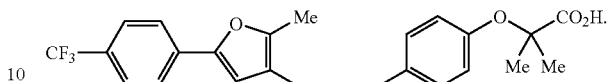

In the same manner as in Example 25, an objective product was obtained from 3-{2-methyl-5-[4-(trifluoromethyl)phenyl]-3-furyl}propan-1-ol obtained in Reference Example 11(1).

An oily matter; $^1$H-NMR (CDCl$_3$) δ 1.59 (6H, s), 1.82-1.90 (2H, m), 2.29 (3H, s), 2.50 (2H, t), 2.87 (2H, t), 6.53 (1H, s), 6.86 (2H, d), 7.27 (2H, d), 7.57 (2H, d), 7.66 (2H, d).

Example 27

2-Methyl-2-{4-[(({2-methyl-5-[4-(trifluoromethyl)phenyl]-3-furyl}methyl)amino]benzyl}thio)propionic acid

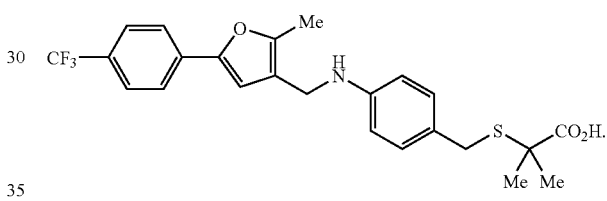

{2-Methyl-5-[4-(trifluoromethyl)phenyl]-3-furyl}methanol (0.7 g) was dissolved in ethyl acetate (7 ml) and concentrated hydrochloric acid (0.73 ml) was added thereto with ice-cooling. The mixture was stirred at room temperature for 1.5 hours. The mixture was poured into an aqueous sodium hydrogen carbonate solution and extracted with ethyl acetate. The organic layer was washed with water and brine and dried over magnesium sulfate, and the solvent was distilled off. The residue was dissolved in DMF (5 ml) and methyl 2-[(4-aminobenzyl)thio]-2-methylpropionate (0.5 g) and sodium hydrogen carbonate (0.5 g) were added. The reaction mixture was heated at 60° C. for 2 hours. The mixture was poured into an aqueous sodium hydrogen carbonate solution and extracted with ethyl acetate. The organic layer was washed with water and brine and dried over magnesium sulfate, and the solvent was distilled off. The residue was purified by silica gel column chromatography (dissolution medium: ethyl acetate/hexane) to obtain an oily matter (0.4 g). The oily matter was dissolved in ethanol (50 ml), a 1 N aqueous sodium hydroxide solution (5 ml) was added thereto, and then the mixture was heated at 80° C. for 2.5 hours. After concentration, a 1 N aqueous citric acid solution was added and extracted with ethyl acetate. The organic layer was washed with water and brine and dried over magnesium sulfate, and the solvent was distilled off to obtain crude crystals. The crude crystals were recrystallized from ethyl acetate-hexane to obtain an objective product (0.33 g) as crystals.

Melting point 139-141° C.; $^1$H-NMR (CDCl$_3$) δ 1.58 (6H, s), 2.37 (3H, s), 3.82 (2H, s), 4.06 (2H, s), 6.60 (2H, d), 6.71 (1H, s), 7.16 (2H, d), 7.58 (2H, d), 7.68 (2H, d).

Formulation Example

Medicines comprising the compound of the present invention as an active ingredient can be prepared according to the following formulations.

Moreover, other ingredients (additives) than the active ingredient in the following formulations, may be ones listed in Japanese Pharmacopoeia, Japanese Standards for Pharmaceutical Ingredients or Regulations for Pharmaceutical Additives

1. Capsule

| | |
|---|---|
| (1) 2-[(3-{[5-(4-fluorophenyl)-2-methyl-3-furyl]methoxy}benzyl)thiol]-2-methylpropionic acid | 10 mg |
| (2) lactose | 90 mg |
| (3) microcrystalline cellulose | 70 mg |
| (4) magnesium stearate | 10 mg |
| 1 capsule | 180 mg |

(1), (2), (3) and ½ of (4) are mixed and then granulated. To the granules is added the remainder of (4), and the whole is filled into a gelatin capsule.

2. Capsule

| | |
|---|---|
| (1) 3-[2-methyl-4-({2-methyl-5-[4-(trifluoromethyl)phenyl]-3-furyl}methoxy)phenyl]propionic acid | 10 mg |
| (2) lactose | 90 mg |
| (3) microcrystalline cellulose | 70 mg |
| (4) magnesium stearate | 10 mg |
| 1 capsule | 180 mg |

(1), (2), (3) and ½ of (4) are mixed and then granulated. To the granules is added the remainder of (4), and the whole is filled into a gelatin capsule.

3. Tablet

| | |
|---|---|
| (1) 2-[(3-{[5-(4-fluorophenyl)-2-methyl-3-furyl]methoxy}benzyl)thio]-2-methylpropionic acid | 10 mg |
| (2) lactose | 35 mg |
| (3) corn starch | 150 mg |
| (4) microcrystalline cellulose | 30 mg |
| (5) magnesium stearate | 5 mg |
| 1 tablet | 230 mg |

(1), (2), (3), ⅔ of (4) and ½ of (5) are mixed and then granulated. To the granules are added the remainders of (4) and (5), followed by subjecting the mixture to compression molding, thereby giving a tablet.

4. Tablet

| | |
|---|---|
| (1) 3-[2-methyl-4-({2-methyl-5-[4-(trifluoromethyl)phenyl]-3-furyl}methoxy)phenyl]propionic acid | 10 mg |
| (2) lactose | 35 mg |
| (3) corn starch | 150 mg |
| (4) microcrystalline cellulose | 30 mg |
| (5) magnesium stearate | 5 mg |
| 1 tablet | 230 mg |

(1), (2), (3), ⅔ of (4) and ½ of (5) are mixed and then granulated. To the granules are added the remainders of (4) and (5), followed by subjecting the mixture to compression molding, thereby giving a tablet.

5. Injection

| | |
|---|---|
| (1) 2-[(3-{[5-(4-fluorophenyl)-2-methyl-3-furyl]methoxy}benzyl)thio]-2-methylpropionic acid | 10 mg |
| (2) inositol | 100 mg |
| (3) benzyl alcohol | 20 mg |
| 1 ampoule | 130 mg |

(1), (2) and (3) were dissolved in distilled water for injection to the total volume of 2 ml, and filled into an ampoule. All processes were carried out under sterile conditions.

6. Injection

| | |
|---|---|
| (1) 3-[2-methyl-4-({2-methyl-5-[4-(trifluoromethyl)phenyl]-3-furyl}methoxy)phenyl]propionic acid | 10 mg |
| (2) inositol | 100 mg |
| (3) benzyl alcohol | 20 mg |
| 1 ampoule | 130 mg |

(1), (2) and (3) were dissolved in distilled water for injection to the total volume of 2 ml, and filled into an ampoule. All processes were carried out under sterile conditions.

INDUSTRIAL APPLICABILITY

Compound (I) of the present invention and a pharmacologically acceptable salt thereof show excellent preventing and treating action for PPAR-related diseases (e.g., lipid metabolism abnormality and sequelae thereof, diabetes mellitus, hyperlipidemia, arteriosclerotic disease and sequelae thereof (for example, ischemic cardiac disease, cerebral disease, peripheral arterial occlusion and the like), impaired glucose tolerance and the like), by acting on PPAR. Therefore, Compound (I) of the present invention is useful as a PPAR controlling agent and a prophylactic or therapeutic agent for PPAR-related diseases (e.g., lipid metabolism abnormality and sequelae thereof, diabetes mellitus, hyperlipidemia, arteriosclerotic diseases (for example, ischemic cardiac disease, cerebral disease or peripheral arterial occlusion and the like), impaired glucose tolerance and the like) in a mammal (e.g., human, monkey, sheep, bovine, horse, dog, cat, rabbit, rat, mouse and the like). Compound (I) of the present invention is also useful as an agent of raising high-density lipoprotein cholesterol, an agent of lowering triglyceride, an agent of lowering a low-density lipoprotein cholesterol, an agent of suppressing progress of arteriosclerotic plaque and the like. Furthermore, Compound (I) of the present invention has regulating action for GPR40 receptor function, and is also useful as an insulin secretion promoter or a prophylactic or therapeutic agent for diabetes mellitus and the like.

The invention claimed is:

1. A compound represented by the formula (I):

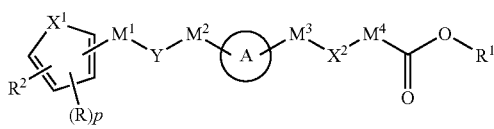

wherein
R is an optionally substituted hydrocarbon group or an optionally substituted heterocyclic group,
p is 0, 1 or 2, and when p is 2, each R may be the same or different,
$R^1$ is a hydrogen atom or an optionally substituted hydrocarbon group,
$R^2$ is an optionally substituted aromatic group,
Ring A is an optionally substituted benzene,
$X^1$ is an oxygen atom or a sulfur atom,
$X^2$ is an oxygen atom or $-S(O)_n-$, wherein n is 0, 1 or 2,
Y is a bond, an oxygen atom, $-S(O)_m-$, $-C(=O)-N(R^3)-$ or $-N(R^3)-C(=O)-$ and $R^3$ is a hydrogen atom, an optionally substituted hydrocarbon group or an optionally substituted heterocyclic group, and m is 0, 1 or 2,
$M^1$ and $M^2$ may be the same or different and are each independently a bond or an optionally substituted divalent aliphatic hydrocarbon group, $M^3$ is an optionally substituted divalent aliphatic hydrocarbon group and $M^4$ is an optionally substituted divalent aliphatic hydrocarbon group,
or a pharmacologically acceptable salt thereof, or a prodrug thereof,
provided that (1) when Y is an oxygen atom or $-S(O)_m-$, $M^1$ is not a bond, and (2) when Y is a bond and one of $M^1$ and $M^2$ is a bond, the other of $M^1$ and $M^2$ is neither a bond nor methylene.

2. The compound according to the claim 1, wherein R is an optionally substituted alkyl, an optionally substituted aralkyl, an optionally substituted cycloalkyl or an optionally substituted aryl.

3. The compound according to the claim 1, wherein p is 1.

4. The compound according to the claim 1, wherein $R^1$ is a hydrogen atom.

5. The compound according to the claim 1, wherein $R^2$ is an optionally substituted phenyl.

6. The compound according to the claim 1, wherein the formula:

is the formula:

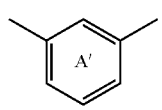

wherein Ring A' is an optionally further substituted benzene ring.

7. The compound according to the claim 1, wherein $X^1$ is an oxygen atom.

8. The compound according to the claim 1, wherein $X^2$ is an oxygen atom or a sulfur atom.

9. The compound according to the claim 1, wherein Y is an oxygen atom or a sulfur atom.

10. The compound according to the claim 1, wherein Y is $-C(=O)-N(R^3)-$, wherein $R^3$ is a hydrogen atom, an optionally substituted hydrocarbon group or an optionally substituted heterocyclic group, and the carbon atom is bonded to $M^1$, and the nitrogen atom to $M^2$.

11. The compound according to the claim 10, wherein $R^3$ is a hydrogen atom, an optionally substituted alkyl, an optionally substituted aralkyl, an optionally substituted cycloalkyl or an optionally substituted aryl.

12. The compound according to the claim 1, wherein $M^1$ is an alkylene having 3 or more carbon atoms.

13. The compound according to the claim 1, wherein $M^1$ and $M^2$ may be the same or different and are each independently a bond, an alkylene, an alkenylene or an alkynylene, $M^3$ is an alkylene, an alkenylene or an alkynylene, and $M^4$ is an alkylene, an alkenylene or an alkynylene.

14. The compound according to the claim 1, wherein the formula (I) is

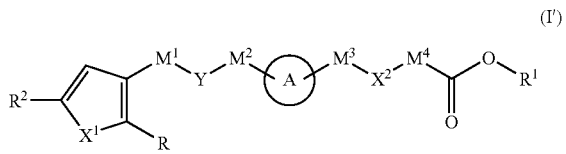

wherein
R is an optionally substituted hydrocarbon group or an optionally substituted heterocyclic group,
$R^1$ is a hydrogen atom or an optionally substituted hydrocarbon group,
$R^2$ is an optionally substituted aromatic group,
Ring A is an optionally substituted benzene,
$X^1$ is an oxygen atom or a sulfur atom,
$X^2$ is an oxygen atom or $-S(O)_n-$, wherein n is 0, 1 or 2,
Y is a bond, an oxygen atom, $-S(O)_m-$, $-C(=O)-N(R^3)-$ or $-N(R^3)-C(=O)-$ and $R^3$ is a hydrogen atom, an optionally substituted hydrocarbon group or an optionally substituted heterocyclic group, and m is 0, 1 or 2,
$M^1$ and $M^2$ may be the same or different and are each independently a bond or an optionally substituted divalent aliphatic hydrocarbon group, $M^3$ is an optionally substituted divalent aliphatic hydrocarbon group, and $M^4$ is an optionally substituted divalent aliphatic hydrocarbon group,
or a pharmacologically acceptable salt thereof,
provided that (1) when Y is an oxygen atom or $-S(O)_m-$, $M^1$ is not a bond, and (2) when Y is a bond and one of $M^1$ and $M^2$ is a bond, the other of $M^1$ and $M^2$ is neither a bond nor methylene.

15. The compound according to the claim 14, wherein the formula (I') is

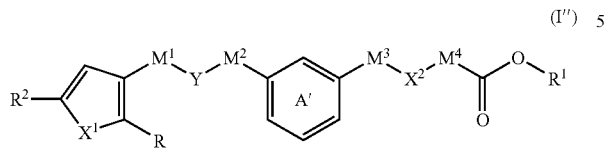

(I'')

wherein
R is an optionally substituted hydrocarbon group or an optionally substituted heterocyclic group,
$R^1$ is a hydrogen atom or an optionally substituted hydrocarbon group,
$R^2$ is an optionally substituted aromatic group,
Ring A' is an optionally further substituted benzene ring,
$X^1$ is an oxygen atom or a sulfur atom,
$X^2$ is an oxygen atom or —S(O)$_n$—, wherein n is 0, 1 or 2,
Y is a bond, an oxygen atom, —S(O)$_m$—, —C(=O)—N(R$^3$)— or —N(R$^3$)—C(=O)— and $R^3$ is a hydrogen atom, an optionally substituted hydrocarbon group or an optionally substituted heterocyclic group, and m is 0, 1 or 2,
$M^1$ and $M^2$ may be the same or different and are each independently a bond or an optionally substituted divalent aliphatic hydrocarbon group, $M^3$ is an optionally substituted divalent aliphatic hydrocarbon group, and $M^4$ is an optionally substituted divalent aliphatic hydrocarbon group,
or a pharmacologically acceptable salt thereof,
provided that (1) when Y is an oxygen atom or —S(O)$_m$—, $M^1$ is not a bond, and (2) when Y is a bond and one of $M^1$ and $M^2$ is a bond, the other of $M^1$ and $M^2$ is neither a bond nor methylene.

16. The compound according to the claim 15, wherein $X^1$ is an oxygen atom, $X^2$ is an oxygen atom or —S(O)$_n$— wherein n is 0, 1 or 2, Y is an oxygen atom, $M^1$ is an optionally substituted $C_{1-3}$ alkylene, $M^2$ is a bond, $M^3$ is an optionally substituted methylene, and $M^4$ is an optionally substituted methylene.

17. The compound according to the claim 16, wherein $M^1$ and $M^3$ may be the same or different and are each independently an optionally substituted methylene.

18. The compound according to the claim 14, wherein the formula (I') is

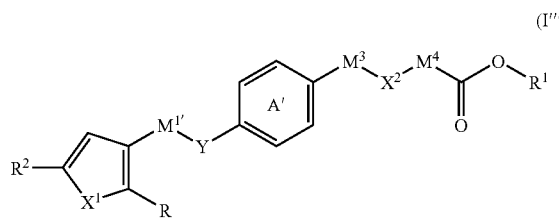

(I''')

wherein
R is an optionally substituted hydrocarbon group or an optionally substituted heterocyclic group,
$R^1$ is a hydrogen atom or an optionally substituted hydrocarbon group,
$R^2$ is an optionally substituted aromatic group,
Ring A' is an optionally further substituted benzene ring,
$X^1$ is an oxygen atom or a sulfur atom,
$X^2$ is an oxygen atom or —S(O)$_n$—, wherein n is 0, 1 or 2,
Y is a bond, an oxygen atom, —S(O)$_m$—, —C(=O)—N(R$^3$)— or —N(R$^3$)—C(=O)— and $R^3$ is a hydrogen atom, an optionally substituted hydrocarbon group or an optionally substituted heterocyclic group, and m is 0, 1 or 2,
$M^{1'}$ is an alkylene group having 3 or more carbon atoms,
$M^3$ is a optionally substituted divalent aliphatic hydrocarbon group, and
$M^4$ is an optionally substituted divalent aliphatic hydrocarbon group,
or a pharmacologically acceptable salt thereof,
provided that (1) when Y is an oxygen atom or —S(O)$_m$—, $M^{1'}$ is not a bond, and (2 when Y is a bond $M^1$ is neither a bond nor methylene.

19. The compound according to the claim 1, wherein R is an optionally substituted alkyl, aryl or cycloalkyl group, p is 0 or 1, $R^1$ is a hydrogen atom, $R^2$ is an optionally substituted phenyl group, Ring A is an optionally substituted benzene ring, $X^1$ is an oxygen atom, $X^2$ is an oxygen atom, Y is an oxygen atom or —C(=O)—N(R$^3$)— wherein $R^3$ is a hydrogen atom, alkyl or aralkyl, and the carbon atom is bonded to $M^1$, and the nitrogen atom to $M^2$, $M^1$ and $M^2$ may be the same or different and are each independently a bond or alkylene, $M^3$ is alkylene, and $M^4$ is alkylene.

20. The compound according to the claim 1, wherein R is an optionally substituted alkyl, aryl or cycloalkyl group, p is 0 or 1, $R^1$ is a hydrogen atom, $R^2$ is an optionally substituted phenyl group, Ring A is an optionally substituted benzene ring, $X^1$ is an oxygen atom, $X^2$ is —S(O)$_n$—, wherein n is 0, 1 or 2, Y is an oxygen atom or —C(=O)—N(R$^3$)—, wherein $R^3$ is a hydrogen atom, alkyl or aralkyl, and the carbon atom is bonded to $M^1$, and the nitrogen atom to $M^2$, $M^1$ and $M^2$ may be the same or different and are each independently a bond or alkylene, $M^3$ is alkylene, and $M^4$ is alkylene.

21. A pharmaceutical medicine composition comprising the compound according to the claim 1 or a prodrug thereof and a pharmaceutically acceptable carrier, excipient, or diluent.

22. An agent of regulating nuclear receptor PPAR comprising the compound according to the claim 1 or a prodrug thereof.

23. The agent according to the claim 22, which is a therapeutic agent for lipid metabolism abnormality or sequelae thereof, arteriosclerotic disease or sequelae thereof, diabetes mellitus, or impaired glucose tolerance.

24. The medicine according to the claim 21, which is an agent of raising high-density lipoprotein cholesterol, an agent of lowering triglyceride, an agent of lowering low-density lipoprotein cholesterol or an agent of suppressing progress of arteriosclerotic plaque.

25. An agent of regulating GPR40 receptor function comprising the compound according to the claim 1 or a prodrug thereof.

26. The agent according to claim 25, which is an agent of regulating insulin secretion, an agent of lowering blood glucose or an agent of protecting pancreatic β cells.

27. The agent according to claim 25, which is a therapeutic agent for diabetes mellitus, glucose intolerance, diabetic neuropathy, diabetic nephropathy, diabetic retinopathy, hyperlipidemia, arteriosclerosis, obesity, hypoglycemia, insulin resistant syndrome, unstable diabetes mellitus, or insulin allergy.

* * * * *